US008716493B2

(12) United States Patent
Chatterjee et al.

(10) Patent No.: US 8,716,493 B2
(45) Date of Patent: *May 6, 2014

(54) MULTICYCLIC COMPOUNDS AND THE USE THEREOF

(75) Inventors: Sankar Chatterjee, Wynnewood, PA (US); Reddeppa reddy Dandu, Downingtown, PA (US); James L. Diebold, Eagleville, PA (US); Derek D. Dunn, Coatesville, PA (US); Robert L. Hudkins, Chester Springs, PA (US); Gregory J. Wells, West Chester, PA (US); Allison L. Zulli, Wayne, PA (US)

(73) Assignee: Cephalon, Inc., Frazer, PA (US)

( * ) Notice: Subject to any disclaimer, the term of this patent is extended or adjusted under 35 U.S.C. 154(b) by 631 days.

This patent is subject to a terminal disclaimer.

(21) Appl. No.: 12/949,254

(22) Filed: Nov. 18, 2010

(65) Prior Publication Data

US 2011/0059959 A1     Mar. 10, 2011

Related U.S. Application Data

(63) Continuation of application No. 11/455,356, filed on Jun. 19, 2006, now abandoned, which is a continuation-in-part of application No. 09/850,858, filed on May 8, 2001, now Pat. No. 7,122,679.

(60) Provisional application No. 60/202,947, filed on May 9, 2000.

(51) Int. Cl.
| *A61K 31/5377* | (2006.01) |
| *C07D 471/14* | (2006.01) |
| *A61K 31/407* | (2006.01) |
| *C07D 487/04* | (2006.01) |
| *A61K 31/437* | (2006.01) |
| *C07D 413/14* | (2006.01) |
| *C07D 249/08* | (2006.01) |
| *A61K 31/4196* | (2006.01) |
| *C07D 403/14* | (2006.01) |
| *A61K 31/496* | (2006.01) |
| *A61P 25/00* | (2006.01) |
| *A61P 25/16* | (2006.01) |
| *A61P 25/28* | (2006.01) |
| *A61P 9/10* | (2006.01) |
| *A61P 3/00* | (2006.01) |
| *A61P 19/02* | (2006.01) |
| *A61P 17/06* | (2006.01) |
| *A61P 35/00* | (2006.01) |
| *C12N 5/02* | (2006.01) |

(52) U.S. Cl.
USPC ........... 548/418; 548/416; 548/417; 548/420; 548/427; 514/232.5

(58) Field of Classification Search
USPC ....................................... 514/232.5, 338, 183
See application file for complete search history.

(56) References Cited

U.S. PATENT DOCUMENTS 7,122,679 B2 * 10/2006 Ator et al. .................... 548/418

* cited by examiner

*Primary Examiner* — Walter Webb

(57) ABSTRACT

The present invention is directed to novel multicyclic molecules that mediate enzymatic activity. In particular, the compounds may be effective in the treatment of diseases or disease states related to the activity of PARP, VEGFR2, and MLK3 enzymes, including, for example, neurodegenerative diseases, inflammation, ischemia, and cancer.

27 Claims, 9 Drawing Sheets

V = O or S

MULTICYCLIC COMPOUNDS AND THE USE THEREOF

CROSS REFERENCE TO RELATED APPLICATIONS

This application is a continuation application of U.S. application Ser. No. 11/455,356, filed Jun. 19, 2006 which, in turn is a continuation-in-part of U.S. application Ser. No. 09/850,858, filed May 8, 2001, now U.S. Pat. No. 7,122,679 which, in turn, claims the benefit of U.S. Provisional Application No. 60/202,947, filed May 9, 2000.

FIELD OF THE INVENTION

The present invention relates to novel multicyclic compounds and the use thereof. More particularly, the present invention relates to novel multicyclic compounds and their use, for example, for the mediation of enzyme activity.

BACKGROUND OF THE INVENTION

Poly(ADP-ribose) polymerase (PARP, also called poly (ADP-ribose) synthetase, or PARS) is a nuclear enzyme which catalyzes the synthesis of poly(ADP-ribose) chains from $NAD^+$ in response to single-stranded DNA breaks as part of the DNA repair process (de Murcia et al. *Trends Biochem. Sci.* 1994, 19, 172; Alvarez-Gonzalez et al. *Mol. Cell. Biochem.* 1994, 138, 33). The chromatin-associated protein substrates for ADP-ribosylation, which include histones, DNA metabolizing enzymes and PARP itself, are modified on surface glutamate residues. PARP catalyzes attachment of one ADP-ribose unit to the protein (initiation), followed by polymerization of as many as 200 ADP-ribose monomers (elongation) via 2'-1" glycosidic linkages. In addition, PARP catalyzes branching of the polymer at a lower frequency.

The role of PARP in the DNA repair process is incompletely defined. The binding of PARP to nicked double-stranded DNA is suggested to facilitate the repair process by transiently blocking DNA replication or recombination. The subsequent poly(ADP-ribosyl)ation of PARP and histones may result in introduction of a substantial negative charge, causing repulsion of the modified proteins from the DNA. The chromatin structure is then proposed to relax, enhancing the access of DNA repair enzymes to the site of damage.

Excessive activation of PARP in response to cell damage or stress is hypothesized to result in cell death (Sims et al. *Biochemistry* 1983, 22, 5188; Yamamoto et al. *Nature* 1981, 294, 284). Activation of PARP by DNA strand breaks may be mediated by nitric oxide (NO) or various reactive oxygen intermediates. When the degree of DNA damage is large, PARP may catalyze a massive amount of poly(ADP-ribosyl) ation, depleting the cell's levels of $NAD^+$. As the cell attempts to maintain homeostasis by resynthesizing $NAD^+$, levels of ATP may decrease precipitously (since synthesis of one molecule of $NAD^+$ requires four molecules of ATP) and the cell may die through depletion of its energy stores.

Activation of PARP has been reported to play a role in cell death in a number of disease states, suggesting that PARP inhibitors would have therapeutic efficacy in those conditions. Enhanced poly(ADP-ribosyl)ation has been observed following focal cerebral ischemia in the rat, consistent with activation of PARP in stroke (Tokime et al. *J. Cereb. Blood Flow Metab.* 1998, 18, 991). A substantial body of published pharmacological and genetic data supports the hypothesis that PARP inhibitors would be neuroprotective following cerebral ischemia, or stroke. Inhibitors of PARP protected against NMDA- or NO-induced neurotoxicity in rat cerebral cortical cultures (Zhang et al., *Science* 1994, 263, 687; Eliasson et al. *Nature Med.* 1997, 3, 1089). The degree of neuroprotection observed for the series of compounds directly paralleled their activity as PARP inhibitors.

Inhibitors of PARP may also display neuroprotective efficacy in animal models of stroke. The potent PARP inhibitor DPQ (3,4-dihydro-5-[4-(1-piperidinyl)butoxy]-1(2H)-isoquinolinone) (Suto et al., U.S. Pat. No. 5,177,075) provided a 54% reduction in infarct volume in a rat model of focal cerebral ischemia (permanent MCAo and 90 min bilateral occlusion of the common carotid artery) following i.p. dosing (10 mg/kg) two hours prior to and two hours after the initiation of ischemia (Takahashi et al. *Brain Res.* 1997, 829, 46). Intracerebroventricular administration of a less potent PARP inhibitor, 3-aminobenzamide (3-AB), yielded a 47% decrease in infarct volume in mice following a two hour occlusion of the MCA by the suture thread method (Endres et al. *J. Cereb. Blood Flow Metab.* 1997, 17, 1143). Treatment with 3-AB also enhanced functional recovery 24 hours after ischemia, attenuated the decrease in $NAD^+$ levels in ischemic tissues, and decreased the synthesis of poly(ADP-ribose) polymers as determined by immunohistochemistry. Similarly, 3-AB (10 mg/kg) significantly reduced infarct volume in a suture occlusion model of focal ischemia in the rat (Lo et al. *Stroke* 1998, 29, 830). The neuroprotective effect of 3-AB (3-30 mg/kg, i.c.v.) was also observed in a permanent middle cerebral artery occlusion model of ischemia in the rat (Tokime et al. *J. Cereb. Blood Flow Metab.* 1998, 18, 991).

The availability of mice in which the PARP gene has been rendered non-functional (Wang, *Genes Dev.* 1995, 9, 509) has also helped to validate the role of PARP in neurodegeneration. Neurotoxicity due to NMDA, NO, or oxygen-glucose deprivation was virtually abolished in primary cerebral cortical cultures from $PARP^{-/-}$ mice (Eliasson et al. *Nature Med.* 1997, 3, 1089). In the mouse suture thread model of ischemia, an 80% reduction in infarct volume was observed in $PARP^{-/-}$ mice, and a 65% reduction was noted in $PARP^{+/-}$ mice. In Endres et al. (1997), there was reported a 35% reduction in infarct volume in $PARP^{-/-}$ mice and a 31% reduction in $PARP^{+/-}$ animals. In addition to neuroprotection, $PARP^{-/-}$ mice demonstrated an improvement in neurological score and displayed increased $NAD^+$ levels following ischemia.

Preclinical evidence also exists which suggests that PARP inhibitors may be efficacious in the treatment of Parkinson's disease. This is because loss of dopaminergic neurons in the substantia nigra is a hallmark of Parkinson's disease. Treatment of experimental animals or humans with the neurotoxin 1-methyl-4-phenyl-1,2,3,6-tetrahydropyridine (MPTP) replicates the loss of dopaminergic neurons and the motor symptoms of Parkinson's disease. MPTP activates PARP in the substantia nigra, and mice lacking PARP are resistant to the neurodegenerative effects of MPTP (Mandir et al. *Proc. Nat. Acad. Sci.* 1999, 96, 5774). Similarly, the PARP inhibitor 3-aminobenzamide is reported to attenuate the loss of $NAD^+$ in the striatum following administration of MPTP to mice (Cosi et al. *Brain Res.* 1998, 809, 58).

Activation of PARP has been implicated in the functional deficits that may result from traumatic brain injury and spinal cord injury. In a controlled cortical impact model of traumatic brain injury, $PARP^{-/-}$ mice displayed significantly improved motor and cognitive function as compared to $PARP^{+/+}$ mice (Whalen et al. *J. Cereb. Blood Flow Metab.* 1999, 19, 835). Peroxynitrite production and PARP activation have also been demonstrated in spinal cord-injured rats (Scott et al. *Ann.*

*Neurol.* 1999, 45, 120). These results suggest that inhibitors of PARP may provide protection from loss of function following head or spinal trauma.

The role of PARP as a mediator of cell death following ischemia and reperfusion may not be limited to the nervous system. In this connection, a recent publication reported that a variety of structurally distinct PARP inhibitors, including 3-AB and related compounds, reduce infarct size following cardiac ischemia and reperfusion in the rabbit (Thiemermann et al. *Proc. Nat. Acad. Sci.* 1997, 94, 679). In the isolated perfused rabbit heart model, inhibition of PARP reduced infarct volume and contractile dysfunction following global ischemia and reperfusion. Skeletal muscle necrosis following ischemia and reperfusion was also attenuated by PARP inhibitors. Similar cardioprotective effects of 3-AB in a rat myocardial ischemia/reperfusion model were reported by Zingarelli and co-workers (Zingarelli et al. *Cardiovascular Research* 1997, 36, 205). These in vivo results are further supported by data from experiments in cultured rat cardiac myocytes (Gilad et al. *J. Mol. Cell. Cardiol.* 1997, 29, 2585). Inhibitors of PARP (3-AB and nicotinamide) protected the myocytes from the reductions in mitochondrial respiration observed following treatment with oxidants such as hydrogen peroxide, peroxynitrite, or nitric oxide donors. The genetic disruption of PARP in mice was recently demonstrated to provide protection delayed cellular injury and production of inflammatory mediators following myocardial ischemia and reperfusion (Yang et al. *Shock* 2000, 13, 60). These data support the hypothesis that administration of a PARP inhibitor could contribute to a positive outcome following myocardial infarction. A particularly useful application of a PARP inhibitor might involve administration concurrent with a treatment designed to reperfuse the affected area of the heart, including angioplasty or a clot-dissolving drug such as tPA.

The activity of PARP is also implicated in the cellular damage that occurs in a variety of inflammatory diseases. Activation of macrophages by pro-inflammatory stimuli may result in the production of nitric oxide and superoxide anion, which combine to generate peroxynitrite, resulting in formation of DNA single-strand breaks and activation of PARP. The role of PARP as a mediator of inflammatory disease is supported by experiments employing PARP$^{-/-}$ mice or inhibitors of PARP in a number of animal models. For example, joints of mice subjected to collagen-induced arthritis contain nitrotyrosine, consistent with generation of peroxynitrite (Szabo et al. *J. Clin. Invest.* 1998, 100, 723). The PARP inhibitor 5-iodo-6-amino-1,2-benzopyrone reduced the incidence and severity of arthritis in these animals, decreasing the severity of necrosis and hyperplasia of the synovium as indicated by histological examination. In the carrageenan-induced pleurisy model of acute local inflammation, 3-AB inhibited the histological injury, pleural exudate formation and mononuclear cell infiltration characteristic of the inflammatory process (Cuzzocrea et al. *Eur. J. Pharmacology* 1998, 342, 67).

Results from rodent models of colitis suggest that PARP activation may be involved in the pathogenesis of inflammatory bowel disease (Zingarelli et al. *Gastroenterology* 1999, 116, 335). Administration of trinitrobenzene sulfonic acid into the lumen of the bowel causes mucosal erosion, neutrophil infiltration, and the appearance of nitrotyrosine. Deletion of the PARP gene or inhibition of PARP by 3-AB decreased tissue damage and attenuated neutrophil infiltration and nitrotyrosine formation, suggesting that PARP inhibitors may be useful in the treatment of inflammatory bowel disease.

A role for PARP in the pathogenesis of endothelial dysfunction in models of endotoxic shock has also been proposed (Szabo et al. *J. Clin. Invest.* 1997, 100, 723). This is because PARP inhibition or genetic deletion of PARP may protect against the decrease in mitochondrial respiration that occurs following treatment of endothelial cells with peroxynitite.

The activation of PARP is involved in the induction of experimental diabetes initiated by the selective beta cell toxin streptozocin (SZ). Substantial breakage of DNA may be induced by SZ, resulting in the activation of PARP and depletion of the cell's energy stores as described above in Yamamoto et al. (1981). In cells derived from PARP$^{-/-}$ mice, exposure to reactive oxygen intermediates results in attenuated depletion of NAD$^+$ and enhanced cell viability relative to wild-type cells (Heller et al. *J. Biol. Chem.* 1995, 270, 11176). Similar effects were observed in wild-type cells treated with 3-AB. Subsequent studies in mice treated with SZ indicated that deletion of the PARP gene provides protection against loss of beta cells (Burkart et al. *Nature Med.* 1999, 5, 314; Pieper et al. *Proc. Nat. Acad. Sci.* 1999, 96, 3059). These observations support the hypothesis that an inhibitor of PARP may have therapeutic utility in the treatment of type I diabetes.

Another potential therapeutic utility of PARP inhibitors involves enhancement of the anti-tumor activity of radiation or DNA-damaging chemotherapeutic agents (Griffin et al. *Biochemie* 1995, 77, 408). Since polyADP-ribosylation occurs in response to these treatments and is part of the DNA repair process, a PARP inhibitor might be expected to provide a synergistic effect.

Like PARP, protein kinases play a critical role in the control of cells. In particular, kinases are known to be involved in cell growth and differentiation. Aberrant expression or mutations in protein kinases have been shown to lead to uncontrolled cell proliferation, such as malignant tumor growth, and various defects in developmental processes, including cell migration and invasion, and angiogenesis. Protein kinases are therefore critical to the control, regulation, and modulation of cell proliferation in diseases and disorders associated with abnormal cell proliferation. Protein kinases have also been implicated as targets in central nervous system disorders such as Alzheimer's disease, inflammatory disorders such as psoriasis, bone diseases such as osteoporosis, atherosclerosis, restenosis, thrombosis, metabolic disorders such as diabetes, and infectious diseases such as viral and fungal infections.

One of the most commonly studied pathways involving kinase regulation is cellular signaling from receptors at the cell surface to the nucleus. Generally, the pattern of expression, ligand availability, and the array of downstream signal transduction pathways that are activated by a particular receptor, determine the function of each receptor. One example of a pathway includes a cascade of kinases in which members of the growth factor receptor tyrosine kinases deliver signals via phosphorylation to other kinases such as Src tyrosine kinase, and the Raf, Mek and Erk serine/threonine kinase families. Each of these kinases is represented by several family members that play related but functionally distinct roles. The loss of regulation of the growth factor signaling pathway is a frequent occurrence in cancer as well as other disease states (Fearon, *Genetic Lesions in Human Cancer, Molecular Oncology* 1996, 143-178).

One receptor tyrosine kinase signaling pathway includes the vascular endothelial growth factor (VEGF) receptor kinase. It has been shown that binding of VEGF to the receptor VEGFR2 affects cell proliferation. For instance, binding of VEGF to the VEGFR-2/flt-1 receptor, which is expressed primarily on endothelial cells, results in receptor dimerization and initiation of a complex cascade which results in growth of new blood vessels (Korpelainen and Alitalo, *Curr.*

Opin. Cell. Biol. 1998, 10, 159). Suppression of formation of new blood vessels by inhibition of the VEGFR tyrosine kinases would have utility in a variety of diseases, including treatment of solid tumors, diabetic retinopathy and other intraocular neovascular syndromes, macular degeneration, rheumatoid arthritis, psoriasis, and endometriosis.

An additional kinase signal transduction is the stress-activated protein kinase (SAPK) pathway (Ip and Davis *Curr. Opin. Cell Biol.* 1998, 10, 205). In response to stimuli such as cytokines, osmotic shock, heat shock, or other environmental stress, the pathway is activated and dual phosphorylation of Thr and Tyr residues within a Thr-Pro-Tyr motif of the c-jun N-terminal kinases (JNKs) is observed. Phosphorylation activates the JNKs for subsequent phosphorylation and activation of various transcription factors, including c-Jun, ATF2 and ELK-1.

The JNKs are mitogen-activated protein kinases (MAPKs) that are encoded by three distinct genes, jnk1, jnk2 and jnk3, which can be alternatively spliced to yield a variety of different JNK isoforms (Gupta et al., *EMBO J.* 1996, 15, 2760). The isoforms differ in their ability to interact with and phosphorylate their target substrates. Activation of JNK is performed by two MAPK kinases (MAPKK), MKK4 and MKK7. MKK4 is an activator of JNK as well as an additional MAPK, p38, while MKK7 is a selective activator of JNK. A number of MAPKK kinases are responsible for activation of MKK4 and MKK7, including the MEKK family and the mixed lineage kinase, or MLK family. The MLK family is comprised of six members, including MLK1, MLK2, MLK3, MLK6, dual leucine zipper kinase (DLK) and leucine zipper-bearing kinase (LZK). MLK2 is also known as MST (Katoh, et al. *Oncogene*, 1994, 10, 1447). Multiple kinases are proposed to be upstream of the MAPKKKs, including but not restricted to germinal center kinase (GCK), hematopoietic progenitor kinase (HPK), and Rac/cdc42. Specificity within the pathway is contributed, at least in part, by scaffolding proteins that bind selected members of the cascade. For example the JNK interacting protein-1 (JIP-1) binds HPK1, DLK or MLK3, MKK7 and JNK, resulting in a module which enhances JNK activation (Dickens et al. *Science* 1997, 277, 693).

Manipulation of the activity of the SAPK pathway can have a wide range of effects, including promotion of both cell death and cell survival in response to various pro-apoptotic stimuli. For example, down-regulation of the pathway by genetic disruption of the gene encoding JNK3 in the mouse provided protection against kainic acid-induced seizures and prevented apoptosis of hippocampal neurons (Yang et al. *Nature* 1997, 389, 865). Similarly, inhibitors of the JNK pathway such as JIP-1 inhibit apoptosis (Dickens, supra). In contrast, the activity of the JNK pathway appears to be protective in some instances. Thymocytes in which MKK4 has been deleted display increased sensitivity to CD95- and CD3 mediated apoptosis (Nishina et al. *Nature* 1997, 385, 350). Overexpression of MLK3 leads to transformation of NIH 3T3 fibroblasts (Hartkamp et al. *Cancer Res.* 1999, 59, 2195).

An area the present invention is directed toward is identification of compounds that modulate the MLK members of the SAPK pathway and promote either cell death or cell survival Inhibitors of MLK family members would be anticipated to lead to cell survival and demonstrate therapeutic activity in a variety of diseases, including chronic neurodegenerative diseases such as Alzheimer's disease, Parkinson's disease and Huntington's disease and acute neurological conditions such as cerebral ischemia, traumatic brain injury and spinal injury. Inhibitors of MLK members leading to inhibition of the SAPK pathway (JNK activity) would also display activity in inflammatory diseases and cancer.

An additional member of the MAP kinase family of proteins is the p38 kinase. Activation of this kinase has been implicated in the production of proinflammatory cytokines such as IL-1 and TNF. Inhibition of this kinase could therefore offer a treatment for disease states in which disregulated cytokine production is involved.

The signals mediated by kinases have also been shown to control cell growth, cell death and differentiation in the cell by regulating the processes of the cell cycle. A family of kinases called cyclin dependent kinases (CDKs) controls progression through the eukaryotic cell cycle. The loss of control of CDK regulation is a frequent event in hyperproliferative diseases and cancer.

Inhibitors of kinases involved in mediating or maintaining particular disease states represent novel therapies for these disorders. Examples of such kinases include Src, raf, the cyclin-dependent kinases (CDK) 1, 2, and 4 and the checkpoint kinases Chk1 and Cds1 in cancer, CDK2 or PDGF-R kinase in restenosis, CDK5 and GSK3 kinases in Alzheimer's Disease, c-Src kinase in osteoporosis, GSK3 kinase in type-2 diabetes, p38 kinase in inflammation, VEGFR 1-3 and TIE-1 and -2 kinases in angiogenesis, UL97 kinase in viral infections, CSF-1R kinase in bone and hematopoietic diseases, and Lck kinase in autoimmune diseases and transplant rejection.

A variety of compounds which are described as PARP or kinase inhibitors have been reported in the literature including Banasik et al. *J. Biol. Chem.* 1992, 267, 1569 and Banasik et al. *Mol. Cell. Biochem.* 1994, 138, 185. Many other PARP inhibiting compounds have been the subject of patents. For example, compounds that are described as PARP inhibitors are disclosed in WO 99/08680, WO 99/11622, WO 99/11623, WO 99/11624, WO 99/11628, WO 99/11644, WO 99/11645, WO 99/11649, WO 99/59973, WO 99/59975 and U.S. Pat. No. 5,587,384.

Structurally related compounds, which are described as having activities other than PARP inhibition, are disclosed in WO 99/47522, EP 0695755, and WO 96/28447. Other structurally related compounds, their syntheses and precursors are disclosed in Piers et al. *J. Org. Chem.* 2000, 65, 530, Berlinck et al. *J. Org. Chem.* 1998, 63, 9850, McCort et al. *Tetrahedron Lett.* 1999, 40, 6211, Mahboobi et al. *Tetrahedron* 1996, 52, 6363, Rewcastle et al. *J. Med. Chem.* 1996, 39, 918, Harris et al. *Tetrahedron Lett.* 1993, 34, 8361, Moody et al. *J. Org. Chem.* 1992, 57, 2105, Ohno et al. *Heterocycles* 1991, 32, 1199, Eitel et al. *J. Org. Chem.* 1990, 55, 5368, Krutošíková et al. *Coll. Czech. Chem. Commun.* 1988, 53, 1770, Muchowski et al. *Tetrahedron Lett.* 1987, 28, 3453, Jones et al. *J. Chem. Soc., Perkin Trans. I* 1984, 2541, Noland et al. *J. Org. Chem.* 1983, 48, 2488, Jones et al. *J. Org. Chem.* 1980, 45, 4515, Leonard et al. *J. Am. Chem. Soc.* 1976, 98, 3987, Rashidan et al. *Arm. Khim. Zh.* 1968, 21, 793, Abrash et al. *Biochemistry* 1965, 4, 99, U.S. Pat. No. 5,728,709, U.S. Pat. No. 4,912,107, EP 0768311, JP 04230385, WO 99/65911, WO 99/41276, WO 98/09967, and WO 96/11933.

Because of the potential role in therapeutically treating neurodegenerative disorders, cancers, and other PARP and kinase related diseases, PARP and kinase inhibitors are an important class of compounds requiring further discovery, exploration, and development. Although, a wide variety of PARP and kinase inhibitors are known, many suffer from problems such as toxicity, poor solubility, and limited efficacy, which prevent practical therapeutic use and preclude further development into effective drugs. Thus, there is a current and immediate need for new PARP and kinase inhibitors for the treatment of PARP and kinase related diseases. The present invention is directed to this, as well as other important ends.

SUMMARY OF THE INVENTION

The present invention is directed, in part, to novel multicyclic compounds. Specifically, in one embodiment, there are provided compounds of formula I:

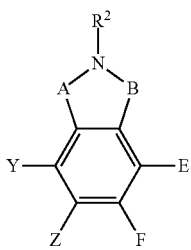

I wherein constituent members of formula I are disclosed in detail, infra.

Another aspect of the invention relates to compounds of formula Ia:

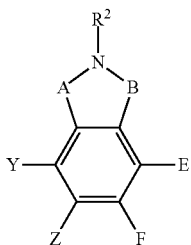

Ia wherein constituent members of formula Ia are disclosed in detail, infra.

Another aspect of the invention relates to multicyclic compounds of formula IIa:

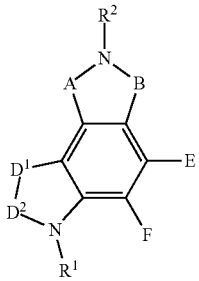

IIa wherein constituent members of formula IIa are disclosed in detail, infra.

A further aspect of the invention relates to compounds of formula IIaa:

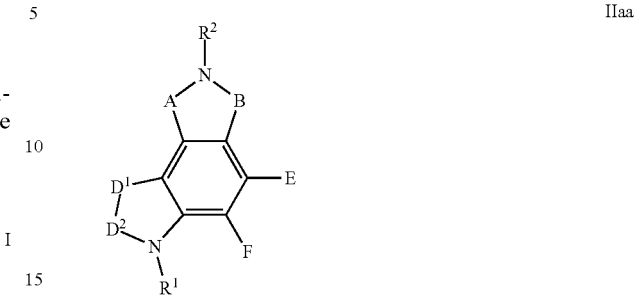

IIaa wherein constituent members of formula IIaa are disclosed in detail, infra.

In yet another embodiment of the present invention, there are provided multicyclic compounds of formula IIb:

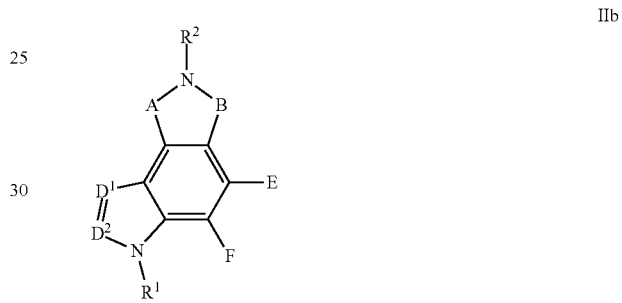

IIb wherein constituent members of formula IIb are disclosed in detail, infra.

In yet another embodiment of the present invention, there are provided multicyclic compounds of formula IIbb:

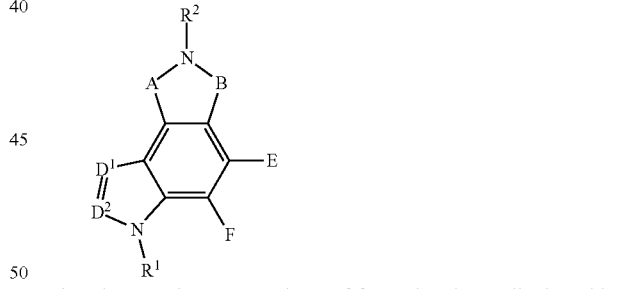

IIbb wherein constituent members of formula IIb are disclosed in detail, infra.

In an additional embodiment of the invention, there are provided compounds of formula III:

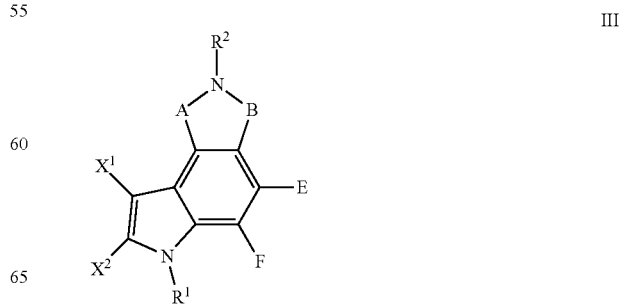

III wherein constituent members of formula III are disclosed in detail, infra.

In an additional embodiment of the invention, there are provided compounds of formula IIIa:

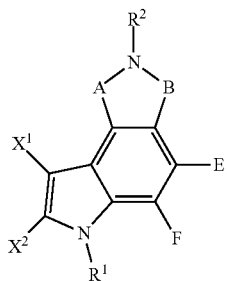

IIIa wherein constituent members of formula IIIa are disclosed in detail, infra.

In still another embodiment of the invention, there are provided compounds of formula IV:

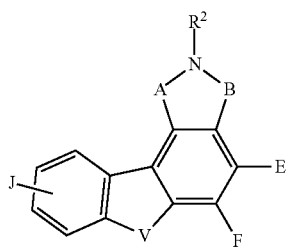

IV wherein constituent members of formula IV are disclosed in detail, infra.

In a further embodiment of the invention, there are provided compounds of formula IVa:

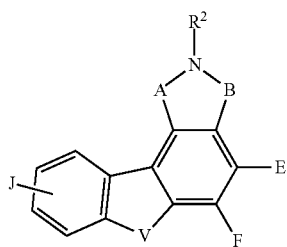

IVa wherein constituent members of formula IVa are disclosed in detail, infra.

The present invention further encompasses a method of inhibiting PARP, VEGFR2, or MLK3 activity comprising contacting said PARP, VEGFR2, or MLK3 with a compound of formula I:

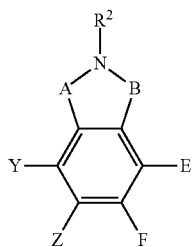

I wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;

Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a C$_3$ to C$_5$ heteroaryl group;

each of E and F is, independently,
lower alkyl; or

E and F, together with the atoms to which they are attached, form:
a substituted or unsubstituted C$_4$ to C$_7$ cycloalkyl group wherein said substituted cycloalkyl group has at least one substituent J;
a substituted or unsubstituted C$_3$ to C$_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group, wherein said substituted aryl group has at least one group J; or
a substituted or unsubstituted heteroaryl group, wherein said substituted heteroaryl group has at least one group J;

R$^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of R$^3$ and R$^4$ is, independently,
hydrogen, lower alkyl, aryl, lower alkyl having at least one substituent J, or aryl having at least one substituent J;

G is:
O, S, SO, SO$_2$, NR$^2$, NR$^3$, NR$^2$CO, NR$^2$CONR$^3$, NR$^2$SO$_2$, or NR$^3$SO$_2$;

J is:
J$^3$-(J$^2$)$_n$-(J$^1$)$_m$ wherein each n and m is, independently, 0 or 1;

each of J$^1$ and J$^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:

hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid.

In yet another aspect of the present invention, a method is provided for treating or preventing a neurodegenerative disease comprising administering to a mammal a therapeutically effective amount of a compound of formula I:

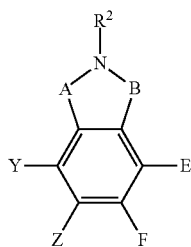

I wherein:

each of A and B is, independently,
C(=O), CH($OR^3$), CH($SR^3$),
$CH_2$, $CHR^3$, $CHR^3CHR^4$, $CR^3R^4$,
C(=O)$NR^3$, N=$CR^3$,
SO, or $SO_2$;

Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a $C_3$ to $C_5$ heteroaryl group;

each of E and F is, independently,
lower alkyl; or

E and F, together with the atoms to which they are attached, form:
a substituted or unsubstituted $C_4$ to $C_7$ cycloalkyl group wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group, wherein said substituted aryl group has at least one group J; or
a substituted or unsubstituted heteroaryl group, wherein said substituted heteroaryl group has at least one group J;

$R^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently,
hydrogen, lower alkyl, aryl, lower alkyl having at least one substituent J, or aryl having at least one substituent J;

G is:
O, S, SO, $SO_2$, $NR^2$, $NR^3$, $NR^2CO$, $NR^2CONR^3$, $NR^2SO_2$, or $NR^3SO_2$;

J is:
$J^3$-($J^2$)$_n$-($J^1$)$_m$ wherein each n and m is, independently, 0 or 1;

each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid.

In a further aspect of the present invention, a method is provided for treating traumatic central nervous system injuries or preventing neuronal degradation associated with traumatic central nervous system injuries comprising administering to a mammal a therapeutically effective amount of a compound of formula I:

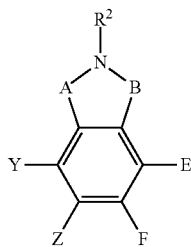

I wherein:

each of A and B is, independently,
C(=O), CH($OR^3$), CH($SR^3$),
$CH_2$, $CHR^3$, $CHR^3CHR^4$, $CR^3R^4$,
C(=O)$NR^3$, N=$CR^3$,
SO, or $SO_2$;

Y and Z, together with the carbon atoms to which they are attached, form:
a substituted or unsubstituted aryl group, wherein said aryl group is monocyclic or bicyclic and said substituted aryl group has at least one substituent J;

a substituted or unsubstituted bicyclic heteroaryl group, wherein said substituted bicyclic heteroaryl group has at least one substituent J; or a $C_3$ to $C_5$ heteroaryl group;

each of E and F is, independently, lower alkyl; or

E and F, together with the atoms to which they are attached, form:

a substituted or unsubstituted $C_4$ to $C_7$ cycloalkyl group wherein said substituted cycloalkyl group has at least one substituent J;

a substituted or unsubstituted $C_3$ to $C_6$ heterocycloalkyl group wherein said substituted heterocycloalkyl group has at least one substituent J;

a substituted or unsubstituted heterocycloalkyl group endocyclically comprising at least one group G wherein said substituted heterocycloalkyl group comprising G has at least one substituent J;

a substituted or unsubstituted aryl group, wherein said substituted aryl group has at least one group J; or a substituted or unsubstituted heteroaryl group, wherein said substituted heteroaryl group has at least one group J;

$R^2$ is:

hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently, hydrogen, lower alkyl, aryl, lower alkyl having at least one substituent J, or aryl having at least one substituent J;

G is:

O, S, SO, $SO_2$, $NR^2$, $NR^3$, $NR^2CO$, $NR^2CONR^3$, $NR^2SO_2$, or $NR^3SO_2$;

J is:

$J^3$-$(J^2)_n$-$(J^1)_m$ wherein each n and m is, independently, 0 or 1;

each of $J^1$ and $J^2$ is, independently, carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:

hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid.

In another aspect of the present invention, a method is provided for treating cerebral ischemia, cardiac ischemia, inflammation, endotoxic shock, or diabetes comprising administering to a mammal a pharmaceutically effective amount of a compound of formula I:

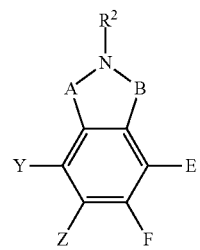

wherein:

each of A and B is, independently,

C(=O), $CH(OR^3)$, $CH(SR^3)$, $CH_2$, $CHR^3$, $CHR^3CHR^4$, $CR^3R^4$, $C(=O)NR^3$, N=$CR^3$, SO, or $SO_2$;

Y and Z, together with the carbon atoms to which they are attached, form:

a substituted or unsubstituted aryl group, wherein said aryl group is monocyclic or bicyclic and said substituted aryl group has at least one substituent J;

a substituted or unsubstituted bicyclic heteroaryl group, wherein said substituted bicyclic heteroaryl group has at least one substituent J; or a $C_3$ to $C_5$ heteroaryl group;

each of E and F is, independently, lower alkyl; or

E and F, together with the atoms to which they are attached, form:

a substituted or unsubstituted $C_4$ to $C_7$ cycloalkyl group wherein said substituted cycloalkyl group has at least one substituent J;

a substituted or unsubstituted $C_3$ to $C_6$ heterocycloalkyl group wherein said substituted heterocycloalkyl group has at least one substituent J;

a substituted or unsubstituted heterocycloalkyl group endocyclically comprising at least one group G wherein said substituted heterocycloalkyl group comprising G has at least one substituent J;

a substituted or unsubstituted aryl group, wherein said substituted aryl group has at least one group J; or a substituted or unsubstituted heteroaryl group, wherein said substituted heteroaryl group has at least one group J;

$R^2$ is:

hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently, hydrogen, lower alkyl, aryl, lower alkyl having at least one substituent J, or aryl having at least one substituent J;

G is:

O, S, SO, $SO_2$, $NR^2$, $NR^3$, $NR^2CO$, $NR^2CONR^3$, $NR^2SO_2$, or $NR^3SO_2$;

J is:

$J^3$-$(J^2)_n$-$(J^1)_m$ wherein each n and m is, independently, 0 or 1;

each of $J^1$ and $J^2$ is, independently, carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:

hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid.

In a yet a further aspect of the present invention, a method is provided for suppressing the formation of blood vessels in a mammal comprising administering to a mammal a pharmaceutically effective amount of a compound of formula I:

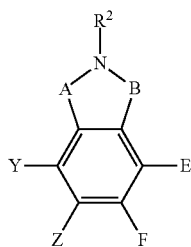

I wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;

Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a $C_3$ to $C_5$ heteroaryl group;

each of E and F is, independently,
lower alkyl; or

E and F, together with the atoms to which they are attached, form:
a substituted or unsubstituted $C_4$ to $C_7$ cycloalkyl group wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group, wherein said substituted aryl group has at least one group J; or
a substituted or unsubstituted heteroaryl group, wherein said substituted heteroaryl group has at least one group J;

$R^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently,
hydrogen, lower alkyl, aryl, lower alkyl having at least one substituent J, or aryl having at least one substituent J;

G is:
O, S, SO, SO$_2$, NR$^2$, NR$^3$, NR$^2$CO, NR$^2$CONR$^3$, NR$^2$SO$_2$, or NR$^3$SO$_2$;

J is:
$J^3$-$(J^2)_n$-$(J^1)_m$ wherein each n and m is, independently, 0 or 1;

each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid.

In a further aspect of the present invention, a method is provided for treating cellular proliferative disorders comprising administering to a mammal a pharmaceutically effective amount of a compound of formula I:

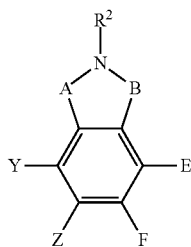

I wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;

Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a $C_3$ to $C_5$ heteroaryl group;

each of E and F is, independently,
lower alkyl; or

E and F, together with the atoms to which they are attached, form:
   a substituted or unsubstituted $C_4$ to $C_7$ cycloalkyl group wherein said substituted cycloalkyl group has at least one substituent J;
   a substituted or unsubstituted $C_3$ to $C_6$ heterocycloalkyl group wherein said substituted heterocycloalkyl group has at least one substituent J;
   a substituted or unsubstituted heterocycloalkyl group endocyclically comprising at least one group G wherein said substituted heterocycloalkyl group comprising G has at least one substituent J;
   a substituted or unsubstituted aryl group, wherein said substituted aryl group has at least one group J; or
   a substituted or unsubstituted heteroaryl group, wherein said substituted heteroaryl group has at least one group J;

$R^2$ is:
   hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently,
   hydrogen, lower alkyl, aryl, lower alkyl having at least one substituent J, or aryl having at least one substituent J;

G is:
   O, S, SO, $SO_2$, $NR^2$, $NR^3$, $NR^2CO$, $NR^2CONR^3$, $NR^2SO_2$, or $NR^3SO_2$;

J is:
   $J^3$-$(J^2)_n$-$(J^1)_m$ wherein each n and m is, independently, 0 or 1;

each of $J^1$ and $J^2$ is, independently,
   carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:
   hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid.

In yet another aspect of the present invention, a method for treating cancer comprising administering to a mammal a pharmaceutically effective amount of a compound of formula I:

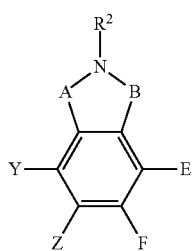

I wherein:
   each of A and B is, independently,
      C(=O), CH($OR^3$), CH($SR^3$),
      $CH_2$, $CHR^3$, $CHR^3CHR^4$, $CR^3R^4$,
      C(=O)$NR^3$, N=$CR^3$,
      SO, or $SO_2$;
   Y and Z, together with the carbon atoms to which they are attached, form:
      a substituted or unsubstituted aryl group, wherein said aryl group is monocyclic or bicyclic and said substituted aryl group has at least one substituent J;
      a substituted or unsubstituted bicyclic heteroaryl group, wherein said substituted bicyclic heteroaryl group has at least one substituent J; or
      a $C_3$ to $C_5$ heteroaryl group;
   each of E and F is, independently,
      lower alkyl; or
   E and F, together with the atoms to which they are attached, form:
      a substituted or unsubstituted $C_4$ to $C_7$ cycloalkyl group wherein said substituted cycloalkyl group has at least one substituent J;
      a substituted or unsubstituted $C_3$ to $C_6$ heterocycloalkyl group wherein said substituted heterocycloalkyl group has at least one substituent J;
      a substituted or unsubstituted heterocycloalkyl group endocyclically comprising at least one group G wherein said substituted heterocycloalkyl group comprising G has at least one substituent J;
      a substituted or unsubstituted aryl group, wherein said substituted aryl group has at least one group J; or
      a substituted or unsubstituted heteroaryl group, wherein said substituted heteroaryl group has at least one group J;

$R^2$ is:
   hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently,
   hydrogen, lower alkyl, aryl, lower alkyl having at least one substituent J, or aryl having at least one substituent J;

G is:
   O, S, SO, $SO_2$, $NR^2$, $NR^3$, $NR^2CO$, $NR^2CONR^3$, $NR^2SO_2$, or $NR^3SO_2$;

J is:
   $J^3$-$(J^2)_n$-$(J^1)_m$ wherein each n and m is, independently, 0 or 1;

each of $J^1$ and $J^2$ is, independently,
   carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:
   hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid.

The present invention further encompasses a method of inhibiting PARP, VEGFR2, or MLK3 activity comprising contacting said PARP, VEGFR2, or MLK3 with compounds of formula Ia:

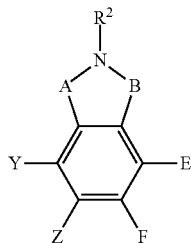

wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;
Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a C$_3$ to C$_5$ heteroaryl group;
each of E and F is, independently,
lower alkyl; or
E and F, together with the atoms to which they are attached, form:
a substituted or unsubstituted C$_4$ to C$_7$ cycloalkyl group, wherein said substituted cycloalkyl group has at least one substituent J;
a substituted or unsubstituted C$_3$ to C$_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;
R$^2$ is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;
each of R$^3$ and R$^4$ is, independently,
hydrogen, lower alkyl, aryl, lower alkyl having at least one substituent J, or aryl having at least one substituent J.

G is:
O, S, SO, SO$_2$, NR$^2$, NR$^3$, NR$^2$CO, NR$^2$CONR$^3$, NR$^2$SO$_2$, or NR$^3$SO$_2$;
J is:
J$^3$-(J$^2$)$_n$-(J$^1$)$_m$ wherein each of n and m is, independently, 0 or 1;
each of J$^1$ and J$^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, C$_3$ to C$_7$ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and
J$^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and
any two adjacent J groups can combine to form —X—(CH$_2$)$_p$—X—, wherein X is independently O or NH, and p is 1 or 2.

In yet another aspect of the present invention, a method is provided for treating or preventing a neurodegenerative disease comprising administering to a mammal a therapeutically effective amount of a compound of formula Ia:

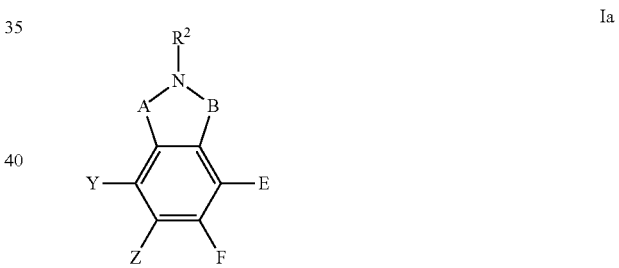

wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;
Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a C$_3$ to C$_5$ heteroaryl group;
each of E and F is, independently,
lower alkyl; or
E and F, together with the atoms to which they are attached, form:
a substituted or unsubstituted C$_4$ to C$_7$ cycloalkyl group, wherein said substituted cycloalkyl group has at least one substituent J;

a substituted or unsubstituted C₃ to C₆ heterocycloalkyl group wherein said substituted heterocycloalkyl group has at least one substituent J;

a substituted or unsubstituted heterocycloalkyl group endocyclically comprising at least one group G wherein said substituted heterocycloalkyl group comprising G has at least one substituent J;

a substituted or unsubstituted aryl group wherein said substituted aryl group has at least one group J; or a substituted or unsubstituted heteroaryl group wherein said substituted heteroaryl group has at least one group J;

R² is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;

each of R³ and R⁴ is, independently,
hydrogen, lower alkyl, aryl, lower alkyl having at least one substituent J, or aryl having at least one substituent J.

G is:
O, S, SO, SO₂, NR², NR³, NR²CO, NR²CONR³, NR²SO₂, or NR³SO₂;

J is:
J³-(J²)ₙ-(J¹)ₘ wherein each of n and m is, independently, 0 or 1;

each of J¹ and J² is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, C₃ to C₇ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and J³ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and any two adjacent J groups can combine to form —X—(CH₂)ₚ—X—, wherein X is independently O or NH, and p is 1 or 2.

In a further aspect of the present invention, a method is provided for treating traumatic central nervous system injuries or preventing neuronal degradation associated with traumatic central nervous system injuries comprising administering to a mammal a therapeutically effective amount of a compound of formula Ia:

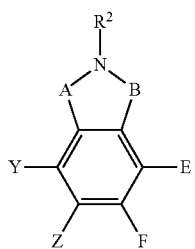

Ia wherein:
each of A and B is, independently,
C(=O), CH(OR³), CH(SR³),
CH₂, CHR³, CHR³CHR⁴, CR³R⁴,
C(=O)NR³, N=CR³,
SO, or SO₂;

Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a C₃ to C₅ heteroaryl group;

each of E and F is, independently,
lower alkyl; or

E and F, together with the atoms to which they are attached, form:
a substituted or unsubstituted C₄ to C₇ cycloalkyl group, wherein said substituted cycloalkyl group has at least one substituent J;
a substituted or unsubstituted C₃ to C₆ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;

R² is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;

each of R³ and R⁴ is, independently,
hydrogen, lower alkyl, aryl, lower alkyl having at least one substituent J, or aryl having at least one substituent J.

G is:
O, S, SO, SO₂, NR², NR³, NR²CO, NR²CONR³, NR²SO₂, or NR³SO₂;

J is:
J³-(J²)ₙ-(J¹)ₘ wherein each of n and m is, independently, 0 or 1;

each of J¹ and J² is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and any two adjacent J groups can combine to form —X—$(CH_2)_p$—X—, wherein X is independently O or NH, and p is 1 or 2.

In another aspect of the present invention, a method is provided for treating cerebral ischemia, cardiac ischemia, inflammation, endotoxic shock, or diabetes comprising administering to a mammal a pharmaceutically effective amount of a compound of formula Ia:

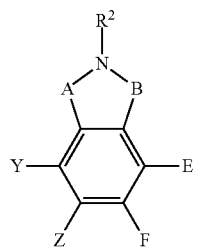

wherein:
each of A and B is, independently,
$C(=O)$, $CH(OR^3)$, $CH(SR^3)$,
$CH_2$, $CHR^3$, $CHR^3CHR^4$, $CR^3R^4$,
$C(=O)NR^3$, $N=CR^3$,
SO, or $SO_2$;

Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a $C_3$ to $C_5$ heteroaryl group;

each of E and F is, independently,
lower alkyl; or

E and F, together with the atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J; a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or a substituted or unsubstituted heteroaryl group wherein said substituted heteroaryl group has at least one group J;

$R^2$ is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;

each of $R^3$ and $R^4$ is, independently,
hydrogen, lower alkyl, aryl, lower alkyl having at least one substituent J, or aryl having at least one substituent J.

G is:
O, S, SO, $SO_2$, $NR^2$, $NR^3$, $NR^2CO$, $NR^2CONR^3$, $NR^2SO_2$, or $NR^3SO_2$;

J is:
$J^3$-$(J^2)_n$-$(J^1)_m$ wherein each of n and m is, independently, 0 or 1;

each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and any two adjacent J groups can combine to form —X—$(CH_2)_p$—X—, wherein X is independently O or NH, and p is 1 or 2.

In a yet a further aspect of the present invention, a method is provided for suppressing the formation of blood vessels in a mammal comprising administering to a mammal a pharmaceutically effective amount of a compound of formula Ia:

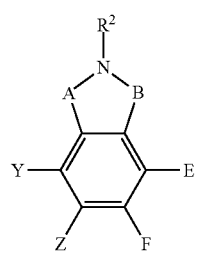

wherein:
each of A and B is, independently,
$C(=O)$, $CH(OR^3)$, $CH(SR^3)$,
$CH_2$, $CHR^3$, $CHR^3CHR^4$, $CR^3R^4$,
$C(=O)NR^3$, $N=CR^3$,
SO, or $SO_2$;

Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a $C_3$ to $C_5$ heteroaryl group;
each of E and F is, independently,
lower alkyl; or
E and F, together with the atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;
$R^2$ is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;
each of $R^3$ and $R^4$ is, independently,
hydrogen, lower alkyl, aryl, lower alkyl having at least one substituent J, or aryl having at least one substituent J.
G is:
O, S, SO, $SO_2$, $NR^2$, $NR^3$, $NR^2CO$, $NR^2CONR^3$, $NR^2SO_2$, or $NR^3SO_2$;
J is:
$J^3$-$(J^2)_n$-$(J^1)_m$ wherein each of n and m is, independently, 0 or 1;
each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and
$J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and
any two adjacent J groups can combine to form —X—$(CH_2)_p$—X—, wherein X is independently O or NH, and p is 1 or 2.

In a further aspect of the present invention, a method is provided for treating cellular proliferative disorders comprising administering to a mammal a pharmaceutically effective amount of a compound of formula Ia:

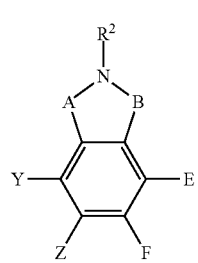

wherein:
each of A and B is, independently,
C(=O), $CH(OR^3)$, $CH(SR^3)$, $CH_2$, $CHR^3$, $CHR^3CHR^4$, $CR^3R^4$, $C(=O)NR^3$, $N=CR^3$, SO, or $SO_2$;
Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a $C_3$ to $C_5$ heteroaryl group;
each of E and F is, independently,
lower alkyl; or
E and F, together with the atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;
$R^2$ is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;
each of $R^3$ and $R^4$ is, independently,
hydrogen, lower alkyl, aryl, lower alkyl having at least one substituent J, or aryl having at least one substituent J.
G is:
O, S, SO, $SO_2$, $NR^2$, $NR^3$, $NR^2CO$, $NR^2CONR^3$, $NR^2SO_2$, or $NR^3SO_2$;
J is:
$J^3$-$(J^2)_n$-$(J^1)_m$ wherein each of n and m is, independently, 0 or 1;
each of $J^1$ and $J^2$ is, independently, carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and
any two adjacent J groups can combine to form —X—$(CH_2)_p$—X—, wherein X is independently O or NH, and p is 1 or 2.

In yet another aspect of the present invention, a method for treating cancer comprising administering to a mammal a pharmaceutically effective amount of a compound of formula Ia:

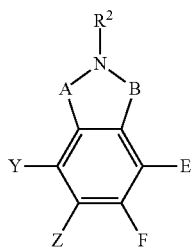

Ia wherein:
each of A and B is, independently,
C(=O), CH($OR^3$), CH($SR^3$),
$CH_2$, $CHR^3$, $CHR^3CHR^4$, $CR^3R^4$,
C(=O)$NR^3$, N=$CR^3$,
SO, or $SO_2$;
Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a $C_3$ to $C_5$ heteroaryl group;
each of E and F is, independently,
lower alkyl; or
E and F, together with the atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;

$R^2$ is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;

each of $R^3$ and $R^4$ is, independently,
hydrogen, lower alkyl, aryl, lower alkyl having at least one substituent J, or aryl having at least one substituent J.

G is:
O, S, SO, $SO_2$, $NR^2$, $NR^3$, $NR^2CO$, $NR^2CONR^3$, $NR^2SO_2$, or $NR^3SO_2$;

J is:
$J^3$-$(J^2)_n$-$(J^1)_m$ wherein each of n and m is, independently, 0 or 1;

each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and
any two adjacent J groups can combine to form —X—$(CH_2)_p$—X—, wherein X is independently O or NH, and p is 1 or 2.

DESCRIPTION OF PREFERRED EMBODIMENTS

Figure 1:
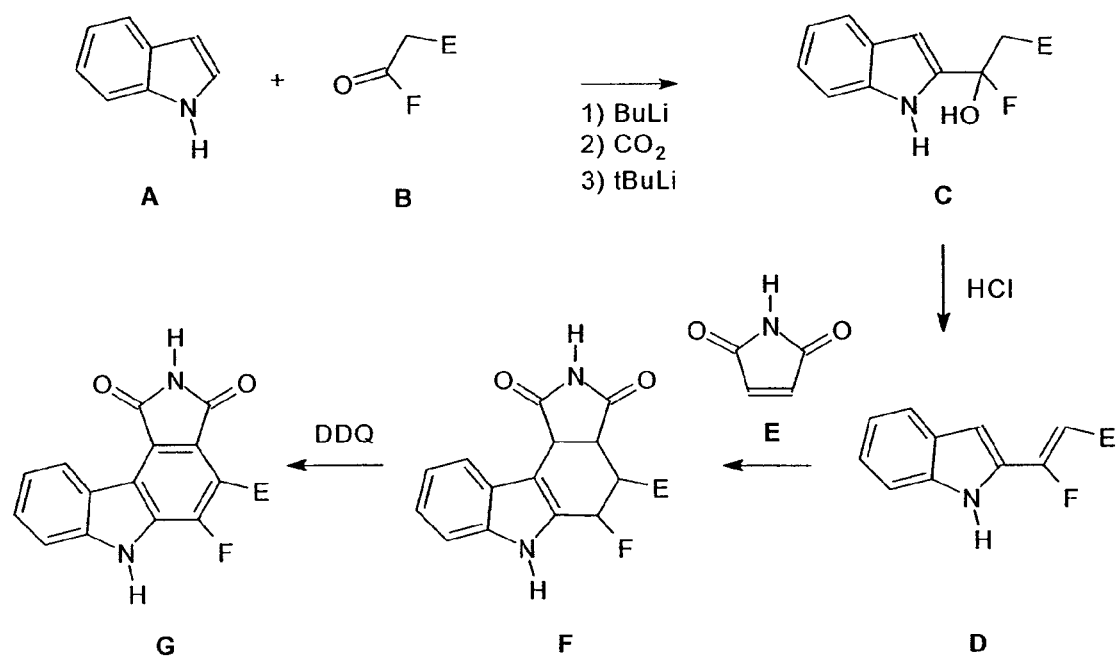
FIG. 1 shows a schematic including a compound within the scope of the present invention and precursors thereto.

The present invention is directed, in part, to new multicyclic compounds that may be highly useful in connection with the inhibition of PARP, VEGFR2, MLK3, or other enzymes. The new compounds are described in more detail below.

Specifically, in one embodiment, the present invention relates to novel multicyclic compounds of formula I:

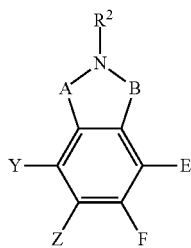

I wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;
Y and Z, together with the carbon atoms to which they are attached, form:
a substituted or unsubstituted aryl group, wherein said aryl group is monocyclic or bicyclic and said substituted aryl group has at least one substituent J;
a substituted or unsubstituted bicyclic heteroaryl group, wherein said substituted bicyclic heteroaryl group has at least one substituent J; or
a C$_3$ to C$_5$ heteroaryl group;
each of E and F is, independently,
lower alkyl; or
E and F, together with the atoms to which they are attached, form:
a substituted or unsubstituted C$_4$ to C$_7$ cycloalkyl group, wherein said substituted cycloalkyl group has at least one substituent J;
a substituted or unsubstituted C$_3$ to C$_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;
R$^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;
each of R$^3$ and R$^4$ is, independently,
hydrogen, lower alkyl, aryl, lower alkyl having at least one substituent J, or aryl having at least one substituent J.
G is:
O, S, SO, SO$_2$, NR$^2$, NR$^3$, NR$^2$CO, NR$^2$CONR$^3$, NR$^2$SO$_2$, or NR$^3$SO$_2$;
J is:
J$^3$-(J$^2$)$_n$-(J$^1$)$_m$ wherein each of n and m is, independently, 0 or 1;
each of J$^1$ and J$^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, C$_3$ to C$_7$ cycloalkyl, heterocycloalkyl, aryl, heteroaryl, sulfonylamido, alkylsulfonylamido, arylsulfonylamido, an amino acid, or a protected amino acid; and
J$^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid;
with the provisos that when one of A and B is C(=O) and E and F, together with the atoms to which they are attached, form phenyl, then the other of A and B is other than C(=O), and when A and B are C(=O), and Y and Z, together with the atoms to which they are attached, form unsubstituted indol-2,3-diyl, and R$^2$ is hydrogen, then E and F, together with the atoms to which they are attached, form a group other than unsubstituted imidazole or N-methylimidazole.

In another embodiment, the present invention provides compounds of formula Ia:

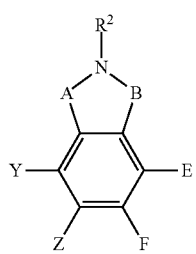

Ia wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;
Y and Z, together with the carbon atoms to which they are attached, form:
a substituted or unsubstituted aryl group, wherein said aryl group is monocyclic or bicyclic and said substituted aryl group has at least one substituent J;

a substituted or unsubstituted bicyclic heteroaryl group, wherein said substituted bicyclic heteroaryl group has at least one substituent J; or
a $C_3$ to $C_5$ heteroaryl group;
each of E and F is, independently,
lower alkyl; or
E and F, together with the atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;
$R^2$ is:
hydrogen, lower alkyl, lower alkyl having at least one substituent J, formyl, acetyl, lower alkanoyl, lower alkanoyl having at least one substituent J, lower alkylsulfonyl, arylsulfonyl, an amino acid, or a protected amino acid;
each of $R^3$ and $R^4$ is, independently,
hydrogen, lower alkyl, aryl, lower alkyl having at least one substituent J, or aryl having at least one substituent J.
G is:
O, S, SO, $SO_2$, $NR^2$, $NR^3$, $NR^2CO$, $NR^2CONR^3$, $NR^2SO_2$, or $NR^3SO_2$;
J is:
$J^3$-$(J^2)_n$-$(J^1)_m$ wherein each of n and m is, independently, 0 or 1;
each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, a protected amino acid, aminocarbonyloxy, arylaminocarbonyloxy, or heteroarylaminocarbonyloxy; and
$J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and
any two adjacent J groups can combine to form —X—$(CH_2)_p$—X—, wherein X is independently O or NH, and p is 1 or 2;
with the provisos that when one of A and B is C(=O) and E and F, together with the atoms to which they are attached, form phenyl, then the other of A and B is other than C(=O), and when A and B are C(=O), and Y and Z, together with the atoms to which they are attached, form unsubstituted indol-2,3-diyl, and $R^2$ is hydrogen, then E and F, together with the atoms to which they are attached, form a group other than unsubstituted imidazole or N-methylimidazole.

In other preferred embodiments, the present invention includes compounds of formula I or Ia where E and F combined together with the carbon atoms to which they are attached, form a $C_5$ cycloalkyl group.

In a preferred embodiment of the present invention, there are provided multicyclic compounds of formula IIa:

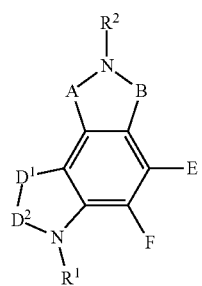

IIa wherein:
each of A and B is, independently,
C(=O), CH($OR^3$), CH($SR^3$),
$CH_2$, $CHR^3$, $CHR^3CHR^4$, $CR^3R^4$,
C(=O)$NR^3$, N=$CR^3$,
SO, or $SO_2$;
each of E and F is, independently,
lower alkyl; or
E and F, together with the carbon atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;
G is:
O, S, SO, $SO_2$, $NR^2$, $NR^3$, $NR^2CO$, $NR^2CONR^3$, $NR^2SO_2$, or $NR^3SO_2$;
$R^1$ is:
hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;
$R^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;
each of $R^3$ and $R^4$ is, independently,
hydrogen, lower alkyl, aryl, lower alkyl having at least one substituent J, or aryl having at least one substituent J;

J is:
J$^3$-(J$^2$)$_n$-(J$^1$)$_m$ wherein each of n and m is, independently, 0 or 1;

each of J$^1$ and J$^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, C$_3$ to C$_7$ cycloalkyl, heterocycloalkyl, aryl, heteroaryl, sulfonylamido, alkylsulfonylamido, arylsulfonylamido, an amino acid, or a protected amino acid; and J$^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid;

each of D$^1$ and D$^2$ is, independently,
N(X$^1$), N(X$^2$), C(R$^1$)(X$^1$), C(R$^1$)(X$^2$), C(=O), S, or O; and each of X$^1$ and X$^2$ is, independently,
hydrogen, halo, group J, lower alkyl,
lower alkyl having at least one substituent J,
substituted or unsubstituted C$_3$ to C$_7$ cycloalkyl wherein said substituted cycloalkyl group has at least one substituent J,
substituted or unsubstituted C$_2$ to C$_6$ heterocycloalkyl wherein said substituted heterocycloalkyl group has at least one substituent J,
substituted or unsubstituted aryl wherein said substituted aryl group has at least one substituent J,
substituted or unsubstituted heteroaryl wherein said substituted heteroaryl group has at least one substituent J; or X$^1$ and X$^2$, together with the atoms to which they are attached, form:
a substituted or unsubstituted C$_4$ to C$_7$ cycloalkyl group wherein said substituted cycloalkyl group has at least one substituent J;
a substituted or unsubstituted aryl group wherein said substituted aryl group has at least one substituent J; or
a substituted or unsubstituted heteroaryl group wherein said substituted heteroaryl group has at least one substituent J.

In a preferred embodiment of the present invention, there are provided multicyclic compounds of formula IIaa:

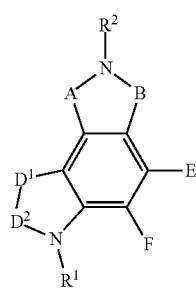

IIaa wherein:
each of A and B is, independently,
C(=O), CH(OR$^3$), CH(SR$^3$),
CH$_2$, CHR$^3$, CHR$^3$CHR$^4$, CR$^3$R$^4$,
C(=O)NR$^3$, N=CR$^3$,
SO, or SO$_2$;

each of E and F is, independently,
lower alkyl; or

E and F, together with the carbon atoms to which they are attached, form:
a substituted or unsubstituted C$_4$ to C$_7$ cycloalkyl group, wherein said substituted cycloalkyl group has at least one substituent J;
a substituted or unsubstituted C$_3$ to C$_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;

G is:
O, S, SO, SO$_2$, NR$^2$, NR$^3$, NR$^2$CO, NR$^2$CONR$^3$, NR$^2$SO$_2$, or NR$^3$SO$_2$;

R$^1$ is:
hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;

R$^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of R$^3$ and R$^4$ is, independently,
hydrogen, lower alkyl, aryl, lower alkyl having at least one substituent J, or aryl having at least one substituent J;

J is:
J$^3$-(J$^2$)$_n$-(J$^1$)$_m$ wherein each of n and m is, independently, 0 or 1;

each of J$^1$ and J$^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, C$_3$ to C$_7$ cycloalkyl, heterocycloalkyl, aryl, heteroaryl, sulfonylamido, alkylsulfonylamido, arylsulfonylamido, an amino acid, or a protected amino acid; and J$^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and any two adjacent J groups can combine to form —X—(CH$_2$)$_p$—X—, wherein X is independently O or NH, and p is 1 or 2;

each of $D^1$ and $D^2$ is, independently,
$N(X^1)$, $N(X^2)$, $C(R^1)(X^1)$, $C(R^1)(X^2)$, $C(=O)$, S, or O; and each of $X^1$ and $X^2$ is, independently,
hydrogen, halo, group J, lower alkyl,
lower alkyl having at least one substituent J,
substituted or unsubstituted $C_3$ to $C_7$ cycloalkyl wherein said substituted cycloalkyl group has at least one substituent J,
substituted or unsubstituted $C_2$ to $C_6$ heterocycloalkyl wherein said substituted heterocycloalkyl group has at least one substituent J,
substituted or unsubstituted aryl wherein said substituted aryl group has at least one substituent J,
substituted or unsubstituted heteroaryl wherein said substituted heteroaryl group has at least one substituent J; or $X^1$ and $X^2$, together with the atoms to which they are attached, form:
a substituted or unsubstituted $C_4$ to $C_7$ cycloalkyl group wherein said substituted cycloalkyl group has at least one substituent J;
a substituted or unsubstituted aryl group wherein said substituted aryl group has at least one substituent J; or
a substituted or unsubstituted heteroaryl group wherein said substituted heteroaryl group has at least one substituent J.

Preferred embodiments of the present invention include compounds of formula IIa or IIaa wherein:
each of A and B is, independently,
$C(=O)$, $CH_2$, $CH(OR^3)$, or $CH(SR^3)$; and
E and F, together with the atoms to which they are attached, form:
a substituted or unsubstituted $C_4$ to $C_7$ cycloalkyl group wherein said substituted cycloalkyl group has at least one substituent J;
a substituted or unsubstituted $C_3$ to $C_5$ heterocycloalkyl group wherein said substituted heterocycloalkyl group has at least one substituent J; or
a substituted or unsubstituted heterocycloalkyl group endocyclically comprising within at least one group G wherein said substituted heterocycloalkyl group comprising G has at least one substituent J; and G is O, S, SO, $SO_2$, $NR^2$, $NR^3$, $NR^2CO$, $NR^2CONR^3$, $NR^2SO_2$, or $NR^3SO_2$.

Preferred embodiments of the present invention include compounds of formula IIa or IIaa wherein:
each of A and B is, independently,
$C(=O)$, $CH_2$, $CH(OR^3)$, or $CH(SR^3)$; and
E and F, together with the atoms to which they are attached, form:
a substituted or unsubstituted aryl group, wherein said substituted aryl group has at least one group J; or
a substituted or unsubstituted heteroaryl group, wherein said substituted heteroaryl group has at least one group J.

In an alternate preferred embodiment of the present invention, there are provided compounds of formula IIb:

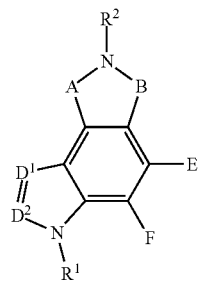

IIb wherein:
each of A and B is, independently,
$C(=O)$, $CH(OR^3)$, $CH(SR^3)$,
$CH_2$, $CHR^3$, $CHR^3CHR^4$, $CR^3R^4$,
$C(=O)NR^3$, $N=CR^3$,
SO, or $SO_2$;
each of E and F is, independently,
lower alkyl; or
E and F, together with the carbon atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;
G is:
O, S, SO, $SO_2$, $NR^2$, $NR^3$, $NR^2CO$, $NR^2CONR^3$, $NR^2SO_2$, or $NR^3SO_2$;
$R^1$ is:
hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;
$R^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;
each of $R^3$ and $R^4$ is, independently,
hydrogen, lower alkyl, aryl, lower alkyl having at least one substituent J, or aryl having at least one substituent J.
J is:
$J^3$-$(J^2)_n$-$(J^1)_m$ wherein each of n and m is, independently, 0 or 1;
each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid;

each of $D^1$ and $D^2$ is, independently,
$C(X^1)$, $C(X^2)$, or N; and each of $X^1$ and $X^2$ is, independently,
hydrogen, halo, group J, lower alkyl,
lower alkyl having at least one substituent J,
substituted or unsubstituted $C_3$ to $C_7$ cycloalkyl wherein said substituted cycloalkyl group has at least one substituent J,
substituted or unsubstituted $C_2$ to $C_6$ heterocycloalkyl wherein said substituted heterocycloalkyl group has at least one substituent J,
substituted or unsubstituted aryl wherein said substituted aryl group has at least one substituent J,
substituted or unsubstituted heteroaryl wherein said substituted heteroaryl group has at least one substituent J; or $X^1$ and $X^2$, together with the atoms to which they are attached, form:
a substituted or unsubstituted $C_4$ to $C_7$ cycloalkyl group wherein said substituted cycloalkyl group has at least one substituent J;
a substituted or unsubstituted aryl group wherein said substituted aryl group has at least one substituent J; or
a substituted or unsubstituted heteroaryl group wherein said substituted heteroaryl group has at least one substituent J;

with the provisos that when one of A and B is C(=O) and E and F, together with the atoms to which they are attached, form phenyl, then the other of A and B is other than C(=O), and when A and B are C(=O), and $D^1$ and $D^2$ are $C(X^1)$ or $C(X^2)$ in which $X^1$ and $X^2$, together with the atoms to which they are attached, form unsubstituted phenyl, and $R^2$ is hydrogen, then E and F, together with the atoms to which they are attached, form a group other than unsubstituted imidazole or N-methylimidazole.

In an alternate preferred embodiment of the present invention, there are provided compounds of formula IIbb:

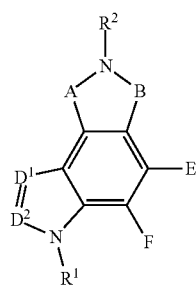

IIbb wherein:
each of A and B is, independently,
C(=O), CH(OR³), CH(SR³),
CH₂, CHR³, CHR³CHR⁴, CR³R⁴,
C(=O)NR³, N=CR³,
SO, or SO₂;

each of E and F is, independently,
lower alkyl; or

E and F, together with the carbon atoms to which they are attached, form:
a substituted or unsubstituted $C_4$ to $C_7$ cycloalkyl group, wherein said substituted cycloalkyl group has at least one substituent J;
a substituted or unsubstituted $C_3$ to $C_6$ heterocycloalkyl group wherein said substituted heterocycloalkyl group has at least one substituent J;
a substituted or unsubstituted heterocycloalkyl group endocyclically comprising at least one group G wherein said substituted heterocycloalkyl group comprising G has at least one substituent J;
a substituted or unsubstituted aryl group wherein said substituted aryl group has at least one group J; or
a substituted or unsubstituted heteroaryl group wherein said substituted heteroaryl group has at least one group J;

G is:
O, S, SO, SO₂, NR², NR³, NR²CO, NR²CONR³, NR²SO₂, or NR³SO₂;

$R^1$ is:
hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;

$R^2$ is:
hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently,
hydrogen, lower alkyl, aryl, lower alkyl having at least one substituent J, or aryl having at least one substituent J.

J is:
$J^3$-$(J^2)_n$-$(J^1)_m$ wherein each of n and m is, independently, 0 or 1;

each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and $J^3$ is:
hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and any two adjacent J groups can combine to form —X—(CH₂)ₚ—X—, wherein X is independently O or NH, and p is 1 or 2;

each of $D^1$ and $D^2$ is, independently,
 $C(X^1)$, $C(X^2)$, or N; and
each of $X^1$ and $X^2$ is, independently,
 hydrogen, halo, group J, lower alkyl,
 lower alkyl having at least one substituent J,
 substituted or unsubstituted $C_3$ to $C_7$ cycloalkyl wherein said substituted cycloalkyl group has at least one substituent J,
 substituted or unsubstituted $C_2$ to $C_6$ heterocycloalkyl wherein said substituted heterocycloalkyl group has at least one substituent J,
 substituted or unsubstituted aryl wherein said substituted aryl group has at least one substituent J,
 substituted or unsubstituted heteroaryl wherein said substituted heteroaryl group has at least one substituent J; or
$X^1$ and $X^2$, together with the atoms to which they are attached, form:
 a substituted or unsubstituted $C_4$ to $C_7$ cycloalkyl group wherein said substituted cycloalkyl group has at least one substituent J;
 a substituted or unsubstituted aryl group wherein said substituted aryl group has at least one substituent J; or
 a substituted or unsubstituted heteroaryl group wherein said substituted heteroaryl group has at least one substituent J;
with the provisos that when one of A and B is C(=O) and E and F, together with the atoms to which they are attached, form phenyl, then the other of A and B is other than C(=O), and when A and B are C(=O), and $D^1$ and $D^2$ are $C(X^1)$ or $C(X^2)$ in which $X^1$ and $X^2$, together with the atoms to which they are attached, form unsubstituted phenyl, and $R^2$ is hydrogen, then E and F, together with the atoms to which they are attached, form a group other than unsubstituted imidazole or N-methylimidazole.

Preferred embodiments of the present invention include compounds of formula IIb or IIbb wherein:
 A is C(=O), $CH_2$, $CH(OR^3)$, or $CH(SR^3)$;
 B is C(=O); and
 each E and F is, independently,
 $CH_3$; or
 E and F, together with the carbon atoms to which they are attached,
 form a $C_5$ cycloalkyl group.

Other preferred embodiments of the present invention include compounds of formula IIb or IIbb wherein:
 A is C(=O);
 B is $CH_2$; and
 E and F, together with the carbon atoms to which they are attached, form
 a $C_5$ cycloalkyl group.

Additional preferred embodiments of the present invention include compounds of formula IIb or IIbb wherein:
 each A and B is, independently,
 C(=O), $CH_2$, $CH(OR^3)$, or $CH(SR^3)$; and
 E and F, together with the atoms to which they are attached, form:
 a substituted or unsubstituted $C_4$ to $C_7$ cycloalkyl group wherein said substituted cycloalkyl group has at least one substituent J;
 a substituted or unsubstituted $C_3$ to $C_5$ heterocycloalkyl group wherein said substituted heterocycloalkyl group has at least one substituent J;
 a substituted or unsubstituted heterocycloalkyl group endocyclically comprising within at least one group G wherein said substituted heterocycloalkyl group comprising G has at least one substituent J.

Group G is as defined previously.

Further preferred embodiments of the present invention include compounds of formula IIb or IIbb wherein:
 each A and B is, independently,
 C(=O), $CH_2$, $CH(OR^3)$, or $CH(SR^3)$; and
 E and F, together with the atoms to which they are attached, form:
 a substituted or unsubstituted aryl group, wherein said substituted aryl group has at least one group J; or
 a substituted or unsubstituted heteroaryl group wherein said substituted heteroaryl group has at least one group J;
with the provisos that when one of A and B is C(=O) and E and F, together with the atoms to which they are attached, form phenyl, then the other of A and B is other than C(=O), and when A and B are C(=O), $D^1$ and $D^2$ are $C(X^1)$ or $C(X^2)$ in which $X^1$ and $X^2$, together with the atoms to which they are attached, form unsubstituted phenyl, and $R^2$ is hydrogen, then E and F, together with the atoms to which they are attached, form a group other than unsubstituted imidazole or N-methylimidazole.

In yet another embodiment of the invention, there are provided compounds of formula III:

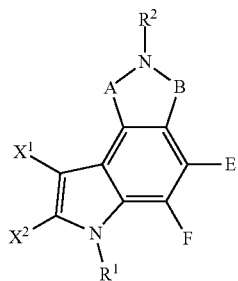

III wherein:
 each of A and B is, independently,
 C(=O), $CH(OR^3)$, $CH(SR^3)$,
 $CH_2$, $CHR^3$, $CHR^3CHR^4$, $CR^3R^4$,
 $C(=O)NR^3$, $N=CR^3$,
 SO, or $SO_2$;
 each of E and F is, independently,
 lower alkyl; or
 E and F, together with the carbon atoms to which they are attached, form:
 a substituted or unsubstituted $C_4$ to $C_7$ cycloalkyl group, wherein said substituted cycloalkyl group has at least one substituent J;
 a substituted or unsubstituted $C_3$ to $C_6$ heterocycloalkyl group wherein said substituted heterocycloalkyl group has at least one substituent J;
 a substituted or unsubstituted heterocycloalkyl group endocyclically comprising within the ring structure at least one group G wherein said substituted heterocycloalkyl group comprising G has at least one substituent J;
 a substituted or unsubstituted aryl group wherein said substituted aryl group has at least one group J; or
 a substituted or unsubstituted heteroaryl group wherein said substituted heteroaryl group has at least one group J;
 G is:
 O, S, SO, $SO_2$, $NR^2$, $NR^3$, $NR^2CO$, $NR^2CONR^3$, $NR^2SO_2$, or $NR^3SO_2$;

R$^1$ is:
  hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;
R$^2$ is:
  hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;
each of R$^3$ and R$^4$ is, independently,
  hydrogen, lower alkyl, aryl, lower alkyl having at least one substituent J, or aryl having at least one substituent J.
J is:
  J$^3$-(J$^2$)$_n$-(J$^1$)$_m$ wherein each of n and m is, independently, 0 or 1;
each of J$^1$ and J$^2$ is, independently,
  carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, C$_3$ to C$_7$ cycloalkyl, heterocycloalkyl, aryl, heteroaryl, sulfonylamido, alkylsulfonylamido, arylsulfonylamido, an amino acid, or a protected amino acid; and
J$^3$ is:
  hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid; and
each of X$^1$ and X$^2$ is, independently,
  hydrogen, halo, group J, lower alkyl,
  lower alkyl having at least one substituent J,
  substituted or unsubstituted C$_3$ to C$_7$ cycloalkyl wherein said substituted cycloalkyl group has at least one substituent J,
  substituted or unsubstituted C$_2$ to C$_6$ heterocycloalkyl wherein said substituted heterocycloalkyl group has at least one substituent J,
  substituted or unsubstituted aryl wherein said substituted aryl group has at least one substituent J,
  substituted or unsubstituted heteroaryl wherein said substituted heteroaryl group has at least one substituent J; or
X$^1$ and X$^2$, together with the atoms to which they are attached, form:
  a substituted or unsubstituted C$_4$ to C$_7$ cycloalkyl group wherein said substituted cycloalkyl group has at least one substituent J;
  a substituted or unsubstituted aryl group wherein said substituted aryl group has at least one substituent J; or
  a substituted or unsubstituted heteroaryl group wherein said substituted heteroaryl group has at least one substituent J;
with the provisos that when one of A and B is C(=O) and E and F, together with the atoms to which they are attached, form phenyl, then the other of A and B is other than C(=O), and when A and B are C(=O), X$^1$ and X$^2$, together with the atoms to which they are attached, form unsubstituted phenyl, and R$^2$ is hydrogen, then E and F, together with the atoms to which they are attached, form a group other than unsubstituted imidazole or N-methylimidazole.

In a preferred embodiment, compounds of formula III have E and F combined together with the atoms to which they are attached to form a C$_5$ cycloalkyl group.

In yet another embodiment of the invention, there are provided compounds of formula IIIa:

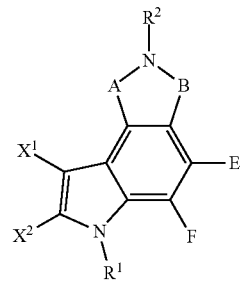

IIIa wherein:
  each of A and B is, independently,
    C(=O), CH(OR$^3$), CH(SR$^3$),
    CH$_2$, CHR$^3$, CHR$^3$CHR$^4$, CR$^3$R$^4$,
    C(=O)NR$^3$, N=CR$^3$,
    SO, or SO$_2$;
  each of E and F is, independently,
    lower alkyl; or
  E and F, together with the carbon atoms to which they are attached, form:
    a substituted or unsubstituted C$_4$ to C$_7$ cycloalkyl group, wherein said substituted cycloalkyl group has at least one substituent J;
    a substituted or unsubstituted C$_3$ to C$_6$ heterocycloalkyl group wherein said substituted heterocycloalkyl group has at least one substituent J;
    a substituted or unsubstituted heterocycloalkyl group endocyclically comprising within the ring structure at least one group G wherein said substituted heterocycloalkyl group comprising G has at least one substituent J;
    a substituted or unsubstituted aryl group wherein said substituted aryl group has at least one group J; or
    a substituted or unsubstituted heteroaryl group wherein said substituted heteroaryl group has at least one group J;
  G is:
    O, S, SO, SO$_2$, NR$^2$, NR$^3$, NR$^2$CO, NR$^2$CONR$^3$, NR$^2$SO$_2$, or NR$^3$SO$_2$;
  R$^1$ is:
    hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;
  R$^2$ is:
    hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;
  each of R$^3$ and R$^4$ is, independently,
    hydrogen, lower alkyl, aryl, lower alkyl having at least one substituent J, or aryl having at least one substituent J.

J is:
  $J^3$-$(J^2)_n$-$(J^1)_m$ wherein each of n and m is, independently, 0 or 1;
  each of $J^1$ and $J^2$ is, independently,
    carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and
  $J^3$ is:
    hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and
  any two adjacent J groups can combine to form —X—$(CH_2)_p$—X—, wherein X is independently O or NH, and p is 1 or 2; and
  each of $X^1$ and $X^2$ is, independently,
    hydrogen, halo, group J, lower alkyl,
    lower alkyl having at least one substituent J,
    substituted or unsubstituted $C_3$ to $C_7$ cycloalkyl wherein said substituted cycloalkyl group has at least one substituent J,
    substituted or unsubstituted $C_2$ to $C_6$ heterocycloalkyl wherein said substituted heterocycloalkyl group has at least one substituent J,
    substituted or unsubstituted aryl wherein said substituted aryl group has at least one substituent J,
    substituted or unsubstituted heteroaryl wherein said substituted heteroaryl group has at least one substituent J; or
  $X^1$ and $X^2$, together with the atoms to which they are attached, form:
    a substituted or unsubstituted $C_4$ to $C_7$ cycloalkyl group wherein said substituted cycloalkyl group has at least one substituent J;
    a substituted or unsubstituted aryl group wherein said substituted aryl group has at least one substituent J; or
    a substituted or unsubstituted heteroaryl group wherein said substituted heteroaryl group has at least one substituent J;
  with the provisos that when one of A and B is C(=O) and E and F, together with the atoms to which they are attached, form phenyl, then the other of A and B is other than C(=O), and when A and B are C(=O), $X^1$ and $X^2$, together with the atoms to which they are attached, form unsubstituted phenyl, and $R^2$ is hydrogen, then E and F, together with the atoms to which they are attached, form a group other than unsubstituted imidazole or N-methylimidazole.
  In a preferred embodiment, compounds of formula IIa have E and F combined together with the atoms to which they are attached to form a $C_5$ cycloalkyl group.
  Additional preferred embodiments of the compounds of formula III or IIIa include those where $X^1$ and $X^2$ are a substituted or unsubstituted heteroaryl group wherein said substituted heteroaryl group has at least one substituent J.
  Further preferred embodiments of the compounds of formula III or IIIa include those where A and B are, independently C(=O) or $CH_2$.
  Other preferred embodiments include compounds of formula III or IIIa, wherein groups E and F, when taken together with the atoms to which they are attached, form a $C_5$ cycloalkyl group; $X^1$ and $X^2$ are a substituted or unsubstituted heteroaryl group wherein said substituted heteroaryl group has at least one substituent J; and A and B are, independently C(=O) or $CH_2$. More preferably, $X^1$ and $X^2$ are a substituted or unsubstituted pyridyl or pyrimidyl group, wherein said substituted pyridyl or pyrimidyl group has at least one substituent J; and A and B are C(=O).
  In still another embodiment of the invention, there are provided compounds of formula IV:

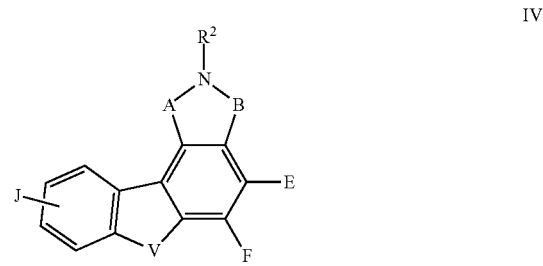

IV wherein:
  each of A and B is, independently,
    C(=O), CH($OR^3$), CH($SR^3$),
    $CH_2$, $CHR^3$, $CHR^3CHR^4$, $CR^3R^4$,
    C(=O)$NR^3$, N=$CR^3$,
    SO, or $SO_2$;
  each of E and F is, independently,
    lower alkyl; or
  E and F, together with the carbon atoms to which they are attached, form:
    a substituted or unsubstituted $C_4$ to $C_7$ cycloalkyl group, wherein said substituted cycloalkyl group has at least one substituent J;
    a substituted or unsubstituted $C_3$ to $C_6$ heterocycloalkyl group wherein said substituted heterocycloalkyl group has at least one substituent J;
    a substituted or unsubstituted heterocycloalkyl group endocyclically comprising within at least one group G wherein said substituted heterocycloalkyl group comprising G has at least one substituent J;
    a substituted or unsubstituted aryl group wherein said substituted aryl group has at least one group J; or
    a substituted or unsubstituted heteroaryl group wherein said substituted heteroaryl group has at least one group J;
  G is:
    O, S, SO, $SO_2$, $NR^2$, $NR^3$, $NR^2CO$, $NR^2CONR^3$, $NR^2SO_2$, or $NR^3SO_2$;
  V is N($R^1$), O, or S;
  $R^1$ is:
    hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;
  $R^2$ is:
    hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;

each of $R^3$ and $R^4$ is, independently,
  hydrogen, lower alkyl, aryl, lower alkyl having at least one substituent J, or aryl having at least one substituent J.
J is:
  $J^3$-$(J^2)_n$-$(J^1)_m$ wherein each of n and m is, independently, 0 or 1;
each of $J^1$ and $J^2$ is, independently,
  carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and
$J^3$ is:
  hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, or aryl ester of phosphonic acid;
with the provisos that when one of A and B is C(=O) and E and F, together with the atoms to which they are attached, form phenyl, then the other of A and B is other than C(=O), and when A and B are C(=O), V is NH, J and $R^2$ are hydrogen, then E and F, together with the atoms to which they are attached, form a group other than unsubstituted imidazole or N-methylimidazole.

In still another embodiment of the invention, there are provided compounds of formula IVa:

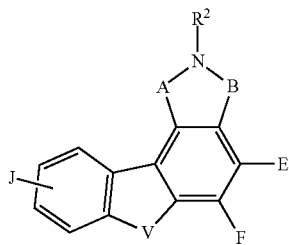

IVa wherein:
  each of A and B is, independently,
    C(=O), CH($OR^3$), CH($SR^3$),
    $CH_2$, $CHR^3$, $CHR^3CHR^4$, $CR^3R^4$,
    C(=O)$NR^3$, N=$CR^3$,
    SO, or $SO_2$;
  each of E and F is, independently,
    lower alkyl; or
  E and F, together with the carbon atoms to which they are attached, form:
    a substituted or unsubstituted $C_4$ to $C_7$ cycloalkyl group, wherein said substituted cycloalkyl group has at least one substituent J;
    a substituted or unsubstituted $C_3$ to $C_6$ heterocycloalkyl group wherein said substituted heterocycloalkyl group has at least one substituent J;
    a substituted or unsubstituted heterocycloalkyl group endocyclically comprising within at least one group G wherein said substituted heterocycloalkyl group comprising G has at least one substituent J;
    a substituted or unsubstituted aryl group wherein said substituted aryl group has at least one group J; or
    a substituted or unsubstituted heteroaryl group wherein said substituted heteroaryl group has at least one group J;
G is:
  O, S, SO, $SO_2$, $NR^2$, $NR^3$, $NR^2CO$, $NR^2CONR^3$, $NR^2SO_2$, or $NR^3SO_2$;
V is N($R^1$), O, or S;
$R^1$ is:
  hydrogen, lower alkyl, lower alkyl having at least one substituent J, formyl, acetyl, lower alkanoyl, lower alkanoyl having at least one substituent J, lower alkylsulfonyl, lower arylsulfonyl, an amino acid, or a protected amino acid;
$R^2$ is:
  hydrogen, lower alkyl, lower alkyl having at least one substituent J; formyl; acetyl, lower alkanoyl, lower alkanoyl having at least one substituent J, lower alkylsulfonyl, arylsulfonyl, an amino acid, or a protected amino acid;
each of $R^3$ and $R^4$ is, independently,
  hydrogen, lower alkyl, aryl, lower alkyl having at least one substituent J, or aryl having at least one substituent J.
J is:
  $J^3$-$(J^2)_n$-$(J^1)_m$ wherein each of n and m is, independently, 0 or 1;
each of $J^1$ and $J^2$ is, independently,
  carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, oxygen, sulphur, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and
$J^3$ is:
  hydrogen, halo, hydroxy, thio, cyano, sulfonic acid, carboxyl, lower alkyl, aryloxycarbonyl, alkyloxycarbonyl, phosphonic acid, lower alkyl, lower alkyl ester of phosphonic acid, aryl ester of phosphonic acid, aminocarbonyloxy, heteroaryl, or heterocycloalkyl; and
any two adjacent J groups can combine to form —X—$(CH_2)_p$—X—, wherein X is independently O or NH, and p is 1 or 2;
with the provisos that when one of A and B is C(=O) and E and F, together with the atoms to which they are attached, form phenyl, then the other of A and B is other than C(=O), and when A and B are C(=O), V is NH, J and $R^2$ are hydrogen, then E and F, together with the atoms to which they are attached, form a group other than unsubstituted imidazole or N-methylimidazole.

Certain preferred embodiments include compounds of formula IV or IVa, wherein V is N($R^1$); groups E and F, when taken together with the atoms to which they are attached, form a $C_5$ cycloalkyl group; and A and B are independently C(=O) or $CH_2$.

Further preferred embodiments include compounds of formula IV, that may be particularly important with regard to inhibition of PARP, in which A and B are both CO, $R^2$ and J are both H, E and F, together with the atoms to which they are attached, form a cyclopentyl group, and V is either NH (1a, see Table 1) or N-(Lysine.2HCl) (1k, see Table 1). Additionally, the compound of formula IV wherein A and B are both CO, $R^2$ is H, V is NH, E and F, together with the atoms to which they are attached, form a cyclopentyl group, and J is $NH_2CH_2$ 3-substituent (2p, see Table 2) comprises a further preferred embodiment.

Preferred embodiments of the present invention which may have particular relevance to the inhibition of VEGFR2 include compounds of formula IV in which both A and B are CO, E and F together are —CH═NCH═CH—, V is NH, $R^2$ is H, and J is either H (12a, see Table 5) or 3-$CH_3$ (12n, see Table 5).

Additional preferred embodiments of the compounds described herein include those where groups E and F, when taken together with the atoms to which they are attached, form a group other than imidazolyl.

Other preferred embodiments of the compounds described herein include those where groups E and F, when taken together with the atoms to which they are attached, form a $C_5$ cycloalkyl group. Further embodiments of the compounds described herein include those where $X^1$ and $X^2$ are a substituted or unsubstituted heteroaryl group wherein said substituted heteroaryl group has at least one substituent J. Another preferred embodiment of the compounds described herein include those where A and B are, independently, C(═O) or $CH_2$.

Additional preferred embodiments of the compounds described herein include those where groups E and F, when taken together with the atoms to which they are attached, form a $C_5$ cycloalkyl group; $X^1$ and $X^2$ are a substituted or unsubstituted heteroaryl group wherein said substituted heteroaryl group has at least one substituent J; and A and B are, independently C(═O) or $CH_2$.

In yet another embodiment of the invention, there are provided compounds of formula IIIa:

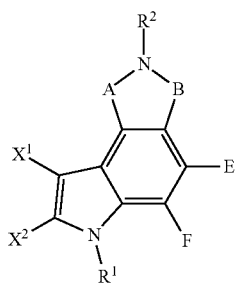

IIIa wherein:
each of A and B is, independently,
C(═O), CH($OR^3$), CH($SR^3$),
$CH_2$, $CHR^3$, $CHR^3CHR^4$, $CR^3R^4$,
C(═O)$NR^3$, SO, or $SO_2$;
E and F, together with the carbon atoms to which they are attached, form a substituted or unsubstituted $C_4$ to $C_7$ cycloalkyl group, wherein said substituted cycloalkyl group has at least one substituent J;
$R^1$ is:
hydrogen, lower alkyl, lower alkyl having at least one substituent J, formyl, acetyl, lower alkanoyl, lower alkanoyl having at least one substituent J, lower alkylsulfonyl, or lower arylsulfonyl;
$R^2$ is:
hydrogen, lower alkyl, lower alkyl having at least one substituent J; formyl; acetyl, lower alkanoyl, lower alkanoyl having at least one substituent J, lower alkylsulfonyl, or arylsulfonyl;

each of $R^3$ and $R^4$ is, independently, hydrogen or lower alkyl;
J is independently at each occurrence:
$J^3$-$(J^2)_n$-$(J^1)_m$- wherein each of n and m is, independently, 0 or 1;
each of $J^1$ and $J^2$ is, independently,
carbonyl, lower alkylcarbonyl, arylcarbonyl, carbonyloxy, sulfonyl, amino, lower alkylamino, lower dialkylamino, amido, lower alkylamido, lower dialkylamido, lower alkyloxycarbonylamino, aryloxycarbonylamino, amidino, guanidino, lower alkoxy, lower aryloxy, aralkoxy, lower alkyl, $C_3$ to $C_7$ cycloalkyl, heterocycloalkyl, aryl, heteroaryl, sulfonylamido, alkylsulfonylamido, arylsulfonylamido, an amino acid, or a protected amino acid; and
$J^3$ is:
hydrogen, halo, hydroxy, thio, cyano, sulfonic acid, $NO_2$, carboxyl, lower alkyl, aryloxycarbonyl, alkyloxycarbonyl, phosphonic acid, lower alkyl ester of phosphonic acid, aryl ester of phosphonic acid, aminocarbonyloxy, heteroaryl, or heterocycloalkyl; and
$X^1$ and $X^2$, together with the atoms to which they are attached, form:
a substituted or unsubstituted aryl group wherein said substituted aryl group has at least one substituent J; or
a substituted or unsubstituted heteroaryl group wherein said substituted heteroaryl group has at least one substituent J.

The compound of the invention as described herein where A and B are independently C(═O).

The compound of the invention as described herein where $X^1$ and $X^2$, together with the atoms to which they are attached, form a substituted or unsubstituted heteroaryl group wherein said substituted heteroaryl group has at least one substituent J.

The compound of the invention as described herein where the substituted or unsubstituted heteroaryl group is pyridyl or pyrimidyl; wherein said heteroaryl group has at least one substituent J.

The compound of the invention as described herein where $J^1$ and $J^2$ is, independently, carbonyl, amino, carbonyloxy, lower alkylamino, lower dialkylamino or lower alkoxy.

The compound of the invention as described herein where $J^3$ is hydrogen, halo, hydroxyl, cyano, $NO_2$, lower alkyl, heteroaryl or heterocycloalkyl.

The compound of the invention as described herein where the substituted or unsubstituted heteroaryl group is pyridine-N-oxide; wherein said heteroaryl group has at least one substituent J.

The compound of the invention as described herein where $J^1$ and $J^2$ is, independently, carbonyl, amino, carbonyloxy, lower alkylamino, lower dialkylamino or lower alkoxy.

The compound of the invention as described herein where $J^3$ is hydrogen, halo, hydroxyl, cyano, $NO_2$, lower alkyl, heteroaryl or heterocycloalkyl.

The compound of the invention as described herein where $X^1$ and $X^2$, together with the atoms to which the are attached, form a substituted or unsubstituted aryl group wherein said substituted aryl group has at least one substituent J.

The compound of the invention as described herein where the substituted or unsubstituted aryl group is phenyl; wherein said phenyl has at least one substituent J.

The compound of the invention as described herein where $J^1$ and $J^2$ is, independently, carbonyl, amino, carbonyloxy, lower alkylamino, lower dialkylamino or lower alkoxy.

The compound of the invention as described herein where $J^3$ is hydrogen, halo, hydroxyl, cyano, $NO_2$, lower alkyl, heteroaryl or heterocycloalkyl.

In still another embodiment of the invention, there are provided compounds based on formula IIIa:
wherein:
each of A and B is, independently, C(=O);
E and F, together with the carbon atoms to which they are attached, form:
a substituted or unsubstituted $C_5$ cycloalkyl group, wherein said substituted cycloalkyl group has at least one substituent J;
$R^1$ is hydrogen;
$R^2$ is hydrogen, lower alkyl or lower alkyl having at least one substituent $J^4$;
J is independently at each occurrence:
$J^3$-$(J^2)_n$-$(J^1)_m$- wherein each of n and m is, independently, 0 or 1;
each of $J^1$ and $J^2$ is, independently,
carbonyl, lower alkylcarbonyl, arylcarbonyl, carbonyloxy, amino, lower alkylamino, lower dialkylamino, amido, lower alkylamido, lower dialkylamido, lower alkoxy, lower alkyl, $C_3$ to $C_7$ cycloalkyl, heterocycloalkyl, aryl, or a heteroaryl; and
$J^3$ is:
hydrogen, halo, hydroxy, cyano, $NO_2$, carboxyl, lower alkyl, aryloxycarbonyl, alkyloxycarbonyl, heteroaryl, or heterocycloalkyl; and
$J^4$ is independently at each occurrence:
$J^7$-$(J^6)_n$-$(J^5)_m$- wherein each of n and m is, independently, 0 or 1;
each of $J^5$ and $J^6$ is, independently,
carbonyl, lower alkylcarbonyl, arylcarbonyl, carbonyloxy, amino, lower alkylamino, lower dialkylamino, amido, lower alkylamido, lower dialkylamido, lower alkoxy, lower alkyl, $C_3$ to $C_7$ cycloalkyl, heterocycloalkyl, aryl, or a heteroaryl; and
$J^7$ is:
hydrogen, halo, hydroxy, cyano, $NO_2$, carboxyl, lower alkyl, aryloxycarbonyl, alkyloxycarbonyl, heteroaryl, or heterocycloalkyl; and
$X^1$ and $X^2$, together with the atoms to which they are attached, form:
a substituted or unsubstituted phenyl group wherein said substituted phenyl group has at least one substituent J; or
a substituted or unsubstituted heteroaryl group wherein said substituted heteroaryl group has at least one substituent J and where said heteroaryl is pyridine or pyridine-N-oxide.

The compound of the invention as described herein where $X^1$ and $X^2$, together with the atoms they are attached, form a phenyl with at least one substituent J.

The compound of the invention as described herein where $J^1$ and $J^2$ is, independently, carbonyl, amino, carbonyloxy, lower alkylamino, lower dialkylamino or lower alkoxy.

The compound of the invention as described herein where $J^3$ is hydrogen, halo, hydroxyl, cyano, $NO_2$, lower alkyl, heteroaryl or heterocycloalkyl.

The compound of the invention as described herein where $X^1$ and $X^2$ together with the atoms they are attached form a pyridine with at least one substituent J.

The compound of the invention as described herein where $J^1$ and $J^2$ is, independently, carbonyl, amino, carbonyloxy, lower alkylamino, lower dialkylamino or lower alkoxy.

The compound of the invention as described herein where $J^3$ is hydrogen, halo, hydroxy, cyano, $NO_2$, lower alkyl, heteroaryl or heterocycloalkyl.

In yet another embodiment of the invention, there are provided compounds of formula IIIa:
wherein:
each of A and B is, independently, C(=O);
E and F, together with the carbon atoms to which they are attached, form:
a substituted or unsubstituted $C_5$ cycloalkyl group;
$R^1$ is hydrogen or lower alkyl having at least one substituent J;
$R^2$ is lower alkyl having at least one substituent $J^4$;
J is independently at each occurrence:
$J^3$-$(J^2)_n$-$(J^1)_m$- wherein each of n and m is, independently, 0 or 1;
each of $J^1$ and $J^2$ is, independently,
carbonyl, lower alkylcarbonyl, arylcarbonyl, carbonyloxy, amino, lower alkylamino, lower dialkylamino, amido, lower alkylamido, lower dialkylamido, lower alkoxy, lower alkyl, $C_3$ to $C_7$ cycloalkyl, heterocycloalkyl, aryl, or a heteroaryl; and
$J^3$ is:
hydrogen, halo, hydroxy, cyano, $NO_2$, carboxyl, lower alkyl, aryloxycarbonyl, alkyloxycarbonyl, heteroaryl, or heterocycloalkyl; and
$J^4$ is independently at each occurrence:
$J^7$-$(J^6)_n$-$(J^5)_m$- wherein each of n and m is, independently, 0 or 1;
each of $J^5$ and $J^6$ is, independently,
carbonyl, lower alkylcarbonyl, arylcarbonyl, carbonyloxy, amino, lower alkylamino, lower dialkylamino, amido, lower alkylamido, lower dialkylamido, lower alkoxy, lower alkyl, $C_3$ to $C_7$ cycloalkyl, heterocycloalkyl, aryl, or a heteroaryl; and
$J^7$ is:
hydrogen, halo, hydroxy, cyano, $NO_2$, carboxyl, lower alkyl, aryloxycarbonyl, alkyloxycarbonyl, heteroaryl, or heterocycloalkyl; and
$X^1$ and $X^2$, together with the atoms to which they are attached, form:
a substituted or unsubstituted phenyl group wherein said substituted phenyl group has at least one substituent J; or
a substituted or unsubstituted heteroaryl group wherein said substituted heteroaryl group has at least one substituent J and where said heteroaryl is pyridine or pyridine-N-oxide.

The compound of the invention as described herein where each of $J^5$ and $J^6$ is, independently, lower alkyl, lower dialkylamino or heterocycloalkyl.

The compound of the invention as described herein where $J^7$ is hydrogen or heterocycloalkyl.

The compound of the invention as described herein where $X^1$ and $X^2$, together with the atoms to which they are attached, form a phenyl with at least one substituent J.

The compound of the invention as described herein where J is lower alkoxy.

The compound of the invention as described herein where $J^4$ is methylaminodimethyl, methylaminodiethyl, 4-methylmorpholine or 4-methylpiperazinyl-$CH_2$.

The compound of the invention as described herein where $J^4$ is 4-methylpiperazinyl-$CH_2$.

The compound of the invention as described herein where $X^1$ and $X^2$, together with the atoms to which they are attached, form a phenyl with at least one substituent J.

The compound of the invention as described herein where J is lower alkoxy.

The term "alkyl", as used herein, unless otherwise specified, refers to a saturated straight, branched, or cyclic hydrocarbon of $C_1$ to $C_{20}$. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

The term "lower alkyl," as used herein, and unless otherwise specified, refers to a $C_1$ to $C_6$ saturated straight chain, branched, or cyclic hydrocarbon. Lower alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl, 2,2-dimethylbutyl, and 2,3-dimethylbutyl.

The terms "cycloalkyl" and "$C_n$ cycloalkyl" are meant to refer to a monocyclic saturated or partially unsaturated hydrocarbon group. The term "$C_n$" in this context, wherein n is an integer, denotes the number of carbon atoms comprising the ring of the cycloalkyl group. For instance, $C_6$ cycloalkyl indicates a six-membered ring. The bonds connecting the endocyclic carbon atoms of a cycloalkyl group may be single or part of a fused aromatic moiety, so long as the cycloalkyl group is not aromatic. Examples of cycloalkyl groups include, but are not limited to, cyclopropyl, cyclobutyl, cyclopentyl, cyclohexyl, and cycloheptyl.

The terms "heterocycloalkyl" or "$C_n$ heterocycloalkyl" are meant to refer to a monocyclic saturated or partially unsaturated cyclic radical which, besides carbon atoms, contains at least one heteroatom as ring members. Typically, heteroatoms include, but are not limited to, oxygen, nitrogen, sulfur, selenium, and phosphorus atoms. In this context, the term "$C_n$," wherein n is an integer, denotes the number of carbon atoms comprising the ring, but is not indicative of the total number of atoms in the ring. For example, $C_4$ heterocycloalkyl includes rings with five or more ring members, wherein four of the ring members are carbon and the remaining ring members are heteroatoms. In addition, the bonds connecting the endocyclic atoms of a heterocycloalkyl group may be part of a fused aromatic moiety, so long as the heterocycloalkyl group is not aromatic. Examples of heterocycloalkyl groups include, but are not limited to, 2-pyrrolidinyl, 3-pyrrolidinyl, piperidinyl, 2-tetrahydrofuranyl, 3-tetrahydrofuranyl, 2-tetrahydrothienyl, and 3-tetrahydrothienyl.

The term "aryl," as used herein, and unless otherwise specified, refers to a mono-, di-, tri-, or multinuclear aromatic ring system of 6 to 10 ring atoms. Non-limiting examples include phenyl, naphthyl, anthracenyl, and phenanthrenyl.

The term "heteroaryl," as used herein, refers to an aromatic ring system having from 5 to 10 ring atoms comprising carbon and at least one heteroatom ring member such as an oxygen, nitrogen or sulfur. The nitrogen heteroatom may be optionally oxidized for example pyridine-N-oxide or 1-oxypyridinyl. Non-limiting examples are pyrryl, pyridinyl, furyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, isoxazolyl, and acridinyl.

The term "aralkyl," as used herein, is meant to refer to aryl-substituted alkyl radicals such as benzyl, diphenylmethyl, triphenylmethyl, phenylethyl, and diphenylethyl.

The term "lower aralkyl," as used herein, is meant to refer to aryl-substituted lower alkyl radicals. Non-limiting examples include benzyl, diphenylmethyl, triphenylmethyl, phenylethyl, and diphenylethyl.

The term "aralkoxy," as used herein, is meant to refer to the group RO— wherein R is an aralkyl group as defined above.

The term "lower aralkoxy," as used herein, is meant to refer to the group RO— wherein R is a lower aralkyl group as defined above.

The term "alkoxy," as used herein, is meant to refer to RO—, wherein R is an alkyl group as defined above.

The term "lower alkoxy," as used herein, is meant to refer to RO—, wherein R is a lower alkyl group as defined above. Non-limiting examples include methoxy, ethoxy, and tert-butyloxy.

The term "aryloxy," as used herein, is meant to refer to RO—, wherein R is an aryl group as defined above.

The terms "lower alkylamino" and "lower dialkylamino" refer to an amino group that bears one or two lower alkyl substituents, respectively.

The terms "amido" and "carbonylamino," as used herein, are meant to refer to —C(O)N(H)—.

The term "alkylamido," as used herein, is meant to refer to —C(O)NR— wherein R is an alkyl group as defined above.

The term "dialkylamido," as used herein, is meant to refer to —C(O)NR'R" wherein R' and R" are, independently, alkyl groups as defined above.

The term "lower alkylamido," as used herein, is meant to refer to —C(O)NR— wherein R is a lower alkyl group as defined above.

The term "lower dialkylamido," as used herein, is meant to refer to —C(O)NR'R" wherein R' and R" are, independently, lower alkyl groups as defined above.

The terms "alkanoyl" and "alkylcarbonyl," as used herein, refer to RC(O)— wherein R is an alkyl group as defined above.

The terms "lower alkanoyl" and "lower alkylcarbonyl" as used herein, refer to RC(O)— wherein R is a lower alkyl group as defined above. Non-limiting examples of such alkanoyl groups include acetyl, trifluoroacetyl, hydroxyacetyl, propionyl, butyryl, valeryl, and 4-methylvaleryl.

The term "arylcarbonyl," as used herein, refers to RC(O)— wherein R is an aryl group as defined above.

The term "aryloxycarbonyl," as used herein, is meant to refer to ROC(O)— wherein R is an aryl group as defined above.

The term "halo," as used herein, refers to fluoro, chloro, bromo, or iodo.

The term "alkylsulfonyl," as used herein, is meant to refer to the group $RSO_2$— wherein R is an alkyl group as defined above.

The term "arylsulfonyl," as used herein, is meant to refer to the group $RSO_2$— wherein R is an aryl group as defined above.

The term "alkyloxycarbonylamino," as used herein, is meant to refer to the group ROC(O)N(H)— wherein R is an alkyl group as defined above.

The term "lower alkyloxycarbonylamino," as used herein, is meant to refer to the group ROC(O)N(H)— wherein R is a lower alkyl group as defined above.

The term "aryloxycarbonylamino," as used herein, is meant to refer to the group ROC(O)N(H)— wherein R is an aryl group as defined above.

The term "sulfonylamido," as used herein, is meant to refer to the group —$SO_2$C(O)NH—.

The term "alkylsulfonylamido," as used herein, is meant to refer to the group $RSO_2$C(O)NH— wherein R is an alkyl group as defined above.

The term "arylsulfonylamido," as used herein, is meant to refer to the group $RSO_2$C(O)NH— wherein R is an aryl group as defined above.

The term "lower alkyl ester of phosphonic acid," as used herein, is meant to refer to the group —P(O)(OR')(OR") wherein R' and R" are lower alkyl as defined above.

The term "aryl ester of phosphonic acid," as used herein, is meant to refer to the group —P(O)(OR')(OR") wherein R' and R" are aryl as defined above.

The term "aminocarbonyloxy," as used herein, is meant to refer to the group RR'N—C(O)—O— wherein R and R' are an alkyl group as defined above.

The term "arylaminocarbonyloxy," as used herein, is meant to refer to the group Ar—N(R)—C(O)—O— wherein Ar is aryl, as defined above, and R is an alkyl group as defined above.

The term "heteroarylaminocarbonyloxy," as used herein, is meant to refer to the group het-Ar—N(R)—C(O)—O— wherein het-Ar is heteroaryl, as defined above, and R is an alkyl group as defined above.

As used herein, the term "amino acid" means a molecule containing both an amino group and a carboxyl group. It includes an "α-amino acid" which is well known to one skilled in the art as a carboxylic acid that bears an amino functionality on the carbon adjacent to the carboxyl group. Amino acids can be naturally occurring or non-naturally occurring.

"Protected amino acids," as used herein refer to amino acids, as described above, comprising protecting groups. For example, the amino group of an amino acid may be protected with t-butoxycarbonyl or benzyloxycarbonyl groups. In addition, the carboxyl group of the amino acid may be protected as alkyl and aralkyl esters. Furthermore, alcohol groups of amino acids can be protected as alkyl ethers, aralkyl ethers, and silyl ethers.

The term "endocyclically comprising" is meant to describe a cyclic chemical moiety that includes a specified chemical group as a ring forming member. As an example, a furanyl group endocyclically comprises an oxygen atom because the oxygen atom is a member of the ring structure. In the context of the present invention, groups E and F may be combined together with the atoms to which they are attached to form a heterocycloalkyl group. This heterocycloalkyl group may endocyclically comprise the chemical group G, meaning that at least one atom of group G is a ring forming member. As a non-limiting example illustrated below, E and F may be combined together with the atoms to which they are attached to form the heterocycloalkyl group endocyclically comprising group G, wherein G, in this instance, is $N(CH_3)$.

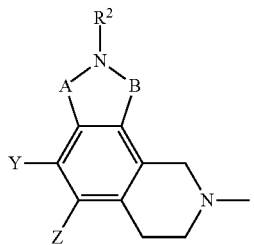

As used herein, the term "therapeutically effective amount" is meant to refer to an amount of compound of the present invention that will elicit a desired therapeutic or prophylactic effect or response when administered according to the desired treatment regimen.

As used herein, the term "contacting" means bringing together, either directly or indirectly, one or more molecules with another, thereby facilitating intermolecular interactions. Contacting may occur in vitro, ex vivo, or in vivo.

As used herein, the term "cellular proliferative disorders" is meant to refer to malignant as well as non-malignant cell populations which differ from the surrounding tissue both morphologically and genotypically. Types of cellular proliferative disorders include, for example, solid tumors, cancer, diabetic retinopathy, intraocular neovascular syndromes, macular degeneration, rheumatoid arthritis, psoriasis, and endometriosis.

All other terms used in the description of compounds of the present invention have their meaning as is well known in the art.

The present invention features methods for preparing the multicyclic compounds described herein which are useful as inhibitors of PARP, VEGFR2, and MLK3. The method consists of a multistep synthesis starting with the necessary heterocyclic compounds. For example, FIG. 1 outlines the general synthesis of compounds of the present invention for the case when the heterocyclic starting material is an indole. Specifically, an indole A, which is unsubstituted or substituted in positions 4-7 on the indole ring, is treated serially, for example, with butyllithium, carbon dioxide, t-butyllithium and a ketone B (having substituents E and F) to provide a 2-substituted indolyl tertiary alcohol C. This tertiary alcohol is eliminated, for example, under acidic conditions using hydrochloric acid or toluenesulfonic acid, to afford a substituted 2-vinylindole, D. Diels-Alder cycloaddition of D with a dienophile such as, but not limited to, maleimide (E) affords the cycloaddition intermediate F. Aromatization of the cycloaddition intermediate, for example, with oxygen in the presence of a catalyst such as palladium or platinum or with an oxidant such as DDQ or tetrachloroquinone, produces carbazole G.

Figure 2:
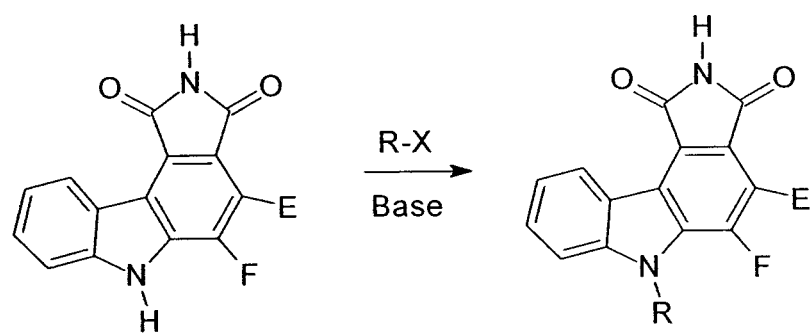
FIG. 2 shows a general synthetic strategy for preparing compounds within the scope of the present invention.

Further treatment of G with an alkylating or acylating reagent gives imide-N-substituted carbazole derivatives of the present invention as shown in FIG. 2.

Figure 3:
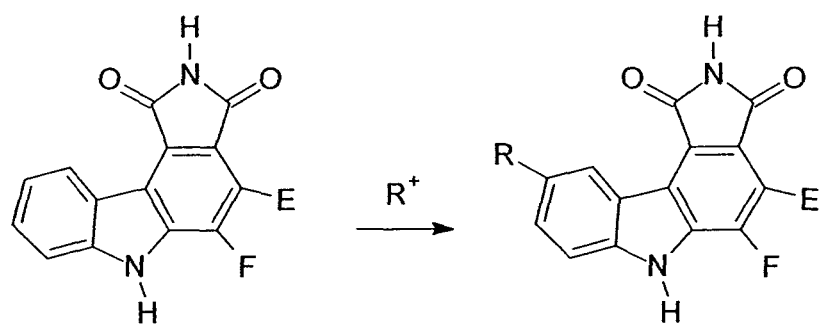
FIG. 3 shows another general synthetic strategy for preparing compounds within the scope of the present invention.
Figure 5:
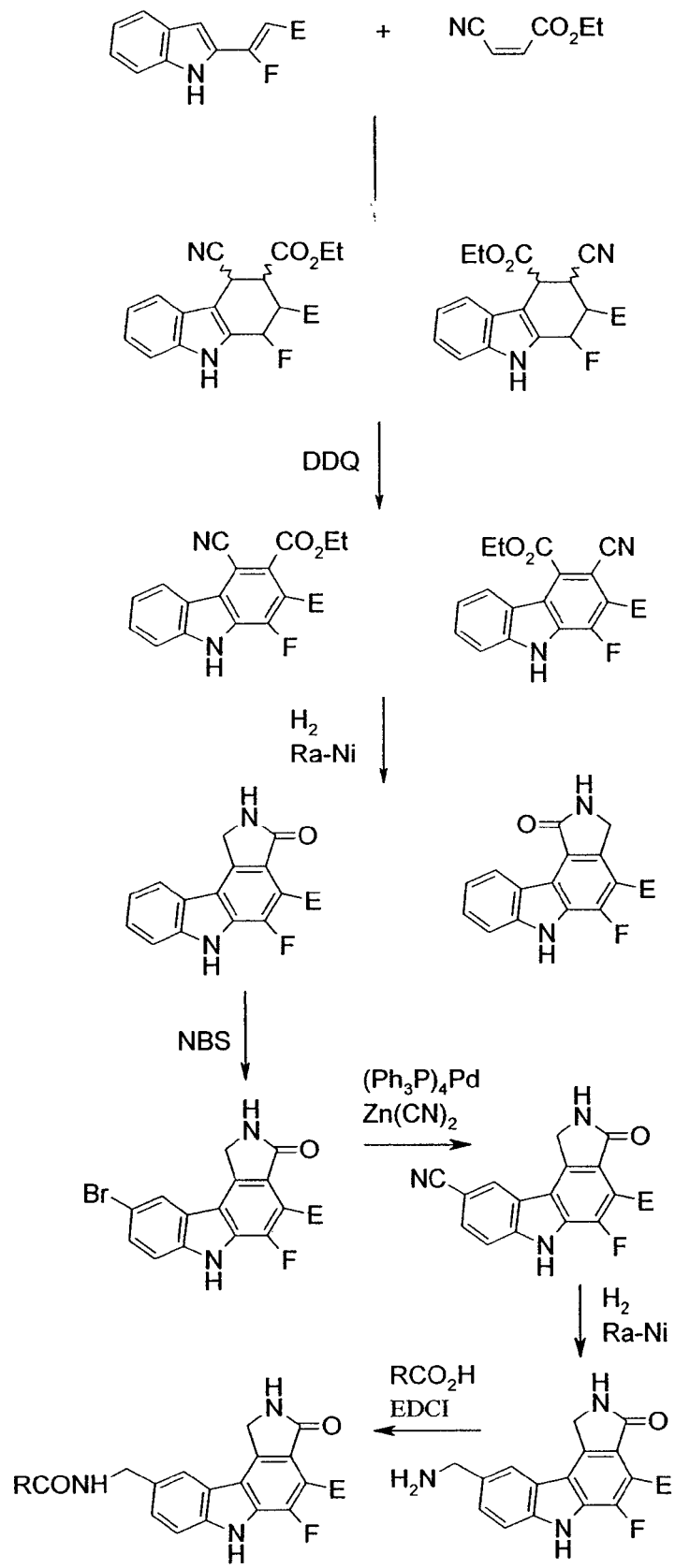
FIG. 5 shows still another general synthetic strategy for preparing compounds within the scope of the present invention.

Treatment of carbazole G (or the carbazole lactams in FIG. 5) with various electrophiles, such as $R^+$, affords 3-substituted carbazole derivatives as shown in FIG. 3. In this manner, halogen or acyl groups can be introduced, and the halogen can be displaced by various nucleophiles including cyano, as shown in FIG. 5. The halogen can also be replaced by various alkyl, aryl, and heteroalkyl groups. The 3-cyano substituent can be reduced to give the 3-aminomethyl substituent which can be alkylated or acylated on the amino group.

Figure 4:
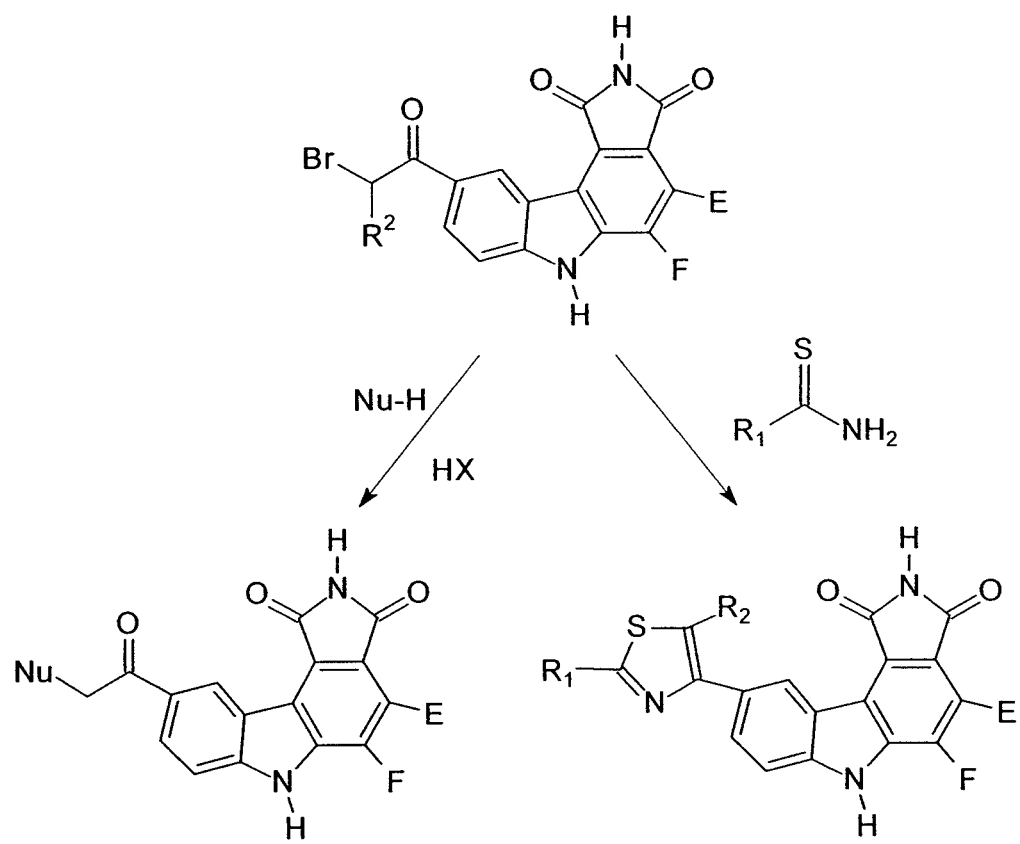
FIG. 4 shows yet another general synthetic strategy for preparing compounds within the scope of the present invention.

When carbazole G contains bromoacetyl or substituted 2-bromoacyl substituents, as shown in FIG. 4, the bromine can be displaced by various nucleophiles to give further embodiments of the present invention. Alternately, the 2-bromoacyl group may be reacted with various thioamides to give substituted thiazoles.

As discussed, using substituted indoles as starting material affords functionalized derivatives of G; however, an intramolecular Wittig reaction can also be used to prepare substituted vinyl indoles D. Furthermore, dienophiles other than maleimide (E) may be used in the Diels-Alder reaction, and include for example, dialkyl fumarate, fumaric acid, dialkyl maleate, maleic acid, maleic anhydride, dialkyl acetylenedicarboxylate or alkyl 3-cyanoacrylate. The intermediates resulting from cycloaddition with these dienophiles give imides, or the corresponding lactams as shown in FIG. 5. For example, anyhdrides, obtained from maleic anhydride cycloaddition or by dehydration of diacids, afford imides when treated with bis(trimethylsilyl)amine or urea. The anhydrides afford six-membered hydrazones when treated with hydrazine. The lactams are obtained by separating the cyano ester isomers, aromatizing each isomer, and reducing the cyano ester to the lactam, as shown in FIG. 5. Imides may also be reduced to lactams by well established methods known to those skilled in the art.

Figure 6:
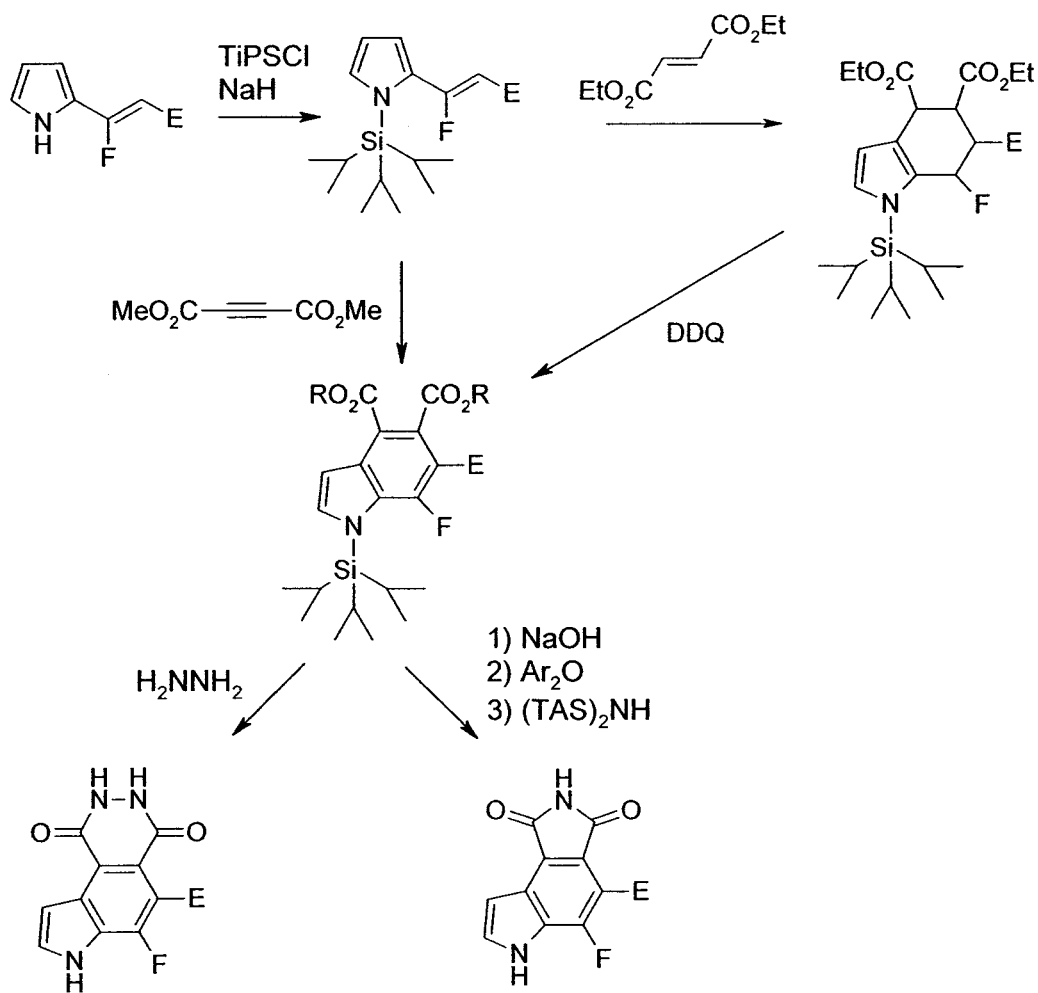
FIG. 6 shows yet another general synthetic strategy for preparing compounds within the scope of the present invention.

Indole-type compounds of the present invention are prepared according to the scheme shown in FIG. 6. Here, substituted vinyl pyrrole starting materials are prepared by the reaction of a pyrrole with an enamine of a ketone as described in the literature (*Heterocycles* 1974, 2, 575-584). A substituted 2-vinyl pyrrole is reacted with various dienophiles, such as those described above, to afford a cycloaddition intermediate which is a precursor to embodiments of the present invention. A nitrogen protecting group such as a silyl protecting group, particularly triisopropyl silyl, may used throughout as depicted in FIG. 6.

Figure 7:
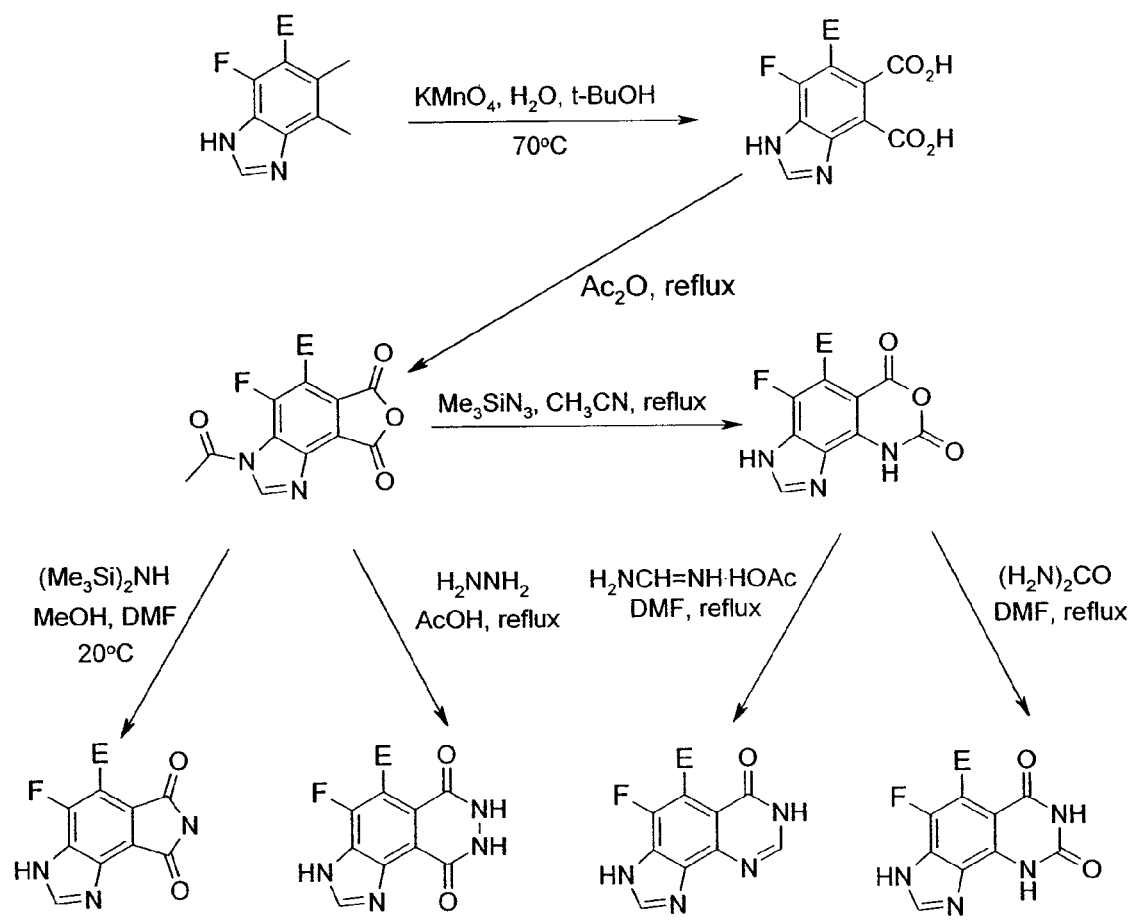
FIG. 7 shows a synthetic strategy for preparing benzimidazole derivatives within the scope of the present invention.

Other heterocyclic precursors may be prepared by analogous reactions. For example, a substituted 5-vinyl imidazole is reacted with various dienophiles, such as those described above, to afford a cycloaddition intermediate which can be further modified by reactions well known to those skilled in the art to give benzimidazole precursors. Likewise, for example, a substituted 5-vinyl 1,2,3-triazole or 4-vinyl thiazole can be reacted with various dienophiles as above to also afford cycloaddition intermediates leading to embodiments of the invention. The benzimidazole-type compounds of the present invention can also be prepared according to the method shown in FIG. 7, in which preformed benzimidozoles serve as starting materials.

Figure 8:
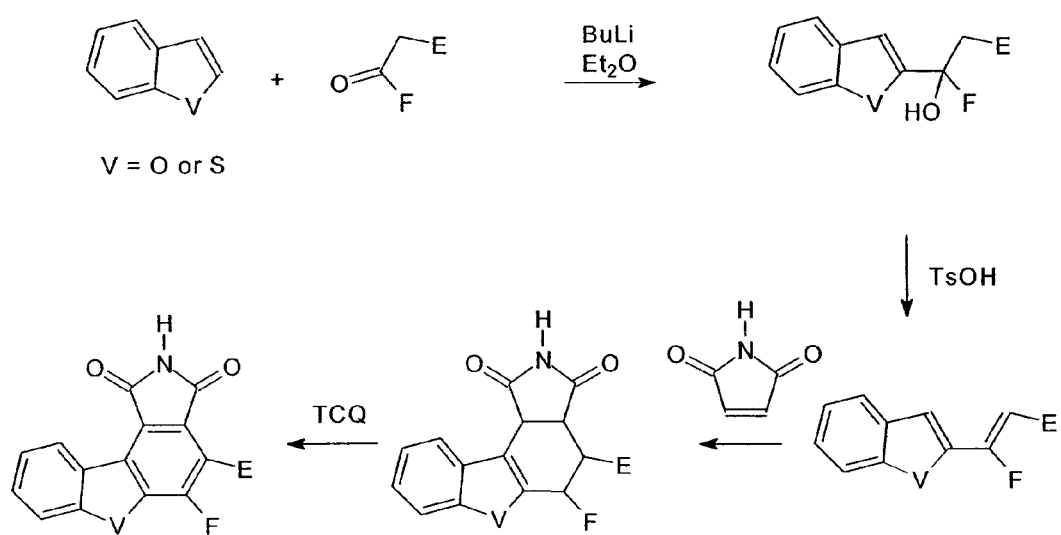
FIG. 8 shows a synthetic strategy for preparing compounds within the scope of the invention.

Furthermore, as shown in FIG. 8, an optionally substituted 2-vinyl benzofuran or 2-vinyl benzothiophene can be reacted with various dienophiles, such as those listed previously, to afford a cycloaddition intermediate. Modification of the cycloaddition intermediate can lead to imides, lactams, and related compounds of the present invention.

In certain preferred embodiments, the compounds of the present invention are PARP inhibitors. The potency of the inhibitor can be tested by measuring PARP activity in vitro or in vivo. A preferred assay monitors transfer of radiolabeled ADP-ribose units from [$^{32}$P]NAD$^+$ to a protein acceptor such as histone or PARP itself. Routine assays for PARP are disclosed in Purnell and Whish, *Biochem. J.* 1980, 185, 775, incorporated herein by reference.

In other preferred embodiments, the compounds of the present invention are also VEGFR2 or MLK3 inhibitors. The potency of the inhibitor can be tested by measuring VEGFR2 or MLK3 activity in vitro or in vivo. A preferred assay for VEGFR2 kinase activity involves the phosphorylation of a protein substrate immobilized on a microtiter plate. The resulting phosphotyrosine residue is detected with an anti-phosphotyrosine antibody conjugated to a europium chelate, allowing quantitation of the product by time-resolved fluorometry. Similar assay methods have been employed for the detection of the tyrosine kinase c-src, as described in Braunwalder et al. *Anal. Biochem.* 1996, 238, 159, incorporated herein by reference. A preferred assay method for MLK3 utilizes phosphorylation of a protein substrate, such as myelin basic protein, with [$\gamma$-$^{32}$P]ATP, followed by isolation of the acid-insoluble $^{32}$P-phosphoprotein product on a filtration plate. Analogous methods were employed for the assay of protein kinase C, as reported in Pitt and Lee, *J. Biomol. Screening* 1996, 1, 47, incorporated herein by reference.

Methods for the inhibition of PARP, VEGFR2, and MLK3 enzyme activities are also contemplated by the present invention. Enzyme activity can be reduced or inhibited by contacting the enzyme with at least one compound described herein. The contacting can occur either in vitro, in vivo, or ex vivo. Contacting can also be promoted by use of contacting media which enhances the rate of mixing of enzyme and inhibitor. Preferred media include water, water-based solutions, buffered solutions, water-miscible solvents, enzyme-solubilizing solutions, and any combination thereof. Contacting cells containing the enzyme in vivo, preferably employs the inhibitor to be delivered in proximity to the enzyme associated with the cell in a biologically compatible medium. Preferred biologically compatible media include water, water-based solutions, saline, biological fluids and secretions, and any other non-toxic material that may effectively deliver inhibitor to the vicinity of the enzyme in a biological system.

The compounds described herein can be used to prevent or treat the onset or progression of any disease or condition related to PARP activity in mammals, especially humans. Such conditions include traumatic injury to the central nervous system, such as brain and spinal cord injuries, and the neuronal degradation associated with traumatic injury to the central nervous system. Related conditions and diseases treatable by methods of the present invention include vascular strokes, cardiac ischemia, cerebral ischemia, cerebrovascular disorders such as multiple sclerosis, and neurodegenerative diseases such as Alzheimer's, Huntington's, and Parkinson's diseases. Other PARP related conditions or diseases treatable by the compounds described herein include inflammation such as pleurisy and colitis, endotoxic shock, diabetes, cancer, arthritis, cardiac ischemia, retinal ischemia, skin aging, chronic and acute pain, hemorrhagic shock, and others. For example, following the symptoms of a stroke, a patient can be administered one or more compounds described herein to prevent or minimize damage to the brain. Patients with symptoms of Alzheimer's, Huntington's, or Parkinson's disease can be treated with compounds of the present invention to halt the progression of the disease or alleviate symptoms. PARP inhibitors may also be used to treat patients suffering from cancer. For instance, cancer patients can be administered the present compounds in order to augment the anti-tumor effects of chemotherapy.

The compounds described herein can be used to prevent or treat the progression of any disease or condition related to kinase activity (such as VEGFR2 or MLK3 activities) in mammals, especially humans. For instance, the compounds described herein may be used to treat conditions related to MLK3 activity such as chronic neurodegenerative diseases as, for example, Alzheimer's disease, Parkinson's disease, and Huntington's disease, and acute neurological conditions such as cardiac ischemia, cerebral ischemia, as well as traumatic brain and spinal injuries. Further, the compounds described herein, can also be useful in the treatment of inflammatory diseases and cancer related to MLK3 activity. Similarly, the compounds described herein, can be used to inhibit VEGFR2 which may lead to suppression of formation of new blood vessels. Such compounds can therefore be useful in the treatment of conditions associated with new blood vessel formations such as, for example, solid tumors, diabetic retinopathy, and other intraocular neovascular syndromes, macular degeneration, rheumatoid arthritis, psoriasis, and endometriosis.

The compounds described herein are preferably administered to mammals in a therapeutically effective amount. Dosage may vary depending on the compound, the potency of the compound, the type of disease, and the diseased state of the patient, among other variables. Dosage amount can be measured by administration of pre-measured dosing means or unit dosages in the form of tablets, capsules, suppositories, powders, emulsions, elixirs, syrups, ointments, creams, or solutions.

In therapeutic or prophylactic use, PARP or kinase inhibitors may be administered by any route that drugs are conventionally administered. Such routes of administration include intraperitoneal, intravenous, intramuscular, subcutaneous, intrathecal, intracheal, intraventricular, oral, buccal, rectal, parenteral, intranasal, transdermal or intradermal. Administration may be systemic or localized.

Compounds described herein may be administered in pure form, combined with other active ingredients, or combined with pharmaceutically acceptable nontoxic excipients or carriers. Oral compositions will generally include an inert diluent carrier or an edible carrier. Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings.

Alternative preparations for administration include sterile aqueous or nonaqueous solutions, suspensions, and emulsions. Examples of nonaqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

Preferred methods of administration of the present compounds to mammals include intraperitoneal injection, intramuscular injection, and intravenous infusion. Various liquid formulations are possible for these delivery methods, including saline, alcohol, DMSO, and water based solutions. The concentration of inhibitor may vary according to dose and volume to be delivered and can range from about 1 to about 1000 mg/mL. Other constituents of the liquid formulations can include, preservatives, inorganic salts, acids, bases, buffers, nutrients, vitamins, or other pharmaceuticals such as analgesics or additional PARP and kinase inhibitors. Particularly preferred formulations for administration of the present compounds are detailed in the following publications that describe administration of known PARP inhibitors and are incorporated herein by reference in their entireties; Kato, T. et al. *Anticancer Res.* 1988, 8(2), 239, Nakagawa, K. et al. *Carcinogenesis* 1988, 9, 1167, Brown, D. M. et al. *Int. J. Radiat. Oncol. Biol. Phys.* 1984, 1665, Masiello, P. et al. *Diabetologia* 1985, 28(9), 683, Masiello, P. et al. *Res. Commun. Chem. Pathol. Pharmacol.* 1990, 69(1), 17, Tsujiuchi, T. et al. Jpn. *J. Cancer Res.* 1992, 83(9), 985, and Tsujiuchi, T. et. al *Jpn. J. Cancer Res.* 1991, 82(7), 739.

Compounds of the present invention also may take the form of a pharmacologically acceptable salt, hydrate, solvate, or metabolite. Pharmacologically acceptable salts include basic salts of inorganic and organic acids, including but not limited to hydrochloric acid, hydrobromic acid, sulphuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function, such as a carboxy group, then suitable pharmaceutically acceptable cation pairs for the carboxy group are well known to those skilled in the art and include alkaline, alkaline earth, ammonium, quaternary ammonium cations and the like.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

EXAMPLES

Example 1

Measurement of PARP Enzymatic Activity

PARP activity was monitored by transfer of radiolabeled ADP-ribose units from [$^{32}$]NAD$^+$ to a protein acceptor such as histone or PARP itself. The assay mixtures contained 100 mM Tris (pH 8.0), 2 mM DTT, 10 mM MgCl$_2$, 20 ug/ml DNA (nicked by sonication), 20 mg/ml histone H1, 5 ng recombinant human PARP, and inhibitor or DMSO (<2.5% (v/v)) in a final volume of 100 uL. The reactions were initiated by the addition of 100 μM NAD$^+$ supplemented with 2 uCi [$^{32}$] NAD$^+$/mL and maintained at room temperature for 12 minutes. Assays were terminated by the addition of 100 μM of 50% TCA and the radiolabeled precipitate was collected on a 96-well filter plate (Millipore, MADP NOB 50), washed with 25% TCA. The amount of acid-insoluble radioactivity, corresponding to polyADP-ribosylated protein, was quantitated in a Wallac MicroBeta scintillation counter.

Example 2

Measurement of VEGFR2 Kinase Enzymatic Activity

A 96-well FluoroNUNC MaxiSorp plate was coated with 100 μL/well of recombinant human PLC-γ/GST substrate solution at a concentration of 40 μg/mL in Tris-buffered saline (TBS). The VEGFR2 activity was assayed in a 100 μL assay mixture containing 50 mM HEPES (pH 7.4), 30 μM ATP, 10 mM MnCl$_2$, 0.1% BSA, 2% DMSO, and 150 ng/mL recombinant human baculovirus-expressed human VEGFR2 cytoplasmic domain (prephosphorylated for 60 min at 4° C. in the presence of 30 μM ATP and 10 mM MnCl$_2$ prior to use). The kinase reaction was allowed to proceed at 37° C. for 15 min. The europium-labeled anti-phosphotyrosine detection antibody was added at 1:5000 dilution in block buffer (3% BSA in TBST). After 1 hour of incubation at 37° C., 100 μL of enhancement solution (Wallac #1244-105) was added and the plate was gently agitated. After 5 min, the time-resolved fluorescence of the resulting solution was measured using the BMG PolarStar (Model #403) using excitation and emission wavelengths of 340 nm and 615 nm, respectively, a collection delay of 400 μsec and an integration time of 400 μsec.

Example 3

Measurement of MLK3 Enzymatic Activity

The activity assay for MLK3 was performed in Millipore Multiscreen plates. Each 50 μL assay mixture contained 50 mM HEPES (pH 7.0), 1 mM EGTA, 10 mM MgCl$_2$, 1 mM DTT, 25 mM β-glycerophosphate, 100 μM ATP, 1 μCi [γ-$^{32}$P]

ATP, 0.1% BSA, 500 µg/mL myelin basic protein, 2% DMSO, various concentrations of test compounds, and 2 µg/mL of baculoviral human GST-MLK1 kinase domain. Samples were incubated for 15 min at 37° C. The reaction was stopped by adding ice-cold 50% TCA and the proteins were allowed to precipitate for 30 min at 4° C. The plates were allowed to equilibrate for 1-2 hours prior to counting in the Wallac MicroBeta 1450 Plus scintillation counter.

Example 4

Determination of $IC_{50}$ for Inhibitors

Single-point inhibition data were calculated by comparing PARP, VEGFR2, or MLK3 activity in the presence of inhibitor to activity in the presence of DMSO only. Inhibition curves for compounds were generated by plotting percent inhibition versus $\log_{10}$ of the concentration of compound. $IC_{50}$ values were calculated by nonlinear regression using the sigmoidal dose-response (variable slope) equation in GraphPad Prism as follows:

$$y = \text{bottom} + (\text{top} - \text{bottom})/(1 + 10^{(\log IC_{50} - x) \cdot \text{Hillslope}})$$

where y is the % activity at a given concentration of compound, x is the logarithm of the concentration of compound, bottom is the % inhibition at the lowest compound concentration tested, and top is the % inhibition at the highest compound concentration examined. The values for bottom and top were fixed at 0 and 100, respectively. $IC_{50}$ values were reported as the average of at least three separate determinations.

The following Examples 5 to 10 present PARP, VEGFR2, and MLK3 inhibiting data for compounds of the present invention. $IC_{50}$ values were determined as described in Examples 1 and 2. For some compounds, inhibiting data is presented as percent inhibition at a specified concentration. Compounds are tabulated together with compound number, substituents, and enzyme inhibition data.

Example 5

PARP Inhibiting Data for Compounds 1a to 1v of Formula IV wherein B is CO, J is H, V is $NR^1$ and E and F, Together with the Atoms to which they are Attached, Form a Cyclopentyl Group. A, $R^2$ and $R^1$ Vary as Listed Below

TABLE 1

| No. | A | $R^1$ | $R^2$ | PARP $IC_{50}$ (nM) |
|---|---|---|---|---|
| 1a | CO | H | H | 36 |
| 1b | CO | H | —$(CH_2)_3OCH_2Ph$ | 720 |
| 1c | CO | H | —$(CH_2)_3CN$ | 38% @ 10 µM |
| 1d | CO | H | —$(CH_2)_3Cl$ | 64% @ 10 µM |
| 1e | CO | H | —$(CH_2)_3OH$ | 946 |
| 1f | CO | H | —$(CH_2)_3$-piperidine | 68% @ 10 µM |
| 1g | CO | H | —$(CH_2)_3$-morpholine | 67% @ 10 µM |
| 1h | CO | H | —$(CH_2)_3$—$NEt_2$ | 819 |
| 1i | CO | H | —$(CH_2)_4$—$NHCOCH_3$ | 10% @ 10 µM |
| 1j | CO | H | —$SO_2Ph$ | 250 |
| 1k | CO | H | Lysine (2 HCl) | 22 |
| 1l | CO | H | β-Alanine (HCl) | 160 |
| 1m | CO | H | Glycine (HCl) | 38 |
| 1n | CO | H | —$(CH_2)_2OCH_2Ph$ | 1600 |
| 1o | CO | H | —$(CH_2)_2NEt_2$ | 12% @ 10 µM |
| 1p | CO | H | —$CH_2COOCH_2Ph$ | 14% @ 10 µM |
| 1q | CO | H | —$CH_2COOH$ | 52% @ 10 µM |
| 1r | CO | H | —$CH_2CONH_2$ | 63% @ 10 µM |

TABLE 1-continued

| No. | A | $R^1$ | $R^2$ | PARP $IC_{50}$ (nM) |
|---|---|---|---|---|
| 1s | CO | H | —$CH_2$-phthalimide | 25% @ 10 µM |
| 1t | $CH_2$ | $CH_3$ | H | 800 |
| 1u | $CH_2$ | $(BOC)_2Lys$ | H | 1500 |
| 1v | $CH_2$ | Lys | H | 1400 |

Example 6

PARP Inhibiting Data for Compounds 2a to 5g of Formula IV Wherein B is CO, $R^2$ is H, V is NH, and E and F, Together with the Atoms to which they are Attached, Form a Cyclopentyl Group. A and J Vary as Listed Below

TABLE 2

| No. | A | J (3-Substituent) | PARP $IC_{50}$ (nM) |
|---|---|---|---|
| 2a | CO | Br | 25 |
| 2b | CO | Cl | 39 |
| 2c | CO | F | 39 |
| 2d | CO | $CH_3CO$— | 17 |
| 2e | CO | $BrCH_2CO$— | 13 |
| 2f | CO | $CH_3BrCHCO$— | 21 |
| 2g | CO | N-Methylpiperizino-$CH_2CO$— | 16 |
| 2h | CO | Morpholino-$CH_2CO$— | 13 |
| 2i | CO | Piperidino-$CH_2CO$— | 20 |
| 2j | CO | Diethylamino-$CH_2CO$— | 21 |
| 2k | CO | $tBuO_2CCH_2N(CH_3)CH_2CO$— | 19 |
| 2l | CO | $HO_2CCH_2N(CH_3)CH_2CO$— | 8 |
| 2m | CO | $HO_2CCH_2CH_2CO$— | 3 |
| 2n | CO | 1,2,4-Triazol-2-yl$CH_2CO$— | 15 |
| 2o | CO | —CN | 14 |
| 2p | CO | $NH_2CH_2$— | 13 |
| 2q | CO | Hexahydrocyclopent[a]pyrrolo[3,4-c]carbazole-7(6H)-one-3-$NHCH_2$— | 167 |
| 2r | CO | $CH_3CONHCH_2$— | 13 |
| 2s | CO | $CH_3CH_2CONHCH_2$— | 28 |
| 2t | CO | $CH_3CH_2CH_2CONHCH_2$— | 44 |
| 2u | CO | Benzoyl-$NHCH_2$— | 37 |
| 2v | CO | BOC—$NHCH_2CONHCH_2$— | 33 |
| 2w | CO | BOC—$NH(CH_2)_3CONHCH_2$— | 33 |
| 2x | CO | $H_2NCH_2CONHCH_2$— | 45 |
| 2y | CO | $H_2N(CH_2)_3CONHCH_2$— | 54 |
| 2z | CO | $CH_3O_2C(CH_2)_2CONHCH_2$— | 10 |
| 2aa | CO | $CH_3O_2C(CH_2)_3CONHCH_2$— | 9 |
| 2ab | CO | $HO_2C(CH_2)_2CONHCH_2$— | 50 |
| 2ac | CO | $HO_2C(CH_2)_3CONHCH_2$— | 48 |
| 2ad | CO | BOC-$NHCH_2$— | 93 |
| 2ae | CO | —$SO_3H$ | 8 |
| 2af | $CH_2$ | Cl | 120 |
| 2ag | $CH_2$ | —$CO_2H$ | 80 |
| 2ah | $CH_2$ | —$CO_2CH_3$ | 59 |
| 2ai | $CH_2$ | —$CONHCH_2CH_2NMe_2$ | 165 |
| 2aj | $CH_2$ | —$CONHCH_2CH_2NC_4H_8O$ | 162 |
| 2ak | $CH_2$ | —$CONC_4H_8O$ | 83 |
| 2al | $CH_2$ | —$CON(CH_3)CH_2(4\text{-Pyr})$ | 65 |
| 2am | $CH_2$ | —$CON(CH_3)CH_2CH_2(1\text{-imidazole})$ | 161 |
| 2an | $CH_2$ | —$CON(CH_3)CH_2(2\text{-Pyr})$ | 237 |
| 2ao | CO | —OH | 27 |
| 2ap | CO | —$OCH_3$ | 32 |
| 2aq | CO | —$OCH_2CH_2OCH_2CH_3$ | 59 |
| 2ar | CO | —$OCH_2CH_2NEt_2$ | 88 |
| 2as | CO | —$OCH_2CH_2CH_2NMe_2$ | 100 |
| 2at | CO | —$OCH_2CH_2NC_4H_8O$ | 22 |
| 2au | CO | —OAc | 33 |
| 2av | CO | —CHO | 29 |
| 2aw | CO | —$CH_2OH$ | 22 |
| 2ax | CO | —$CHOHCH_3$ | 102 |
| 2ay | CH—OH | H | 408 |
| 2az | CO | —$CH_2CH_3$ | 116 |

TABLE 2-continued

| No. | A | J (3-Substituent) | PARP IC$_{50}$ (nM) |
|---|---|---|---|
| 2ba | CO | —COCO$_2$CH$_3$ | 12 |
| 2bb | CO | —COCO$_2$H | 5 |
| 2bc | CO | —CH$_2$CN | 24 |
| 2bd | CO | —CO$_2$H | 85 |
| 2be | CO | —CH$_2$CH$_2$NH$_2$ | 36 |
| 2bf | CO | —CH$_3$ | 82 |
| 2bg | CO | —CH$_2$OCOCH$_2$NMe$_2$ | 31 |
| 2bh | CO | —CONH$_2$ | 31 |
| 2bi | CO | —CO$_2$CH$_3$ | 27 |
| 2bj | CO | —CH$_2$NMe$_2$ | 29 |
| 2bk | CO | —CH$_2$NHEt | 32 |
| 2bl | CO | —CH$_2$N$^n$Pr | 16 |
| 2bm | CO | —CH$_2$NEt$_2$ | 17 |
| 2bn | CO | —CH$_2$N$^n$Bu$_2$ | 28 |
| 2bo | CO | —CH$_2$N(CH$_2$Ph)$_2$ | 293 |
| 2bp | CO | —CH$_2$NH$^n$Bu | 25 |
| 2bq | CO | —CH$_2$NHCH$_2$Ph | 26 |
| 2br | CO | —CH$_2$NH$^i$Pr | 25 |
| 2bs | CO | —CH$_2$N$^i$Pr$_2$ | 25 |
| 2bt | CO | —CH$_2$NHMe | 25 |
| 2bu | CO | —CH$_2$NMe$_3$ | 73 |
| 2bv | CO | —CH$_2$NC$_4$H$_8$O | 32 |
| 2bw | CO | —CH$_2$NcC$_4$H$_8$ | 35 |
| 2bx | CO | —CH$_2$NcC$_5$H$_{10}$ | 35 |
| 2by | CO | —CH$_2$NHCOCH$_2$(1-tetrazole) | 14 |
| 2bz | CO | —CH$_2$NHCO(CH$_2$)$_4$CO$_2$CH$_3$ | 62 |
| 2ca | CO | —CH$_2$NHCO(CH$_2$)$_2$NHCO$_2$tBu | 95 |
| 2cb | CO | —CH$_2$NHCO(CH$_2$)$_2$NH$_2$ | 75 |
| 2cc | CO | —CH$_2$NHSO$_2$CH$_3$ | 29 |
| 2cd | CO | —CH$_2$NHSO$_2$Ph | 39 |
| 2ce | CO | —CH$_2$NHCHO | 34 |
| 2cf | CHOH | —CH$_2$NHCHO | 124 |
| 2cg | CO | —CONHCH$_2$CH$_2$NMe$_2$ | 31 |
| 2ch | CO | —CONHCH$_2$CH$_2$CH$_2$NMe$_2$ | 33 |
| 2ci | CO | —CONHCH$_2$(4-Pyr) | 13 |
| 2cj | CO | —CONHCH$_2$CH$_2$(4-imidazole) | 15 |
| 2ck | CO | —CONH(CH$_2$)$_5$NMe$_2$ | 51 |
| 2cl | CO | —CONHCH$_2$(3-Pyr) | 21 |
| 2cm | CO | —CONHCH$_2$CH$_2$NC$_5$H$_{10}$ | 148 |
| 2cn | CO | —CONHCH$_2$CH$_2$NC$_4$H$_8$O | 26 |
| 2co | CO | —CONH(CH$_2$)$_2$OCH$_3$ | 18 |
| 2cp | CO | —CONC$_4$H$_8$O | 12 |
| 2cq | CO | —CONC$_4$H$_8$NCH$_3$ | 12 |
| 2cr | CO | —CONHCH$_2$(2-THF) | 14 |
| 2cs | CO | —CONHNC$_4$H$_8$NCH$_3$ | 42 |
| 2ct | CO | —CONMeCH$_2$CH$_2$CH$_2$NMe$_2$ | 89 |
| 2cu | CO | —CONMeCH$_2$CH$_2$NMe$_2$ | 151 |
| 2cv | CO | —CONHCH$_2$CH$_2$(2-Pyr) | 18 |
| 2cw | CO | —CONMeCH$_2$CH$_2$(2-Pyr) | 24 |
| 2cx | CO | —CONMeCH$_2$(4-Pyr) | 10 |
| 2cy | CO | —CONMeCH$_2$(4-Piperdinyl) | 23 |
| 2cz | CO | —CO$_2$CH$_2$CH$_2$NMe$_2$ | 30 |
| 2da | CO | —CONH(CH$_2$)$_2$OH | 15 |
| 2db | CO | —CONC$_4$H$_8$C(ethyleneketal) | 11 |
| 2dc | CO | —CONH[(CH$_2$)$_2$OH]$_2$ | 18 |
| 2dd | CO | —CONC$_4$H$_8$CO | 14 |
| 2de | CO | —CH$_2$OEt | 43 |
| 2df | CO | —CH$_2$OCH$_2$CH$_2$(2-Pyr) | 104 |
| 3a | CO | 2-Aminothiazol-4-yl- | 25 |
| 3b | CO | 2-Methylthiazol-4-yl- | 40 |
| 3c | CO | 2-Methyl-5-bromothiazol-4-yl- | 84 |
| 3d | CO | 2-Amino-5-methylthiazol-4-yl- | 50 |
| 3e | CO | 2-[(BOCNH)CH(CO$_2$tBu)(CH$_2$)$_3$NH]thiazol-4-yl- | 46 |
| 3f | CO | 2-[NH2CH(CO$_2$H)(CH$_2$)$_3$NH]thiazol-4-yl- | 22 |
| 3g | CO | 2-Guanidinothiazol-4-yl- | 19 |
| 3h | CO | 2-(Methylamino)thiazol-4-yl- | 54 |
| 3i | CO | 2-(Acetamino)thiazol-4-yl- | 54 |
| 3j | CO | 2-(PhCH$_2$CONHCH$_2$)thiazol-4-yl- | 20 |
| 3k | CO | 2-(Aminomethyl)thiazol-4-yl- | 42 |
| 3l | CO | 2-(Acetamino)imidazol-2-yl- | 47 |
| 3m | CO | 2-(Methanesulfonylaminomethyl)thiazol-4-yl- | 18 |
| 3n | CO | 2-(Acetaminomethyl)thiazol-4-yl- | 20 |
| 3o | CO | 2-(EtNHCONHCH$_2$)thiazol-4-yl- | 20 |
| 3p | CO | 2-(tBuSO$_2$CH$_2$)thiazol-4-yl- | 21 |
| 3q | CO | 2-(tBuO$_2$CCH$_2$)thiazol-4-yl- | 29 |
| 3r | CO | 2-(IsopentanoylNHCH$_2$)thiazol-4-yl- | 56 |
| 3s | CO | 2-(PropanoylNHCH$_2$)thiazol-4-yl- | 56 |
| 3t | CO | 2-(IsobutanoylNHCH$_2$)thiazol-4-yl- | 32 |
| 3u | CO | 2-(ButanoylNHCH$_2$)thiazol-4-yl- | 42 |
| 3v | CO | 2-(PentanoylNHCH$_2$)thiazol-4-yl- | 56 |
| 3w | CO | 2-(CyclopropanecarbonylNHCH$_2$)-thiazol-4-yl- | 49 |
| 3x | CO | 2-(CyclopentanecarbonylNHCH$_2$)-thiazol-4-yl- | 52 |
| 3y | CO | 2-(tButylCO$_2$CH$_2$)thiazol-4-yl- | 60 |
| 3z | CO | 2-(CH$_3$SO$_2$CH$_2$)thiazol-4-yl- | 38 |
| 3aa | CO | 2-(Oxazol-5-yl)thiazol-4-yl- | 66 |
| 3ab | CO | 2-(Glucosamino)thiazol-4-yl- | 17 |
| 4a | CO | 2-(CH$_3$O$_2$C)pyrrolidine-CH$_2$CO— | 12 |
| 4b | CO | 2-(tBuO$_2$C)pyrrolidine-CH$_2$CO— | 12 |
| 4c | CO | 2-(HO$_2$C)pyrrolidine-CH$_2$CO— | 7 |
| 4d | CO | tBocNH(CH$_2$)$_2$NHCO(CH$_2$)$_2$CO— | 16 |
| 4e | CO | H$_2$N(CH$_2$)$_2$NHCO(CH$_2$)$_2$CO— | 22 |
| 4f | CO | Morpholino-CO(CH$_2$)$_2$CO— | 13 |
| 4g | CO | HO(CH$_2$)$_2$NHCO(CH$_2$)$_2$CO— | 9 |
| 4h | CO | 2-(tBuO$_2$C)pyrrolidin-1-yl-CO(CH$_2$)$_2$CO— | 7 |
| 4i | CO | Et$_2$NCO(CH$_2$)$_2$CO— | 12 |
| 4j | CO | 2-(HO$_2$C)pyrrolidin-1-yl-CO(CH$_2$)$_2$CO— | 2 |
| 4k | CO | 3-(HO2C)pyrazin-2-yl-CO— | 1 |
| 4l | CO | 6-Keto-4,5-dihydropyridazin-3-yl- | 17 |
| 4m | CO | 6-Keto-1-methyl-4,5-dihydropyridazin-3-yl- | 12 |
| 4n | CO | HO$_2$C(CH$_2$)$_3$CO— | 2 |
| 4o | CO | 2-(H$_2$NCO)pyrrolidin-1-yl-CO(CH$_2$)$_2$CO— | 13 |
| 4p | CO | Piperidin-1-yl-CO(CH$_2$)$_2$CO— | 10 |
| 4q | CO | 4-BOC-Piperazin-1-yl-CO(CH$_2$)$_2$CO— | 10 |
| 4r | CO | Piperazin-1-yl-CO(CH$_2$)$_2$CO— | 15 |
| 4s | CO | Octahydroazocin-1-yl-CO(CH$_2$)$_2$CO— | 26 |
| 4t | CO | Pyrrolidin-1-yl-CO(CH$_2$)$_2$CO— | 16 |
| 5a | CH$_2$ | H | 108 |
| 5b | CH$_2$ | —Br | 30 |
| 5c | CH$_2$ | —CN | 18 |
| 5d | CH$_2$ | —CH$_2$NH$_2$ | 27 |
| 5e | CH$_2$ | —CH$_3$ | 800 |
| 5f | CH$_2$ | (BOC)$_2$Lys-NHCH$_2$— | 670 |
| 5g | CH$_2$ | Lys-NHCH$_2$— | 80 |

Example 7

PARP Inhibiting Data for Compounds 1a, 5a, and 6b-p of Formula IV Wherein V is NR$^1$

TABLE 3

| No. | A | B | E | F | J | R$^1$ | R$^2$ | PARP IC$_{50}$ (nM) |
|---|---|---|---|---|---|---|---|---|
| 1a | CO | CO | | (CH$_2$)$_3$ | H | H | H | 36 |
| 5a | CH$_2$ | CO | | (CH$_2$)$_3$ | H | H | H | 108 |
| 6b | CO | CO | CH$_3$ | CH$_3$ | H | H | H | 700 |
| 6e | CO | CO | | (CH$_2$)$_3$ | 3-Br | H | Lys | 69 |
| 6f | CO | CO | | (CH$_2$)$_3$ | 3-Cl | H | Lys | 62 |
| 6g | CO | CO | | (CH$_2$)$_3$ | 3-F | H | Lys | 48 |
| 6h | CH$_2$ | CO | | (CH$_2$)$_3$ | H | H | —CHO | 3000 |
| 6i | CH$_2$ | CO | | (CH$_2$)$_3$ | 3-Br | Lys | H | [35% @ 3 uM] |
| 6j | CH$_2$ | CO | | (CH$_2$)$_3$ | 3-CN | Lys | H | 460 |
| 6k | CO | CO | | (CH$_2$)$_3$ | H | H | —CHO | 78 |
| 6l | CO | CO | | (CH$_2$)$_3$ | H | H | —CH$_2$OH | 138 |
| 6n | CO—NH | CO | | (CH$_2$)$_3$ | H | H | H | 60% (10 μM) |
| 6o | CH—OH/CO | CO/CH—OH | | (CH$_2$)$_3$ | CO$_2$H | H | H | 287 |
| 6p | CO | CO | | (CH$_2$)$_3$ | CH$_2$NMe$_2$ | CH$_2$OH | H | 55 |

Example 8

PARP Inhibiting Data for Compounds 8b-j of Formula IIb Wherein R$^1$ is H, and R$^2$ is H

TABLE 4

| No. | A | B | D$^1$ | D$^2$ | E, F | PARP IC$_{50}$ (nM) |
|---|---|---|---|---|---|---|
| 8b | CO | CO | CH | CH | (CH$_2$)$_3$ | 40 |
| 8c | CO | CO | Br—C | CH | (CH$_2$)$_3$ | 5 |
| 8d | CO | CO | NC—C | CH | (CH$_2$)$_3$ | 6 |
| 8e | CONH | CO | CH | CH | (CH$_2$)$_3$ | 1820 |
| 8f | CO | CO | C—Br | C—Br | (CH$_2$)$_3$ | 20 |
| 8g | CO | CO | C—CH$_2$NH$_2$ | H | (CH$_2$)$_3$ | 89 |
| 8h | CO | CO | C—CH=CH—HC=N—C | | (CH$_2$)$_3$ | 3 |
| 8i | CO | CO | C—CH=CH—CH=N(CH$_3$)—C | | (CH$_2$)$_3$ | 1523 |
| 8j | CH$_2$ | CH$_2$ | C—HC=CH—CH=CH—C | | (CH$_2$)$_3$ | 42% (10 uM) |
| 8k | CO | CO | C—CH=CH—C(CH$_3$)=N—C | | (CH$_2$)$_3$ | 2 |

Example 9

VEGFR2 and MLK3 Inhibiting Data for Compounds 11a to 13b of Formula IV Wherein V is NR$^1$ Table 5 contains percent inhibition data for MLK3 and VEGFR2 enzymes at the concentrations specified unless indicated otherwise. For some entries, an IC$_{50}$ value is reported.

TABLE 5

| No. | A | B | E | F | J | R$^1$ | R$^2$ | MLK3 % @ 1 μM | VEGFR2 % @ 300 nM |
|---|---|---|---|---|---|---|---|---|---|
| 11a | CO | CH$_2$ | | (CH$_2$)$_3$ | H | H | H | 19 | IC$_{50}$ 477 (nM) |
| 11b | CO | CO | | (CH$_2$)$_4$ | H | H | H | 26 | IC$_{50}$ 698 (nM) |
| 11c | CO | CO | Pr | Et | H | H | H | 46 | 0% @100 nM |
| 11d | CO | CO | | (CH$_2$)$_4$ | H | CH$_3$ | H | 52 | IC$_{50}$ 778 (nM) |
| 11e | CO | CO | CH=CHCH=CH | | H | H | H | 35 | IC$_{50}$ 166 (nM) |
| 11f | CO | CO | OCH$_2$CH$_2$ | | H | H | H | 62 | 3 |
| 11g | CO | CO | O—CH=CH | | H | H | H | 16 | 8 |
| 11h | CO | CO | CH=CH—O | | H | H | H | — | — |
| 12a | CO | CO | CH=NCH=CH | | H | H | H | 74 | IC$_{50}$ 235 (nM) |

TABLE 5-continued

| No. | A | B | E F J | | | $R^1$ | $R^2$ | MLK3 @ 1 μM | VEGFR2 @ 300 nM |
|---|---|---|---|---|---|---|---|---|---|
| 12b | $CH_2$ or CO | CO or $CH_2$ | CH=NCH=CH | H | H | H | | 34 | 4 |
| 12c | $CH_2$ | CO | CH=NCH=CH | H | H | H | | 54 | 22 |
| 12d | CO | CH(OH) | CH=NCH=CH | H | H | H | | 5 | 27% @ 10 uM |
| 12e | CO | CO | CH=NCH=CH | H | H | $CH_2CH_2CO_2Et$ | | 20 | 0 |
| 12f | CO | CO | CH=NCH=CH | H | H | $CH_2CH_2CH_2$—OH | | 14 | 10 |
| 12g | CO | CO | CH=NCH=CH | H | | H | $CH_2CH_2OH$ | 15 | 22 |
| 12h | CO | CO | CH=NCH=CH | H | | H | $CH_2CO_2Et$ | 35 | 24 |
| 12i | CO | CO | CH=NCH=CH | H | | H | Pyrid-2-yl-$CH_2$ | 40 | 26 |
| 12j | CO | CO | CH=NCH=CH | H | | H | $CH_2CH_2CO_2H$ | 2 | 18 |
| 12k | CO | CO | CH=NCH=CH | H | | H | $CH_2CH_2CN$ | 4 | 9 |
| 12l | CO | CO | CH=NCH=CH | H | | H | 4-HO-Bn | 26 | 10 |
| 12m | CO | CO | CH=NCH=CH | H | | 4-HO—Bn | 4-HO—Bn | 7 | 3 |
| 12n | CO | CO | CH=NCH=CH | 3-$CH_3$ | | H | H | 86 | $IC_{50}$ 94(nM) |
| 12o | CO | CO | CH=NCH=CH | 1-$CH_3$ | | H | H | 73 | 45 |
| 12p | CO | CO | CH=NCH=CH | 3-Br | | H | H | 72 | 22 |
| 12q | CO | CO | CH=NCH=CH | 3-(MeO—$CH_2CH_2O_2C$) | | H | H | 45 | 15 |
| 12r | CH(OH) | CO | CH=NCH=CH | 3-(MeO—$CH_2CH_2O_2C$) | | H | H | 0 | 2 |
| 12s | CO | CO | CH=NCH=CH | 3-(Thiophen-2-yl) | | H | H | 80 | 13 |
| 12t | CO | CO | CH=NCH=CH | 3-(1-Me-pyrrol-2-yl) | | H | H | 67 | 19 |
| 12u | CO | CO | CH=NCH=CH | 3-(Pyrid-4-yl) | | H | H | 47 | 16 |
| 12v | CO | CO | CH=NCH=CH | 3-$COCH_2CH_2$—$CO_2CH_3$ | | H | H | | 28 |
| 12w | CO | CO | CH=NCH=CH | 3-CH=CH—$CO_2Et$ | | H | H | | 21 |
| 12x | CO | CO | CH=NCH=CH | 3-CH=CH—$CONC_4H_8O$ | | H | H | | 34 |
| 12y | CO | CO | CH=NCH=CH | 3-CH=CH—$CONEt_2$ | | H | H | | 26 |
| 12z | CO | CO | CH=NCH=CH | 3-CH=CH—$CONH_2$ | | H | H | | 22 |
| 12aa | CO | CO | CH=NCH=CH | 3-CH=CHCN | | H | H | | 42 |
| 12ab | CO | CO | CH=NCH=CH | 3-CH=CH(3-Pyr) | | H | H | | 15 |
| 12ac | CO | CO | CH=NCH=CH | 3-CH=CH(4-Pyr) | | H | H | | 23 |
| 13a | CO | CO | $CH_2NMeCH_2CH_2$ | H | | H | H | 19 | 0 |
| 13b | CO | CO | $CH_2NBnCH_2CH_2$ | H | | H | H | 20 | 1 |

Example 10

PARP, VEGFR2, and MLK3 Inhibiting Data for Compounds 14 and 15 of Formula IV Wherein J is H, and $R^2$ is H

TABLE 6

| No. | A | B | E, F | V | PARP % @ 10 μM | MLK3 % @ 1 μM |
|---|---|---|---|---|---|---|
| 14 | CO | CO | $(CH_2)_3$ | S | 19 | 18 |
| 15 | CO | CO | $(CH_2)_3$ | O | 18 | 13 |

Example 10a

PARP Inhibiting Data for Compounds 14a and 14b of Formula IV Wherein $R^2$ is H

TABLE 7

| No. | A | B | E, F | J | V | PARP $IC_{50}$ (nM) |
|---|---|---|---|---|---|---|
| 14a | CO | CO | $(CH_2)_3$ | 2-$OCH_3$ | NH | 224 |
| 14b | CO | CO | $(CH_2)_3$ | 4-$OCH_3$ | NH | 19 |

Example 10b

PARP Inhibiting Data for Compounds 15a-15m of Formula IV Wherein B is CO, V is NH, $R^2$ is H, and E-F=$(CH_2)_3$

TABLE 8

| Example | A | J | PARP $IC_{50}$ (nM) |
|---|---|---|---|
| 15a | CO | -3-$OCONC_4H_8O$ | 35 |
| 15b | CO | -3-$OCONC_4H_8NCH_3$ | 51 |
| 15c | CO | -3-$OCONH(CH_2)_2OCH_3$ | 40 |
| 15d | CO | -3-$OCONH(CH_2)_3$(1-imidazol) | 32 |
| 15e | CO | -3-$OCONH(CH_2)_3$(1-butyrolactam) | 28 |
| 15f | CO | -3-$OCONHCH_2$(3-pyridyl) | 34 |
| 15g | CO | -3-$OCONH(CH_2)_2$(2-pyridyl) | 36 |
| 15h | CO | -3-$OCONCH_3(CH_2)_2$(2-pyridyl) | 39 |
| 15i | CO | -3-$OCONCH_3[CH_2$(4-pyridyl)] | 30 |
| 15j | CO | -3-$OCONHCH_2$(5-tetrazole) | 16 |
| 15k | CO | -3-$OCONHNC_4H_8O$ | 20 |
| 15l | CO | -3-$OCONC_4H_8N(CH_2)_2OH$ | 15 |
| 15m | CO | -3-$OCONH(CH_2)_2$(2-pyridyl) | 31 |

Example 11

Synthesis of Starting Materials and Intermediates

Methods and materials employed in the synthesis of starting materials, intermediates, and inhibitors are as follows. Thin layer chromatography was performed on silica gel plates (MK6F 60A, size 1×3 in, layer thickness 250 mm;

Whatman Inc., Whatman House, UK). Preparative thin layer chromatography was performed on silica gel plates (size 20×20 in, layer thickness 1000 micron; Analtech, Newark, N.J.). Preparative column chromatography was carried out using Merck, Whitehouse Station, N.J., silica gel, 40-63 mm, 230-400 mesh. HPLC was run under the following conditions: 1) solvents; A=0.1% TFA in water; B=0.1% TFA in acetonitrile (10 to 100% B in 20 min or 10 to 95% B in 20.5 min), 2) column; zorbax Rx-C8 (4.6 mm×15 cm), 3) flow rate; 1.6 mL/min. $^1$H NMR spectra were recorded on a GE QE Plus instrument (300 MHz) using tetramethylsilane as an internal standard. Electrospray mass spectra were recorded on a VG platform II instrument (Fisons Instruments).

FIG. 1 depicts the syntheses of intermediates, precursors, and starting materials for compounds of the present invention. The synthesis of 1a is also depicted therein.

Intermediate C was prepared in the following manner. To a cooled (−78° C.) solution of indole (A, 20 g, 171 mmol) in dry THF (80 mL) was slowly (over 30 min) added 2.5 M nBuLi in hexanes (68.40 mL, 171 mmol). The mixture was stirred at −78° C. for another 30 min, brought to room temperature and stirred for 10 min and cooled back to −78° C. Carbon dioxide gas was then bubbled into the reaction mixture for 15 min, followed by additional stirring of 15 min. Excess $CO_2$ (with some concomitant loss of THF) was removed at room temperature from the reaction flask by applying house vacuum. Additional dry THF (25 mL) was added to the reaction mixture that was cooled back to −78° C. 1.7 M t-BuLi (100.6 mL, 171 mmol) was slowly added to the reaction mixture over 30 min. Stirring was continued for 2 h at −78° C., followed by slow addition of a solution of cyclopentanone (B, 15.79 g, 188 mmol) in dry THF (80 mL). After an additional stirring of 1 h at −78° C., the reaction mixture was quenched by dropwise addition of water (10 mL) followed by saturated $NH_4Cl$ solution (100 mL). Ethyl ether (300 mL) was added to the flask and the mixture was stirred for 10 min at room temperature. The organic layer was separated, dried ($MgSO_4$), concentrated and triturated with ethyl ether (40 mL). The separated solid was filtered, washed with cold ether and dried under high vacuum to give 22.40 g of compound C as a white solid. Another crop of 4.88 g was obtained from mother liquor and washings. Physical properties include mp 133-141° C.; $R_t$ 8.68 min; $^1$H-NMR (DMSO-$d_6$) δ 8.46 (br. s, 1H), 7.58 (d, 1H), 7.36 (d, 1H), 7.17 (t, 1H), 7.09 (t, 1H), 6.34 (s, 1H), 2.2-1.6 (m, 8H). An analytical sample was recrystallized from refluxing methanol-water. Anal. Calcd. for $C_{13}H_{15}NO$: C, 77.58; H, 7.51; N, 6.96. Found: C, 77.13; H, 7.12; N, 6.96.

Intermediate D was prepared in the following manner. To a solution of compound C (20 g, 99.50 mmol) in acetone (150 mL) was added slowly 2 N HCl (20 mL) over a period of 10 min. The mixture was stirred for another 10 min and water (300 mL) was added to it. On standing, slowly a precipitate appeared. The precipitate was filtered washed with a mixture of water-acetone (2:1, 3×50 mL) and dried under vacuum to generate 13.57 g of D that was used in the next step without any further purification. The combined mother liquor and washings, on standing, generated another 3.72 g of white solid. Physical properties for D include; mp 166-167° C.;. $^1$H-NMR (DMSO-$d_6$) δ 8.12 (br. s, 1H), 7.57 (d, 1H), 7.33 (d, 1H), 7.16 (t, 1H), 7.06 (t, 1H), 6.42 (s, 1H), 6.01 (s, 1H), 2.79 (m, 2H), 2.60 (m, 2H), 2.08 (quintet, 2H). An analytical sample was purified by chromatography on silica gel (hexanes-ether, 80:20). Anal. Calcd for $C_{13}H_{13}N$: C, 85.21; H, 7.15; N, 7.64. Found: C, 85.08; H, 7.16; N, 7.64.

Intermediate F was prepared in the following manner. A mixture of compound D (13.57 g, 74.20 mmol) and E (14.4 g, 148 mmol) was mixed thoroughly and heated neat at 190° C. in a sealed tube for 1 h, cooled to room temperature, triturated with cold methanol and filtered. The residue was washed several times with cold methanol and dried under high vacuum to generate 10.30 g of compound F that was used in the next step without any further purification. Compound F is characterized as a yellow amorphous solid; $^1$H-NMR (DMSO-$d_6$) δ 11.15 (s, 1H), 10.89 (s, 1H), 7.65 (d, 1H), 7.23 (d, 2H), 6.91 (m, 2H), 4.24 (d, 1H), 3.30 (m, 2H), 2.60 (m, 1H), 2.14 (m, 1H), 1.92 (m, 1H), 1.45 (m, 3H), 1.13 (m, 1H). MS m/e 279 (M−H)$^-$.

Compound G (1a, 5,7,8,9,10,11-hexahydrocyclopent[a]pyrrolo[3,4-c]carbazole-5(6H), 7-dione) was prepared in the following manner. A mixture of compound F (10.20 g, 36.42 mmol), DDQ (20.7 g, 91.18 mmol), and toluene (100 mL) was heated at 60° C. in a sealed tube overnight, cooled to room temperature and filtered. The filtrate was washed several times with methanol (total volume 250 mL) to remove all the by-products. Drying under high vacuum generated 7.8 g of compound G (1a) that was used without any further purification. Compound G, also identified as 1a, occurs as a yellow amorphous solid showing $R_t$ 10.90 min; $^1$H-NMR (DMSO-$d_6$) δ 11.80 (s, 1H), 10.90 (s, 1H), 8.70 (s, 1H), 7.50 (m, 2H), 7.20 (t, 1H), 3.25 (2 sets of t, 4H), 2.25 (broad m, 2H); MS m/e 275 (M−H).

The following examples are preparations of precursors and compounds within the scope of the present invention.

Example 12

Preparation of 1b

To a slurry of sodium hydride (60% in oil, 0.016 g, 0.4 mmol) in dry DMF (2 mL) was slowly added 1a (0.1 g, 0.36 mmol) in dry DMF (3 mL). After the evolution of $H_2$-gas ceased, benzyl 3-mesylpropyl ether (0.11 g, 0.45 mmol) in dry DMF (1 mL) was added to the reaction flask. The mixture was stirred at 60° C. for 1.5 h, poured into ice-water (ca. 10 g) and extracted into ethyl acetate (2×15 mL). The combined organic layer was washed with water (1×10 mL), brine (1×10 mL) and concentrated to give a residue that was triturated with ether-hexane (1; 1, 5 mL) to give a solid. The solid was washed with methanol and dried to give 0.046 g of 1b. Compound 1b is characterized as a yellow amorphous solid; $R_t$ 17.92 min; $^1$H-NMR (DMSO-$d_6$) δ 11.90 (s, 1H), 8.70 (d, 1H), 7.50 (m, 2H), 7.25 (t, 1H), 7.10 (m, 5H), 4.30 (s, 2H), 3.70 (t, 2H), 3.50 (t, 2H), 3.25 (2 sets of t, 4H), 2.25 (m, 2H), 1.80 (m, 2H); MS m/e 423 (M−H).

Example 13

Preparation of 1c

To a slurry of sodium hydride (60% in oil, 0.016 g, 0.4 mmol) in dry DMF (2 mL) was slowly added 1a (0.1 g, 0.36 mmol) in dry DMF (3 mL). After the evolution of $H_2$-gas ceased, benzyl 4-bromobutyronitrile (0.08 g, 0.54 mmol) in dry DMF (1 mL) was added to the reaction flask. The mixture was stirred at 60° C. for 1.5 h, poured into a mixture of ice and water (ca. 10 g) and filtered. The residue was washed with methanol and dried to give 0.08 g of 1c. 1c is characterized as a yellow amorphous solid; $R_t$ 14.31 min; $^1$H-NMR (DMSO-$d_6$) δ 11.90 (s, 1H), 8.70 (d, 1H), 7.50 (m, 2H), 7.25 (t, 1H), 3.70 (t, 2H), 3.25 (2 sets of t, 4H), 2.50 (t, 2H), 2.25 (m, 2H), 1.90 (m, 2H); MS m/e 342 (M−H).

Example 14

Preparation of 1d

To a slurry of sodium hydride (60% in oil, 0.088 g, 2.2 mmol) in dry DMF (4 mL) was slowly added 1a (0.55 g, 2 mmol) in dry DMF (3 mL). After the evolution of $H_2$-gas ceased, 1-chloro-3-iodopropane (0.49 g, 0.54 mmol) in dry DMF (3 mL) was added to the reaction flask. The mixture was stirred at 100° C. for 6 h, concentrated to a smaller volume and poured into a mixture of ice and water (ca. 20 g) and filtered. The residue was washed with methanol and dried to give 0.4 g of 1d. Compound 1d is characterized as a yellow amorphous solid; $R_t$ 16.59 min; $^1$H-NMR (DMSO-$d_6$) δ 11.90 (s, 1H), 8.70 (d, 1H), 7.50 (m, 2H), 7.25 (t, 1H), 3.70 (m, 4H), 3.25 (2 sets of t, 4H), 2.25 (m, 2H), 2.10 (m, 2H); MS m/e 351 and 353 (M–H for different isotopes of chlorine).

Example 15

Preparation of 1e

A solution of 1b (0.042 g, 0.1 mmol) in DMF (10 mL) was hydrogenated in a Paar apparatus in presence of Pd(OH)$_2$ (0.020 g) and 1 drop of conc. HCl at 40 psi for 2 h. The reaction mixture was then filtered through a Celite® pad and concentrated to give a residue that was triturated with methanol to generate 0.018 g of 1e. Compound 1e is characterized as a yellow amorphous solid; $R_t$ 12.18 min; $^1$H-NMR (DMSO-$d_6$) δ 11.90 (s, 1H), 8.70 (d, 1H), 7.50 (m, 2H), 7.25 (t, 1H), 3.70 (t, 2H), 3.50 (t, 2H), 3.40 (broad, 1H), 3.25 (2 sets of t, 4H), 2.25 (m, 2H), 1.80 (m, 2H); MS m/e 333 (M–H).

Example 16

Preparation of 1f

A mixture of 1d (0.062 g, 0.18 mmol) and piperidine (0.06 g, 0.7 mmol) in ethanol (4 mL) was heated (80-85° C.) in a sealed tube for 3 days. After cooling, the reaction mixture was poured over a mixture of ice and water (ca. 20 g) and filtered. The residue was dried, dissolved in methanol (5 mL) and treated with black carbon. Filtration and solvent evaporation generated 0.005 g of 1f. Compound 1f is characterized as a yellow amorphous solid; $R_t$ 10.63 min; MS m/e 402 (M+H).

Example 17

Preparation of 1g

A mixture of 1d (0.066 g, 0.19 mmol) and excess morpholine in ethanol (2 mL) was heated (80-85° C.) in a sealed tube for 3 days. After cooling, the reaction mixture was concentrated, taken into methanol (3 mL) and cooled to 0° C. Dropwise addition of water to the above solution then generated a solid that was filtered and redissolved in ethyl acetate. Drying and solvent evaporation gave 0.019 g of 1g. Compound 1g is characterized as a yellow amorphous solid; $R_t$ 12.91 min; $^1$H-NMR (DMSO-$d_6$) δ 11.90 (s, 1H), 8.70 (d, 1H), 7.50 (m, 2H), 7.25 (t, 1H), 3.70 (t, 2H), 3.25 (m, 6H), 2.25 (m, 10H), 1.80 (m, 2H); MS m/e 404 (M+H).

Example 18

Preparation of 1 h

A mixture of 1d (0.052 g, 0.15 mmol) and excess diethylamine in ethanol (2 mL) was heated (80-85° C.) in a sealed tube for 3 days. After cooling, the reaction mixture was poured over a mixture of ice and water (ca. 20 g) and filtered. The residue was washed several times with water and dried under high vacuum to generate 0.015 g of 1 h. Combined mother liquor and washings, on standing, produced another 0.014 g of 1 h. Compound 1h is characterized as a yellow amorphous solid; $R_t$ 10.47 min; $^1$H-NMR (CDCl$_3$) δ 9.00 (d, 1H), 8.30 (s, 1H), 7.50 (m, 2H), 7.25 (t, 1H), 3.70 (t, 2H), 3.30 (t, 2H), 3.10 (t, 2H), 2.25 (m, 6H), 2.30 (m, 2H), 1.90 (m, 2H), 1.00 (t, 6H); MS m/e 390 (M+H).

Example 19

Preparation of 1j

To a slurry of sodium hydride (60% in oil, 0.008 g, 0.2 mmol) in dry DMF (1 mL) was slowly added 1a (0.05 g, 0.18 mmol) in dry DMF (2 mL). After the evolution of $H_2$-gas ceased, phenylsulfonyl chloride (0.035 g, 0.2 mmol) in dry DMF (3 mL) was added to the reaction flask. The mixture was stirred at 60° C. for 1 h, poured into ice-water (ca. 20 g) and filtered. The residue was successively washed with water and methanol and dried to give 0.036 g of 1j. Compound 1j is characterized as a yellow amorphous solid; $R_t$ 16.19 min; $^1$H-NMR (DMSO-$d_6$) δ 12.10 (s, 1H), 8.70 (d, 1H), 8.10 (d, 2H), 7.70 (m, 3H), 7.50 (m, 2H), 7.30 (t, 1H), 3.25 (2 sets of t, 4H), 2.25 (m, 2H); MS m/e 415 (M–H).

Example 20

Preparation of 1k

To a slurry of sodium hydride (60% in oil, 0.048 g, 1.2 mmol) in dry DMF (2 mL) was slowly added 1a (0.3 g, 1.1 mmol) in dry DMF (4 mL) and the mixture was stirred for 30 min. In a separate flask, a mixture of Boc-Lys(Boc) dicyclohexylamine salt (1.16 mmol, 2.2 mmol), TBTU (0.71 g, 2.2 mmol), NMM (0.22 g, 2.2 mmol) in dry DMF (5 mL) was stirred for 30 min and added to the first reaction-flask. The mixture was stirred for 1 h (HPLC showed 70% of a new product), poured into a mixture of ice and water (ca. 20 g) and filtered. The residue was washed several times with water, dried under high vacuum, dissolved in dioxane (3 mL) and to it added 4 N HCl in dioxane (3 mL). After stirring for 1 h at room temperature, the reaction mixture was filtered and the residue was washed several times with dioxane, followed by ether. Drying under high vacuum generated 0.1 g of 1k. Compound 1k is characterized as a yellow amorphous solid; $R_t$ 5.93 min; $^1$H-NMR (DMSO-$d_6$) δ 12.20 (s, 1H), 8.80 (d, 1H), 8.70 (broad, 3H), 8.00 (broad, 3H), 7.60 (m, 2H), 7.30 (t, 1H), 5.00 (broad, 1H), 3.25 (m, 4H), 2.70 (broad, 2H), 2.25 (m, 2H), 2.00 (2 sets of broad, 2H), 1.50 (broad m, 4H); MS m/e 406 (M+2H).

Example 21

Preparation of 1l

This compound was prepared following the same procedure as described before for the synthesis of 1k. Thus, starting from 0.1 g of 1a and 0.14 g of Boc-beta-alanine, 0.025 g of 1l was obtained. 1l is characterized as a yellow amorphous solid; $R_t$ 7.45 min; $^1$H-NMR (DMSO-$d_6$) δ 12.20 (s, 1H), 8.70 (d, 1H), 8.00 (broad, 3H), 7.50 (m, 2H), 7.25 (t, 1H), 3.30 (t, 2H), 3.25 (m, 6H), 2.25 (m, 2H); MS m/e 348 (M+H).

Example 22

Preparation of 1m

This compound was prepared following the same procedure as described before for the synthesis of 1k. Thus, starting from 0.1 g of 1a and 0.13 g of Boc-glysine, 0.028 g of 1m was obtained. Compound 1m is characterized as a yellow amorphous solid; $R_t$ 7.14 min; $^1$H-NMR (DMSO-$d_6$) δ 12.20 (s, 1H), 8.70 (d, 1H), 8.30 (broad, 3H), 7.60 (m, 2H), 7.30 (t, 1H), 4.30 (s, 2H), 3.25 (m, 4H), 2.25 (m, 2H); MS m/e 334 (M+H).

Example 23

Preparation of 1p

To a slurry of sodium hydride (60% in oil, 0.08 g, 2 mmol) in dry DMF (2 mL) was slowly added 1a (0.5 g, 1.8 mmol) in dry DMF (4 mL). After the evolution of $H_2$-gas ceased, benzyl 2-bromoacetate (0.46 g, 2 mmol) in dry DMF (2 mL) was added to the reaction flask. The mixture was stirred at 60° C. for 1 h, poured into a mixture of ice and water (ca. 20 g) and filtered. The crude residue was then purified by flash column chromatography (20% THF in toluene) to generate 0.2 g of 1p. Compound 1p is characterized as a yellow amorphous solid; $R_t$ 14.59 min; $^1$H-NMR (DMSO-$d_6$) δ 12.00 (s, 1H), 8.50 (d, 1H), 7.50 (m, 2H), 7.25 (m, 6H), 5.10 (s, 2H), 4.50 (s, 2H), 3.25 (m, 4H), 2.25 (m, 2H); MS m/e 423 (M−H).

Example 24

Preparation of 1n

To a slurry of sodium hydride (60% in oil, 0.029 g, 0.73 mmol) in dry DMF (2 mL) was slowly added 1a (0.17 g, 0.6 mmol) in dry DMF (3 mL). After the evolution of $H_2$-gas ceased, benzyl 2-bromoethyl ether (0.16 g, 0.73 mmol) in dry DMF (1 mL) was added to the reaction flask. The mixture was stirred at 60° C. for 4 h, poured into a mixture of ice and water (ca. 10 g) and filtered. The crude residue was then purified by flash column chromatography (20% THF in toluene) to generate 0.13 g of 1n. Compound 1n is characterized as a yellow amorphous solid; $R_t$ 14.62 min; $^1$H-NMR (DMSO-$d_6$) δ 11.90 (s, 1H), 8.50 (d, 1H), 7.50 (m, 2H), 7.20 (m, 6H), 4.50 (s, 2H), 3.70 (overlapping dd, 2H), 3.60 (overlapping dd, 2H), 3.25 (2 sets of t, 4H), 2.25 (broad m, 2H); MS m/e 409 (M−H).

Example 25

Preparation of 1o

A solution of 1n (0.1 g, 0.24 mmol) in DMF (8 mL) was hydrogenated in a Paar apparatus in presence of Pd(OH)$_2$ (0.025 g) and 1 drop of conc. HCl at 45 psi for 16 h. The reaction mixture was then filtered through a Celite® pad and concentrated to give 0.077 g of the corresponding debenzylated product as a yellow amorphous solid; $R_t$ 10.37 min; $^1$H-NMR (DMSO-$d_6$) δ 11.90 (s, 1H), 8.75 (d, 1H), 7.50 (m, 2H), 7.25 (t, 1H), 4.80 (t, 1H), 3.60 (m, 4H), 3.25 (2 sets of t, 4H), 2.25 (m, 2H). MS m/e 319 (M−H).

The above product (0.052 g, 0.163 mmol) was converted, in the presence of p-toluenesulfonyl chloride (0.214 g, 1.122 mol) and pyridine (3 mL) to corresponding p-toluenesulfonyl derivative (0.07 g). A solution of this compound (0.05 g) in THF (2 mL) and excess diethylamine was then refluxed in a sealed tube for 2 days. Excess solvent and reagent were removed. The residue was washed several times with methanol and dried under high vacuum to generate 0.20 g of 1o.

Compound 1o is characterized as a yellow amorphous solid; $R_t$ 9.06 min; $^1$H-NMR (DMSO-$d_6$) δ 11.90 (s, 1H), 8.75 (d, 1H), 7.50 (m, 2H), 7.25 (t, 1H), 3.60 (t, 2H), 3.25 (2 sets of t, 4H), 2.60 (t, 2H), 2.50 (q, 4H), 2.25 (m, 2H), 0.80 (t, 6H); MS m/e 376 (M+H).

Example 26

Preparation of 1q

A solution of 1p (0.030 g, 0.071 mmol) in MeOH-DMF (1:1, 10 mL) was hydrogenated in a Paar apparatus in presence of 10% Pd—C (DeGussa type, 50% water content) at 40 psi for 15 min. The reaction mixture was then filtered through a Celite® pad and concentrated to give 0.025 g of 1p. Compound 1p is characterized as a yellow amorphous solid; $R_t$ 10.36 min; $^1$H-NMR (DMSO-$d_6$) δ 12.00 (s, 1H), 8.75 (d, 1H), 7.50 (m, 2H), 7.25 (t, 1H), 4.25 (s, 2H), 4.00-3.00 (broad, 1H), 3.25 (m, 4H), 2.25 (m, 2H); MS m/e 333 (M−H).

Example 27

Preparation of 1r

To a solution of 1q (0.20 g, 0.060 mmol) in dry DMF (2 mL) at 0° C. was added EDCI (0.012 g, 0.063 mmol). The mixture was stirred for 10 min and to it added HOBt-ammonia complex (0.017 g, 0.112 mmol; 1.12 g of the complex was prepared by reacting 1.30 g of HOBt and 1.1 mL of 28% ammonium hydroxide in 10 mL of acetone, followed by removal of the solvents). The ice-bath was removed and the mixture was stirred overnight. It was then poured into a mixture of ice and water (ca. 10 g) and filtered. The residue was washed several times with water and dried under high vacuum to generate 0.012 g of 1r. Compound 1r is characterized as a yellow solid; $R_t$ 9.28 min; MS m/e 332 (M−H).

Example 28

Preparation of 1s

To a slurry of sodium hydride (60% in oil, 0.016 g, 0.4 mmol) in dry DMF (2 mL) was slowly added 1a (0.1 g, 0.36 mmol) in dry DMF (3 mL). After the evolution of $H_2$-gas ceased, N-bromomethylphthalimide (0.096 g, 0.4 mmol) in dry DMF (1 mL) was added to the reaction flask. The mixture was stirred at 60° C. for overnight, poured into a mixture of ice and water (ca. 10 g) and filtered. The residue was washed several times with water and dried under high vacuum to generate 0.1 g of 1s. 1s characterized as a yellow solid; $R_t$ 13.07 min $^1$H-NMR (DMSO-$d_6$) δ 12.00 (s, 1H), 8.75 (d, 1H), 7.80 (m, 4H), 7.50 (m, 2H), 7.25 (t, 1H), 5.50 (s, 2H), 3.25 (m, 4H), 2.25 (m, 2H); MS m/e 434 (M−H).

Example 29

Preparation of 1t

11-Methyl-5,7,8,9,10,11-hexahydrocyclopent[a]pyrrolo[3,4-c]carbazole-7(6H)-one

Compound 5a (20 mg, 0.076 mmol) in DMF (0.2 mL) was treated with MeI (11.4 mg, 0.08 mmol) and NaH (8.1 mg of 60%, 0.2 mmol) for 18 h. Water (1 mL) was added. The resulting precipitate was refluxed with acetone, cooled, and the precipitate was collected to afford the product as an off-white solid (9 mg, 43% yield). MS m/e 277 (M+H)⁺. NMR (DMSO-d₆) δ 8.45 (s, 1H), 7.95 (d, 1H), 7.70 (d, 1H), 7.55 (t, 1H), 7.30 (t, 1H), 4.82 (s, 2H), 4.12 (s, 3H), 3.52 (t, 2H), 3.40 (t, 2H), 2.25 (quintet, 2H).

Example 30

Preparation of 1u

11-[Bis(t-butoxycarbonyl)-L-lysyl]-5,7,8,9,10,11-hexahydrocyclopent[a]pyrrolo[3,4-c]carbazole-7(6H)-one The bis(t-butoxycarbonyl)-lysyl derivative was prepared as described for 1k, and purified by chromatography (CH₂Cl₂-Et₂O) to give a yellow glass. MS m/e 613 (M+Na)⁺.

Example 31

Preparation of 1v

11-L-Lysyl-5,7,8,9,10,11-hexahydrocyclopent[a]pyrrolo[3,4-c]carbazole-7(6H)-one dihydrochloride The BOC groups of 1u were hydrolyzed with 2M HCl in dioxane to afford the product as a tan solid. MS m/e 391 (M+H)⁺, 263 (M+H-Lysyl)⁺. NMR (DMSO-d₆) δ 12.1 (s, 1H), 8.6 (s, 3H), 8.4 (s, 3H), 8.08 (1H, d), 8.0 (s, 3H), 7.62 (d, 1H), 7.50 (t, 1H), 7.32 (t, 1H), 5.35 (s, 2H), 5.15 (m, 1H), 3.85 (m, 1H), 2.75 (m, 2H), 2.2-1.5 (m, 6H).

Example 32

Preparation of 2a

A mixture of 1a (1 g, 3.6 mmol), N-bromosuccinimide (0.64 g, 3.62 mmol) and dry DMF (20 mL) was stirred at room temperature for 1 h. The reaction mixture was then poured into methanol (100 mL) and filtered. The precipitated solid was washed several times with methanol and dried under high vacuum to generate 0.97 g of 2a. The product is characterized as a yellow amorphous solid with properties; $R_t$ 12.39 min; ¹H-NMR (DMSO-d₆) δ 12.00 (s, 1H), 11.00 (s, 1H), 8.70 (s, 1H), 7.60 (d, 1H), 7.50 (d, 1H), 3.25 (2 sets of t, 4H), 2.25 (broad m, 2H); MS m/e 353 and 355 (M−H for different isotopes of bromine).

Example 33

Preparation of 2b

A mixture of 1a (0.20 g, 0.72 mmol), N-chlorosuccinimide (0.106 g, 0.75 mmol) and dry DMF (5 mL) was heated in a sealed tube at 60° C. for 1 h. After cooling, the reaction mixture was poured into methanol (10 mL) and filtered. The precipitated solid was washed several times with methanol and dried under high vacuum to generate 0.11 g of 2b. Compound 2b is a yellow amorphous solid; $R_t$ 14.06 min; ¹H-NMR (DMSO-d₆) δ 12.00 (s, 1H), 11.00 (s, 1H), 8.70 (s, 1H), 7.50 (m, 2H), 3.25 (2 sets of t, 4H), 2.25 (broad m, 2H); MS m/e 309 and 301 (M−H for different isotopes of chlorine).

Example 34

Preparation of 2c

Starting with 5-fluoroindole, this compound was prepared following the same multistep procedure as described for the synthesis of 1a from indole. The compound 2c is characterized as an orange amorphous solid; $R_t$ 11.50 mm; ¹H-NMR (DMSO-d₆) δ 12.00 (s, 1H), 11.00 (s, 1H), 8.50 (d, 1H), 7.50 (m, 1H), 7.30 (t, 1H), 3.25 (2 sets of t, 4H), 2.25 (broad m, 2H). MS m/e 293 (M−H).

Example 35

Preparation of 2d

To a suspension of AlCl₃ (0.072 g, 0.54 mmol) in 1,2-dichloroethane (2 mL) at 0° C. was added acetyl chloride (0.042 g, 0.54 mmol). A suspension of 1a (0.050 g, 0.18 mmol) in 1,2-dichloroethane (4 mL) was slowly added to the reaction flask. The cooling bath was removed and the mixture was stirred for 4 h, poured over a mixture of ice (ca. 10 g) and 2 N HCl (10 mL) and filtered. The residue was washed with water, stirred overnight in a mixture of methanol-water (4:1, 5 mL) and filtered. It was washed with small volumes of methanol and ether, respectively and dried under vacuum to generate 0.023 g of 2d. Compound 2d is characterized as a yellow amorphous solid; $R_t$ 9.82 min (broad); ¹H-NMR (DMSO-d₆) δ 12.25 (s, 1H), 11.00 (s, 1H), 9.30 (s, 1H), 8.00 (d, 1H), 7.50 (d, 1H), 3.25 (2 sets of t, 4H), 2.70 (s, 3H), 2.25 (broad m, 2H); MS m/e 317 (M−H).

Example 36

Preparation of 2e

This compound was prepared following the same procedure as described before for the synthesis of 2d. Thus, starting from 0.050 g of 1a and 0.10 g of bromoacetyl bromide, 0.045 g of 2e was obtained. 2e is characterized as a yellow amorphous solid; $R_t$ 10.76 min; ¹H-NMR (DMSO-d₆) δ 12.30 (s, 1H), 11.00 (s, 1H), 9.40 (s, 1H), 8.10 (d, 1H), 7.60 (d, 1H), 4.80 (s, 2H), 3.25 (2 sets of t, 4H), 2.25 (broad m, 2H). MS m/e 396 (M−H).

Example 37

Preparation of 2f

This compound was prepared following the same procedure as described before for the synthesis of 2e. Based on 0.2 g of 1a starting material, 0.2 g of 2f was obtained. The compound 2f is characterized as a yellow amorphous solid; $R_t$ 11.96 min; ¹H-NMR (DMSO-d₆) δ 12.20 (s, 1H), 11.00 (s, 1H), 9.50 (s, 1H), 8.20 (d, 1H), 7.50 (d, 1H), 5.70 (q, 1H), 3.25 (2 sets of t, 4H), 2.25 (broad m, 2H), 1.80 (d, 3H). MS m/e 410 (M−H).

Example 38

Preparation of 2g

A mixture of 2e (0.036 g, 0.09 mmol), triethylamine (0.010 g, 0.10 mmol) and N-methylpiperizine (0.010 g, 0.10 mmol) in dry DMF (2 mL) was stirred at room temperature for 0.5 h, poured into a mixture of ice and water (ca. 10 g) and filtered. The residue was washed several times with water and dried under high vacuum to generate 0.010 g of 2 g. Compound 2g is characterized as a yellow amorphous solid; $R_t$ 5.77 min; ¹H-NMR (DMSO-d₆) δ 12.25 (s, 1H), 11.00 (s, 1H), 9.50 (s, 1H), 8.20 (d, 1H), 7.50 (d, 1H), 3.70 (s, 2H), 3.25 (2 sets of t, 4H), 2.50 (broad, 4H), 2.25 (broad m, 6H), 2.10 (t, 3H). MS m/e 417 (M+H).

Example 39

Preparation of 2h

A mixture of 2e (0.040 g, 0.10 mmol), triethylamine (0.011 g, 0.11 mmol) and morpholine (0.0096 g, 0.11 mmol) in dry DMF (2 mL) was stirred at room temperature for 1 h, poured into a mixture of ice and water (ca. 10 g) and filtered. The residue was washed several times with water and dried under high vacuum to generate 0.019 g of 2h. Compound 2h is characterized as a yellow amorphous solid; $R_t$ 6.50 min; $^1$H-NMR (DMSO-$d_6$) δ 12.25 (s, 1H), 11.00 (s, 1H), 9.50 (s, 1H), 8.20 (d, 1H), 7.60 (d, 1H), 3.70 (s, 2H), 3.50 (broad, 4H), 3.25 (2 sets of t, 4H), 2.40 (broad, 4H), 2.25 (broad m, 2H); MS m/e 404 (M+H).

Example 40

Preparation of 2i

A mixture of 2e (0.040 g, 0.1 mmol), triethylamine (0.011 g, 0.11 mmol) and piperidine (0.009 g, 0.11 mmol) in dry DMF (3 mL) was stirred at room temperature for 0.5 h, poured into a mixture of ice and water (ca. 10 g) and filtered. The residue was washed several times with water and dried under high vacuum to generate 0.034 g of 2i. Compound 2i is characterized as a yellow amorphous solid; $R_t$ 7.32 min; $^1$H-NMR (DMSO-$d_6$) δ 12.25 (broad, 1H), 11.00 (broad, 1H), 9.50 (s, 1H), 8.20 (d, 1H), 7.50 (d, 1H), 3.50 (s, 2H), 3.25 (2 sets of t, 4H), 2.40 (broad, 4H), 2.25 (broad m, 2H), 1.50 (broad, 4H), 1.30 (broad, 2H). MS m/e 402 (M+H).

Example 41

Preparation of 2j

A mixture of 2e (0.040 g, 0.1 mmol), triethylamine (0.012 g, 0.12 mmol) and diethylamine (0.009 g, 0.12 mmol) in dry DMF (3 mL) was stirred at room temperature for 1 h, poured into a mixture of ice and water (ca. 10 g) and filtered. The residue was washed several times with water and dried under high vacuum to generate 0.026 g of 2j. Compound 2j is characterized as a dark brown amorphous solid; $R_t$ 7.04 min; $^1$H-NMR (DMSO-$d_6$) δ 12.25 (broad, 1H), 11.00 (broad, 1H), 9.50 (s, 1H), 8.20 (d, 1H), 7.50 (d, 1H), 3.70 (s, 2H), 3.25 (2 sets of t, 4H), 2.60 (q, 4H), 2.25 (broad m, 2H), 1.00 (t, 6H). MS m/e 390 (M+H).

Example 42

Preparation of 2k

A mixture of 2e (0.050 g, 0.13 mmol), triethylamine (0.028 g, 0.27 mmol) and sarcosine t-butyl ester hydrochloride (0.025 g, 0.135 mmol) in dry DMF (3 mL) was stirred at room temperature for 72 h, poured into a mixture of ice and water (ca. 10 g) and filtered. The residue was washed several times with water and dried under high vacuum to generate 0.035 g of 2k. Compound 2k is characterized as a yellow amorphous solid; $R_t$ 9.20 min (broad); $^1$H-NMR (DMSO-$d_6$) δ 12.20 (s, 1H), 11.00 (s, 1H), 9.40 (s, 1H), 8.20 (d, 1H), 7.60 (d, 1H), 4.10 (s, 2H), 3.40 (s, 2H), 3.25 (2 sets of t, 4H), 2.40 (s, 3H), 2.25 (broad m, 2H), 1.40 (s, 9H); MS m/e 461 (M+H).

Example 43

Preparation of 2l

A mixture of compound 2k (0.018 g, 0.039 mmol) and trifluoroacetic acid (0.3 mL) was stirred overnight at room temperature. Excess trifluoroacetic acid was removed and ethyl acetate (5 mL) was added to the reaction flask. Slowly a solid appeared that was filtered, washed several times with ethyl acetate and dried under high vacuum to generate 0.016 g of 2l. Compound 2l is characterized as a yellow amorphous solid; $R_t$ 6.34 min (broad); $^1$H-NMR (DMSO-$d_6$) δ 12.20 (s, 1H), 11.00 (s, 1H), 9.40 (s, 1H), 8.10 (d, 1H), 7.60 (d, 1H), 4.70 (s, 2H), 3.70 (s, 2H), 3.50 (broad, 2H), 3.25 (2 sets of t, 4H), 2.70 (s, 3H), 2.25 (broad m, 2H); MS m/e 406 (M+H).

Example 44

Preparation of 2m

To a suspension of AlCl$_3$ (2.89 g, 21.7 mmol) in 1,2-dichloroethane (5 mL) at 0° C. was added succinic anhydride (1.086 g, 10.86 mmol) in 1,2-dichloroethane (5 mL). A suspension of 1a (1 g, 3.62 mmol) in 1,2-dichloroethane (10 mL) was slowly added to the reaction flask. The cooling bath was removed and the mixture was stirred for 5 h, poured over a mixture of ice (ca. 10 g) and 2 N HCl (10 mL) and filtered. The residue was washed with water, stirred overnight in a mixture of methanol-water (4:1, 10 mL) and filtered. The product was washed with small volumes of water and ether, sequentially, and dried under vacuum to generate 1.16 g of 2m. The compound 2m is characterized as a yellow amorphous solid; $R_t$ 9.17 min; $^1$H-NMR (DMSO-$d_6$) δ 12.30 (s, 1H), 12.10 (broad, 1H), 11.00 (s, 1H), 9.30 (s, 1H), 8.00 (d, 1H), 7.50 (d, 1H), 3.40 (m, 2H), 3.25 (2 sets of t, 4H), 2.60 (m, 2H), 2.25 (broad m, 2H). MS m/e 375 (M–H).

Example 45

Preparation of 2n

To a solution of compound 2e (0.040 g, 0.1 mmol) in dry DMF (2 mL) was added 1,2,4-triazole, sodium derivative (0.014 g, 0.14 mmol). The mixture was stirred for 30 min at room temperature, poured into a mixture of ice and water (ca. 10 g) and filtered. The residue was washed several times with water and dried under high vacuum to generate 0.024 g of 2n. Compound 2n is characterized as a yellow amorphous solid; $R_t$ 9.28 min; $^1$H-NMR (DMSO-$d_6$) δ 12.50 (s, 1H), 11.00 (s, 1H), 9.30 (s, 1H), 8.50 (s, 1H), 8.20 (d, 1H), 8.00 (s, 1H), 7.50 (d, 1H), 6.00 (s, 2H), 3.25 (2 sets of t, 4H), 2.25 (broad m, 2H); MS m/e 386 (M+H).

Example 46

Preparation of 2o

CuCN method: A mixture of 2a (0.1 g, 0.28 mmol), CuCN (0.075 g, 0.85 mmol) and 1-methyl-2-pyrrolidinone (4 mL) was heated at 175° C. in a sealed tube overnight, cooled to room temperature, passed through a silica pad, concentrated to a small volume and poured into water (20 mL). The precipitated solid was filtered, washed with water, dried and purified by column chromatography (eluant: EtOAc) to generate 0.006 g of 2o.

Zn(CN)$_2$ method: A mixture of 2a (2.33 g, 6.56 mmol) and Zn(CN)$_2$ (1.56 g, 13.3 mmol) were dissolved in DMF (22 mL) under nitrogen. Pd(Ph$_3$P)$_4$ (1.17 g, 0.10 mmol, 15 mol %) was added, and the mixture was stirred at 125° C. for 80 min. The warm solution was vacuum filtered through Celite® and the pad rinsed with hot DMF. The filtrate was diluted with two volumes of water. The resulting precipitate was collected, dried, and triturated with ethyl acetate and rinsed with ethyl acetate, then ether, affording the slightly impure product as a brownish-orange solid (2.17 g). This could be purified by column chromatography as above. Compound 2o is characterized as a yellow amorphous solid; $R_t$ 10.51 min; $^1$H-NMR (DMSO-$d_6$) δ 12.40 (s, 1H), 11.00 (s, 1H), 9.00 (s, 1H), 7.80 (d, 1H), 7.60 (d, 1H), 3.25 (2 sets of t, 4H), 2.25 (broad m, 2H); MS m/e 300 (M–H).

Example 47

Preparation of 2p 3-(Aminomethyl)-5,7,8,9,10,11-hexahydrocyclopent[a]pyrrolo[3,4-c]carbazole-5(6H), 7-dione hydrochloride 3-Cyano-5,7,8,9,10,11-hexahydrocyclopent[a]pyrrolo[3,4-c]carbazole-5(6H), 7-dione 2o (580 mg) was dissolved in DMF (58 mL). The solution was saturated with ammonia and hydrogenated at 55 psi over freshly prepared (R. Mozingo, Org. Synth. 1955 3, 181-183) W-2 Raney nickel (2.4 g) for 7 days. Additional Raney nickel was added as required. The precipitate, containing catalyst and some product, was removed and the solvent evaporated from the filtrate to afford the orange crude product (408 mg). The crude product was suspended in water (70 mL) and 1M HCl (1.5 mL) and mixed with Celite® 521 then filtered. The residue was lyophilized to give the product as a yellow solid (288 mg, 44% yield). NMR (DMSO-$d_6$) δ 12.20 (s, 1H), 11.02 (s, 1H), 8.85 (s, 1H), 8.36 (br. s, 3H), 7.65 (m, 2H), 4.19 (br. s, 2H), 4.00 (s, 2H), 3.28 (t, 2H), 3.21 (t, 2H), 2.31 (quintet, 2H). NMR ($D_2O$) δ 7.58 (s, 1H), 7.24 (d, 1H), 7.03 (d, 1H), 4.07 (s, 2H), 2.10 (m, 2H), 1.90 (m, 2H), 1.65 (m, 2H). MS m/e 289 (M+H–$NH_3$)$^+$, 306 (M+H)$^+$. Anal. Calcd for $C_{18}H_{15}N_3O_2$-2.1HCl-1.6$H_2O$: C, 52.64; H, 4.98; N, 10.23; Cl, 18.13. Found: C, 52.38; H, 4.61; N, 10.03; Cl, 18.29.

Example 48

Preparation of 2q

Bis-[5(6H), 7-dioxo-5,7,8,9,10,11-hexahydrocyclopent[a]pyrrolo[3,4-c]carbazol-3-ylmethyl]amine hydrochloride When 3-cyano-5,7,8,9,10,11-hexahydrocyclopent[a]pyrrolo[3,4-c]carbazole-5(6H), 7-dione 2o (115 mg) dissolved in DMF was hydrogenated as above but in the absence of ammonia, HPLC indicated a 60:40 mixture of dimer 2q and monomer 2p. The mixture was stirred with 0.01 M HCl (50 mL) and filtered. The precipitate was extracted with DMF (15 mL) to give the product as a yellow solid. NMR (DMSO-$d_6$) δ 10.09 (s, 2H), 9.31 (s, 2H), 8.03 (d, 2H), 7.73 (d, 2H), 4.13 (br. s, 4H), 3.28 (t, 4H), 3.21 (t, 4H), 2.30 (quintet, 4H). MS m/e 594 (M+H)$^+$.

Example 49

Preparation of 2r 3-(Acetylaminomethyl)-5,7,8,9,10,11-hexahydrocyclopent[a]pyrrolo[3,4-c]carbazole-5(6H), 7-dione EDCI (30 mg, 0.156 mmol) was added to a suspension of 3-(aminomethyl)-5,7,8,9,10,11-hexahydrocyclopent[a]pyrrolo[3,4-c]carbazole-5(6H), 7-dione hydrochloride (2p, 31 mg, 0.10 mmol), NMM (15 uL, 13 mmol), HOBT-$H_2O$ (16 mg, 0.10 mmol), and acetic acid (10 mg, 0.17 mmol) in DMF (0.5 mL). All solids dissolved 10 min. After 2 days, water (4 mL) was added. The precipitate was collected and rinsed with water, saturated $NaHCO_3$, water, 1 M HCl, and water, then dried to afford the product (2r, 23 mg, 73% yield) as a golden-brown solid. NMR (DMSO-$d_6$) δ 11.92 (s, 1H), 10.95 (s, 1H), 8.71 (s, 1H), 8.43 (t, 1), 7.54 (d, 1H), 7.43 (d, 1H), 4.43 (d, 2H), 3.27 (t, 2H), 3.19 (t, 2H), 2.30 (quintet, 2H), 1.91 (s, 3H). MS m/e 346 (M–H)$^-$.

Example 50

Preparation of 2s 3-(Propanoylaminomethyl)-5,7,8,9,10,11-hexahydrocyclopent[a]pyrrolo[3,4-c]carbazole-5(6H), 7-dione Prepared from 2p and propionic acid by a similar procedure to that used in the preparation of 2r. NMR (DMSO-$d_6$) δ 11.93 (s, 1H), 10.96 (s, 1H), 8.71 (s, 1H), 8.40 (t, 1), 7.52 (d, 1H), 7.44 (d, 1H), 4.42 (d, 2H), 3.30 (t, 2H), 3.22 (t, 2H), 2.35 (quintet, 2H), 2.22 (q, 2H), 1.11 (t, 3H). MS m/e 360 (M–H)$^-$.

Example 51

Preparation of 2t 3-(Butanoylaminomethyl)-5,7,8,9,10,11-hexahydrocyclopent[a]pyrrolo[3,4-c]carbazole-5(6H), 7-dione Prepared from 2p and butyric acid by a procedure analogous for the preparation of 2r. NMR (DMSO-$d_6$) δ 11.90 (s, 1H), 10.96 (s, 1H), 8.70 (s, 1H), 8.40 (t, 1), 7.52 (d, 1H), 7.42 (d, 1H), 4.42 (d, 2H), 3.35 (t, 2H), 3.26 (t, 2H), 2.28 (quintet, 2H), 2.15 (t, 2H), 1.60 (m, 2H), 0.89 (t, 3H). MS m/e 374 (M–H)$^-$.

Example 52

Preparation of 2u 3-(Benzoylaminomethyl)-5,7,8,9,10,11-hexahydrocyclopent[a]pyrrolo[3,4-c]carbazole-5(6H), 7-dione Prepared from 2p and benzoic acid by a similar procedure to that described for the preparation of 2r. NMR (DMSO-$d_6$) δ 11.94 (s, 1H), 10.95 (s, 1H), 9.18 (t, 1H), 9.82 (s, 1H), 7.95 (d, 1H), 7.50 (m, 6H), 4.67 (d, 2H), 3.27 (t, 2H), 3.19 (t, 2H), 2.30 (quintet, 2H). MS m/e 408 (M–H)$^-$.

Example 53

Preparation of 2v 3-(N-(2-(N-Boc-amino)acetyl)aminomethyl)-5,7,8,9,10,11-hexahydrocyclopent[a]pyrrolo[3,4-c]carbazole-5(6H), 7-dione Prepared from 2p and BOC-glycine by a similar procedure to that described for the preparation of 2r. NMR (DMSO-$d_6$) δ 11.93 (s, 1H), 10.96 (s, 1H), 8.71 (s, 1H), 8.38 (t, 1), 7.54 (d, 1H), 7.46 (d, 1H), 6.96 (br. s, 1H), 4.45 (d, 2H), 3.61 (d, 2H), 3.27 (t, 2H), 3.19 (t, 2H), 2.33 (quintet, 2H), 1.40 (s, 9H). MS m/e 461 (M–H)⁻.

Example 54

Preparation of 2w 3-(N-(4-(N-Boc-amino)butanoyl)aminomethyl)-5,7,8,9,10,11-hexahydrocyclopent[a]pyrrolo[3,4-c]carbazole-5(6H), 7-dione Prepared from 2p and BOC-4-aminobutyric acid by a similar procedure to that described for 2r. NMR (DMSO-$d_6$) δ 11.87 (s, 1H), 10.90 (s, 1H), 8.70 (s, 1H), 8.36 (t, 1), 7.52 (d, 1H), 7.43 (d, 1H), 6.77 (br. s, 1H), 4.41 (d, 2H), 3.24 (t, 2H), 3.17 (t, 2H), 2.93 (q, 2H), 2.29 (quintet, 2H), 2.15 (t, 2H), 1.65 (quintet, 2H), 1.37 (s, 9H). MS m/e 489 (M–H)⁻.

Example 55

Preparation of 2x 3-(N-(2-(Amino)acetyl)aminomethyl)-5,7,8,9,10,11-hexahydrocyclopent[a]pyrrolo[3,4-c]carbazole-5(6H), 7-dione This compound was prepared by treatment of 2v with 2 M HCl in dioxane. NMR (D$_2$O) δ 7.40 (s, 1H), 7.07 (d, 1H), 6.89 (d, 1H), 4.32 (br. s, 2H), 3.90 (br. s, 2H), 3.76 (m, 4H), 1.99 (m, 4H), 1.65 (m, 2H). MS m/e 363 (M+H)⁺.

Example 56

Preparation of 2y 3-(N-(4-(Amino)butanoyl)aminomethyl)-5,7,8,9,10,11-hexahydrocyclopent[a]pyrrolo[3,4-c]carbazole-5(6H), 7-dione This compound was prepared by treatment of 2w with 2 M HCl in dioxane. NMR (D$_2$O) δ 7.36 (s, 1H), 7.03 (d, 1), 6.85 (d, 1H), 4.26 (s, 2H), 3.84 (t, 2H), 3.76 (m, 2H), 3.68 (t, 2H), 3.09 (t, 2H), 2.45 (t, 2H), 2.02 (m, 4H). 2.15 (t, 2H), 1.61 (m, 2H). MS m/e 391 (M+H)⁺.

Example 57

Preparation of 2z 3-(N-(3-(Methoxycarbonyl)propanoyl)aminomethyl)-5,7,8,9,10,11-hexahydrocyclopent[a]pyrrolo[3,4-c]carbazole-5(6H), 7-dione Prepared from 2p and monomethyl succinate by a similar procedure to that described for the preparation of 2r. MS m/e 418 (M–H)⁻.

Example 58

Preparation of 2aa 3-(N-(4-(Methoxycarbonyl)butanoyl)aminomethyl)-5,7,8,9,10,11-hexahydrocyclopent[a]pyrrolo[3,4-c]carbazole-5(6H), 7-dione Prepared from 2p and monomethyl glutarate by a similar procedure to that described for the preparation of 2r. MS m/e 432 (M–H)⁻.

Example 59

Preparation of 2ab 3-(N-(3-(Carboxy)propanoyl)aminomethyl)-5,7,8,9,10,11-hexahydrocyclopent[a]-pyrrolo[3,4-c]carbazole-5(6H), 7-dione Succinic anhydride (3.1 mg, 0.031 mmol) was added to a suspension of 3-(aminomethyl)-5,7,8,9,10,11-hexahydrocyclopent[a]pyrrolo[3,4-c]carbazole-5(6H), 7-dione hydrochloride (9.8 mg, 0.029 mmol) and NMM (9 uL, 0.082 mmol) in DMF (0.2 mL). The solid dissolved within 30 min, and then a new precipitate formed. After 1 h, 1 M HCl was added. The precipitate was collected, rinsed with water, and then dried to afford the product 2ab (11.4 mg, 98% yield) as a yellow solid. MS m/e 404 (M–H)⁻.

Example 60

Preparation of 2ac 3-(N-(4-(Carboxy)butanoyl)aminomethyl)-5,7,8,9,10,11-hexahydrocyclopent[a]-pyrrolo[3,4-c]carbazole-5(6H), 7-dione Prepared from glutaric anhydride by a similar procedure as described for 2ab. MS m/e 418 (M–H)⁻.

Example 61

Preparation of 2ad 3-(N-Boc-aminomethyl)-5,7,8,9,10,11-hexahydrocyclopent[a]pyrrolo[3,4-c]carbazole-5(6H), 7-dione NMM (14 mg, 0.14 mmol) was added to a mixture of 3-(aminomethyl)-5,7,8,9,10,11-hexahydrocyclopent[a]pyrrolo[3,4-c]carbazole-5(6H), 7-dione hydrochloride (2p, 15 mg, 0.045 mmol) and di-t-butyl dicarbonate (18 mg, 0.082 mmol) in DMF (1 mL). After 2 hr, the mixture was filtered, and water (5 mL) was added. The precipitate was collected and rinsed with 3% citric acid, saturated NaHCO$_3$, and water, then dried to afford the product (12 mg, 67% yield) as a golden-brown solid. This solid could be purified by chromatography on silica gel (EtOAc) to give a yellow solid. NMR (CDCl$_3$) δ 8.78 (s, 1H), 8.34 (s, 1H), 7.49 (m, 1H), 7.31 (m, 1H), 5.00 (m, 1H), 4.51 (s, 1H), 3.40 (t, 2H), 3.16 (t, 2H), 2.39 (quintet, 2H), 1.53 (s, 9H). MS m/e 404 (M–H)⁻.

Example 62

Preparation of 2ae

To a suspension of 5a (0.1 g, 0.36 mmol) in methylene chloride (2 mL) at 0° C., was slowly added chlorosulfonic acid (0.05 g, 0.4 mmol). The reaction mixture was stirred at 0° C. for another 30 min, then stirred at room temperature overnight and filtered. The residue was washed successively with methylene chloride and ether. It was then purified by preparative HPLC to generate 0.008 g of 2ae. Compound 2ae is a yellow amorphous solid; R$_t$ 4.89 min (broad); ¹H-NMR (DMSO-$d_6$) δ 12.00 (s, 1H), 11.00 (s, 1H), 9.10 (s, 1H), 7.75 (d, 1H), 7.40 (d, 1H), 3.25 (2 sets of t, 4H), 2.50 (s, 1H), 2.25 (broad m, 2H); MS m/e 355 (M–H).

Example 62a

Preparation of 2af

To a solution of example 5a (26 mg, 0.10 mmol) in DMF (2 ml) was added N-chlorosuccinimide (15 mg, 0.11 mmol). The mixture was stirred at room temperature for 18 h before being added dropwise to a stirred flask of water (10 ml). The resulting precipitate was collected by suction filtration, washed with water (3×5 ml) and dried to constant weight to give 15 mg (52%) of the title compound as an off-white solid. MS: m/e=295/297 (M+H)$^+$.

Example 62b

Preparation of 2ag

A slurry of example 5c (305 mg, 1.06 mmol) in 1,4-dioxane (15 ml) and concentrated hydrochloric acid (15) was heated to reflux for 72 h. The dioxane was removed by rotary evaporation and the product was collected by suction filtration, washed with water to neutrality and air-dried to constant weight to give 315 mg (97%) of the title compound as a tan to light brown solid. MS: m/e=305 (M−H)$^+$.

Example 62c

Preparation of 2ah

To a solution of example 2ag (75 mg, 0.25 mmol) in DMF (5 ml) and ethanol (1 ml) was added a solution of (trimethylsilyl)diazomethane (2M in hexanes, 0.6 ml, 1.2 mmol). After being stirred for 4 h a few drops of glacial acetic acid was added, the solvents were removed in-vacuo, and the residue was slurried in water (5 ml) and freeze-dried to provide 11 mg (91%) of the title compound as a tan or light-brown solid. MS: m/e=319 (M−H)$^+$.

Example 62d

Preparation of 2ai

To a solution of example 2ag (20 mg, 0.065 mmol) in DMF (3 ml) was added 1-hydroxybenzotriazole (HOBt, 13 mg, 0.098) and benzotriazol-1-yloxy-tris(dimethylamino)phosphonium hexafluorophosphate (BOP, 43 mg, 0.098 mmol). The mixture was stirred for 2 h, N,N-dimethyethylenediamine (9 mg, 0.098 mmol) was added and stirring was continued for 1-3 h or until deemed complete by HPLC analysis. The mixture was concentrated to an oily residue, washed thoroughly with ether, dissolved into 0.5N HCl (5 ml), filtered to clarify and freeze-dried to give 25 mg (93%) of the title compound. MS: m/e=377 (M+H)$^+$.

Example 62e

Preparation of 2aj

This compound was prepared according to the procedure described above for example 2ai. From 2ag (20 mg, 0.065 mmol) and 4-(2-aminoethyl)morpholine (13 mg, 0.098 mmol) was obtained 29 mg (97%) of the title compound. MS: m/e=419 (M+H)$^+$.

Example 62f

Preparation of 2ak

This compound was prepared according to the procedure described above for example 2ai except product isolation was achieved by dilution of the reaction mixture with ethyl acetate (15 ml) and washing the resulting precipitate with ethyl acetate (2×5 ml) and ether (5 ml). From example 2ag (20 mg, 0.065 mmol) and morpholine (7 mg, 0.078 mmol) was obtained 4 mg (17%) of the title compound as a tan solid. MS: 376 (M+H)$^+$.

Example 62g

Preparation of 2al

This compound was prepared according to the procedure described above for example 2ai except product isolation was achieved by evaporation of DMF, stirring the residue with methanol (3 ml) and washing the resulting precipitate with 50% methanol/ether (5 ml) and ether (5 ml). From example 2ag (20 mg, 0.065 mmol) and 4-(N-methyl-aminomethyl)pyridine (12 mg, 0.098 mmol) was obtained 18 mg (67%) of the title compound as a light brown solid. MS: 411 (M+H)$^+$.

Example 62h

Preparation of 2am

This compound was prepared according to the procedure described above for example 2ai except product isolation was achieved by evaporation of DMF, stirring the residue with 50% methanol/ether (2 ml) and washing the resulting precipitate with ether (2×3 ml). From example 2ag (20 mg, 0.065 mmol) and N-methylhistamine dihydrochloride (21 mg, 0.104 mmol) was obtained 5 mg (19%) of the title compound as a light brown solid. MS: 414 (M+H)$^+$.

Example 62i

Preparation of 2an

This compound was prepared according to the procedure described above for example 2ai. From example 2ag (20 mg, 0.065 mmol) and 2-(N-methyl-aminomethyl)pyridine (13 mg, 0.104 mmol) was obtained 27 mg (99%) of the title compound as a light brown solid. MS: m/e 411 (M+H)$^+$.

Example 62j

Preparation of 2ao

A mixture of 5-triisopropylsilyloxy-2-(1-hydroxycyclopentyl)indole (0.4 g, 1 mmol) and maleimide (0.15 g, 1.6 mmol) in acetic acid were stirred for 24 hours at room temperature. The mixture was concentrated at reduced pressure. The residue was dissolved in methylene chloride, washed with 10% NaHCO$_3$ solution and dried (MgSO$_4$). The drying agent was removed by filtration and the solvent concentrated to give 0.31 g MS: m/e 451 (M−H)$^+$. The Diels-Alder adduct (1.2 g, 2.6 mmol) in HOAc (60 mL) was added 30% H$_2$O$_2$ (15 mL) followed by heating for 90 minutes at 50° C. The mixture was concentrated then water added and a tan solid collected, 1.07 g; MS: m/e 447 (M−H)$^+$. The above carbazole (0.3 g, 0.66 mmol) and TBAF (1.67 mL of 1 M solution, 1.67 mmol) in CH$_3$CN (40 mL) were stirred for 0.5 hours at room temperature. The solvent was concentrated at reduced pressure and the residue was partitioned between ethyl acetate and water. The ethyl acetate layer was dried (MgSO$_4$) and concentrated to give 0.13 g of 2ao. MS: m/e 291 (M−H)$^-$.

Example 62k

Preparation of 2ap

This compound was prepared by the same general procedure as described for 2ao or 1a starting with 5-methoxy-2-(1-hydroxycyclopentyl)indole to give 2ap. MS m/e=305 (M−H).

Example 62l

Preparation of 2aq

This compound was prepared by the same general procedure as described for 2ao or 1a starting with 5-ethoxyethoxy-2-(1-hydroxycyclopentyl)indole to give 2aq. MS m/e=363 (M−H).

Example 62m

Preparation of 2ar

This compound was prepared by the same general procedure as described for 2ao or 1a starting with 5-diethylaminoethyloxy-2-(1-hydroxycyclopentyl)indole to give the title compound. MS m/e=392 (M−H)$^+$.

Example 62n

Preparation of 2as

This compound was prepared by the same general procedure as described for 2ao or 1a starting with 5-dimethylaminoethyloxy-2-(1-hydroxycyclopentyl)indole to give the title compound. MS m/e=378 (M+H).

Example 62o

Preparation of 2at

This compound was prepared by the same general procedure as described for 2ao or 1a starting with 5-morpholinoethoxy-2-(1-hydroxycyclopentyl)indole to give the title compound. MS m/e=406 (M+H).

Examples 62p-62x

Data for 2au-2bc

TABLE 9

| Example | Compound | Mass Spec (m/e) |
|---------|----------|-----------------|
| 62p | 2au | 333 (M − H)$^-$ |
| 62q | 2av | 303 (M + H)$^+$ |
| 62r | 2aw | 305 (M − H)$^-$ |
| 62s | 2ax | 319 (M − H)$^-$ |
| 62t | 2ay | 279 (M + H)$^+$ |
| 62u | 2az | 303 (M − H)$^-$ |
| 62v | 2ba | 361 (M − H)$^-$ |
| 62w | 2bb | 347 (M − H)$^-$ |
| 62x | 2bc | 314 (M − H)$^-$ |

Example 62y

Preparation of 2bd

The carboxylation procedure of Neubert and Fishel [Org. Synth. Col. Vol. 7, 420-424 (1990)] was followed. Oxalyl chloride (1.0 mL, 1.45 g, 11.4 mmol) was added to a stirred suspension of aluminum chloride (1.50 g, 11.3 mmol) in 1,2-dichloroethane (20 mL) at 20° C. After 1 min, 1a (1.00 g, 3.62 mmol) was added and the mixture was stirred for 40 min, then poured into 20 g of ice and water (gas evolution) and stirred for 10 min. The precipitate was collected by vacuum filtration and rinsed with water, 1M HCl, and water, then dried to give 1.11 g (95% yield) of crude 2bd contaminated with 17% of the dimeric ketone. A pure sample of 2bd was obtained by suspension in dilute aqueous $Na_2CO_3$ and filtration followed by acidification with HCl. After several days, the resulting gel yielded a solid precipitate which was collected and dried. MS m/e 319 (M−H)$^-$; $^1$H NMR (DMSO-d$_6$) δ 2.29 (2H, m), 3.18 (2H, t), 3.26 (2H, t), 7.62 (1H, d), 8.11 (1H, d), 9.48 (1H, s), 11.02 (1H, s), 12.27 (1H, s).

Examples 62z-62ad

Data for 2be-2bi

TABLE 10

| Example | Compound | Mass Spec (m/e) |
|---------|----------|-----------------|
| 62z | 2be | 320 (M + H)$^+$ |
| 62aa | 2bf | 289 (M − H)$^-$ |
| 62ab | 2bg | 392 (M + H)$^+$ |
| 62ac | 2bh | 318 (M − H)$^-$ |
| 62ad | 2bi | 333 (M − H)$^-$ |

Example 62ae

Preparation of 2bj

NaBH$_3$CN (60 mg, 0.95 mmol) was added to a solution of the hydrochloride salt of 2p (300 mg, 0.88 mmol) and aqueous formaldehyde (0.10 mL, 37%, 1.23 mmol) in water (6 mL). After 2.5 h, the solution was basified with saturated Na$_2$CO$_3$. The precipitate was collected, rinsed with water, and dried to afford 2bj (207 mg, 71% yield). MS m/z 334 (M+H)$^+$, 289 (M-Me$_2$N)$^+$; NMR (DMSO-d$_6$) δ 2.30 (2H, m), 3.18 (2H, t), 3.26 (2H, t), 4.08 (2H, br.), 7.58 (2H, Abq), 8.82 (1H, s), 10.95 (1H, s), 12.01 (1H, s).

Examples 62af-62as

General Procedure for Preparation of 2bk-2bx

TABLE 11

| Example | Compound | Mass Spec (m/e) |
|---------|----------|-----------------|
| 62af | 2bk | 334 (M + H)$^+$ |
| 62ag | 2bl | 390 (M + H)$^+$ |
| 62ah | 2bm | 362 (M + H)$^+$ |
| 62ai | 2bn | 418 (M + H)$^+$ |
| 62aj | 2bo | 486 (M + H)$^+$ |
| 62ak | 2bp | 362 (M + H)$^+$ |
| 62al | 2bq | 396 (M + H)$^+$ |
| 62am | 2br | 348 (M + H)$^+$ |
| 62an | 2bs | 418 (M + H)$^+$ |
| 62ao | 2bt | 320 (M + H)$^+$ |
| 62ap | 2bu | 348 (M + H)$^+$ |
| 62aq | 2bv | 376 (M + H)$^+$ |
| 62ar | 2bw | 360 (M + H)$^+$ |
| 62as | 2bx | 374 (M + H)$^+$ |

Examples 62at-62ba

General Procedure for Preparation of 2by-2cf

TABLE 12

| Example | Compound | Mass Spec (m/e) |
|---|---|---|
| 62at | 2by | 416 (M + H)+ |
| 62au | 2bz | 448 (M + H)+ |
| 62av | 2ca | 475 (M − H)− |
| 62aw | 2cb | 377 (M − H)− |
| 62ax | 2cc | 482 (M − H)− |
| 62ay | 2cd | 444 (M − H)− |
| 62az | 2ce | 356 (M + Na) |
| 62ba | 2cf | 336 (M + H) |

Example 62bb

Preparation of 2cg

Oxalyl chloride (0.010 mL, 14.5 mg, 0.114 mmol) was added to crude 2bd (28 mg, 0.0875 mmol) in DMF (0.28 mL) 0° C. After 1 h at 20° C., excess HCl was removed with a nitrogen stream, and 2-(N,N-dimethylamino)ethylamine (24 mg, 0.27 mmol) was added. After 1 h, the precipitate was collected, dried, and suspended in 0.5 mL 0.1 M HCl. The precipitate (consisting of dimeric ketone in the crude starting material) was discarded and the supernatant was lyophilized to give the hydrochloride of 2cg. MS m/z 391 (M+H)+; NMR (DMSO-$d_6$) δ 2.31 (2H, m), 2.88 (6H, d), 3.20 (2H, t), 3.27 (2H, t), 7.62 (1H, d), 8.04 (1H, d), 8.71 (1H, br. S), 9.37 (1H, s), 9.65 (1H, br. s), 11.02 (1H, s), 12.24 (1H, s).

Examples 62bc-62ca

General Procedure for Preparation of 2ch-2df

TABLE 13

| Example | Compound | Mass Spec (m/e) |
|---|---|---|
| 62bc | 2ch | 405 (M + H) |
| 62bd | 2ci | 411 (M + H) |
| 62be | 2cj | 414 (M + H) |
| 62bf | 2ck | 451 (M + H) |
| 62bg | 2cl | 411 (M + H) |
| 62bh | 2cm | 431 (M + H |
| 62bi | 2cn | 433 (M + H |
| 62bj | 2co | 376 (M − H) |
| 62bk | 2cp | 388 (M − H) |
| 62bl | 2cq | 403 (M + H) |
| 62bm | 2cr | 404 (M + H) |
| 62bn | 2cs | 388 (M + H) |
| 62bo | 2ct | 418 (M + H) |
| 62bp | 2cu | 405 (M + H) |
| 62bq | 2cv | 425 (M + H) |
| 62br | 2cw | 439 (M + H) |
| 62bs | 2cx | 425 (M + H) |
| 62bt | 2cy | 431 (M + H) |
| 62bu | 2cz | 392 (M + H) |
| 62bv | 2da | 392 (M + H) |
| 62bw | 2db | 446 (M + H) |
| 62bx | 2dc | 408 (M + H) |
| 62by | 2dd | 400 (M − H) |
| 62bz | 2de | 333 (M − H) |
| 62ca | 2df | 412 (M + H) |

Example 63

Preparation of 3a

A mixture of 2e (0.03 g, 0.08 mmol), thiourea (0.006 g, 0.08 mmol) and ethanol (1 mL) was heated at 70° C. in a sealed tube for 1 h. On cooling, a precipitate appeared that was filtered, washed several times with cold ethanol and ether, respectively and dried under high vacuum to generate 0.025 g of 3a. Compound 3a is characterized as a yellow amorphous solid; $R_t$ 6.68 min; $^1$H-NMR (DMSO-$d_6$) δ 12.00 (s, 1H), 11.00 (s, 1H), 9.00 (s, 1H), 7.75 (d, 1H), 7.50 (d, 1H), 7.00 (s, 1H), 3.50 (broad, 2H), 3.25 (2 sets of t, 4H), 2.25 (broad m, 2H). MS m/e 375 (M+H).

Example 64

Preparation of 3b

A mixture of 2e (0.05 g, 0.13 mmol), thioacetamide (0.01 g, 0.13 mmol) and ethanol (1 mL) was heated at 70° C. in a sealed tube for 1 h. On cooling, a precipitate appeared that was filtered, washed several times with cold ethanol and ether, respectively and dried under high vacuum to generate 0.025 g of 3b. Compound 3b is characterized as a yellow amorphous solid; $R_t$ 10.14 min; $^1$H-NMR (DMSO-$d_6$) δ 12.00 (s, 1H), 11.00 (s, 1H), 9.30 (s, 1H), 8.00 (d, 1H), 7.70 (s, 1H), 7.50 (d, 1H), 3.25 (2 sets of t, 4H), 2.70 (s, 3H), 2.25 (broad m, 2H); MS m/e 374 (M+H).

Example 65

Preparation of 3e

A mixture of 2e (0.03 g, 0.07 mmol), Boc-L-thiocitruline-OtBu (0.01 g, 0.13 mmol) and ethanol (1 mL) was heated at 70° C. in a sealed tube for 1 h. On cooling, a precipitate appeared that was filtered, washed several times with cold ethanol and dried under high vacuum to generate 0.010 g of 3e. Compound 3e is characterized as a yellow amorphous solid; $R_t$ 12.23 min; $^1$H-NMR (DMSO-$d_6$) δ 12.00 (s, 1H), 10.90 (s, 1H), 9.20 (s, 1H), 8.20 (broad, 3H), 8.00 (d, 1H), 7.80 (broad, 1H), 7.50 (d, 1H), 6.80 (s, 1H), 4.00 (m, 1H), 3.50 (broad, 2H), 3.25 (2 sets of t, 4H), 2.25 (broad m, 2H), 1.70 (broad, 4H); MS m/e 646 (M+H).

Example 66

Preparation of 3c

A mixture of 3b (0.051 g, 0.136 mmol), N-bromosuccinamide (0.027 g, 0.152 mmol) and DMF (3 mL) was stirred at room temperature for 72 h, poured into cold MeOH (6 mL) and filtered. The precipitated solid was washed several times with small portions of cold methanol and dried under high vacuum to generate 0.041 g of 3c. Compound 3c is characterized as a yellow amorphous solid; $R_t$ 12.90 min; $^1$H-NMR (DMSO-$d_6$) δ 12.00 (s, 1H), 10.90 (s, 1H), 9.40 (s, 1H), 8.00 (d, 1H), 7.60 (s, 1H), 3.25 (2 sets of t, 4H), 2.70 (s, 3H), 2.25 (broad m, 2H); MS m/e 452 and 454 (M+H for different isotopes of bromine).

Example 67

Preparation of 3d

A mixture of Example 2f (0.1 g, 0.24 mmol), thiourea (0.03 g, 0.4 mmol) and ethanol (3 mL) was heated at 75-80° C. in a sealed tube overnight. On cooling, a precipitate appeared that was filtered, washed several times with cold ethanol and ether and dried under high vacuum to generate 0.075 g of 3d. Compound 3d is characterized as a yellow amorphous solid; $R_t$ 8.07 min; $^1$H-NMR (DMSO-$d_6$) δ 12.20 (s, 1H), 11.00 (s, 1H), 9.00 (s, 1H), 8.80 (b, 2H), 7.70 (dd, 2H), 3.25 (2 sets of t, 4H), 2.40 (s, 3H), 2.25 (broad m, 2H). MS m/e 389 (M+H).

Example 68

Preparation of 3f

A mixture of 3e (0.060 g, 0.093 mmol), trifluoroacetic acid (1 mL) and water (2 drops) was stirred at room temperature for 2 h. Excess reagents were removed and the residue was triturated with ethyl acetate (5 mL) to generate a solid. Filtration and drying under high vacuum generated 0.048 g of 3f. Compound 3f is characterized as a yellow amorphous solid. $R_t$ 6.64 min; $^1$H-NMR (DMSO-$d_6$) δ 12.00 (s, 1H), 10.90 (s, 1H), 9.20 (s, 1H), 7.90 (d, 1H), 7.60 (d, 1H), 6.90 (s, 1H), 3.70 (broad, 1H), 3.60 (broad, 4H), 3.25 (2 sets of t, 4H), 2.25 (broad m, 2H), 1.70 (broad, 4H); MS m/e 490 (M+H).

Example 69

Preparation of 3g

A mixture of 2e (0.053 g, 0.133 mmol), 2-imino-4-thiobiuret (0.017 g, 0.144 mmol) and ethanol (3 mL) was heated at 70° C. in a sealed tube for overnight. On cooling, a precipitate appeared that was filtered, washed several times with cold ethanol and dried under high vacuum to generate 0.055 g of 3g. Compound 3g is characterized as a yellow amorphous solid; $R_t$ 8.25 min; $^1$H-NMR (DMSO-$d_6$) δ 12.00 (s, 1H), 10.90 (s, 1H), 9.30 (s, 1H), 8.20 (broad, 4H), 8.00 (d, 1H), 7.60 (d, 1H), 7.50 (s, 1H), 3.25 (2 sets of t, 4H), 2.25 (broad m, 2H); MS m/e 417 (M+H).

Example 70

Preparation of 3h

A mixture of 2e (0.05 g, 0.126 mmol), methylthiourea (0.016 g, 0.133 mmol) and ethanol (3 mL) was heated at 75-80° C. in a sealed tube for 1 h. On cooling, a precipitate appeared that was filtered, washed several times with cold ethanol and dried under high vacuum to generate 0.03 g of 3h. Compound 3h is characterized as a yellow amorphous solid; $R_t$ 7.92 min; $^1$H-NMR (DMSO-$d_6$) δ 12.00 (s, 1H), 11.00 (s, 1H), 9.10 (s, 1H), 7.80 (d, 1H), 7.50 (d, 1H), 7.00 (s, 1H), 3.75 (broad, 1H), 3.25 (2 sets of t, 4H), 2.40 (s, 3H), 2.25 (broad m, 2H). MS m/e 389 (M+H).

Example 71

Preparation of 3i

A mixture of 2e (0.05 g, 0.126 mmol), acetylthiourea (0.012 g, 0.133 mmol) and ethanol (3 mL) was heated at 75-80° C. in a sealed tube for 1 h. On cooling, a precipitate appeared that was filtered, washed several times with cold ethanol and dried under high vacuum to generate 0.044 g of 3i. Compound 3i is characterized as a yellow amorphous solid; $R_t$ 10.57 min; $^1$H-NMR (DMSO-$d_6$) δ 12.20 (s, 1H), 12.00 (s, 1H), 11.00 (s, 1H), 9.30 (s, 1H), 8.00 (d, 1H), 7.60 (d, 1H), 7.40 (s, 1H), 3.25 (2 sets of t, 4H), 2.25 (broad m, 2H), 2.10 (s, 3H). MS m/e 415 (M–H).

Example 72

Preparation of 3j

A mixture of 2e (0.037 g, 0.093 mmol), N-benzyloxythioglycinamide (0.028 g, 0.125 mmol) and ethanol (3 mL) was heated at 75-80° C. in a sealed tube for 1 h. On cooling, a precipitate appeared that was filtered and washed with ether to give 0.029 g of 3j. Compound 3j is characterized as a brown amorphous solid; $R_t$ 12.81 min; $^1$H-NMR (DMSO-$d_6$) δ 12.00 (s, 1H), 11.00 (s, 1H), 9.30 (s, 1H), 8.30 (t, 1H), 8.00 (d, 1H), 7.80 (s, 1H), 7.60 (d, 1H), 7.30 (m, 5H), 5.00 (s, 2H), 4.50 (broad, 2H), 3.25 (2 sets of t, 4H), 2.25 (broad m, 2H). MS m/e 545 (M+Na), 523 (M+H).

Example 73

Preparation of 3k

A mixture of 3j (0.06 g, 0.115 mmol) and 30% HBr in HOAc (0.8 mL) was stirred at room temperature for 30 min. Excess reagent was removed and the residue was triturated with ether to give 0.052 g of 3k. Compound 3k is characterized as a yellow amorphous solid; $R_t$ 7.36 min; $^1$H-NMR (DMSO-$d_6$) δ 12.00 (s, 1H), 11.00 (s, 1H), 9.30 (s, 1H), 8.60 (broad, 3H), 8.10 (d, 1H), 8.00 (s, 1H), 7.60 (d, 1H), 4.50 (broad, 2H), 3.25 (2 sets of t, 4H), 2.25 (broad m, 2H). MS m/e 389 (M+H).

Example 74

Preparation of 3l

A mixture of 2e (0.2 g, 5.037 mmol), acetylguanidine (0.153 g, 1.51 mmol) and DMF (3 mL) was heated at 60° C. in a sealed tube for 1.5 h, concentrated at high vacuum and triturated with water to give 0.189 g of a crude material. This material was washed with hot ethanol (3×75 mL) and dried under high vacuum to generate 0.039 g of 3l. Compound 3l is characterized as a brown amorphous solid; $R_t$ 7.41 min; $^1$H-NMR (DMSO-$d_6$) δ 11.80 (s, 1H), 11.60 (s, 1H), 11.30 (s, 1H), 10.80 (s, 1H), 9.10 (s, 1H), 7.80 (d, 1H), 7.50 (d, 1H), 7.20 (s, 1H), 3.25 (2 sets of t, 4H), 2.25 (broad m, 2H), 2.10 (s, 3H). MS m/e 400 (M+H).

Example 75

Preparation of 3m

To a mixture of 3k (0.015 g, 0.032 mmol) and triethylamine (0.007 g, 0.07 mmol) in DMF (1 mL) at room temperature was added methanesulfonyl chloride (0.004 g, 0.035 mmol). The mixture was stirred for 30 min, poured over ice-water (1 mL) and filtered. The residue was washed with water and ether and dried to generate 0.005 g of 3m. Compound 3m is characterized as a yellow amorphous solid; $R_t$ 9.95 min; $^1$H-NMR (DMSO-$d_6$) δ 12.00 (s, 1H), 11.00 (s, 1H), 9.30 (s, 1H), 8.10 (m, 2H), 7.80 (s, 1H), 7.60 (d, 1H), 4.50 (s, 2H), 3.25 (2 sets of t, 4H), 2.40 (s, 3H), 2.25 (broad m, 2H). MS m/e 489 (M+Na), 467 (M+H).

Example 76

Preparation of 3n

To a mixture of 3k (0.04 g, 0.085 mmol) and triethylamine (0.019 g, 0.18 mmol) in DMF (1 mL) at room temperature was added acetyl chloride (0.007 g, 0.09 mmol). The mixture was stirred for 30 min, poured over ice-water (1 mL) and filtered. The residue was washed with water and ether and dried to generate 0.01 g of 3n. The compound 3n is characterized as a yellow amorphous solid; $R_t$ 9.31 min; $^1$H-NMR (DMSO-$d_6$) δ 12.00 (s, 1H), 11.00 (s, 1H), 9.30 (s, 1H), 8.70 (t, 1H), 8.00 (d, 1H), 7.80 (s, 1H), 7.60 (d, 1H), 4.60 (s, 2H), 3.25 (2 sets of t, 4H), 2.25 (broad m, 2H), 1.90 (s, 3H). MS m/e 453 (M+Na), 431 (M+H).

Example 77

Preparation of 3o

To a mixture of 3k (0.04 g, 0.085 mmol) and triethylamine (0.01 g, 0.094 mmol) in DMF (1 mL) at room temperature was added ethyl isocyanate (0.0066 g, 0.09 mmol). The mixture was stirred for 30 min, poured over ice-water (1 mL) and filtered. The residue was washed with water and ether and dried to generate 0.008 g of 3o. Compound is characterized as a yellow amorphous solid; $R_t$ 9.38 min; $^1$H-NMR (DMSO-$d_6$) δ 12.00 (s, 1H), 11.00 (s, 1H), 9.30 (s, 1H), 8.00 (d, 1H), 7.80 (s, 1H), 7.60 (d, 1H), 7.40 (broad, 1H), 6.70 (broad, 1H), 4.50 (s, 2H), 3.25 (2 sets of t, 4H), 3.10 (q, 2H), 2.25 (broad m, 2H), 1.00 (t, 3H). MS m/e 482 (M+Na), 460 (M+H), Example 78

Preparation of 3p

A mixture of 2e (0.05 g, 0.126 mmol), 2-(t-butanesulfonyl)thioacetamide (0.026 g, 0.132 mmol) and ethanol (2 mL) was heated at 75-80° C. in a sealed tube overnight. On cooling, a precipitate appeared that was filtered, washed several times with ethyl acetate and ether and dried under high vacuum to generate 0.02 g of 3p. Compound 3p is characterized as a yellow amorphous solid; $R_t$ 11.73 min; $^1$H-NMR (DMSO-$d_6$) δ 12.00 (s, 1H), 11.00 (s, 1H), 9.30 (s, 1H), 8.10 (d, 1H), 8.00 (s, 1H), 7.60 (d, 1H), 5.00 (s, 2H), 3.25 (2 sets of t, 4H), 2.25 (broad m, 2H), 1.30 (s, 9H). MS m/e 516 (M+Na), 494 (M+H).

Example 79

Preparation of 3q

A mixture of 2e (0.05 g, 0.126 mmol), 2-(t-butoxycarbonyl)thioacetamide (0.024 g, 0.137 mmol) and ethanol (2 mL) was heated at 75-80° C. in a sealed tube overnight. On cooling, a precipitate appeared that was filtered, washed several times with ethyl acetate and ether and dried under high vacuum to generate 0.02 g of 3q. Compound 3q yellow amorphous solid; $R_t$ 14.48 min; $^1$H-NMR (DMSO-$d_6$) δ 12.00 (s, 1H), 11.00 (s, 1H), 9.30 (s, 1H), 8.10 (d, 1H), 7.90 (s, 1H), 7.60 (d, 1H), 5.50 (s, 2H), 3.25 (2 sets of t, 4H), 2.25 (broad m, 2H), 1.20 (s, 9H). MS m/e 496 (M+Na), 474 (M+H).

Example 80

Preparation of 3r

To a mixture of 3k (0.04 g, 0.085 mmol) and triethylamine (0.019 g, 0.18 mmol) in DMF (1 mL) at room temperature was added isovaleryl chloride (0.011 g, 0.094 mmol). The mixture was stirred overnight, concentrated at the rotavap, triturated with water (1 mL) and filtered. The residue was washed with water and ether and dried to generate 0.019 g of 3r. Compound 3r is characterized as a yellow amorphous solid; $R_t$ 11.25 min; $^1$H-NMR (DMSO-$d_6$) δ 12.00 (s, 1H), 11.00 (s, 1H), 9.30 (s, 1H), 8.70 (t, 1H), 8.00 (d, 1H), 7.70 (s, 1H), 7.50 (d, 1H), 4.60 (d, 2H), 3.25 (2 sets of t, 4H), 2.20 (m, 3H), 2.00 (broad, 2H), 0.90 (d, 6H). MS m/e 495 (M+Na), 473 (M+H).

Example 81

Preparation of 3s

To a mixture of 3k (0.04 g, 0.085 mmol) and triethylamine (0.019 g, 0.18 mmol) in DMF (1 mL) at room temperature was added propionyl chloride (0.009 g, 0.094 mmol). The mixture was stirred overnight, concentrated at the rotavap, triturated with water (1 mL) and filtered. The residue was washed with water and ether and dried to generate 0.019 g of 3s. Compound 3s is characterized as a yellow amorphous solid; $R_t$ 9.97 min; $^1$H-NMR (DMSO-$d_6$) δ 12.00 (s, 1H), 11.00 (s, 1H), 9.30 (s, 1H), 8.70 (t, 1H), 8.00 (d, 1H), 7.70 (s, 1H), 7.50 (d, 1H), 4.60 (d, 2H), 3.25 (2 sets of t, 4H), 2.25 (broad m, 4H), 1.00 (d, 3H). MS m/e 467 (M+Na), 445 (M+H).

Example 82

Preparation of 3t

To a mixture of 3k (0.04 g, 0.085 mmol) and triethylamine (0.019 g, 0.18 mmol) in DMF (1 mL) at room temperature was added isobutyryl chloride (0.010 g, 0.094 mmol). The mixture was stirred overnight, concentrated at the rotavap, triturated with water (1 mL) and filtered. The residue was washed with water and ether and dried to generate 0.007 g of 3t. Compound 3t is characterized as a yellow amorphous solid; $R_t$ 10.52 min; $^1$H-NMR (DMSO-$d_6$) δ 12.00 (s, 1H), 11.00 (s, 1H), 9.30 (s, 1H), 8.70 (broad t, 1H), 8.00 (d, 1H), 7.70 (s, 1H), 7.50 (d, 1H), 4.60 (d, 2H), 3.25 (2 sets of t, 4H), 3.00 (m, 1H), 2.25 (broad m, 2H), 1.00 (d, 6H). MS m/e 481 (M+Na), 458 (M+H).

Example 83

Preparation of 3u

To a mixture of 3k (0.04 g, 0.085 mmol) and triethylamine (0.019 g, 0.18 mmol) in DMF (1 mL) at room temperature was added butyryl chloride (0.010 g, 0.094 mmol). The mixture was stirred overnight, concentrated at the rotavap, triturated with water (1 mL) and filtered. The residue was washed with water and ether and dried to generate 0.019 g of 3u. Compound 3u is characterized as a yellow amorphous solid; $R_t$ 10.64 min; $^1$H-NMR (DMSO-$d_6$) δ 12.00 (s, 1H), 11.00 (s, 1H), 9.30 (s, 1H), 8.70 (broad t, 1H), 8.00 (d, 1H), 7.70 (s, 1H), 7.50 (d, 1H), 4.60 (d, 2H), 3.25 (2 sets of t, 4H), 2.25 (broad m, 2H), 2.10 (t, 2H), 1.50 (m, 2H), 0.70 (t, 3H). MS m/e 481 (M+Na), 458 (M+H).

Example 84

Preparation of 3v

To a mixture of 3k (0.04 g, 0.085 mmol) and triethylamine (0.019 g, 0.18 mmol) in DMF (1 mL) at room temperature was added valeryl chloride (0.011 g, 0.094 mmol). The mixture was stirred overnight, concentrated at the rotavap, triturated with water (1 mL) and filtered. The residue was washed with water and ether and dried to generate 0.021 g of 3v. Compound 3v is characterized as a yellow amorphous solid; $R_t$ 11.40 min; $^1$H-NMR (DMSO-$d_6$) δ 12.00 (s, 1H), 11.00 (s, 1H), 9.30 (s, 1H), 8.70 (t, 1H), 8.00 (d, 1H), 7.70 (s, 1H), 7.50 (d, 1H), 4.60 (d, 2H), 3.25 (2 sets of t, 4H), 2.25 (broad m, 2H), 2.10 (t, 2H), 1.50 (m, 2H), 1.20 (m, 2H), 0.70 (t, 3H). MS m/e 495 (M+Na), 473 (M+H).

Example 85

Preparation of 3w

To a mixture of 3k (0.04 g, 0.085 mmol) and triethylamine (0.019 g, 0.18 mmol) in DMF (1 mL) at room temperature was added cyclopropanecarbonyl chloride (0.010 g, 0.094 mmol). The mixture was stirred overnight, concentrated at the rotavap, triturated with water (1 mL) and filtered. The residue was washed with water and ether and dried to generate 0.017 g of 3w. Compound 3w is characterized as a yellow amorphous solid; $R_t$ 10.34 min; $^1$H-NMR (DMSO-$d_6$) δ 12.00 (s, 1H), 11.00 (s, 1H), 9.30 (s, 1H), 9.00 (broad t, 1H), 8.00 (d, 1H), 7.75 (s, 1H), 7.60 (d, 1H), 4.60 (d, 2H), 3.25 (m, 4H), 2.25 (broad m, 2H), 1.60 (m, 1H), 0.70 (broad, 4H). MS m/e 479 (M+Na), 457 (M+H).

Example 86

Preparation of 3x

To a mixture of 3k (0.04 g, 0.085 mmol) and triethylamine (0.019 g, 0.18 mmol) in DMF (1 mL) at room temperature was added cyclopentanecarbonyl chloride (0.012 g, 0.094 mmol). The mixture was stirred overnight, concentrated at the rotavap, triturated with water (1 mL) and filtered. The residue was washed with water and ether and dried to generate 0.016 g of 3x. Compound 3x is characterized as a yellow amorphous solid; $R_t$ 11.59 min. $^1$H-NMR (DMSO-$d_6$) δ 12.00 (s, 1H), 11.00 (s, 1H), 9.30 (s, 1H), 8.70 (broad t, 1H), 8.00 (d, 1H), 7.75 (s, 1H), 7.50 (d, 1H), 4.50 (d, 2H), 3.25 (m, 4H), 2.60 (m, 1H), 2.25 (broad m, 2H), 1.80-1.30 (m, 8H). MS m/e 507 (M+Na), 485 (M+H).

Example 87

Preparation of 3y

A mixture of 2e (0.042 g, 0.106 mmol), 2-(t-butylcarbonyloxy)thioacetamide (0.022 g, 0.126 mmol) and ethanol (3 mL) was heated at 75-80° C. in a sealed tube for 2 h. On cooling, a precipitate appeared that was filtered and washed several times with cold ethanol. The combined filtrate and washings were concentrated at high vacuum to generate 0.018 g of 3y. Compound 3y is characterized as a yellow amorphous solid; $R_t$ 15.67 min; $^1$H-NMR (DMSO-$d_6$) δ 12.00 (s, 1H), 11.00 (s, 1H), 9.30 (s, 1H), 8.10 (d, 1H), 7.90 (s, 1H), 7.60 (d, 1H), 5.50 (s, 2H), 3.25 (2 sets of t, 4H), 2.25 (broad m, 2H), 1.20 (s, 9H). MS m/e 472 (M–H).

Example 88

Preparation of 3z

A mixture of 2e (0.04 g, 0.1 mmol), 2-(methylsulfonyl)thioacetamide (0.019 g, 0.12 mmol) and ethanol (3 mL) was heated at 75-80° C. in a sealed tube for 2 h. On cooling, a precipitate appeared that was filtered, washed several times with cold ethanol and dried under high vacuum to generate 0.033 g of 3z. Compound 3z is characterized as a yellow amorphous solid; $R_t$ 11.24 min; $^1$H-NMR (DMSO-$d_6$) δ 12.00 (s, 1H), 11.00 (s, 1H), 9.40 (s, 1H), 8.10 (d, 1H), 8.00 (s, 1H), 7.60 (d, 1H), 5.20 (s, 2H), 3.60 (s, 3H), 3.25 (2 sets of t, 4H), 2.25 (broad m, 2H). MS m/e 450 (M–H).

Example 89

Preparation of 3aa

A mixture of 2e (0.044 g, 0.1108 mmol), isoxazole-5-thiocarboxamide (0.017 g, 0.1328 mmol) and ethanol (3 mL) was heated at 75-80° C. in a sealed tube for 2 h. On cooling, a precipitate appeared that was filtered, washed several times with cold ethanol and dried under high vacuum to generate 0.036 g of 3aa. Compound 3aa is characterized as a yellow amorphous solid; $R_t$ 13.77 min; $^1$H-NMR (DMSO-$d_6$) δ 12.00 (s, 1H), 11.00 (s, 1H), 9.40 (s, 1H), 8.80 (s, 1H), 8.20 (s, 1H), 8.10 (d, 1H), 7.60 (d, 1H), 7.20 (s, 1H), 3.25 (2 sets of broad, 4H), 2.25 (broad m, 2H). MS m/e 425 (M–H).

Example 90

Preparation of 3ab

A mixture of 2e (0.044 g, 0.1108 mmol), N-[3,4,5-trihydroxy-6-(hydroxymethyl)tetrahydro-2H-pyran-2-yl]thiourea (0.032 g, 0.1344 mmol) and ethanol (3 mL) was heated at 75-80° C. in a sealed tube for 2 h. On cooling, a precipitate appeared that was filtered, washed several times with cold ethanol and dried under high vacuum to generate 0.053 g of 3ab. Compound 3ab is characterized as a yellow amorphous solid; $R_t$ 6.88 min; $^1$H-NMR (DMSO-$d_6$) spectrum is a complex one. MS m/e 537 (M+H).

Example 91

Preparation of 4a

A mixture of 2e (0.042 g, 0.106 mmol), L-proline methyl ester hydrochloride (0.028 g, 0.169 mmol) and N-methylmorpholine (0.032 g, 0.32 mmol) in dry DMF (3 mL) was stirred at 60° C. for 4 h, poured into a mixture of ice and water (ca. 20 g) and filtered. The filtrate was then extracted into ethyl acetate-THF (1:1, 2×20 mL). The combined organic layer was dried (MgSO$_4$) and concentrated to give a residue, which on trituration with ethyl acetate (4 mL) generated 0.008 g of 4a. Compound 4a is characterized as a yellow amorphous solid; $R_t$ 8.82 min (broad); $^1$H-NMR (DMSO-$d_6$) δ 12.20 (s, 1H), 11.00 (s, 1H), 9.40 (s, 1H), 8.10 (d, 1H), 7.50 (d, 1H), 4.30 (d, 1H), 4.10 (d, 1H), 3.60 (m, 1H), 3.50 (s, 3H), 3.25 (2 sets of t, 4H), 2.70 (q, 1H), 2.25 (broad m, 2H), 2.10 (m, 1H), 1.70 (m, 4H); MS m/e 446 (M+H).

Example 92

Preparation of 4b

A mixture of 2e (0.1 g, 0.25 mmol), L-Pro-OtBu (0.048 g, 0.28 mmol), triethylamine (0.028 g, 0.28 mmol) in DMF (2 mL) was stirred at room temperature for 1 h, poured over ice-water (4 mL) and filtered. The residue was washed with water and ether, respectively, and dried under high vacuum to generate 0.068 g of 4b. Compound 4b is characterized as a yellow amorphous solid; $R_t$ 9.73 min; $^1$H-NMR (DMSO-$d_6$) δ 12.20 (s, 1H), 11.00 (s, 1H), 9.50 (s, 1H), 8.20 (d, 1H), 7.60 (d, 1H), 4.20 (dd, 2H), 3.50 (m, 1H), 3.30 (m, 1H), 3.25 (2 sets of t, 4H), 3.00 (m, 1H), 2.80 (m, 1H), 2.25 (broad m, 2H), 2.00 (m, 1H), 1.80 (m, 2H), 1.30 (s, 9H). MS m/e 488 (M+H).

Example 93

Preparation of 4c

A mixture of 4b (0.063 g, 0.13 mmol) and TFA (1 mL) was stirred at room temperature overnight. Excess reagent was removed and the residue was triturated with ethyl acetate to generate 0.05 g of 4c. Compound 4c is characterized as a yellow amorphous solid; $R_t$ 6.64 min; $^1$H-NMR (DMSO-$d_6$) δ 12.20 (s, 1H), 11.00 (s, 1H), 9.40 (s, 1H), 8.20 (d, 1H), 7.60 (d, 1H), 4.80 (dd, 2H), 4.20 (broad, 1H), 3.50 (broad, 1H), 3.40-2.80 (m, 6H), 2.25 (broad m, 2H). 2.00 (m, 4H). MS m/e 432 (M+H).

Example 94

Preparation of 4d

A mixture of 2m (0.02 g, 0.053 mmol), NMM (0.011 g, 0.1 mmol), TBTU (0.034 g, 0.1 mmol) in dry DMF (2 mL) was stirred for 5 min. A solution of H$_2$N(CH$_2$)$_2$NHtBoc (0.01 g, 0.054 mmol) in DMF (1 mL) was added to the reaction flask and the mixture was stirred at room temperature overnight. It was then poured into water (5 mL) and filtered. The residue was washed with small volumes of water and ether, respectively, and dried under high vacuum to generate 0.015 g of 4d. Compound 4d is characterized as a yellow amorphous solid; $R_t$ 11.19 min; $^1$H-NMR (DMSO-$d_6$) δ 12.20 (s, 1H), 11.00 (s, 1H), 9.40 (s, 1H), 8.10 (d, 1H), 8.00 (broad, 1H), 7.50 (d, 1H), 6.70 (broad, 1H), 3.40-2.70 (a series of m, 8H), 2.50 (m, 4H), 2.25 (broad m, 2H), 1.20 (s, 9H). MS m/e 517 (M−H).

Example 95

Preparation of 4e

A mixture of 4d (0.012 g, 0.02 mmol) and 4 N HCl in dioxane (3 mL) was stirred at room temperature for 30 min and filtered. The residue was washed with small volumes of dioxane and ether and dried under high vacuum to generate 0.008 g of 4e. Compound 4e is characterized as a yellow amorphous solid; $R_t$ 7.23 min; $^1$H-NMR (DMSO-$d_6$) δ 12.30 (s, 1H), 11.00 (s, 1H), 9.40 (s, 1H), 8.10 (d, 1H), 8.20 (broad t, 1H), 8.00 (broad, 3H), 7.60 (d, 1H), 3.40-2.50 (a series of m, 12H), 2.25 (broad m, 2H). MS m/e 417 (M−H).

Example 96

Preparation of 4f

This compound was prepared in a similar procedure to that described for 4d. Accordingly, the reaction between 2m (0.05 g) and morpholine (0.015 g) in presence of TBTU and NMM in DMF generated 0.012 g of 4f. Compound 4f is characterized as a yellow amorphous solid; $R_t$ 9.84 min; $^1$H-NMR (DMSO-$d_6$) δ 12.20 (s, 1H), 11.00 (s, 1H), 9.50 (s, 1H), 8.10 (d, 1H), 7.60 (d, 1H), 3.70-3.00 (a series of m, 14H), 2.70 (m, 2H), 2.25 (broad m, 2H). MS m/e 444 (M−H).

Example 97

Preparation of 4g

This compound was prepared in the same manner as described for 4d. Accordingly, the reaction between 2m (0.05 g) and ethanolamine (0.011 g) in presence of TBTU and NMM in DMF generated 0.027 g of 4g. Compound 4g is characterized as a yellow amorphous solid; $R_t$ 7.62 min; $^1$H-NMR (DMSO-$d_6$) δ 12.20 (s, 1H), 11.00 (s, 1H), 9.40 (s, 1H), 8.10 (d, 1H), 7.90 (broad, 1H), 7.50 (d, 1H), 4.60 (t, 1H), 3.50-3.00 (a series of m, 10H), 2.50 (t, 2H), 2.25 (broad m, 2H). MS m/e 418 (M−H).

Example 98

Preparation of 4h

This compound was prepared in the same manner as described for 4d. Accordingly, the reaction between 2m (0.05 g) and L-Pro-OtBu (0.030 g) in presence of TBTU and NMM in DMF generated 0.058 g of 4 h. Compound 4h is characterized as a yellow amorphous solid; $R_t$ 11.58 min; $^1$H-NMR (DMSO-$d_6$) δ 12.20 (s, 1H), 11.00 (s, 1H), 9.40 (s, 1H), 8.10 (d, 1H), 7.50 (d, 1H), 4.60 and 4.20 (2 sets of rotameric m, 1H), 3.70-1.70 (a series of m, 16H), 1.50 and 1.30 (2 sets of rotameric s, 9H). MS m/e 528 (M−H).

Example 99

Preparation of 4i

This compound was prepared in the same manner as for 4d. Accordingly, the reaction between 2m (0.05 g) and diethylamine (0.013 g) in presence of TBTU and NMM in DMF generated 0.030 g of 4i. Compound 4i is characterized as a yellow amorphous solid; $R_t$ 9.95 min; $^1$H-NMR (DMSO-$d_6$) δ 12.20 (s, 1H), 11.00 (s, 1H), 9.40 (s, 1H), 8.10 (d, 1H), 7.50 (d, 1H), 3.50-3.00 (a series of m, 10H), 2.70 (m, 2H), 2.20 (m, 2H), 1.20 and 1.00 (2 sets of rotameric t, 6H). MS m/e 430 (M−H).

Example 100

Preparation of 4j

A mixture of 4h (0.05 g, 0.09 mmol), TFA (1 mL) and H$_2$O (2 drops) was stirred at room temperature for 45 min. Excess reagents were removed and the residue was triturated with methanol. Precipitated solid was filtered, washed with ether and dried under high vacuum to generate 0.017 g of 4j. Compound 4j is characterized as a yellow amorphous solid; $R_t$ 7.99 min; $^1$H-NMR (DMSO-$d_6$) δ 12.20 (s, 1H), 11.00 (s, 1H), 9.40 (s, 1H), 8.10 (d, 1H), 7.50 (d, 1H), 4.60 and 4.20 (2 sets of rotameric m, 1H), 3.70-1.70 (a series of m, 16H). MS m/e 472 (M−H).

Example 101

Preparation of 4k

To a suspension of AlCl$_3$ (0.8 g, 0.006 mol) in 1,2-dichloroethane (5 mL) at 0° C. was added 2,3-pyrazinedicarboxylic anhydride (0.49 g, 0.0033 mol) and the mixture was stirred for 5 min. A suspension of 1a (0.3 g, 0.0011 mol) in 1,2-dichloroethane (15 mL) was slowly added to the reaction flask. The cooling bath was removed and the mixture was stirred at room temperature overnight; TLC of the reaction mixture showed unreacted starting materials. The reaction mixture was then heated at 80° C. for 72 h, poured over a mixture of ice (ca. 10 g) and 2 N HCl (10 mL) and filtered. The residue was washed with water and ether, respectively and dried under vacuum to generate 0.372 g of 4k. Compound 4k

Example 102

Preparation of 4l

A mixture of 2m (0.05 g, 0.133 mmol), hydrazine (0.006 g) and ethanol was heated at 80° C. in a sealed-tube overnight, cooled to 0° C. and filtered. The residue was washed with cold ethanol and ether, respectively and dried under high vacuum to generate 0.023 g of 4l. Compound 4l is characterized as a yellow amorphous solid; $R_t$ 8.03 min; $^1$H-NMR (DMSO-$d_6$) δ 12.00 (s, 1H), 10.90 (s, 1H), 10.80 (s, 1H), 9.10 (s, 1H), 8.00 (d, 1H), 7.50 (d, 1H), 3.40-3.25 (3 sets of t, 6H), 2.50 (t, 2H), 2.25 (broad m, 2H). MS m/e 371 (M–H).

Example 103

Preparation of 4m

This compound was prepared following the same procedure as described for 4l. Accordingly, the reaction between 2m (0.05 g) and methyl hydrazine (0.012 g) in ethanol generated 0.017 g of 4m. Compound 4m is characterized as a yellow amorphous solid; $R_t$ 10.21 min; $^1$H-NMR (DMSO-$d_6$) δ 12.10 (s, 1H), 11.00 (s, 1H), 9.20 (s, 1H), 8.00 (d, 1H), 7.50 (d, 1H), 3.40-3.25 (m, 6H), 2.60 (t, 2H), 2.50 (s, 3H), 2.25 (broad m, 2H). MS m/e 385 (M–H).

Example 104

Preparation of 4n

To a suspension of $AlCl_3$ (0.667 g, 0.005 mol) in 1,2-dichloroethane (5 mL) at 0° C. was added glutaric anhydride (0.57 g, 0.005 mol) and the mixture was stirred for 5 min. A suspension of 1a (0.276 g, 0.001 mol) in 1,2-dichloroethane (15 mL) was slowly added to the reaction flask. The cooling bath was removed and the mixture was stirred at room temperature overnight; TLC of the reaction mixture showed unreacted starting materials. The reaction mixture was then heated at 80° C. for 24 h, poured over a mixture of ice (ca. 10 g) and 2 N HCl (10 mL) and filtered. The residue was washed with water and ether, respectively and dried under vacuum to generate 0.243 g of 4n. Compound 4n is characterized as a yellow amorphous solid; $R_t$ 8.84 min; $^1$H-NMR (DMSO-$d_6$) δ 12.30 (s, 1H), 12.00 (s, 1H), 11.00 (s, 1H), 9.40 (s, 1H), 8.10 (d, 1H), 7.50 (d, 1H), 3.50-3.25 (m, 6H), 2.30 (t, 2H), 2.25 (broad m, 2H), 2.00 (m, 2H). MS m/e 389 (M–H).

Example 105

Preparation of 4o

This compound was prepared following the same procedure as for 4d. Accordingly, the reaction between 2m (0.03 g) and L-Pro-$NH_2$ (0.016 g) in the presence of TBTU and NMM in DMF generated 0.007 g of 4o. Compound 4o is characterized as a yellow amorphous solid; $R_t$ 7.61 min; $^1$H-NMR (DMSO-$d_6$) δ 12.20 (s, 1H), 11.00 (s, 1H), 9.40 (s, 1H), 8.10 (d, 1H), 7.50 (d, 1H), 7.20 (d, 1H), 6.80 (s, 1H), 4.40 and 4.20 (2 sets of rotameric m, 1H), 3.70-2.50 (a series of m, 10H), 2.25 (broad m, 2H), 1.80 (m, 4H). MS m/e 471 (M–H).

Example 106

Preparation of 4p

This compound was prepared following the same procedure as for 4d. Accordingly, the reaction between 2m (0.03 g) and piperidine (0.009 g) in the presence of TBTU and NMM in DMF generated 0.011 g of 4p. Compound 4p is characterized as a yellow amorphous solid; $R_t$ 11.61 min; $^1$H-NMR (DMSO-$d_6$) δ 12.20 (s, 1H), 11.00 (s, 1H), 9.40 (s, 1H), 8.10 (d, 1H), 7.50 (d, 1H), 3.50 (m, 2H), 3.30-3.00 (m, 8H), 2.60 (m, 2H), 2.25 (broad m, 2H), 1.60 (broad m, 4H), 1.40 (broad m, 2H). MS m/e 442 (M–H).

Example 107

Preparation of 4q

This compound was prepared following the same procedure as described for 4d. Accordingly, the reaction between 2m (0.1 g) and 4-t-butoxycarbonylpiperizine (0.1 g) in the presence of TBTU and NMM in DMF generated 0.112 g of 4q. Compound 4q is characterized as a yellow amorphous solid; $R_t$ 11.87 min; $^1$H-NMR (DMSO-$d_6$) δ 12.20 (s, 1H), 11.00 (s, 1H), 9.40 (s, 1H), 8.10 (d, 1H), 7.50 (d, 1H), 3.50-2.70 (a series of m, 16H), 2.25 (broad m, 2H), 1.40 (s, 9H). MS m/e 543 (M–H).

Example 108

Preparation of 4r

A mixture of 4q (0.1 g, 0.184 mmol) and 4 N HCl in dioxane (3 mL) was stirred at room temperature for 30 min and filtered. The residue was washed with small volumes of dioxane and ether and dried under high vacuum to generate 0.071 g of 4r. Compound 4r is characterized as a yellow amorphous solid; $R_t$ 6.68 min; $^1$H-NMR (DMSO-$d_6$) δ 12.20 (s, 1H), 11.00 (s, 1H), 9.40 (s, 1H), 9.30 (2 sets of broad, 2H), 8.10 (d, 1H), 7.50 (d, 1H), 3.70-2.80 (a series of m, 16H), 2.25 (broad m, 2H). MS m/e 443 (M–H).

Example 109

Preparation of 4s

This compound was prepared following the same procedure as described for 4d. Accordingly, the reaction between 2m (0.05 g) and heptamethyleneimine (0.02 g) in the presence of TBTU and NMM in DMF generated 0.037 g of 4s. Compound 4s is characterized as a yellow amorphous solid; $R_t$ 12.95 min; $^1$H-NMR (DMSO-$d_6$) δ 12.20 (s, 1H), 11.00 (s, 1H), 9.40 (s, 1H), 8.10 (d, 1H), 7.50 (d, 1H), 3.50 (m, 2H), 3.30-3.00 (m, 8H), 2.60 (m, 2H), 2.25 (broad m, 2H), 1.80 (broad m, 2H), 1.60 (2 sets of m, 8H). MS m/e 470 (M–H).

Example 110

Preparation of 4t

This compound was prepared following the same procedure as described for 4d. Accordingly, the reaction between 2m (0.05 g) and pyrrolidine (0.013 g) in the presence of TBTU and NMM in DMF generated 0.033 g of 4t. Compound 4t is characterized as a yellow amorphous solid; $R_t$ 10.18 min; $^1$H-NMR (DMSO-$d_6$) δ 12.20 (s, 1H), 11.00 (s, 1H), 9.40 (s, 1H), 8.10 (d, 1H), 7.50 (d, 1H), 3.50 (m, 2H), 3.30-3.00 (m, 8H), 2.60 (m, 2H), 2.25 (broad m, 2H), 1.80 (2 sets of m, 4H). MS m/e 428 (M–H).

Example 111

Preparation of Precursors to 5a

Ethyl 5-Cyano-1,2,3,4,5,10-hexahydrocyclopenta[a]carbazole-4-carboxylate and Ethyl 4-Cyano-1,2,3,4,5,10-hexahydrocyclopenta[a]carbazole-5-carboxylate 2-(Cyclopenten-1-yl)indole (13.6 g, 74 mmol), ethyl cis-3-cyanoacrylate (17.8 g, 142 mmol) and BHT (70 mg) were heated to 180° C. under nitrogen for 30 min. The volatiles were removed by kugelrohr distillation at 110° C. and 0.8 mm to afford 19.7 g of an amber-brown tar. Addition of ether (50 mL) afforded a precipitate of a single isomer of white crystalline ethyl 4-cyano-1,2,3,4,5,10-hexahydrocyclopenta[a]carbazole-5-carboxylate (1.89 g, 8.2% yield); mp 192-195° C. NMR (CDCl$_3$) δ 7.91 (s, 1H), 7.46 (d, 1H), 7.34 (d, 1H), 7.12 (m, 2H), 4.31 (d, 1H0, 4.32 (m, 2H), 4.20 (d, 1H), 3.46 (t, 1H), 3.30 (q, 1H), 2.80 (m, 1H), 2.3-1.4 (m, 6H), 1.34 (t, 3H). Anal. Calcd for $C_{19}H_{20}N_2O_2$: C, 74.00; H, 6.54; N, 9.08. Found: C, 73.84; H, 6.53; N, 9.03.

The filtrate was chromatographed on 500 g silica gel (ether-hexanes, 50:50 to 60:40) to afford 6.4 g (28% yield) of diastereomeric ethyl 5-cyano-1,2,3,4,5,10-hexahydrocyclopenta[a]carbazole-4-carboxylate as a yellow glass, a single white crystalline isomer of which (1.07 g, 4.7% yield) could be obtained by precipitation from ether (20 mL); mp 164-167° C. MS m/e 309 (M+H)$^+$. NMR (CDCl$_3$) δ 8.08 (s, 1H), 7.58 (d, 1H), 7.33 (d, 1H), 7.20 (m, 2H), 4.40 (d, 1H0, 4.32 (m, 2H), 3.16 (q, 1H), 3.02 (q, 1H), 2.80 (dd, 1H), 2.1 (m, 3H), 1.9-1.4 (m, 7H), 1.39 (t, 3H). Anal. Calcd for $C_{19}H_{20}N_2O_2$-0.3Et$_2$O: C, 73.39; H, 7.01; N, 8.47. Found: C, 73.43; H, 6.54; N, 8.04.

Further elution (ether-hexanes, 60:40) afforded more than 1.5 g (6.6%) of diastereomeric ethyl 4-cyano-1,2,3,4,5,10-hexahydrocyclopenta[a]carbazole-5-carboxylate. MS m/e 309 (M+H)$^+$.

Example 112

Preparation of Precursor to 5a

Ethyl 5-Cyano-1,2,3,10-tetrahydrocyclopenta[a]carbazole-4-carboxylate

DDQ (1.35 g, 5.95 mmol) was added to solution of 5-cyano-1,2,3,4,5,10-hexahydrocyclopenta[a]carbazole-4-carboxylate (820 mg, 2.66 mmol) in toluene (12 mL). The solution immediately turned dark brown, and was stirred at 60° C. for 3 hr. The mixture was cooled to 20° C. overnight and filtered. The precipitate was rinsed twice with hexanes to give 2.04 g of a light green solid. This was suspended in methanol (8 mL), filtered, and the precipitate rinsed with methanol (3 mL, in portions), and ether to give 603 mg (75% yield) of product as a light green solid, mp 233-234° C. NMR (CDCl$_3$) δ 8.80 (d, 1H), 8.20 (s, 1H), 7.52 (m, 2H), 7.38 (t, 1H), 4.52 (q, 2H), 3.42 (t, 2H), 3.19 (t, 2H), 2.31 (quintet, 2H), 1.51 (t, 3H). Anal. Calcd for $C_{19}H_{16}N_2O_2$-0.2H$_2$O: C, 74.11; H, 5.37; N, 9.10. Found: C, 74.03; H, 5.06; N, 9.04.

Example 113

Preparation of 5a 5,7,8,9,10,11-Hexahydrocyclopent[a]pyrrolo[3,4-c]carbazole-7(6H)-one Ethyl 5-cyano-1,2,3,10-tetrahydrocyclopenta[a]carbazole-4-carboxylate (950 mg) in DMF (60 mL) was hydrogenated at 55 psi over W2 Raney nickel for two weeks. A total of 15 g Raney nickel was added portionwise during hydrogenation until starting material was consumed. The catalyst was removed by filtration and the DMF was evaporated in vacuo. The solid residue was refluxed for 10 min with 30 mL water and cooled. The precipitate was rinsed with 5 mL acetone to give the product (640 mg, 78% yield) as a white solid, mp 326-327° C. NMR (DMSO-d$_6$) δ 11.6 (s, 1H), 7.96 (d, 1H), 7.56 (d, 1H), 7.43 (t, 1H), 7.24 (t, 1H), 4.79 (s, 2H), 3.30 (t, 2H), 3.11 (t, 2H), 2.26 (quintet, 2H). Anal. Calcd for $C_{17}H_{14}N_2O$: C, 77.84; H, 5.38; N, 10.68. Found: C, 77.35; H, 5.36; N, 10.57.

Example 114

Preparation of 5b

3-Bromo-5,7,8,9,10,11-hexahydrocyclopent[a]pyrrolo[3,4-c]carbazole-7(6H)-one

N-Bromosuccinimide (190 mg, 1.07 mmol) was added to 5,7,8,9,10,11-hexahydrocyclopent[a]pyrrolo[3,4-c]carbazole-7(6H)-one (250 mg, 0.954 mmol) dissolved in DMF (7.5 mL). After 24 hr, the solvent was evaporated and the residue refluxed with water (5 mL) for 5 min. After cooling to 20° C., the precipitate was collected, affording the product (328 mg, 100% yield) as a yellow solid, mp ~350° C. (d). MS m/e 341, 343 (M+H)$^+$. NMR (DMSO-d$_6$) δ 11.72 (s, 1H), 8.29 (s, 1H), 8.07 (s, 1H), 7.51 (ABq, 2H), 4.80 (s, 2H), 3.32 (t, 2H), 3.20 (t, 2H), 2.30 (quintet, 2H). Anal. Calcd for $C_{17}H_{13}N_2$OBr-0.75H$_2$O: C, 57.56; H, 4.12; N, 7.90. Found: C, 57.55; H, 3.89; N, 8.08.

Example 115

Preparation of 5c

3-Cyano-5,7,8,9,10,11-hexahydrocyclopent[a]pyrrolo[3,4-c]carbazole-7(6H)-one

Tetrakis(triphenylphosphine)palladium (70 mg, 0.061 mmol) was added under nitrogen to a mixture of 3-bromo-5,7,8,9,10,11-hexahydrocyclopent[a]pyrrolo[3,4-c]carbazole-7(6H)-one (140 mg, 0.42 mmol) and Zn(CN)$_2$, (100 mg, 0.85 mmol) suspended in DMF (2 mL). (See D. M. Tschaen, R. Desmond, A. O. King, M. C. Fortin, B. Pipik, S. King, and T. R. Verhoeven. *Synth. Commun.* 1994, 24, 887). The mixture was heated to 125° C. for 2 hr, cooled to 20° C., then filtered through a mixture of diatomaceous earth and silica gel. The filtrate was diluted with 3 volumes water. The precipitate was collected and triturated twice with ether to give the product (116 mg, 99% yield) as a yellow solid, mp 369-370° C. NMR (DMSO-d$_6$) δ 12.19 (s, 1H), 8.49 (s, 1H), 8.40 (s, 1H), 7.80 (d, 1H), 7.69 (d, 1H), 4.85 (s, 2H), 3.30 (t, 2H), 3.12 (t, 2H), 2.26 (quintet, 2H). MS m/e 288 (M+H)$^+$.

Example 116

Preparation of 5d 3-(Aminomethyl)-5,7,8,9,10,11-hexahydrocyclopent[a]pyrrolo[3,4-c]carbazole-7(6H)-one 3-Cyano-5,7,8,9,10,11-hexahydrocyclopent[a]pyrrolo[3,4-c]carbazole-7(6H)-one (95 mg, 0.33 mmol) dissolved in DMF (3 mL) was hydrogenated at 55 psi over freshly prepared (R. Mozingo, *Org. Synth. Col.* 1955, 3, 181-183) W-2 Raney nickel (310 mg) for 20 hr. The catalyst was removed and the solvent evaporated to afford a residue which was suspended in water to give crude product (58 mg, 60% yield). NMR (DMSO-$d_6$) δ 11.59 (s, 1H), 8.29 (s, 1H), 7.96 (s, 1H), 7.53 (ABq, 2H), 4.75 (s, 2H), 4.00 (s, 2H), 3.35 (t, 2H), 3.18 (t, 2H), 2.25 (quintet, 2H). MS m/e 275 (M+H–NH$_3$)$^+$, 292 (M+H)$^+$. A portion of the crude product (12 mg) was stirred with 0.1 M HCl (120 mL) and the filtrate was lyophilized to give the hydrochloride salt (9 mg).

Example 117

Preparation of 5e

3-Methyl-5,7,8,9,10,11-hexahydrocyclopent[a]pyrrolo[3,4-c]carbazole-7(6H)-one

Tetrakis(triphenylphosphine)palladium (14 mg, 0.012 mmol) was added under nitrogen to a mixture of 3-bromo-5,7,8,9,10,11-hexahydrocyclopent[a]pyrrolo[3,4-c]carbazole-7(6H)-one (59 mg, 0.17 mmol) and tetramethyltin (38 mg, 0.20 mmol) in DMF (2 mL). The mixture was heated to 140° C. for 4 hr, cooled to 20° C., then filtered through a mixture of diatomaceous earth and silica gel. The solvent was evaporated from the filtrate, and the product, a yellow solid, was isolated by chromatography (EtOAc-EtOH, 75:25). MS m/e 277 (M+H)$^+$.

Example 118

Preparation of 5f

3-[(Bis(t-butoxycarbonyl)-L-lysyl)aminomethyl]-5,7,8,9,10,11-hexahydrocyclo-pent[a]pyrrolo[3,4-c]carbazole-7(6H)-one Di(BOC)-L-lysine dicyclohexylamine salt (70 mg, 0.133 mmol), HOBT hydrate (15 mg, 0.098 mmol), and BOP reagent (60 mg, 0.136 mmol) were added to 3-(aminomethyl)-5,7,8,9,10,11-hexahydrocyclopent[a]pyrrolo[3,4-c]carbazole-7(6H)-one (25 mg, 0.0859 mmol) dissolved in DMF (0.6 mL). After 5 hr, water (2.5 mL) was added. The precipitate was suspended in ethyl acetate (10 mL) and the resulting filtrate was rinsed with 1 M HCl, water, and saturated Na$_2$CO$_3$, then saturated NaCl. Evaporation of the solvent followed by chromatography (EtOAc-EtOH 100:0 to 95:5) gave the product as a light yellow solid (12 mg, 22% yield). MS m/e 620 (M+H)$^+$.

Example 119

Preparation of 5g 3-(L-Lysylaminomethyl)-5,7,8,9,10,11-hexahydrocyclopent[a]pyrrolo[3,4-c]-carbazole-7(6H)-one, dihydrochloride The BOC groups of 5f were hydrolyzed with 2 M HCl in dioxane to afford the product as a beige solid (94% yield). NMR (DMSO-$d_6$) δ 11.67 (s, 1H), 9.70 (t, 1H), 8.45 (br. s, 3H), 8.37 (s, 1H), 8.05 (br. s, 3H), 7.87 (s, 1H), 7.52 (d, 1H), 7.47 (d, 1H), 4.75 (s, 2H), 4.00 (d, 2H), 3.86 (m, 1H), 3.32 (t, 2H), 3.12 (t, 2H), 2.79 (m, 2H), 2.25 (quintet, 2H), 1.85 (m, 2H), 1.78 (m, 2H), 1.45 (m, 2H). MS m/e 420 (M+H)$^+$.

Example 120

Preparation of 6a 5,6,7,10-Tetrahydropyrrolo[3,4-c]carbazole-7(6H)-one

Prepared from 2-vinylindole (U. Pindur and M. Eitel, *Helv. Chim. Acta*, 1988, 71, 1060; M. Eitel and U. Pindur, *Synthesis* 1989, 364-367) by a procedure similar to that reported for synthesis of 1a. NMR (DMSO-$d_6$) δ 12.10 (br. s, 1H), 11.15 (br. s, 1H), 8.83 (d, 1H), 7.94 (m, 2H), 7.60 (m, 2H), 7.32 (t, 1H). MS m/e 237 (M+H)$^+$.

Example 121

Preparation of 6b 8,9-Dimethyl-5,7-dihydropyrrolo[3,4-c]carbazole-5(6H),7(10H)-dione 2-(But-2-en-2-yl)indole (87 mg, 0.51 mmol, prepared according to M. Eitel, and U. Pindur, *Synthesis*, 1989, 364-367) was mixed with maleimide (97 mg, 1.0 mmol), and heated to 190-200° C. in a sealed tube for 0.5 hr. The mixture was cooled to rt and the resulting solid was washed with hot water (10×5 ml) to give the Diels-Alder adduct (91 mg, 68%, MS m/e 267 (M–H)$^-$). The adduct was dried in vacuo for 3 hrs and added to the solution of DDQ (2.5 eq) in 5 ml of toluene. The dark brown solution was stirred at 40° C. for 7 hrs and 20° C. overnight, then evaporated to dryness. The residue was dissolved in EtOAc and washed with saturated NaHCO$_3$ (5×5 ml), H$_2$O, saturated NaCl, and dried over MgSO$_4$. The crude product was triturated with EtOAc to afford 17 mg (28%) of the product as a yellow solid. $^1$H NMR (DMSO-$d_6$) δ 11.72 (s, 1H), 10.98 (s, 1H), 8.76 (d, 1H), 7.54 (d, 1H), 7.48 (t, 1H), 7.23 (t, 1H), 2.69 (s, 3H), 2.53 (s, 3H). MS m/e 263 (M–H)$^-$.

Example 122

Preparation of 6e

This compound was prepared according to the same procedure for 1k using, instead, 2a as starting material. Compound 6e is characterized as a yellow amorphous solid; R$_t$ 6.77 min; $^1$H-NMR (DMSO-$d_6$) δ 12.60 (s, 1H), 8.80 (s, 1H), 8.60 (broad, 3H), 8.00 (broad, 3H), 7.70 (d, 1H), 7.60 (d, 1H), 5.00 (broad, 1H), 3.25 (m, 4H), 2.70 (broad, 2H), 2.25 (m, 2H), 2.00-1.70 (a series of m, 6H). MS m/e 483 and 485 (M+2H for bromine isotopes).

Example 123

Preparation of 6f

This compound was prepared according to the same procedure as for 1k using, instead, 2b as starting material. Compound 6f is characterized as a yellow amorphous solid; $R_t$ 7.13 min; $^1$H-NMR (DMSO-$d_6$) δ 12.60 (s, 1H), 8.80 (s, 1H), 8.60 (broad, 3H), 8.00 (broad, 3H), 7.70 (dd, 2H), 5.00 (broad, 1H), 3.25 (m, 4H), 2.70 (broad, 2H), 2.25 (m, 2H), 2.00 (2 sets of broad, 2H), 1.50 (broad m, 4H). MS m/e 439 and 441 (M+2H, for chlorine isotopes).

Example 124

Preparation of 6g

This compound was prepared according to the same procedure as for 1k using, instead, 2c as starting material. Compound 6g is characterized as a yellow amorphous solid; $R_t$ 6.72 min; $^1$H-NMR (DMSO-$d_6$) δ 12.50 (s, 1H), 8.60 (broad, 3H), 8.50 (d, 1H), 8.00 (broad, 3H), 7.70 (m, 1H), 7.50 (t, 1H), 5.00 (broad, 1H), 3.25 (m, 4H), 2.70 (broad, 2H), 2.25 (m, 2H), 2.00 (2 sets of broad, 2H), 1.50 (broad m, 4H). MS m/e 423 (M+2H).

Example 125

Preparation of 6h

6-Formyl-5,7,8,9,10,11-hexahydrocyclopent[a]pyrrolo[3,4-c]carbazole-7(6H)-one

POCl$_3$ (65.8 mg, 0.43 mmol) and DMF (200 uL, 2.59 mmol) were stirred for 30 min and added to 5,7,8,9,10,11-hexahydrocyclopent[a]pyrrolo[3,4-c]carbazole-7(6H)-one (39 mg, 0.15 mmol) suspended in DMF (200 uL). After stirring 1 hr at 20° C. and 1 hr at 60° C., 4 mL water was added. The precipitate (36 mg) was collected and refluxed with acetone (40 mL). Evaporation of the filtrate gave the product (18 mg, 42% yield) as a yellow-brown solid, mp>300° C. MS m/e 289 (M−H)$^-$. NMR (DMSO-$d_6$) δ 11.6 (br. s, 1H), 9.22 (s, 1H), 8.02 (d, 1H), 7.56 (d, 1H), 7.43 (t, 1H), 7.24 (t, 1H), 5.20 (s, 2H).

Example 126

Preparation of 6i

3-Bromo-11-L-lysyl-5,7,8,9,10,11-hexahydrocyclopent[a]pyrrolo[3,4-c]carbazole-7(6H)-one dihydrochloride The bis(t-butoxycarbonyl)-lysyl derivative was prepared from 5b as described for 1k, and purified by chromatography (CH$_2$Cl$_2$-EtOAc 75:25) to give an orange-yellow glass. The BOC groups were hydrolyzed by treatment with 2M HCl in dioxane for 2.5 hr to afford the product as a tan solid. $R_t$ 8.43 min. MS m/e 469 and 471 (M+H)$^+$, 341 and 343 (M+H-Lysyl)$^+$.

Example 127

Preparation of 6j

3-Cyano-11-L-lysyl-5,7,8,9,10,11-hexahydrocyclopent[a]pyrrolo[3,4-c]carbazole-7(6H)-one dihydrochloride The bis(t-butoxycarbonyl)-lysyl derivative was prepared from 5c as described for 1k. The BOC groups were hydrolyzed by treatment with 2M HCl in dioxane for 2.5 hr to afford the product. $R_t$ 7.40 min. MS m/e 416 (M+H)$^+$, 310 (M+H-Lysyl)$^+$.

Example 127a-127f

Data for 6k-6p

TABLE 14

| Example | Compound | Mass Spec (m/e) |
|---|---|---|
| 127a | 6k | 325 (M − H, +Na) |
| 127b | 6l | 275 (M − CH$_2$OH) |
| 127c | 6m | 334 (M + H$^+$) |
| 127d | 6n | 290 (M − H)$^-$ |
| 127e | 6o | 321 (M − H) |
| 127f | 6p | 364 (M + H)$^+$ |

Example 128

Preparation of Precursor to 8b 2-(Cyclopenten-1-yl)pyrrole and 3-(Cyclopenten-1-yl)pyrrole A modification of a previously reported procedure (M. Tashiro, Y. Yiru, and O. Tsuge, *Heterocycles*, 1974, 2, 575-584) was utilized. Pyrrole (20 g, 300 mmol) and the 1-(cyclopenten-1-yl)pyrrolidine (20 g, 150 mmol, freshly prepared from cyclopentanone and pyrrolidine as described (M. E. Kuehne, *J. Amer. Chem. Soc.* 1989, 81, 5400-5404) were heated to 145° C. for 5 h. The volatile components were distilled off at 40-45° C. and 12 mm Hg, then the product was kugelrohr distilled at 100-140° C. and 1 mm Hg to afford 12.9 g (65%) of a 2:1 mixture of the 2- and 3-isomers. Analytical samples were obtained by chromatography (hexanes-ether, 90:10 to 85:15).

2-(Cyclopenten-1-yl)pyrrole: White solid (darkens in air), mp 68-71° C. NMR (CDCl$_3$) δ 8.24 (br. s, 1H), 6.74 (s, 1H), 6.21 (s, 1H), 6.17 (s, 1H), 5.73 (s, 1H), 2.64 (t, 2H), 2.51 (t, 2H), 1.99 (quintet, 2H). Anal. Calcd for C$_9$H$_{11}$N-0.2H$_2$O: C, 79.02; H, 8.40; N, 10.24. Found: C, 79.00; H, 8.12; N, 10.09.

3-(Cyclopenten-1-yl)pyrrole: Light yellow oil (darkens rapidly in air). NMR (CDCl$_3$) δ 8.10 (br. s, 1H), 6.74 (s, 2H), 6.37 (s, 1H), 5.82 (s, 1H), 2.58 (t, 2H), 2.45 (t, 2H), 1.99 (quintet, 2H).

Example 129

Preparation of Precursors to 8b 2-(Cyclopenten-1-yl)-1-(triisopropylsilyl)pyrrole and 3-(Cyclopenten-1-yl)-1-(triisopropylsilyl)pyrrole Sodium hydride (7.0 g, 60% in mineral oil, 176 mmol) was rinsed with hexane and suspended in ether (150 mL) and cooled to 0° C. Triisopropylsilyl chloride (23.3 g, 121 mmol), a 2:1 mixture of 2-(cyclopenten-1-yl)pyrrole and 3-(cyclopenten-1-yl)pyrrole (3.0 g, 22.5 mmol) and DMF (2 mL) were added. The mixture was stirred beneath a reflux condenser. After hydrogen evolution subsided, the reaction was stirred at 20° C. for 1 hr. The mixture was poured into ice-water, rinsed with water and saturated NaCl, dried, and concentrated to afford the triisopropylsilyl derivatives (35.0 g, 104% crude yield). 2-Isomer: NMR (CDCl$_3$) δ 6.83 (s, 1H), 6.26 (s, 1H), 6.19 (s, 1H), 5.70 (s, 1H), 2.66 (t, 2H), 2.48 (t, 2H), 1.94 (quintet, 2H), 1.53 (m, 3H), 1.11 (d, 18H). 3-Isomer NMR as reported in A. P. Kozikowski and X.-M. Cheng *J. Org. Chem.* 1984, 49, 3239-3240.

Example 130

Preparation of Precursor to 8b

Dimethyl 1-(triisopropylsilyl)-1,6,7,8-tetrahydrocyclopent[g]indole-4,5-dicarboxylate.

A 2:1 mixture of 2-(cyclopenten-1-yl)-1-(triisopropylsilyl)pyrrole and 3-(cyclopenten-1-yl)-1-(triisopropylsilyl)pyrrole (6.2 g, 21.4 mmol) and dimethyl acetylenedicarboxylate (6.2 g, 43.7 mmol) were heated to 110° C. for 22 h. More dimethyl acetylenedicarboxylate (6.2 g, 43.7 mmol) was added and heating was continued for 6 more h. The resulting orange-brown oil was dissolved in ether (25 mL) then treated with hexanes (50 mL). The same process was repeated 3 more times on the precipitate. The combined ether-hexane soluble fractions were evaporated in vacuo, then heated in vacuo to remove excess dimethyl acetylenedicarboxylate. The residue (3.3 g) was chromatographed (hexanes-ether 75:25) to give 490 mg (5.3% yield) product as a light orange oil. The same product was obtained in 10% yield from pure 2-(cyclopenten-1-yl)-1-(triisopropylsilyl)pyrrole. NMR (CDCl$_3$) δ 7.44 (d, 1H), 7.05 (d, 1H), 3.97 (s, 3H), 3.92 (s, 3H), 3.20 (t, 2H), 3.11 (t, 3H), 2.09 (quintet, 2H), 1.70 (septet, 3H), 1.14 (d, 18H). MS m/e 430 (M+H)$^+$. Anal. Calcd for C$_{24}$H$_{35}$NO$_4$Si·0.5H$_2$O: C, 65.71; H, 8.27; N, 3.19. Found: C, 65.51; H, 8.14; N, 2.83.

Example 131

Preparation of Precursor to 8b

Diethyl 1-(triisopropylsilyl)-1,6,7,8-tetrahydrocyclopent[g]indole-4,5-dicarboxylate A 2:1 mixture of 2-(cyclopenten-1-yl)-1-(triisopropylsilyl)pyrrole and 3-(cyclopenten-1-yl)-1-(triisopropylsilyl)pyrrole (1.16 g, 4.01 mmol) and diethyl fumarate (0.75 g, 4.36 mmol) were heated under nitrogen to 150° C. for 64 h, affording the crude Diels-Alder adduct as an amber oil. The pure Diels-Alder adduct could be isolated by chromatography on silica gel (hexanes-ether 90:10). NMR (CDCl$_3$) δ 6.68 (d, 1H), 6.16 (d, 1H), 4.20 (m, 4H), 3.95 (d, 1H), 2.91 (t, 2H), 2.49 (m, 1H), 2.09 (m, 1H), 1.73 (m, 2H), 1.48 (septet, 3H), 1.30 (2t, 6H), 1.27 (d, 9H), 1.07 (d, 9H). MS m/e 462 (M+H)$^+$. DDQ (2.2 g, 9.7 mmol) was added in three portions to a benzene solution (16 mL) of the crude Diels-Alder adduct at 50° C. until no starting material remained (TLC and NMR). After 8 h, the mixture was filtered through Celite®. The precipitate was rinsed with benzene, and the filtrate was evaporated to give 1.52 g of a black solid. This was chromatographed on silica gel (hexanes-ether 15:85 to 20:80) to give the product (380 mg, 21% yield, 35% yield from 2-isomer) as a colorless oil. NMR (CDCl$_3$) δ 7.42 (d, 1H), 7.05 (d, 1H), 4.40 (2q, 4H), 3.20 (t, 2H), 3.12 (t, 2H), 2.17 (quintet, 2H), 1.67 (septet, 3H), 1.39 (t, 3H), 1.36 (t, 3H), 1.20 (d, 18H). MS m/e 458 (M+H)$^+$.

Example 132

Preparation of Precursor to 8b 1,6,7,8-Tetrahydrocyclopent[g]indole-4,5-dicarboxylate A mixture of diethyl 1-(triisopropylsilyl)-1,6,7,8-tetrahydrocyclopent[g]indole-4,5-dicarboxylate (400 mg, 0.875 mmol) and 10 M NaOH (0.4 mL) in ethanol (5 mL) was refluxed under nitrogen for 3 h. The solvent was evaporated and the brown residue dissolved in water and extracted three times with ether. The aqueous layer was acidified with HCl and extracted 3 times with EtOAc, and the combined organic extract was dried over MgSO$_4$ to give the crude product (205 mg, 96%) as a brown solid, mp 311-312° C. NMR (DMSO-d$_6$) δ 12.55 (br. s, 2H), 11.37 (s, 1H), 7.43 (d, 1H), 6.70 (d, 1H), 3.08 (t, 2H), 3.02 (t, 2H), 2.14 (quintet, 2H). Anal. Calcd for C$_{13}$H$_{11}$NO$_4$: C, 63.67; H, 4.52; N, 5.71. Found: C, 63.15; H, 4.46; N, 5.39. Hydrolysis of the dimethyl ester with NaOH in refluxing methanol for 3 days afforded the same product.

Example 133

Preparation of Precursor to 8b 1,6,7,8-Tetrahydrocyclopent[g]indole-4,5-dicarboxylic anhydride A suspension of the diacid (184 mg) in acetic anhydride (3 mL) was heated to 73° C. for 1 h, then cooled to 0° C. The precipitate was collected and washed with 2 mL ether to give the product as a yellow solid (112 mg, 66%), mp 320° C. (sublimes). NMR (CD$_3$COCD$_3$) δ 7.80 (d, 1H), 6.94 (d, 1H), 3.30 (t, 2H), 3.24 (t, 2H), 2.38 (quintet, 2H).

Example 134

Preparation of Precursor to 8b

Diethyl 1-(triisopropylsilyl)-1,6,7,8-tetrahydrocyclopent[g]indole-4,5-dicarboxylate A 2:1 mixture of 2-(cyclopenten-1-yl)-1-(triisopropylsilyl)pyrrole and 3-(cyclopenten-1-yl)-1-(triisopropylsilyl)pyrrole (1.16 g, 4.01 mmol) and diethyl fumarate (0.75 g, 4.36 mmol) was heated under nitrogen to 150° C. for 64 h, affording the crude Diels-Alder adduct as an amber oil. The pure Diels-Alder adduct could be isolated by chromatography on silica gel (hexanes-ether 90:10). NMR (CDCl$_3$) δ 6.68 (d, 1H), 6.16 (d, 1H), 4.20 (m, 4H), 3.95 (d, 1H), 2.91 (t, 2H), 2.49 (m, 1H), 2.09 (m, 1H), 1.73 (m, 2H), 1.48 (septet, 3H), 1.30 (2t, 6H), 1.27 (d, 9H), 1.07 (d, 9H). MS m/e 462 (M+H)$^+$. DDQ (2.2 g, 9.7 mmol) was added in three portions to a benzene solution (16 mL) of the crude Diels-Alder adduct at 50° C. until no starting material remained (TLC and NMR). After 8 h, the mixture was filtered through Celite®. The precipitate was rinsed with benzene, and the filtrate was evaporated to give 1.52 g of a black solid. This was chromatographed on silica gel (hexanes-ether 15:85 to 20:80) to give the product (380 mg, 21% yield, 35% yield from 2-isomer) as a colorless oil. NMR (CDCl$_3$) δ 7.42 (d, 1H), 7.05 (d, 1H), 4.40 (2q, 4H), 3.20 (t, 2H), 3.12 (t, 2H), 2.17 (quintet, 2H), 1.67 (septet, 3H), 1.39 (t, 3H), 1.36 (t, 3H), 1.20 (d, 18H). MS m/e 458 (M+H)$^+$.

Example 135

Preparation of Precursor to 8b 1,6,7,8-Tetrahydrocyclopent[g]indole-4,5-dicarboxylate A mixture of diethyl 1-(triisopropylsilyl)-1,6,7,8-tetrahydrocyclopent[g]indole-4,5-dicarboxylate (400 mg, 0.875 mmol) and 10 M NaOH (0.4 mL) in ethanol (5 mL) was refluxed under nitrogen for 3 h. The solvent was evaporated and the brown residue dissolved in water and extracted three times with ether. The aqueous layer was acidified with HCl and extracted 3 times with EtOAc, and the combined organic extract was dried over MgSO$_4$ to give the crude product (205 mg, 96%) as a brown solid, mp 311-312° C. NMR (DMSO-d$_6$) δ 12.55 (br. s, 2H), 11.37 (s, 1H), 7.43 (d, 1H), 6.70 (d, 1H), 3.08 (t, 2H), 3.02 (t, 2H), 2.14 (quintet, 2H). Anal. Calcd for C$_{13}$H$_{11}$NO$_4$: C, 63.67; H, 4.52; N, 5.71. Found: C, 63.15; H, 4.46; N, 5.39. Hydrolysis of the dimethyl ester with NaOH in refluxing methanol for 3 days afforded the same product.

Example 136

Preparation of 8b 1,6,7,8-Tetrahydrocyclopent[g]indole-4,5-dicarboxylate imide

A mixture of hexamethyldisilazane (1.38 mL, 1.06 g, 6.56 mmol) and methanol (0.135 mL, 107 mg, 3.33 mmol) was added to 1,6,7,8-tetrahydrocyclopent[g]indole-4,5-dicarboxylic anhydride dissolved in DMF (3 mL). The mixture was heated to 73° C. for 4 h, then cooled. The solvent was evaporated and the residue was stirred with dilute HCl. The precipitate was collected and washed with EtOAC to give the product (132 mg, 88% yield) as a yellow solid, mp>350° C. NMR (DMSO-d$_6$) δ 11.81 (br. s, 1H), 10.71 (br. s, 1H), 7.67 (d, 1H), 6.75 (d, 1H), 3.18 (t, 2H), 3.10 (t, 2H), 2.22 (quintet, 2H). MS m/e 225 (M–H)$^-$. Anal. Calcd for C$_{13}$H$_{10}$N$_2$O$_2$·0.2H$_2$O: C, 67.94; H, 4.46; N, 12.19. Found: C, 67.81; H, 4.50; N, 12.04.

Example 137

Preparation of 8c

3-Bromo-1,6,7,8-tetrahydrocyclopent[g]indole-4,5-dicarboxylate imide

Pyridinium bromide perbromide (60 mg, 0.187 mmol) was added to a suspension of 1,6,7,8-tetrahydrocyclopent[g]indole-4,5-dicarboxylate imide (40 mg, 0.177 mmol) in DMF (0.9 mL). Water (3.5 mL) was added after 50 min. The precipitate was collected, rinsed with water, and dried to give the product (54 mg, 100% yield) as a yellow solid, mp>350° C. NMR (DMSO-d$_6$) δ 12.18 (br. s, 1H), 10.71 (br. s, 1H), 7.83 (d, 1H), 3.18 (t, 2H), 3.10 (t, 2H), 2.22 (quintet, 2H). MS m/e 303 and 305 (M–H)$^-$. Anal. Calcd. for C$_{13}$H$_9$N$_2$O$_2$Br: C, 51.17; H, 2.97; N, 9.18; Br, 26.19. Found: C, 50.91; H, 3.19; N, 8.99; Br, 26.40.

Example 138

Preparation of 8d

3-Cyano-1,6,7,8-tetrahydrocyclopent[g]indole-4,5-dicarboxylate imide

A mixture of 3-bromo-1,6,7,8-tetrahydrocyclopent[g]indole-4,5-dicarboxylate imide (36 mg) and CuCN (31 mg) in DMF (0.4 mL) was heated to 155° C. for 4 hr, cooled to 20° C. The grey precipitate containing product and copper salts was chromatographed on silica gel (2×0.5 cm) with DMF. The evaporated eluent was boiled with water for 5 min, and the golden precipitate was collected. Yield 8 mg, 27%.

mp>350° C. H$^1$ NMR (DMSO-d$_6$) δ 12.86 (br s, 1H), 10.94 (s, 1H), 8.55 (s, 1H), 3.17 (m, 4H), 2.24 (quintet, 2H). MS m/e 250 (M–H)$^-$. Additional product eluted with DMSO. Anal. Calcd. for C$_{14}$H$_9$N$_3$O$_2$·1.2H$_2$O: C, 61.63; H, 4.21; N, 15.40. Found: C, 61.33; H, 3.60; N, 14.93.

Example 139

Preparation of 8e 1,6,7,8-Tetrahydrocyclopent[g]indole-4,5-dicarboxylate hydrazide Dimethyl 1-(triisopropylsilyl)-1,6,7,8-tetrahydrocyclopent[g]indole-4,5-dicarboxylate (34 mg, 0.079 mmol) and hydrazine hydrate (83 mg, 1.23 mmol) were refluxed in ethanol (0.6 mL) for 24 h. After evaporation of solvent, the residue was suspended in EtOAc rinsed with water, 1 M HCl, and saturated NaCl, then dried. The solvent was evaporated and the residue was suspended in chloroform, affording a precipitate of the product (2 mg, 10% yield), mp>250° C. NMR (acetone-d$_6$) δ 7.56 (d, 1H), 7.50 (d, 1H), 3.60 (t, 2H), 3.19 (t, 3H), 2.86 (br s. 2H), 2.23 (quintet, 2H). MS m/e 242 (M+H)$^+$.

Example 139a-139b

Data for 8f-8g

TABLE 15

| Example | Compound | Mass Spec (m/e) |
| --- | --- | --- |
| 139a | 8f | 383, 385, 387 (M – H)$^-$ |
| 139b | 8g | 250 (M – H)$^-$ |

Example 139c

Preparation of 8h 2-(1-cyclopentenyl)-7-azaindole (500 mg; 2.72 mmol), maleimide (527 mg; 5.44 mmol) and YbBr$_3$ (113 mg) in toluene (10 mL) were stirred at reflux under nitrogen for 1.5 hours. After cooling to room temperature the product was collected, washed with methanol and dried to give 420 mg (55%). MS m/e 380 (M–1). The tetrahydrocarbazole intermediate (20 mg, 0.07 mmol) was suspended in acetic acid, DDQ (80 mg, 0.36 mmol) added and the mixture maintained at 55° C. for 12 hours. The solvent was removed at reduced pressure, the residue triturated with MeOH and the product collected to give 16 mg (84%) of 8h as a reddish solid. $^1$H-NMR (DMSO-d$_6$) δ 12.50 (s, 1H), 11.02 (s, 1H), 9.0 (m, 1H), 8.55 (m, 1H), 7.35 (m, 1H), 3.21 (m, 4H), 2.28 (broad m, 2H). MS m/e 276 (M–H).

Example 139d

Preparation of 8i

Compound 8h (200 mg) and CH$_3$I (2 mL) in DMF (10 mL) was heated in a sealed reaction tube at 110° C. for 3 hours.

Example 139e

Preparation of 8j

A solution of example 1 (100 mg, 0.36 mmol) in THF (10 mL) was added $BH_3$-THF (1 mL of 1 mol solution) followed by heating for 2 hours at 60° C. An additional 2 ml $BH_3$THF was added and heating continued for 12 hours. The solution was concentrated at reduced pressure to a solid. 2N HCl was added to the residue and stirred for 2 hours. The product was collected and dried to give 35 mgs (39%) of a white solid. MS m/e 249 (M+H).

Example 139f

Preparation of 8k 8k was prepared in a manner similar to that described in Example 139c to give the title compound. MS m/e 301 (M+H).

Example 140

Preparation of Precursor to 11a

Ethyl 4-Cyano-1,2,3,10-tetrahydrocyclopenta[a]carbazole-5-carboxylate

DDQ (39 mg, 0.17 mmol, 220 mol %) was added to solution of ethyl 4-cyano-1,2,3,4,5,10-hexahydrocyclopenta[a] carbazole-5-carboxylate (24 mg, 0.078 mmol) in toluene (12 mL). The solution immediately turned dark brown, and was stirred at 20° C. for 1.5 hr. The solvent was evaporated. The residue was dissolved in EtOAc and rinsed with dilute aqueous ascorbic acid and twice with saturated $NaHCO_3$. Evaporation of the solvent afforded crude product (21 mg) which was recrystallized from EtOAc gave the product (9 mg, 38% yield) as a beige solid, mp 229-231° C. NMR ($CDCl_3$) δ 8.28 (s, 1H), 7.49 (s, 2H), 7.26 (s, 2H), 4.64 (q, 2H), 3.30 (t, 2H), 3.20 (t, 2H), 2.36 (quintet, 2H), 1.54 (t, 3H).

Example 141

Preparation of 11a 5,7,8,9,10,11-Hexahydrocyclopent[a]pyrrolo[3,4-c]carbazole-5(6H)-one Ethyl 4-Cyano-1,2,3,10-tetrahydrocyclopenta[a]carbazole-5-carboxylate (14 mg) in DMF (1.6 mL) was hydrogenated at 55 psi over W2 Raney nickel (150 mg) for 2.5 days. The catalyst was removed by filtration and the DMF was evaporated in vacuo to give the product (12 mg, 100% yield) as light brown crystals. A sample was recrystallized from DMF, boiled with ethanol, cooled, and filtered to give the product as an off-white solid, mp>300° C. NMR (DMSO-$d_6$) δ 11.45 (s, 1H), 9.06 (d, 1H), 8.47 (s, 1H), 7.51 (d, 1H), 7.40 (t, 1H), 7.16 (t, 1H), 4.41 (s, 2H), 3.21 (t, 2H), 3.04 (t, 2H), 2.30 (quintet, 2H). Anal. Calcd for $C_{17}H_{14}N_2O$: C, 77.84; H, 5.38; N, 10.68. Found: C, 77.40; H, 5.66; N, 10.49.

Example 142

Preparation of 11b 5,7,9,10,11,12-Hexahydrocyclohexano[a]pyrrolo[3,4-c]carbazole-5(6H), 7(8H)-dione Prepared from 2-(cyclohexen-1-yl)indole by a procedure similar to that reported for synthesis of 5a. NMR (DMSO-$d_6$) δ 11.73 (br. s, 1H), 10.90 (br. s, 1H), 8.77 (d, 1H), 7.58 (d, 1H), 7.51 (t, 1H), 7.27 (t, 1H), 3.22 (t, 2H), 3.03 (t, 2H), 1.90 (m, 2H). MS m/e 289 (M−H)⁻.

Example 143

Preparation of 11c

9-Ethyl-8-propyl-5,7-dihydropyrrolo[3,4-c]carbazole-5(6H), 7(10H)-dione

Prepared from 2-(hept-3-en-3-yl)indole according to the general procedure described for synthesis of 8,9-dimethyl-5,6,7,10-tetrahydropyrrolo[3,4-c]carbazole-7(6H)-one. Purified by preparative TLC (10% MeOH in $CH_2Cl_2$) to afford 38 mg (40%) of product. ¹H NMR ($CDCl_3$) δ 11.77 (s, 1H), 10.91 (s, 1H), 8.77 (d, 1H), 7.58 (m, 2H), 7.25 (m, 1H), 3.10-3.30 (m, 4H), 1.56 (m, 2H), 1.05 (t, 3H), 1.16 (t, 3H). MS m/e 305 (M−H)⁻.

Example 144

Preparation of 11d

Compound 11d was prepared from 2-(cyclohexen-1-yl)-1-methylindole by a procedure similar to that reported for the synthesis of 1a; mp 242° C. MS m/e 303 (M−H)⁻.

Example 145

Preparation of 11f 5,7,10,11-Tetrahydrofuran[a-3,2]pyrrolo[3,4-c]carbazole-5(6H), 7(9H)-dione Prepared from 2-(2,3-dihydrofuran-4-yl)indole according to the general procedure described for synthesis of 8,9-dimethyl-5,6,7,10-tetrahydropyrrolo[3,4-c]carbazole-7(6H)-one. Purified by preparative TLC (10% MeOH in $CH_2Cl_2$) to afford 0.15 mg (~1%) of product. ¹H NMR ($CD_3COCD_3$) δ 9.08 (d, 1H), 7.68 (d, 1H), 7.48 (t, 1H), 7.26 (t, 1H), 3.58 (m, 2H), 2.30 m, 2H). MS m/e 277 (M−H)⁻.

Example 146

Preparation of 11g 5,7-Dihydrofuran[a-3,2]pyrrolo[3,4-c]carbazole-5(6H), 7(11H)-dione Prepared from 2-(furan-3-yl)indole according to the general procedure described for synthesis of 8,9-dimethyl-5,6,7,10-tetrahydropyrrolo[3,4-c]carbazole-7(6H)-one. Purified by preparative TLC (10% MeOH in $CH_2Cl_2$) to afford 0.57 mg (~1%) of the product. ¹H NMR (DMSO-$d_6$) δ 12.0 (s, 1H), 10.9 (s, 1H), 8.9 (d, 1H), 7.9 (d, 1H), 7.8 (d, 1H), 7.6 (d, 1H), 7.58 (t, 1H), 7.26 (t, 1H). MS m/e 275(M−H)⁻.

Example 147

Preparation of 12a

To a solution of indole (10.72 g, 92.5 mmol) in THF (400 mL) at −78° C. was added 2.0 M n-BuLi (48.0 mL, 96 mmol). After stirring for 25 min, $CO_2$ was bubbled through the solution for 12 min. The mixture was warmed to RT, and solvent (and excess $CO_2$) was reduced by 50% by rotary evaporation. Additional THF (200 mL) was added, and the solution cooled to −78° C. before adding 1.7 M t-BuLi (54 mL, 91.8 mL). After stirring for 2 h, a solution of benzyl 4-oxo-1-piperidinecarboxylate (23.3 g, 99.9 mmol) in THF (30 mL) was added. After 1 h, the reaction was quenched with water (10 mL) and poured into a 10% aqueous solution of $NH_4Cl$ (200 mL). The mixture was extracted into EtOAc, and the organic layer was separated and washed with brine. After drying over $MgSO_4$, filtration followed by rotary evaporation afforded a solid that was triturated with ether (3×25 mL) and yielded the corresponding alcohol (18.5 g, 57%).

To a solution of the above adduct (11.2 g, 32.0 mmol) in acetone (300 mL) was added 2 N HCl (2.0 mL). After stirring for 3 h, more 2 N HCl (1 mL) was added. After 1 h, a saturated aqueous solution of $NaHCO_3$ was added and solvent was reduced by rotary evaporation. The residue was extracted into $CH_2Cl_2$, washed with water and dried over $Na_2SO_4$. After filtration, solvent was removed by rotary evaporation, and the residue was triturated with ether to afford the corresponding diene as a white solid (9.5 g, 89%).

A mixture of the above diene (1.02 g, 3.1 mmol) and maleimide (0.59 g, 6.1 mmol) in xylenes (20 mL) was heated to reflux for 18 h. The cooled mixture was filtered and the solid was successively washed with water (3×20 mL), ether (3×5 mL) and more water (3×10 mL). After drying under vacuum afforded the cycloadduct 1.35 g (100%).

A mixture of the above cycloadduct (325 mg, 0.76 mmol) and 10% Pd on carbon (375 mg) in di(ethylene glycol) diethyl ether (10 mL) was heated to reflux for 3 h. The cooled mixture was filtered through a plug of celite and the filter cake was washed with DMF (3×15 ml). The filtrate was evaporated to dryness and the resulting residue triturated with ether to afford the title compound (175 mg, 81%) as a pale green powder. $^1H$ NMR (DMSO-$d_6$) δ 13.2 (s, 1H), 11.32 (s, 1H), 10.19 (s, 1H), 8.92 (d, J=7.9, 1H), 8.81 (d, J=5.8, 1H), 8.51 (d, J=5.8, 1H), 7.78 (d, J=7.9, 1H), 7.60 (app. t, J=7.3, 1H), 7.41 (app t, J=7.3, 1H). MS m/e 288 (M+H)⁺.

Example 148

Preparation of 12b

A mixture of imide 12a (28.5 mg, 0.10 mmol), Sn powder (31.2 mg, 0.26 mmol), HOAc (4 ml), and conc. HCl (2 ml) was heated to reflux. More Sn was added after 20 h (42.5 mg, 0.35 mmol) and 26 h (65.0 mg, 55 mmol). The solution was decanted and the metallic residue was rinsed with DMF. The supernatent was evaporated and triturated with aqueous $NaHCO_3$ and water. The resulting solid was slurried in DMSO and filtered. The filtrate was extracted into EtOAc and washed with water (3×10 mL) and dried over $MgSO_4$. After filtration, solvent was removed by rotary evaporation, and the residue was triturated with ether to yield a mixture of lactams (1.1 mg, 4%). NMR (DMSO-$d_6$) δ 13.0 (br s, 1H), 10.4 (s, 0.65H), 10.13 (s, 0.35H), 8.88 (d, 0.35H), 8.70 (m, 1.65H), 8.51 (d, 0.35H), 8.44 (d, 0.65H), 8.27 (d, 0.35H), 8.11 (d, 0.65H), 7.76 (m, 1H), 7.53 (m, 1H), 7.34 (m, 1H), 4.97 (s, 2H). MS m/e 274 (M+H)⁺.

Example 149

Preparation of 12c

To a mixture of hydroxylactam 12d (5.2 mg, 0.018 mmol) in $CH_2Cl_2$ (4 mL) was added $Et_3SiH$ (123 uL) and TFA (297 uL). The mixture was stirred for 20 h, and solvent was removed by repeated rotary evaporation from iPrOH. Trituration with ether afforded the lactam product (2.3 mg, 45%). NMR (DMSO-$d_6$) δ 12.90 (s, 1H), 10.40 (s, 1H), 8.70 (m, 2H), 8.44 (d, j=5.65, 1H), 8.11 (d, J=7.8, 1H), 7.76 (d, J=8.3, 1H), 7.53 (m, 1H), 7.34 (m, 1H), 4.97 (s, 2H). MS m/e 274 (M+H)⁺.

Example 150

Preparation of 12d

To a mixture of imide 12a (28.5 mg, 0.10 mmol) in acetone (7 mL) was added iPrI (200 uL). After stirring overnight, solvent was removed by rotary evaporation, and the residue was taken up in MeOH (10 mL) and treated with $NaBH_4$ (22.4 mg, 0.59 mmol). After stirring overnight, the reaction was quenched with 1 N HCl (5 mL) and warmed to 50° C. The mixture was neutralized with aqueous $NaHCO_3$, extracted into EtOAc, washed successively with water and brine and dried over $MgSO_4$. After filtration, solvent was removed by rotary evaporation, and the residue was purified by preparative HPLC with 25% MeCN/$H_2O$ containing 0.1% TFA to afford the product hydroxylactam (7.0 mg, 25%). $^{13}C$ NMR (DMSO-$d_6$) δ 170.5, 148.6, 145.3, 144.0, 140.1, 136.6, 126.7, 124.5, 123.8, 121.9, 121.0, 117.4, 116.1, 116.0, 115.8, 112.4, 78.3. $^1H$ NMR (DMSO-$d_6$) δ 12.90 (s, 1H), 10.37 (s, 1H), 8.95 (s, 1H), 8.70 (s, 1H), 8.44 (s, 1H), 8.37 (d, J=7.9, 1H), 7.73 (d, J=8.2, 1H), 7.52 (app. t, J=7.4, 1H), 7.33 (app t, J=7.4, 1H), 6.63 (d, J=10.0, 1H), 6.40 (d, J=10.0, 1H). MS m/e 290 (M+H)⁺ and m/e 273 (M−OH)⁺.

Example 151

Preparation of 12e

To a mixture of imide 12a (50.1 mg, 0.17 mmol) in MeCN (5.0 mL) was added ethyl acrylate (50 uL) and DBU (50 uL). The reaction was warmed to reflux for 20 h, cooled and diluted with water (10 mL). The solid product was collected by filtration and washed with 50% aqueous EtOH (2×5 mL) and 95% EtOH (3×1 mL) and dried under vacuum (32 mg, 49%). $^{13}C$ NMR (DMSO-$d_6$) δ 171.1, 169.3, 168.8, 149.2, 145.3, 140.7, 138.7, 129.2, 128.1, 125.6, 124.7, 121.8, 121.2, 121.0, 118.3, 116.2, 114.6, 112.8, 60.7, 34.0, 33.2, 14.4. $^1H$ NMR (DMSO-$d_6$) δ 13.19 (s, 1H), 10.10 (s, 1H), 8.83 (d, J=8.0, 1H), 8.76 (d, J=5.8, 1H), 8.42 (d, J=5.8, 1H), 7.73 (d, J=8.0, 1H), 7.59 (app. t, J=7.2, 1H), 7.39 (app t, J=7.2, 1H), 4.00 (q, J=7.1, 2H), 3.88 (t, J=7.0, 2H), 2.73 (t, J=7.0, 2H), 1.07 (t, J=7.1, 3H). MS m/e 388 (M−H)⁺.

Example 152

Preparation of 12f

To a solution of imide 12a (28.9 mg, 0.1 mmol) in DMF (2.0 mL) was added NaH (60%, 5.1 mg, 0.13 mmol). After stirring for 15 min., (3-bromopropoxy)-t-butyldimethylsilane (30 uL) was added and the reaction was warmed to 50° C. for 2 h. The solution was cooled, poured into 10% aqueous $NH_4Cl$ (10 mL) and extracted into EtOAc. The organic layer was separated and washed successively with water, aqueous $NaHCO_3$ and brine, and dried over $Na_2SO_4$. After filtration, solvent was removed by rotary evaporation, and the residue was taken up in MeOH (10 mL) and treated with AcCl (90 uL). After 1 h, solvent was removed by rotary evaporation and the product residue was triturated with ether (2×1 mL) and dried under vacuum (21.7 mg, 57%). $^1$H (DMSO-$d_6$) δ 13.54 (s, 1H), 10.16 (s, 1H), 8.89 (d, J=9.5, 1H), 8.84 (d, J=6.7, 1H), 8.71 (d, J=6.7, 1H), 7.77 (d, 8.2, 1H), 7.63 (app. t, J=7.2, 1H), 7.43 (app t, J=7.2, 1H), 5.00 (m, 1H), 3.72 (t, J=7.0, 2H), 3.48 (d, J=7.0, 2H), 1.82 (p, J=7.4, 2H). MS m/e 404 (M+Na)$^+$.

Example 153

Preparation of 12g

To a solution of imide 12a (28.9 mg, 0.1 mmol) in DMF (2.0 mL) was added NaH (60%, 5.1 mg, 0.13 mmol). After stirring for 15 min., (3-bromoethoxy)-t-butyldimethylsilane (30 uL) was added and the reaction was warmed to 50° C. for 2 h. The solution was cooled, poured into 10% aqueous $NH_4Cl$ (10 mL) and extracted into EtOAc. The organic layer was separated and washed successively with water, aqueous $NaHCO_3$ and brine and dried over $Na_2SO_4$. After filtration, solvent was removed by rotary evaporation, and the residue was taken up in MeOH (10 mL) and treated with AcCl (90 uL). After 1 h, solvent was removed by rotary evaporation and the product residue was triturated with ether (2×1 mL) and dried under vacuum (6.5 mg, 20%). $^1$H (DMSO-$d_6$) δ 13.51 (s, 1H), 10.21 (s, 1H), 8.93 (d, J=8.8, 1H), 8.81 (d, J=5.7, 1H), 8.52 (d, J=5.7, 1H), 7.79 (d, 8.8, 1H), 7.62 (app. t, J=7.2, 1H), 7.43 (app t, J=7.2, 1H), 4.87 (m, 1H), 3.75 (m, 2H), 3.67 (m, 2H). MS m/e 332 (M+H)$^+$.

Example 154

Preparation of 12h

To a solution of imide 12a (28.7 mg, 0.1 mmol) in DMF (2.0 mL) was added NaH (60%, 5.2 mg, 0.13 mmol). After stirring for 15 min., ethyl bromoacetate (14 uL) was added and the reaction was warmed to 60° C. for 1 h. More NaH (5.8 mg) was added followed by more ethyl bromoacetate (15 uL). This mixture was stirred at 60° C. for 1 h. The solution was cooled, poured into 10% aqueous $NH_4Cl$ (10 mL) and extracted into EtOAc. The organic layer was separated and washed successively with water, aqueous $NaHCO_3$ and brine and dried over $Na_2SO_4$. After filtration, solvent was removed by rotary evaporation, and the residue was triturated with MeOH (2×1 mL). The product was dried under vacuum (18.2 mg, 48%). $^1$H (DMSO-$d_6$) δ 13.35 (s, 1H), 10.16 (s, 1H), 8.83 (m, 2H), 8.52 (d, J=5.9, 1H), 7.79 (d, J=8.2, 1H), 7.63 (app. t, J=8.2, 1H), 7.43 (app t, J=8.2, 1H), 4.51 (s, 2H), 4.14 (q, J=7.1, 2H), 1.20 (t, J=7.1, 3H). MS m/e 374 (M+H)$^+$.

Example 155

Preparation of 12i

To a solution of imide 12a (28.7 mg, 0.1 mmol) in DMF (2.0 mL) was added NaH (60%, 12.8 mg, 0.32 mmol). After stirring for 15 min., 2-picolyl chloride hydrochloride (19.6 mg, 0.12 mmol) was added and the reaction was warmed to 65° C. for 3 h. The solution was cooled, poured into 10% aqueous $NH_4Cl$ (10 mL) and the product was collected by filtration. After washing with water (5 mL) and MeOH (2×1 mL), the product was dried under vacuum (20.5 mg, 54%). $^1$H (DMSO-$d_6$) δ 13.38 (s, 1H), 10.12 (s, 1H), 8.87-8.80 (m, 2H), 8.50 (s, 1H), 8.41 (s, 1H), 7.76 (m, 2H), 7.61 (app. t, J=7.4, 1H), 7.47 (d, J=7.7, 1H), 7.39 (app t, J=7.4, 1H), 7.25 (app t, J=5.4), 4.99 (s, 2H). MS m/e 379 (M+H)$^+$.

Example 156

Preparation of 12j

To a solution of ester 12e (2.1 mg, 0.005 mmol) in EtOH (4.0 mL) was added 1 N NaOH (300 uL), and the mixture was warmed to 70° C. for 0.5 h. After the reaction was cooled, solvent was removed by rotary evaporation. The residue was taken up in water (1 mL) and acidified to pH 3 with 1 N aqueous HCl. Solvent was removed by rotary evaporation and the residue triturated with water. The product was dried under vacuum (1.1 mg, 56%). $^1$H (DMSO-$d_6$) δ 12.78 (s, 1H), 9.35 (s, 1H), 8.78-8.53 (m, 2H), 8.39 (d, J=5.5, 1H), 8.14 (d, J=7.9, 1H), 7.70 (d, J=7.9, 1H), 7.49 (app. t, J=7.8, 1H), 7.25 (app t, J=7.8, 1H), 3.54 (t, J=, 2H), 2.57 (t, J=7.1, 2H). MS m/e 360 (M+H)$^+$.

Example 157

Preparation of 12k

To a mixture of imide 12a (28.9 mg, 0.1 mmol) in MeCN (5.0 mL) was added acrylonitrile (50 uL) and DBU (5 uL). The reaction was warmed to reflux for 15 h, cooled and diluted with water (10 mL). The solid product was collected by filtration and washed with 50% aqueous EtOH (2×5 mL) and 95% EtOH (3×1 mL). The filtrate was evaporated and triturated with water (2×1 mL) and ether (2×1 mL) and dried under vacuum (4.0 mg, 12%). $^1$H NMR (DMSO-$d_6$) δ 13.3 (s, 1H), 10.20 (s, 1H), 8.93 (d, J=7.9, 1H), 8.83 (d, J=5.8, 1H), 8.53 (d, J=5.8, 1H), 7.80 (d, J=7.9, 1H), 7.63 (app. t, J=7.2, 1H), 7.44 (app t, J=7.2, 1H), 3.97 (t, J=7.1, 2H), 3.00 (t, J=7.0, 2H). MS m/e 341 (M+H)$^+$.

Example 158

Preparations of 12l and 12m

To a solution of the imide from example 12a (28.6 mg, 0.1 mmol) in DMF (2.0 mL) was added NaH (60%, 5.0 mg, 0.13 mmol). After stirring for 15 min., p-(t-butyldimethylsiloxy)benzyl chloride (29.7 mg) was added and the reaction was warmed to 60° C. for 4 h. The solution was cooled, poured into water (5 mL) and filtered. The solid was taken up in MeOH (10 mL) and treated with AcCl (50 uL). After 1 h, solvent was removed by rotary evaporation and the residue triturated with MeOH (2×1 mL) to afford the mono-alkylated product (12l) that was dried under vacuum (8.9 mg, 23%). $^1$H (DMSO-$d_6$) δ 13.24 (s, 1H), 10.16 (s, 1H), 9.37 (s, 1H), 8.88 (d, J=8.0, 1H), 8.78 (s, 1H), 8.47 (d, J=5.7, 1H), 7.75 (d, J=8.2, 1H), 7.60 (app. t, J=7.8, 1H), 7.40 (app t, J=7.8, 1H), 7.21 (d, J=8.2, 2H), 6.69 (d, J=8.2, 2H), 4.72 (s, 2H). Evaporation of the MeOH washings left a residue that was fractionated by preparative HPLC (45% MeCN/$H_2O$ w/ 0.1% TFA) to afford the di-alkylated product (12m, 8.2 mg, 16%). $^1$H (DMSO-$d_6$) δ 10.28 (s, 1H), 9.36 (s, 2H), 9.14 (d, J=8.0, 1H), 8.63 (s, 1H), 8.35 (d, J=5.7, 1H), 7.93 (d, J=8.4, 1H), 7.66 (app. t, J=7.4, 1H), 7.49 (app t, J=7.4, 1H), 7.22 (d, J=8.2, 2H), 6.83 (d, J=8.2, 2H), 6.69 (d, J=8.2, 2H), 6.61 (d, J=8.2, 2H), 6.15, (s, 2H), 4.75 (s, 2H).

Example 159

Preparation of 12n

The procedure described for 12a was repeated with 5-methylindole in place of indole. $^{13}$C NMR (DMSO-d$_6$) δ 171.3, 170.6, 149.3, 145.1, 139.0, 138.8, 130.6, 130.2, 129.4, 125.8, 124.4, 121.6, 121.1, 119.3, 116.2, 114.2, 112.3, 21.6. $^1$H NMR (DMSO-d$_6$) δ 13.07 (s, 1H), 11.27 (s, 1H), 10.12 (s, 1H), 8.75 (d, J=5.8, 1H), 8.63 (s, 1H), 8.44 (d, J=5.8, 1H), 7.61 (d, J=8.3, 1H), 7.39 (d, J=8.3, 1H), 2.50 (s, 3H).

Example 160

Preparation of 12o

The synthesis described for 12a was performed with 7-methylindole in place of indole for the preparation of 12o. $^1$H NMR (DMSO-d$_6$) δ 12.37 (s, 1H), 11.18 (s, 1H), 10.04 (s, 1H), 8.69 (d, J=5.7, 1H), 8.63-8.50 (m, 2H), 7.29 (d, J=6.9, 1H), 7.20 (ap t, J=7.6, 1H), 2.53 (s, 3H). MS m/e 302 (M+H)$^+$.

Example 161

Preparation of 12p

To a mixture of imide 12a (496 mg, 1.73 mmol) in DMF (30 mL) was added NBS (341 mg, 192 mmol), and the reaction was warmed to 60° C. for 2 h. More NBS (85 mg, 0.48 mmol) was added, and heating was continued for 1 h. More NBS (25 mg, 0.14 mmol) was added, and heating was continued for 1 h. The reaction mixture was cooled, and solvent was removed by rotary evaporation. The residue was triturated with 95% EtOH (3×10 mL) and dried under vacuum (479 mg, 76%). $^1$H NMR (DMSO-d$_6$) δ 13.25 (s, 1H), 11.33 (s, 1H), 10.08 (s, 1H), 8.88 (s, 1H), 8.77 (d, J=5.6, 1H), 8.38 (d, J=5.6, 1H), 7.64 (s, 2H).

Example 162

Preparation of 12q

A mixture of bromide compound 12p (17.1 mg, 0.047 mmol), PdCl$_2$(PPh$_3$)$_2$ (3.2 mg, 0.005 mmol), NaOAc (22.5 mg), and methoxyethanol (2 mL) was purged with CO and warmed to 150° C. for 2 h The reaction mixture was cooled, filtered through a pad of celite with the aid of MeOH (3×1 mL), and the filtrate was reduced by rotary evaporation. The residue was triturated with water (3×10 mL), dried under vacuum, and purified by preparative HPLC (30% MeCN/H$_2$0 w/ 0.1% TFA, 3.1 mg, 17%) $^1$H NMR (DMSO-d$_6$) δ 13.77 (s, 1H), 11.41 (s, 1H), 10.18 (s, 1H), 9.66 (s, 1H), 8.88 (d, J=5.6, 1H), 8.67 (d, J=5.6, 1H), 8.21 (d, J=7.5, 1H), 7.88 (d, J=7.4, 2H), 4.44 (m, 2H), 3.65 (m, 2H), 3.34 (s, 3H). MS m/e 390 (M+H)$^+$.

Example 163

Preparation of 12r

To a mixture of imide compound 12q (20.1 mg, 0.052 mmol), in THF (2 mL) was added a 2M solution of LiBH$_4$ in THF (200 uL). After 2 h, the reaction mixture was quenched with MeOH, then water, then 1 N HCl (5 drops). This mixture was neutralized with a solution of aqueous NaHCO$_3$ and extracted into EtOAc. The organic layer was washed with brine, dried over Na$_2$SO$_4$, and solvent was removed by rotary evaporation.

The residue was purified by preparative HPLC (25% MeCN/H$_2$0 w/ 0.1% TFA, 2.0 mg, 10%) $^1$H NMR (DMSO-d$_6$) δ 13.18 (s, 1H), 10.39 (s, 1H), 8.90 (s, 1H), 8.85 (s, 1H), 8.60 (d, J=5.6, 1H), 8.32 (d, J=5.6, 1H), 7.97 (d, J=7.5, 1H), 7.68 (d, J=7.4, 2H), 6.44 (d, J=6.5, 1H), 6.33 (d, J=6.5, 1H), 4.30 (m, 2H), 3.51 (m, 2H), 3.16 (s, 3H). MS m/e 392 (M+H)$^+$.

Example 164

Preparation of 12s

A mixture of bromide compound 12p (21.2 mg, 0.058 mmol), PdCl$_2$(PPh$_3$)$_2$ (4.6 mg, 0.007 mmol), 2-(tributylstannyl)thiophene (75 uL) and DMF (2 mL) was warmed to 100° C. for 20 h. The reaction mixture was cooled, filtered through a pad of celite with the aid of DMF (3×1 mL) and the filtrate was reduced by rotary evaporation. The residue was triturated with ether (3×3 mL), and pentane (10×2 mL) and dried under vacuum (8.1 mg, 38%) $^1$H NMR (DMSO-d$_6$) δ 13.26 (s, 1H), 11.43 (s, 1H), 10.16 (s, 1H), 9.16 (s, 1H), 8.80 (d, J=5.7, 1H), 8.47 (d, J=5.7, 1H), 7.91 (d, J=8.3, 1H), 7.78 (d, J=8.3, 2H), 7.53 (d, J=4.9, 1H), 7.48 (d, J=3.0, 1H), 7.16 (app t, J=4.2, 1H).

Example 165

Preparation 12t

A mixture of bromide compound 12p (15.1 mg, 0.041 mmol), PdCl$_2$(PPh$_3$)$_2$ (4.6 mg, 0.007 mmol), 2-(tributylstannyl)-1-methylpyrrole (55 uL) and DMF (2 mL) was warmed to 100° C. for 3 h. The reaction mixture was cooled, filtered through a pad of celite with the aid of DMF (3×1 mL) and the filtrate was reduced by rotary evaporation. The residue was triturated with ether (3×3 mL), and pentane (10×2 mL) and purified by chromatography (silica gel, 7% MeOH in CH$_2$Cl$_2$) (3.8 mg, 25%) $^1$H NMR (DMSO-d$_6$) δ 13.26 (s, 1H), 11.43 (s, 1H), 10.24 (s, 1H), 9.03 (s, 1H), 8.86 (d, 1H), 8.57 (d, 1H), 7.85 (d, 1H), 7.71 (dd, 1H), 6.91 (s, 1H), 6.24 (dd, 1H), 6.14 (dd, 1H), 3.75 (s, 3H). MS m/e 367 (M+H)$^+$.

Example 166

Preparation of 12u

A mixture of bromide compound 12p (21.5 mg, 0.059 mmol), PdCl$_2$(PPh$_3$)$_2$ (4.6 mg, 0.007 mmol), 4-(tributylstannyl)pyridine (100 uL) and DMF (2 mL) was warmed to 110° C. for 12 h. The reaction mixture was cooled, filtered through a pad of celite with the aid of DMF (3×1 mL) and the filtrate was reduced by rotary evaporation. The residue was purified by chromatography (silica gel, 20% MeOH in CH$_2$Cl$_2$) (1.8 mg, 8%) $^1$H NMR (DMSO-d$_6$) δ 13.18 (s, 1H), 11.20 (s, 1H), 10.01 (s, 1H), 9.13 (s, 1H), 8.65 (d, 1H), 8.46 (m, 2H), 8.33 (d, 1H), 7.83 (dd, 1H), 7.52 (d 1H), 7.66 (m, 2H). MS m/e 365 (M+H)$^+$.

Examples 166a-166d

Preparation of 12v-12y

The following compounds 12v-12y were prepared in a manner similar to that described in Examples 147-166.

TABLE 16

| Example | Compound | Mass Spec (m/e) |
|---------|----------|-----------------|
| 166a | 12v | 402 (M + H) |
| 166b | 12w | 386 (M + H) |
| 166c | 12x | 427 (M + H) |
| 166d | 12y | 385 (M + H) |

Example 166e

Data for 12z

Compound 12z was prepared in a manner similar to that described in Examples 147-166. $^1$H-NMR (DMSO-$d_6$) δ 13.4 (1H, s), 11.4 (1H, s), 10.2 (1H, s), 9.1 (s, 1H), 8.86 (d, J=5.7 Hz 1H), 8.54, (d, J=5.7 Hz 1H), 7.84 (s, 1H), 7.83-7.67 (m, 2H), 7.66 (d, J=15.8 1H), 7.0 (m, 1H), 6.70 (d, J=15.8 Hz, 1H).

Example 166f

Data for 12aa

Compound 12aa was prepared in a manner similar to that described in Examples 147-166. $^1$H-NMR (DMSO-$d_6$) δ 13.5 (1H, s), 11.4 (1H, s), 10.2 (1H, s), 9.1 (s, 1H), 8.86 (d, J=5.8 Hz 1H), 8.53, (d, J=5.8 Hz 1H), 8.0-7.3 (m, 2H), 6.98 (m, 1H), 6.4 (d, J=16.6 Hz, 1H).

Example 166g

Data for 12ab

Compound 12ab was prepared in a manner similar to that described in Examples 147-166. $^1$H-NMR (DMSO-$d_6$) δ 13.3 (1H, s), 11.4 (1H, s), 10.2 (1H, s), 9.1 (s, 1H), 8.85 (d, J=5.6 Hz 1H), 8.54, (d, J=5.1 Hz 1H), 8.01 (d, J=10.1, 1H), 7.92 (d, J=16.1 Hz, 1H), 7.84-7.80 (m, 2H), 7.65 (d, J=8.0, 1H), 7.34 (d, J=16.1 Hz, 1H), 7.28 (m, 1H).

Example 166h

Data for 12ac

Compound 12ac was prepared in a manner similar to that described in Examples 147-166. $^1$H-NMR (DMSO-$d_6$) δ 13.4 (1H, s), 11.4 (1H, s), 10.2 (1H, s), 9.1 (s, 1H), 8.86 (d, J=5.8 Hz 1H), 8.61-8.50 (m, 2H), 8.01 (d, J=10.1, 1H), 7.85 (d, J=10.1, 1H), 7.80-7.25 (m, 5H).

Example 167

Preparation of 13a

To a mixture of imide 12a (28.5 mg, 0.10 mmol) in acetone (7 mL) was added MeI (250 uL). After stirring overnight, solvent was removed by rotary evaporation, and the residue was taken up in MeOH (7 mL) and treated with NaBH$_4$ (15.2 mg, 0.4 mmol). After stirring overnight, the reaction was quenched with 1 N HCl (5 mL) and warmed to 50° C. The mixture was neutralized with aqueous NaHCO$_3$, extracted into EtOAc, washed successively with water and brine and dried over MgSO$_4$. After filtration, solvent was removed by rotary evaporation, and the residue was triturated with ether (3×3 mL) and dried under vacuum (14.9 mg, 49%). $^1$H NMR (DMSO-$d_6$) δ 11.84 (s, 1H), 10.96 (s, 1H), 8.74 (d, J=7.8, 1H), 7.54 (d, J=7.8, 1H), 7.49 (app. t, J=7.3, 1H), 7.25 (app t, J=7.3, 1H), 3.95 (s, 2H), 3.25-3.00 (m, 2H), 2.85-2.65 (m, 2H), 2.41 (s, 3H). MS m/e 306 (M+H)$^+$.

Example 168

Preparation of 13b

To a mixture of imide 12a (28.5 mg, 0.10 mmol) in acetone (7 mL) was added benzyl bromide (300 uL). After stirring overnight, solvent was removed by rotary evaporation, and the residue was triturated with ether (3×2 mL). This solid was taken up in MeOH (7 mL) and treated with NaBH$_4$ (15.2 mg, 0.4 mmol). After stirring 3.5 h, the reaction was quenched with 1 N HCl (5 mL) and warmed to 50° C. The mixture was neutralized with aqueous NaHCO$_3$, extracted into EtOAc, washed successively with water and brine and dried over MgSO$_4$. After filtration, solvent was removed by rotary evaporation, and the residue was purified by preparative HPLC (45% MeCN/H$_2$O w/ 0.1% TFA, 6.5 mg, 17%). $^1$H NMR (DMSO-$d_6$) δ 11.87 (s, 1H), 10.93 (s, 1H), 8.74 (d, J=7.8, 1H), 7.54 (d, J=7.8, 1H), 7.60-7.20 (series of m, 8H), 4.05 (s, 2H), 3.74 (s, 2H), 3.44-3.10 (m, 2H), 2.85-2.65 (m, 2H). MS m/e 382 (M+H)$^+$.

Example 169

Preparation of 14

Benzofuran was treated with butyllithium in ether followed by cyclopentanone. The resulting alcohol was dehydrated with toluenesulfonic acid in toluene to afford 2-cyclopenten-1-ylbenzofuran. Treatment with maleimide gave a cycloadduct which was aromatized by treatment with tetrachloroquinone. $^1$H NMR (DMSO-$d_6$) δ 11.29 (s, 1H), 8.60 (d, 1H), 7.82 (d, 1H), 7.66 (t, 1H), 7.52 (t, 1H), 3.23 (m, 4H), 2.30 (quintet, 2H). MS m/e 276 (M−H)$^-$.

Example 169a

Preparation of 14a 14a was prepared in a manner similar to that described in Example 62j, starting with 6-methoxy-2-(1-hydroxycyclopentyl)indole to give the title compound. MS m/e 305 (m−1)$^+$.

Example 169b

Preparation of 14b 14b was prepared in a manner similar to that described in Example 62j, starting with 4-methoxy-2-(1-hydroxycyclopentyl)indole to give the title compound. MS m/e 305 (M−H).

Example 170

Preparation of 15

This compound was synthesized from benzothiophene according to the same procedure described for compound 14. $^1$H NMR (DMSO-$d_6$) δ 11.36 (s, 1H), 9.60 (d, 1H), 8.13 (d, 1H), 7.63 (m, 2H), 3.11 (m, 4H), 2.31 (quintet, 2H). MS m/e 292 (M−H)$^-$.

Examples 170a-170m

Preparation of 15a-15m

Carbonate Intermediate:

Compound 2ao (0.55 g, 1.9 mmol) and bis(4-nitrophenyl) carbonate (1.1.4 g, 3.76 mmol) were mixed in a sealed reaction tube and heated at 140° C. for 20 minutes. The solid was triturated with ether and collected to 0.83 g MS m/e 456 (M–H).

Carbamates:

A mixture of amine (0.09 mmol) and nitrophenyl carbonate intermediate (0.18 mmol) in dry THF (2 mL) under nitrogen was heated at 80° C. for 6 hours. The solvent was concentrated at reduced pressure and the residue triturated with ether and the product collected.

TABLE 17

| Example | Compound | Mass Spec (m/e) |
|---------|----------|-----------------|
| 170a | 15a | 404 (M – H) |
| 170b | 15b | 417 (M – H) |
| 170c | 15c | 392 (M – H) |
| 170d | 15d | 442 (M – H) |
| 170e | 15e | 459 (M – H) |
| 170f | 15f | 425 (M – H) |
| 170g | 15g | 439 (M – H) |
| 170h | 15h | 453 (M – H) |
| 170i | 15i | 425 (M – H) |
| 170j | 15j | 402 (M – H) |
| 170k | 15k | 419 (M – H) |
| 170l | 15l | 447 (M – H) |
| 170m | 15m | 439 (M – H) |

Example 171

Preparation of 8l

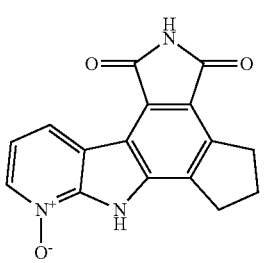 [SMILES: O=C1NC(=O)c2c1c1c(c3[nH]c4c(ccc[n+]4[O-])c23)CCC1]

A mixture of 8h (8.7 g, 0.031 m) and MCPBA (19.34 g, 0.078 m) in acetic acid (500 mL) was heated at 80° C. for 20 hr. Upon cooling to room temperature, a yellow solid was collected, washed with acetic acid, sodium bicarbonate solution, brine and dried (8.5 g 92% yield); $^1$H NMR (DMSO-d$_6$) δ 7.33-7.37 (t, 1H), 8.48-8.49 (d, 1H), 8.62 (d, 1H), 8.64 (s, 1H), 11.14 (m, 1H); MS (m/z)=292 (M–H).

Example 172

Preparation of 8m

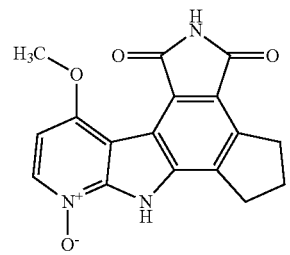 [SMILES: COc1cc[n+]([O-])c2[nH]c3c4c(c5c(c3c12)C(=O)NC5=O)CCC4]

A mixture of 8l (50 mg, 0.15 mmol) and sodium methoxide (40 mg, 0.74 mmol) in anhydrous DMSO (0.4 mL) was heated at 80° C. for 3 hr. The solution was diluted with water (5 mL) and adjusted to pH 3 giving a brown solid. This material was refluxed in methanol, filtered and the filtrate evaporated. Upon triturating the residue with DCM and water, a yellow solid was obtained (6 mg, 12% yield); $^1$H NMR (DMSO-d$_6$) δ 2.22-2.26 (m, 2H), 4.09 (s, 3H), 6.97 (s, 1H), 8.50-8.52 (d, 1H), 10.92 (s, 1H); MS (m/z)=325 (M+).

Example 173

Preparation of 8n

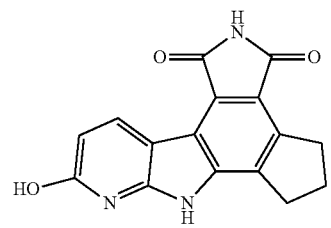 [SMILES: O=C1NC(=O)c2c1c1c(c3[nH]c4nc(O)ccc4c23)CCC1]

A mixture of 8l (15 mg, 0.05 mmol), trifluoroacetic anhydride (0.2 mL) and anhydrous DMF (0.5 mL) was heated at 70° C. for 5 hr. The solvent was evaporated then THF (1 mL) and 3 N HCl (0.2 mL) were added to the residue and heated at 70° C. for 0.5 hr. The solvent was decanted and the residue triturated with water giving a yellow solid (10 mg, 65% yield); $^1$H NMR (DMSO-d$_6$) δ 2.23-2.27 (t, 2H), 3.60 (t, 2H), 6.57 (d, 1H), 8.76-8.78 (d, 1H), 10.89 (s, 1H), 12.13 (s, 1H); MS (m/z)+294 (M+).

Example 174

Preparation of 8o

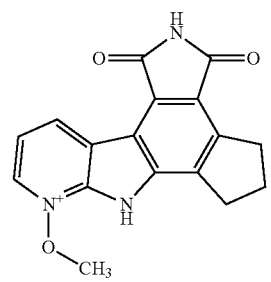 [SMILES: CO[n+]1cccc2c3c4c(c5c(c3[nH]c21)CCC5)C(=O)NC4=O]

A mixture of 8l (20 mg, 0.068 mmol) and dimethylsulfate (0.5 mL) was heated at 140° C. for 10 hr. Upon cooling a gray solid was collected, washed with dimethylsulfate and then ether. The solid was refluxed in THF, then in ethanol giving a tan solid (17 mg, 68% yield); $^1$H NMR (DMSO-$d_6$) δ 2.34-2.35 (m, 2H), 3.23-3.25 (m, 4H), 4.52 (s, 3H), 7.83-7.85 (m, 1H), 9.40 (m, 2H), 11.38 (s, 1H); MS (m/z)=308 (M+).

Example 175

Preparation of 8p

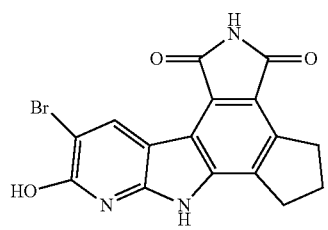 [SMILES: O=C1NC(=O)c2c1c1c(c3[nH]c4nc(O)c(Br)cc4c23)CCC1]

A mixture of 8o (20 mg, 0.068 mmol) and NBS (24 mg, 0.14 mmol) in THF (6 mL) was stirred at rt for 15 hr. After evaporation of the solvent, water was added to the residue and a solid collected (18 mg, 65% yield); $^1$H NMR (DMSO-$d_6$) δ 2.24 (m, 2H), 8.98 (s, 1H), 10.97 (s, 1H), 12.33 (s, 1H); MS (m/z)=371 (M$^+$).

Example 176

Preparation of 8q and 8r

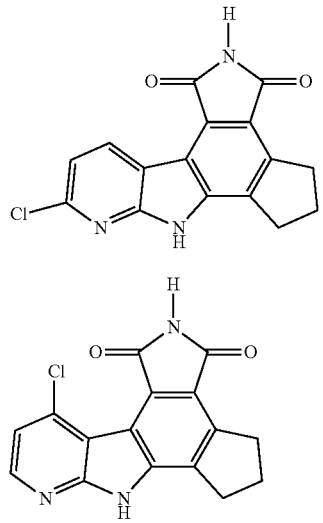

A mixture of 8l (20 mg, 0.068 mmol), methanesulfonyl chloride (0.1 mL, 0.68 mmol), lithium chloride (44 mg, 1.0 mmol) and anhydrous DMF (0.3 mL) was heated at 80° C. for 16 hr. Additional methanesulfonyl chloride (0.1 mL, 0.68 mmol) was added and heated another 10 hr. The mixture was evaporated and the residue stirred with 10% sodium bicarbonate solution giving a solid consisting of isomers 8q and 8r (18 mg); $^1$H NMR (DMSO-$d_6$) δ 2.28 (m, 2H), 7.39-7.44 (m, 2H), 8.46 (d, 1H), 8.47 (d, 1H), 8.96 (d, 1H), 8.98 (d, 1H), 9.18 (s, 1H), 10.95 (s, 1H), 11.02 (s, 1H), 11.08 (s, 1H), 12.74 (s, 1H), 12.91 (s, 1H); MS (m/z)=312 (m$^+$).

Example 177

Preparation of 8s

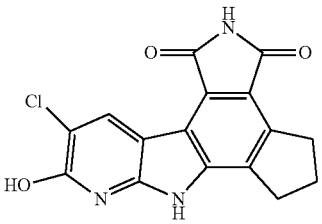 [SMILES: O=C1NC(=O)c2c1c1c(c3[nH]c4nc(O)c(Cl)cc4c23)CCC1]

A mixture of 8n (20 mg, 0.068 mmol) and N-chlorosuccinimde (36 mg, 0.27 mmol) in anhydrous THF (6 mL) was refluxed for 4 hr. The mixture was evaporated and the residue stirred with water, then THF giving a tan solid (4 mg, 18% yield); $^1$H NMR (DMSO-$d_6$) δ 2.25 (m, 1H), 8.82 (s, 1H), 10.97 (s, 1H), 12.33 (m, 1H); MS (m/z)=328 (m$^+$).

Example 178

Preparation of 8t and 8u

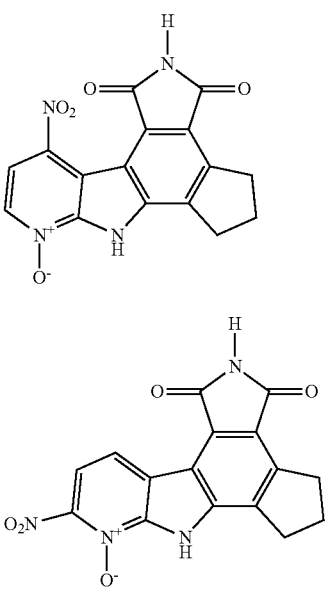

Nitric acid (fuming) (5 mL) was added to a solution of 8l (0.5 g, 0.0016 m) in TFA (5 mL) and stirred at rt for 16 hr. Upon evaporation of the TFA, cold water was added to the residue giving a solid (0.5 g, 75% yield) consisting of isomers 8t and 8u; $^1$HNMR (DMSO-$d_6$) δ 2.25-2.33 (m, 2H), 7.83-

7.85 (d, 1H), 7.88-7.97 (d, 1H), 9.26-9.28 (d, 1H), 11.10 (s, 1H), 14.00 (m, 1H); MS (m/z)=339 (m⁺).

Example 179

Preparation of 8vi and 8vii

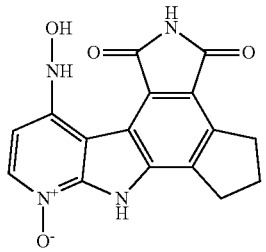

8vi

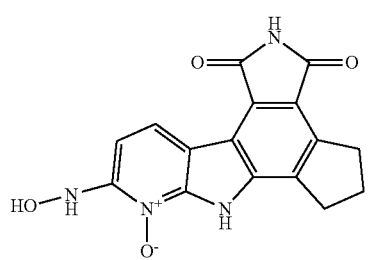

8vii

A mixture of isomers 8t and 8u (25 mg, 0.074 mmol) and stannous chloride dihydrate (50 mg, 0.22 mmol) in acetic acid was heated at 40° C. for 2 hr. The reaction was poured into water and the pH adjusted to 5 giving a solid. The mixture was heated at 60° C. in acetic acid, cooled and a brown solid collected (11 mg, 46% yield); ¹H NMR (DMSO-d₆) δ 2.25-2.35 (m, 2H), 6.72 (d, 1H), 6.78 (d, 2H), 8.11 (d, 1H), 8.19 (d, 1H), 11.27 (s, 1H), 11.39 (s, 1H), 11.83 (s, 1H), 12.00 (s, 1H); MS (m/z)=325 (m⁺).

Example 180

Preparation of 8w

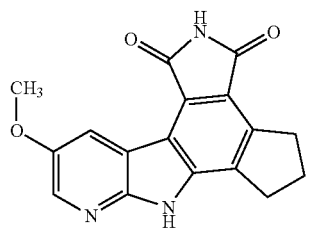 [SMILES: COc1cnc2[nH]c3c4c(c5c(c3c2c1)C(=O)NC5=O)CCC4]

This compounds was prepared using the procedure outlined for 141 starting from 5-methoxy-1H-pyrrolo[2,3-b]pyridine. ¹HNMR (DMSO-d₆) 12.32 (s, 1H), 11.00 (s, 1H), 8.59 (s, 1H), 8.33 (s, 1H), 3.93 (s, 3H), 3.24 (m, 2H), 3.15 (m, 2H), 2.29 (m, 2H); MS (m/z) 308 (M+H).

Figure 9:
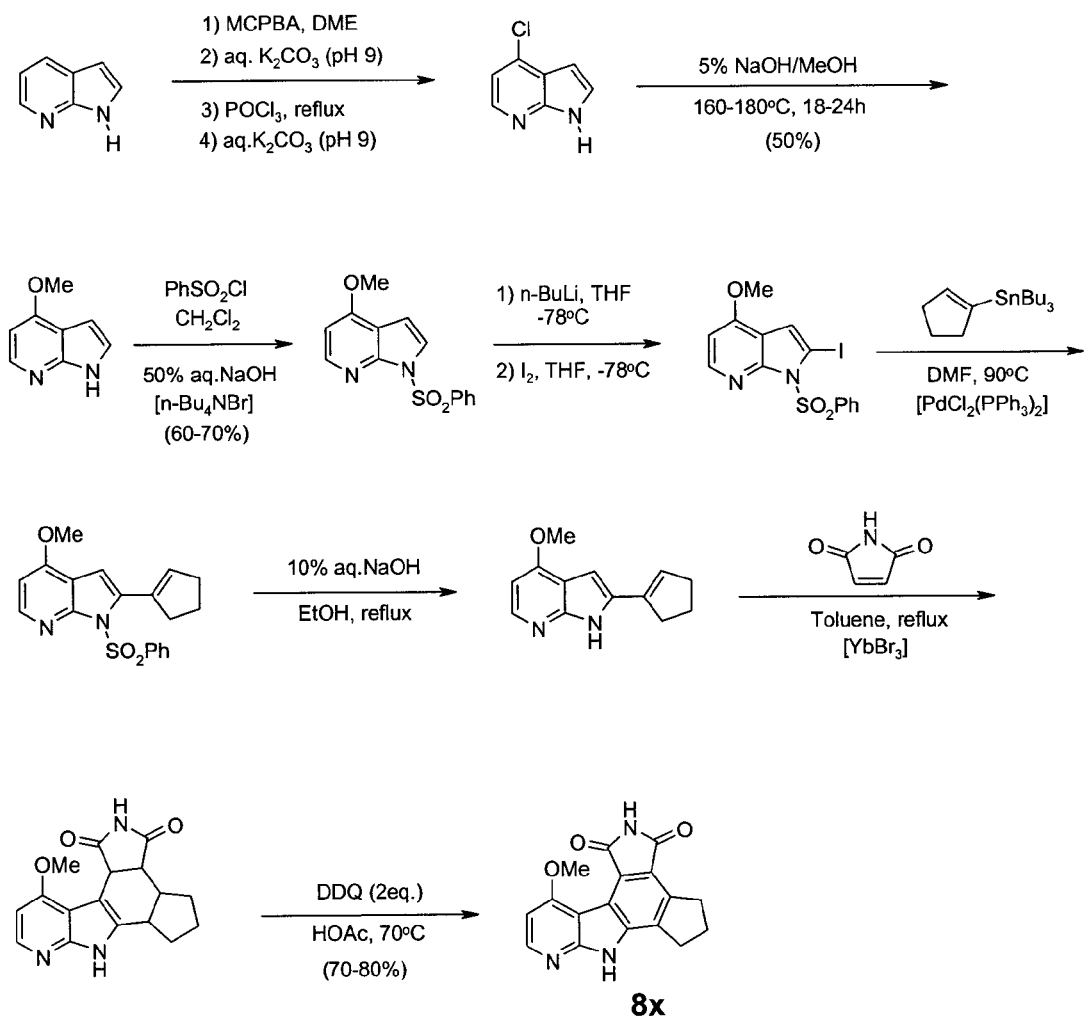
FIG. 9 shows synthetic strategy for preparing compounds within the scope of the present invention.

FIG. 9, which follows, describes the synthesis of Example 181 (compound 8x).

Example 181

Preparation of 8x

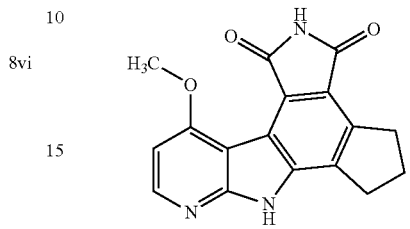

Step 1. To a solution of 7-azaindole (32.0 g, 271 mmol) in 1,2-dimethoxyethane (500 mL) was added 3-chloroperoxybenzoic acid (93.5 g of 70% tech. grade, 379 mmol). After being stirred for two hours at ambient temperature the resulting precipitate was collected by suction filtration onto a sintered glass funnel, washed with ether (3×100 mL) and air-dried to give 50.7 g as the 3-chlorobenzoate salt. The salt was dissolved in water (400 mL), saturated aqueous potassium carbonate was added to pH 9 (~50 mL) and the homogeneous solution was cooled to 5° C. for 18-24 hr. The precipitate was collected to give 20.3 g as a white solid; MS (m/z) 135 (M+H).

Step 2. A mixture of 1H-pyrrolo[2,3-b]pyridin-7-oxide (step 1)(10.0 g, 74.5 mmol) in phosphorous oxychloride (50 mL) was heated to reflux. After 12 h the excess phosphorous oxychloride was evaporated under reduced pressure and the residue was stirred in saturated aqueous sodium bicarbonate (250 mL) for one hour. The solid was collected by suction filtration, washed with water to neutrality, and air-dried to afford 9.8 g of 4-choro-7-azaindole as an off-white solid; MS (m/z) 153/155 (M+H).

Step 3. A solution of sodium hydroxide (11 g) in methanol (250 mL) was stirred with 4-chloro-1H-pyrrolo[2,3-b]pyridine (step 2)(12.2 g, 80 mmol) at 140° C. in a sealed reactor for 16 hr. After being cooled to ambient temperature the mixture was concentrated and residue was slurred in water (100 mL) for one hour. The solid was collected by suction filtration and washed to neutrality with water. After being dried to constant weight, 6.5 g of 4-methoxy-7-azaindole was obtained as a tan solid; MS (m/z) 149 (M+H).

Step 4. To a mixture of 4-methoxy-7-azaindole (6.4 g, 43.2 mmol) in dichloromethane (200 mL) and 50% aqueous sodium hydroxide (200 mL) was added benzenesulfonyl chloride (6.1 mL, 47.5 mmol) and tetrabutylammonium bromide (1.4 g, 4.3 mmol). The mixture was stirred vigorously at room temperature for 18 hours. The organic phase was washed with water and brine, dried (MgSO₄), filtered and concentrated. The crude product was recrystallized from ethyl acetate and hexanes to give 9.2 g of 1-benzenesulfonyl-4-methoxy-7-azaindole as a yellow solid. ¹H NMR (DMSO-d6) δ 8.30 (d, J=5 Hz, 1H), 8.18 (d, 1 Hz, 1H), 7.58 (m, 2H), 7.47 (m, 2H), 6.67 (d, 4 Hz, 1H), 6.61 (d, 4 Hz, 1H), 3.94 (s, 3H). MS (m/z) 289 (M+H).

Step 5. To a solution of 1-benzenesulfonyl-4-methoxy-1H-pyrrolo[2,3-b]pyridine (1.0 g, 3.47 mmol) in THF (50 mL) cooled in a dry ice-acetone bath was added n-BuLi (2.1M in hexanes, 2.0 mL). The mixture was stirred for 20 minutes, warmed to 0° C. and stirred for an additional 30 minutes, then cooled to −78° C. A solution of iodine (1.06 g, 4.16 mmol) in THF (10 mL) was added dropwise over 5 minutes and the mixture was warmed to 0° C. and stirred for one hour. Water (10 mL) was added followed by 10% aq. Na$_2$S$_2$O$_3$ (10 mL) and stirred for 5 minutes. Ethyl acetate (50 mL) was added and the organic phase was washed with water, saturated aqueous sodium bicarbonate and brine, dried (MgSO$_4$), filtered and concentrated to afford 1.0 g of 1-benzenesulfonyl-2-iodo-4-methoxy-7-azaindole as a yellow solid which was carried forward without further purification. MS m/z 415.

Step 6. A mixture of 1-benzenesulfonyl-2-iodo-4-methoxy-1H-pyrrolo[2,3-b]pyridine (1.1 g, 2.65 mmol), tributyl-cyclopent-1-enyl-stannane (1.9 g, 5.31 mmol), and bis(triphenylphosphine)palladium(II) chloride (93 mg) in DMF (10 mL) was heated in a sealed tube to 90° C. for seven hours. The mixture was washed with hexanes (2×10 mL) and the DMF phase was concentrated under reduced pressure. The residue was purified by flash chromatography on silica gel (gradient elution of 10-35% EtOAc/hexanes) to give 0.61 g of 1-benzenesulfonyl-2-cyclopent-1-enyl-4-methoxy-7-azaindole as a yellow solid; MS (m/z) 355 (M+H).

Step 7. A solution of 1-benzenesulfonyl-2-cyclopent-1-enyl-4-methoxy-1H-pyrrolo[2,3-b]pyridine (500 mg, 1.41 mmol) in ethanol (50 mL) was treated with 10% aqueous sodium hydroxide solution (5 mL) and heated to reflux for one hour. The ethanol was evaporated under reduced pressure and the aqueous residue was diluted with water (10 mL). The resulting slurry was filtered, washed with water to pH 7 and dried to constant weight to afford 263 mg; MS (m/z) 215 (M+H).

Step 8. A mixture of 2-cyclopent-1-enyl-4-methoxy-1H-pyrrolo[2,3-b]pyridine (1.8 g, 8.4 mmol), maleimide (8.15 g, 84 mmol), and YbBr$_3$ (350 mg, 0.84 mmol) in toluene was heated to reflux for 29 hours and concentrated. The residue was stirred in water (75 mL) for 30 minutes, filtered, washed with water (3×20 mL), hexanes and finally ether before being dried to constant weight to give 2.4 g of the tetrahydrocarbazole imide as a grey solid; MS (m/z) 312 (M+H).

Step 9. Example 181 (compound 8x): To a solution of the imide from step 8 (1.3 g, 4.2 mmol) in glacial acetic acid (45 mL) was added DDQ (2.0 g, 8.8 mmol). The mixture was heated to 70° C. for 22 hours, an additional 0.50 g of DDQ was added and the mixture was stirred for a further 18 hours. The mixture was concentrated under reduced pressure and the residue was stirred for one hour in 10% MeOH/EtOAc (50 mL), filtered, washed with 10% MeOH/EtOAc (50 mL) and EtOAc before being dried to constant weight to afford 1.1 g of 8x. MS m/e 308; $^1$H NMR (DMSO-d6) δ 12.4 (s, 1H), 10.7 (s, 1H), 8.43 (d, J=4 Hz, 1H), 6.97 (d, J=4 Hz, 1H), 4.08 (s, 3H), 3.27 (t, J=7 Hz, 2H), 3.17 (t, J=7 Hz, 2H), 2.27 (m, 2H); MS (m/z) 308 (M+H).

Example 182

Preparation of 8y

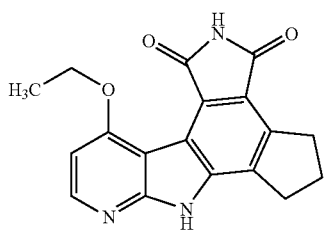 [SMILES: CCOc1ccnc2[nH]c3c4c(c5c(c3c12)C(=O)NC5=O)CCC4]

This compound was prepared as described for 8x. From the tetrahydrocarbazole imide (75 mg, 0.23 mmol) and DDQ (162 mg, 0.71 mmol) in glacial acetic acid at 70° C. for 48 hours was obtained 43 mg of 8y as a light brown solid. (DMSO-d$_6$) δ 12.5 (s, 1H), 10.8 (s, 1H), 8.44 (d, J=4 Hz, 1H), 6.90 (d, J=4 Hz, 1H), 4.35 (q, J=7 Hz, 2H), 3.35 (m, 2H), 3.20 (m, 2H), 2.35 (m, 2H), 1.55 (t, J=7 Hz, 3H). MS m/e 322.

Example 183

Preparation of 8z

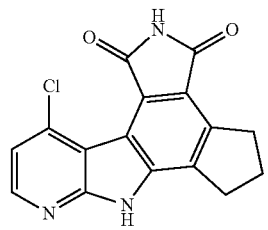 [SMILES: O=C1NC(=O)c2c1c1c(c3[nH]c4nccc(Cl)c4c23)CCC1]

Step 1: To a solution of 4-chloro-7-azaindole (304 mg, 2.0 mmol) in THF (10 mL) cooled to −78° C. was added a solution of 1.5M n-BuLi in hexane (1.5 mL, 2.2 mmol). The mixture was stirred for 20 minutes, purged with a stream of CO$_2$ for 20 minutes and stirred an additional 20 minutes. The mixture was reduced to about half its volume under vacuum to remove residual CO$_2$, THF (5 mL) was added and the mixture was cooled to −78° C. A solution of 1.5M t-BuLi in pentane (1.5 mL, 2.2 mmol) was added dropwise and the mixture was stirred for 45 minutes. A solution of cyclopentanone (195 μL, 2.2 mmol) in THF (1 mL) was added and the mixture was stirred for 45 minutes and poured in 2N HCl (15 mL). The aqueous phase was extracted with ether (2×10 mL), the aqueous phase was adjusted to pH 9 (4N NaOH) and extracted with ethyl acetate (2×25 mL). The combined ethyl acetate phase was washed with brine, dried (MgSO$_4$), filtered and concentrated. Preparative tlc (50% EtOAc/hexanes) gave 36 mg of the tertiary alcohol as a white solid. This was heated with glacial acetic acid to 100° C. for 1.5 hours and concentrated to give 32 mg of 4-chloro-2-cyclopent-1-enyl-1H-pyrrolo[2,3-b]pyridine as a white solid; MS m/e 219; $^1$H NMR (CDCl$_3$) δ 8.10 (d, J=5 Hz, 1H), 7.10 (d, J=5 Hz, 1H), 6.45 (s, 1H), 6.21 (s, 1H), 2.78 (t, J=7 Hz, 2H), 2.62 (t, J=7 Hz, 2H), 2.10 (m, 2H).

Step 2: To a solution of 4-chloro-2-cyclopent-1-enyl-1H-pyrrolo[2,3-b]pyridine (step 1) (20 mg, 0.09 mmol) in cumene was added 88 mg (0.9 mmol) of maleimide and 8 mg of YbBr$_3$. The mixture was heated to reflux for 48 hrs., the solvent was evaporated under reduced pressure, and the residue was stirred in water, filtered, washed with water and dried to give 15 mg of the tetrahydrocarbazole; MS m/e 316.

Step 3. To the tetrahydrocarbazole from step 2 (15 mg, 0.05 mmol) in glacial acetic acid was added 24 mg (0.1 mmol) of DDQ. The mixture was heated to 90° C. for 48 hours. The solvent was evaporated under reduced pressure and residue was washed with 20% MeOH/EtOAc (3×5 mL) and dried to give 10 mg of 8z as a light brown solid. 1H NMR (DMSO-d6) δ 12.9 (s, 1H), 10.9 (s, 1H), 8.45 (s, 1H), 7.40 (s, 1H); MS m/e 310 (M−H)$^+$.

Example 184

Preparation of 8aa

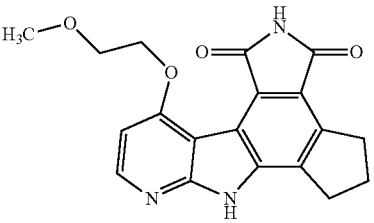 [SMILES: COCCOc1ccnc2[nH]c3c4c(c5c(c3c12)C(=O)NC5=O)CCC4]

This compound was prepared as described for 8x. From the 7-(2-methoxy-ethoxy)-tetrahydrocarbazole-4,6-dione (100 mg, 0.28 mmol) and DDQ (134 mg, 0.59 mmol) was obtained 33 mg of 8aa as a tan solid. (DMSO-d$_6$) δ 12.5 (s, 1H), 10.8 (s, 1H), 8.44 (d, J=4 Hz, 1H), 6.90 (d, J=4 Hz, 1H), 4.45 (m, 2H), 4.05 (m, 2H), 3.35 (s, 3H), 3.25 (m, 2H), 2.35 (m, 2H), 2.05 (m, 2H). MS (m/e) 352.

Example 185

Preparation of 8ab

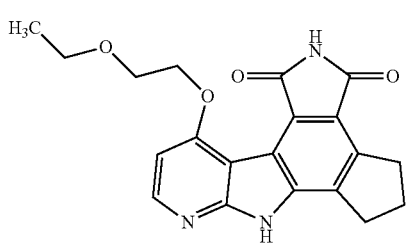 [SMILES: CCOCCOc1ccnc2[nH]c3c4c(c5c(c3c12)C(=O)NC5=O)CCC4]

This compound was prepared as described for 8x. From 7-(2-Ethoxy-ethoxy)-tetrahydrocarbazole-4,6-dione (150 mg, 0.41 mmol) and DDQ (319 mg, 1.40 mmol) was obtained 21 mg of 8ab as a tan solid. (DMSO-d$_6$) δ 12.7 (s, 1H), 10.8 (s, 1H), 8.40 (d, J=4 Hz, 1H), 7.00 (d, J=4 Hz, 1H), 4.45 (m, 2H), 3.95 (m, 2H), 3.60 (q, J=7 Hz, 2H), 3.25 (m, 2H), 2.25 (m, 2H), 2.05 (m, 2H), 1.10 (t, J=7 Hz, 3H). MS m/e 366.

Example 186

Preparation of 8ac

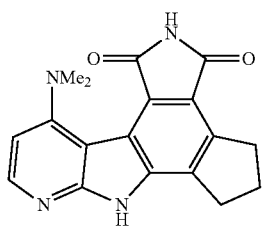 [SMILES: CN(C)c1ccnc2[nH]c3c4c(c5c(c3c12)C(=O)NC5=O)CCC4]

This compound was prepared using the same general procedure as outlined for 1a starting with 4-dimethylamino-7-azaindole. To a 25 mL round-bottomed flask containing a magnetic stirring bar equipped with a reflux condenser and a three-way stopcock connected to an argon balloon was charged with (2-cyclopent-1-enyl-1H-pyrrolo[2,3-b]pyridine-4-yl)-dimethylamine (12 mg, 0.05 mmol) followed by toluene (2 mL), maleimide (157 mg, 0.79 mmol) and ytterbium(III) bromide (19 mg, 0.04 mmol). The reaction mixture was refluxed for 1 h and the toluene evaporated under vacuum. The crude material was triturated with methanol (10 mL) filtered and washed with methanol. The filtrate was concentrated and purified by silica gel column chromatography to obtain tetrahydrocarbazole (15 mg, 88% yield). An oven dried, 25 mL round-bottomed flask containing a magnetic stirring bar was charged with 7-dimethylamino-1,2,3,3a,3b,6a,11,11b-octahydro-5,10,11-triaza-benzo[a]trindene-4,6-dione (15 mg, 0.04 mmol) followed by acetonitrile (4 mL). DDQ (35 mg, 0.15 mmol) was added at 15° C. and then stirred at rt for 1 h and at reflux for 6 h. Acetonitrile was evaporated under vacuum and dissolved in ethyl acetate then washed with saturated sodium bicarbonate, brine, dried (MgSO$_4$) and concentrated to give a crude material. The crude material was purified by silica gel column chromatography to give 8ac (2.3 mg, 15% yield). MS (m/z): 321 (M+1).

Example 187

Preparation of 14c

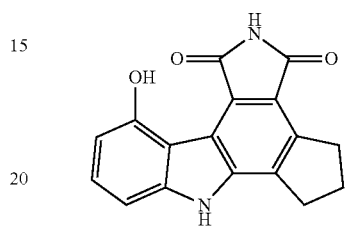

Compound 14c was prepared using the same general procedure as outlined for 1a and 2ao using 4-triisopropylsilyloxyindole addition to cyclopentanone to the alcohol, dehydration to the diene, Diels-Alder reaction with maleimide and oxidation to the carbazole with DDQ. To the TIPS protected carbazole (20 mg, 0.044 mmol) in anhydrous THF (1.5 mL) was added 1 M TBAF (0.1 mL) at 10° C. and stirred at rt for 1 hr. The solvent was evaporated, the residue diluted with water (2 mL) and a tan solid collected (11 mg, 83% yield); $^1$H NMR (DMSO-d$_6$) δ 2.18-2.29 (m, 2H), 3.14-3.26 (m, 2H), 6.58-6.60 (d, 1H), 7.00-7.01 (d, 1H), 7.35 (t, 1H), 12.13 (s, 3H); MS (m/z)=291 (M$^-$).

Example 188

Preparation of 14d

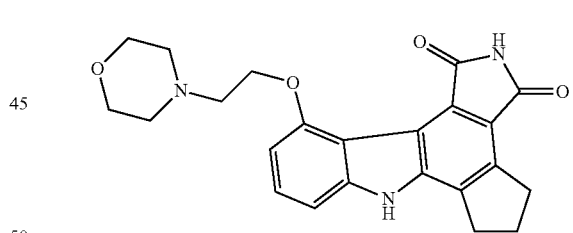

Step 1: 2-Cyclopent-1-enyl-1H-indol-4-ol was prepared from 4-triisopropylsilyloxy-1H-indole and cyclopentanone as described for 14c.

Step 1: To 3.1 g (8.29 mmol) alcohol intermediate was added 100 mL AcOH and the reaction was stirred at room temperature for 30 minutes. The reaction mixture was then concentrated, partitioned between EtOAc and H$_2$O, washed with aqueous NaCl solution, dried (MgSO$_4$), and concentrated under vacuum to yield 3 g of 2-cyclopent-1-enyl-4-triisopropylsilyloxy-1H-indole. To 3.1 g (8.76 mmol) the silyl intermediate in 20 mL THF at 0° C. was added 10 mL TBAF (1 M THF). After 30 minutes at 0° C. the reaction was concentrated, partitioned between EtOAc and H$_2$O, the EtOAc layer washed with aqueous NaCl solution, dried (MgSO$_4$) and concentrated. The product was purified by column chromatography (CH$_2$Cl$_2$) to yield 2 g of 2-cyclopent-1-enyl-1H-indol-4- ol as a white solid. This material was stirred in a mixture of hexane-cyclohexane (1:1) overnight, collected and dried.

Step 2: To 100 mg (0.503 mmol) of the intermediate 2-cyclopent-1-enyl-1H-indol-4-ol in 2 mL CH$_3$CN was added 819 mg (2.51 mmol, 5 eq) cesium carbonate, 94 mg (0.503 mmol) of 4-(2-chloroethyl)morpholine hydrochloride and a catalytic amount of NaI. The reaction mixture was heated at 50° C. for 3 h, partitioned between EtOAc and H$_2$O, washed with aqueous NaCl solution, dried (MgSO$_4$), and concentrated under vacuum to yield 81 mg (52%) of 2-cyclopent-1-enyl-4-(2-morpholin-4-yl-ethoxy)-1H-indole.

Step 3: To 81 mg (0.26 mmol) of the diene intermediate from step 2 in 2 mL AcOH was added 50 mg (0.519 mmol, 2 eq) of maleimide and the reaction was stirred at room temperature overnight. The reaction mixture was concentrated, partitioned between EtOAc and H$_2$O. The EtOAc layer was washed with aqueous NaCl solution, dried (MgSO$_4$), and concentrated under vacuum to yield 64 mg of the tetrahydrocarbazole intermediate as a dark oil (64%).

Step 4: To 64 mg (0.166 mmol) of the imide intermediate from step 3 in 2 mL of toluene and 0.5 mL of AcOH was added 77 mg (0.34 mmol, 2.05 eq) of DDQ at 0° C. and the reaction was stirred at room temperature overnight. The reaction was then concentrated, EtOAc was added and stirred with aqueous ascorbic acid for 30 minutes. The solution was extracted with EtOAc and the organic layer was washed with 2N Na$_2$CO$_3$ solution, H$_2$O, aqueous NaCl solution, dried (MgSO$_4$), and concentrated. The product was purified by preparative plate chromatography (5-10% MeOH/CH$_2$Cl$_2$). The product was collected and then triturated with MeOH to yield 11 mg of 14d as a yellow solid (16%). $^1$H NMR (DMSO-d$_6$) δ 11.95 (br s, 1H), 10.65 (br s, 1H), 7.43 (t, J=8.1 Hz, 1H), 7.13 (d, J=8.1 Hz, 1H), 6.78 (d, J=8.1 Hz, 1H), 4.30 (t, J=6.3 Hz, 2H), 4.08 (m, 2H), 3.56 (m, 4H), 3.30 (m, 2H), 3.17 (m, 4H), 2.96 (t, J=6.3 Hz, 2H), 2.27 (m, 2H); MS 406 (m/z) (M+H)$^+$.

Examples 14e-14h were prepared as described for 14d.

Example 189

Preparation of 14e

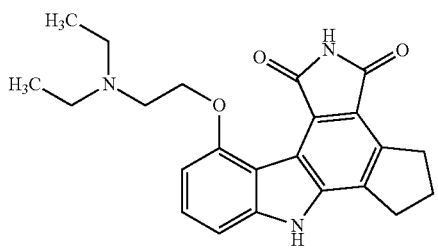 [SMILES: CCN(CC)CCOc1cccc2[nH]c3c4c(c5c(c3c12)C(=O)NC5=O)CCC4]

This compound was prepared by the same general procedure as described for 14d. $^1$HNMR (DMSO-d$_6$) δ 11.93 (s, 1H), 10.67 (s, 1H), 7.43 (t, J=8.1 Hz, 1H), 7.12 (d, J=8.1 Hz, 1H), 6.77 (d, J=8.1 Hz, 1H), 4.26 (br m, 2H), 3.36 (br m, 4H), 3.17 (br m, 2H), 2.63 (br m, 4H), 2.28 (br m, 2H), 1.1 (br m, 6H); MS (m/z) 392 (M+H)$^+$.

Example 190

Preparation of 14f

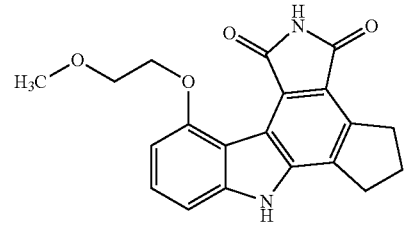 [SMILES: COCCOc1cccc2[nH]c3c4c(c5c(c3c12)C(=O)NC5=O)CCC4]

This compound was prepared by the same general procedure as described for 14d. $^1$HNMR (DMSO-d$_6$) δ 11.94 (s, 1H), 10.66 (s, 1H), 7.42 (t, J=8.1 Hz, 1H), 7.13 (d, J=8.1 Hz, 1H), 6.77 (d, J=8.1 Hz, 1H), 4.31 (t, J=5.3 Hz, 2H), 3.92 (t, J=5.3 Hz, 2H), 3.29 (br m, 5H), 3.17 (t, J=7.5 Hz, 2H), 2.28 (m, 2H); MS (m/z) 349 (M–H).

Example 191

Preparation of 14g

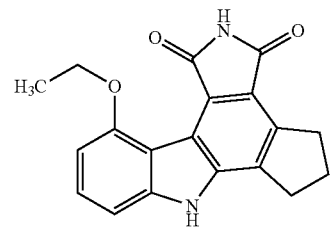

This compound was prepared by the same general procedure as described for 14d. $^1$HNMR (DMSO-d$_6$) δ 11.90 (s, 1H), 10.63 (s, 1H), 7.41 (t, J=8.1 Hz, 1H), 7.11 (d, J=8.1 Hz, 1H), 6.74 (d, J=7.8 Hz, 1H), 4.24 (m, 2H), 4.08 (m, 2H), 3.17 (m, 2H), 2.28 (m, 2H), 1.50 (t, J=6.8 Hz, 3H); MS ((m/z)) 319 (M–H).

Example 192

Preparation of 14h

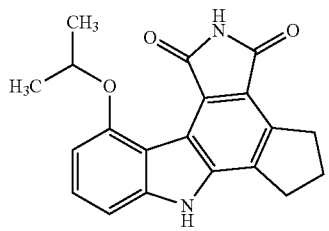 [SMILES: CC(C)Oc1cccc2[nH]c3c4c(c5c(c3c12)C(=O)NC5=O)CCC4]

This compound was prepared by the same general procedure as described for 14d. $^1$HNMR (DMSO-d$_6$) δ 11.89 (s, 1H), 10.61 (s, 1H), 7.41 (t, J=8.1 Hz, 1H), 7.07 (d, J=8.1 Hz, 1H), 6.76 (d, J=8.1 Hz, 1H), 4.86 (m, 1H), 3.30 (m, 2H), 3.15 (m, 2H), 2.28 (m, 2H), 1.43 (d, J=6.1 Hz, 6H); MS (m/z) 333 (M−H).

Example 193

Preparation of 14i

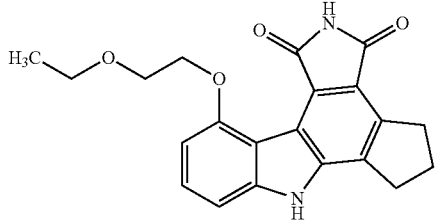 [SMILES: CCOCCOc1cccc2[nH]c3c4c(c5c(c3c12)C(=O)NC5=O)CCC4]

Step 1: To 500 mg (1.41 mmol) of 2-cyclopent-1-enyl-4-triisopropylsilyloxy-1H-indole (14d step 1) in 5 mL AcCN was added 255 mg (1.68 mmol, 1.2 eq) of CsF and 479 µL (4.23 mmol, 3 eq) 2-bromoethylethyl ether. The reaction was heated at 60° C. overnight then cooled to rt, diluted with $CH_2Cl_2$ and filtered through celite and concentrated. The residue was partitioned between ether and $H_2O$, the ether layer was then washed with aqueous NaCl solution, dried ($MgSO_4$), and concentrated under vacuum to yield 282 mg (74%) of 2-cyclopent-1-enyl-4-(2-ethoxy-ethoxy)-1H-indole.

Step 2: To the diene intermediate from step 1 and 2 eq of maleimide in 2 mL AcOH was stirred at room temperature overnight. The reaction mixture was concentrated, partitioned between EtOAc and $H_2O$. The EtOAc layer was washed with aqueous NaCl solution, dried ($MgSO_4$), and concentrated under vacuum to yield the tetrahydrocarbazole.

Step 3: To 323 mg (0.878 mmol) imide intermediate from step 2 in 20 mL AcOH was added 432 mg (1.76 mmol, 2 eq) of chloranil and the reaction was heated to 95° C. for 1.5 h. The reaction mixture was then concentrated, dissolved in EtOAc and stirred with aqueous ascorbic acid for 30 minutes and extracted with EtOAc. The organic layer was washed with 2N $Na_2CO_3$ solution, $H_2O$, aqueous NaCl solution, dried ($MgSO_4$), and concentrated. The product was purified by silica gel chromatography (5-10% MeOH/$CH_2Cl_2$) followed by triturating the product with ether to give 14i as a yellow solid $^1$H NMR (DMSO-$d_6$) δ 11.92 (s, 1H), 10.65 (s, 1H), 7.42 (t, J=8.1 Hz, 1H), 7.13 (d, J=8.1 Hz, 1H), 6.78 (d, J=8.1 Hz, 1H), 4.29 (m, 2H), 3.96 (m, 2H), 3.53 (m, 2H), 3.17 (m, 4H), 2.28 (m, 2H), 1.10 (t, J=7.1 Hz, 3H); MS 363 ((m/z)) (M−H).

Example 194

Preparation of 14j

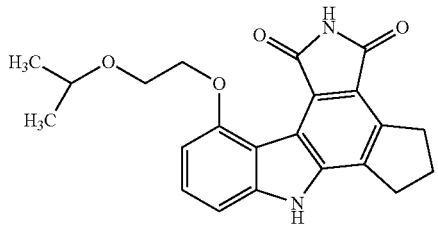 [SMILES: CC(C)OCCOc1cccc2[nH]c3c4c(c5c(c3c12)C(=O)NC5=O)CCC4]

This compound was prepared by the same general procedure as 14i. $^1$HNMR (DMSO-$d_6$) δ 11.92 (s, 1H), 10.65 (s, 1H), 7.42 (t, J=8.1 Hz, 1H), 7.13 (d, J=7.8 Hz, 1H), 6.77 (d, J=8.1 Hz, 1H), 4.26 (m, 2H), 3.95 (m, 2H), 3.65 (m, 1H), 3.28 (m, 2H), 3.17 (m, 2H), 2.26 (m, 2H), 1.09 (d, J=3.8 Hz, 6H); MS ((m/z)) 377 (M−H).

Example 195

Preparation of 14k

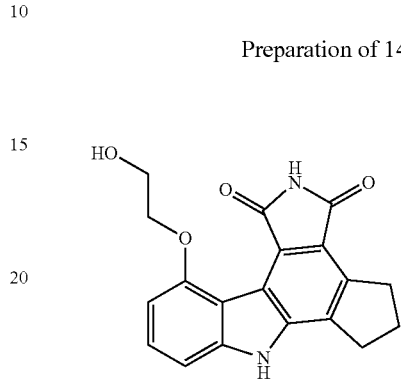

Step 1: To 300 mg (0.845 mmol) of 2-cyclopent-1-enyl-4-triisopropylsilyloxy-1H-indole (14d step 1) in 3 mL AcCN was added 154 mg (1.01 mmol, 1.2 eq) of CsF and 282 µL (2.54 mmol, 3 eq) ethylbromoacetate and the reaction was stirred at 50° C. overnight. The reaction was diluted with $CH_2Cl_2$ and filtered through celite. The $CH_2Cl_2$ layer was washed with 2N $Na_2CO_3$ solution, $H_2O$, aqueous NaCl solution, dried ($Na_2SO_4$), and concentrated in vacuole to yield 239 mg (99%) of (2-cyclopent-1-enyl-1H-indol-4-yloxy)-acetic acid ethyl ester as a dark oil.

Step 2: To 216 mg (0.758 mmol) of the ester from step 1 in 5 mL THF at 0° C. was added 455 µL (0.91 mmol, 1.2 eq) of LiBH$_4$ solution (1M THF) and the reaction was stirred at room temperature overnight. The reaction was quenched with 1N HCl, extracted with EtOAc, washed with $H_2O$, aqueous NaCl solution, dried (Mg $SO_4$), and concentrated in vacuo to yield 167 mg (91%) of 2-(2-cyclopent-1-enyl-1H-indol-4-yloxy)-ethanol.

Step 3: To the diene intermediate from step 2 and 2 eq of maleimide in 2 mL AcOH was stirred at room temperature overnight. The reaction mixture was concentrated, partitioned between EtOAc and $H_2O$. The EtOAc layer was washed with aqueous NaCl solution, dried ($MgSO_4$), and concentrated under vacuum to yield the tetrahydrocarbazole.

Step 4: To 125 mg (0.368 mmol) of the imide from step 3 in 2 mL MeOH at 0° C. was added 171 mg (0.754 mmol, 2.05 eq) of DDQ. The reaction was stirred at room temperature overnight, then concentrated, stirred with ice cold MeOH, filtered, and dried to yield 29 mg (23%) 14k. $^1$H NMR (DMSO-$d_6$) 12.15 (s, 1H), 10.77 (s, 1H), 7.43 (t, J=8.1 Hz, 1H), 7.15 (d, J=8.1 Hz, 1H), 6.76 (d, J=8.1 Hz, 1H), 4.20 (m, 2H), 3.93 (m, 2H), 3.51 (br m, 1H), 3.28 (m, 2H), 3.18 (m, 2H), 2.28 (m, 2H); MS (m/z) 335 (M−H).

Example 196

Preparation of 14l

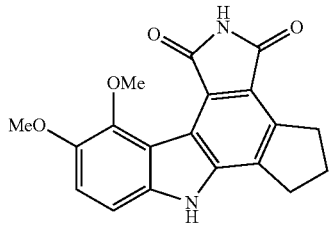 [SMILES: COc1ccc2[nH]c3c4c(c5c(c3c2c1OC)C(=O)NC5=O)CCC4]

Step 1: To 4,5-dimethoxyindole (241 mg, 1.36 mmol) in 5 mL THF at 0° C. was added 82 mg (2.04 mmol, 1.5 eq) of sodium hydride, followed by benzenesulfonyl chloride (260 μL, 2.04 mmol, 1.5 eq). The reaction was warmed to room temperature over 5 h then quenched with $H_2O$ and concentrated. The residue was dissolved in $CH_2Cl_2$ and extracted with $NaHCO_3$, $H_2O$, aqueous NaCl, dried ($Na_2SO_4$), and concentrated. The product was purified by silica gel column chromatography (7/3 hexanes/EtOAc) to give 369 mg of 1-benzenesulfonyl-4,5-dimethoxy-1H-indole (86%).

Step 2: To 541 mg (1.71 mmol) of the protected indole from step 1 in 20 mL dry THF at −20° C. was added 269 μL (1.8 mmol, 1.05 eq) TMEDA, then LDA (1.1 mL, 2.22 mmol, 1.3 eq) dropwise. The reaction was stirred for 45 minutes and iodine (879 mg, 3.42 mmol, 2 eq) in 4 mL THF was added slowly, and stirred an additional 45 minutes at −20° C. The reaction was then quenched with $H_2O$, concentrated and partitioned with EtOAc and 2N $Na_2CO_3$ solution. The EtOAc layer was washed with $H_2O$, aqueous NaCl, dried ($MgSO_4$), and concentrated under vacuum to yield 750 mg of 1-benzenesulfonyl-2-iodo-4,5-dimethoxy-1H-indole.

Step 3: To 539 mg (1.22 mmol) the iodo intermediate from step 2 in 5 mL dry DMF was added 43 mg (0.061 mmol, 5 mol %) of $PdCl_2(PPh_3)_2$, followed by 870 mg (2.44 mmol, 2 eq) tributylstannylcyclopentene. The reaction was heated to 90° C. for 4 h, concentrated, dissolved in EtOAc and filtered through celite. The EtOAc layer was washed with $H_2O$, aqueous NaCl solution, dried ($MgSO_4$), and concentrated. The product was purified by silica gel chromatography (5-15% EtOAc/hexane) to yield 302 mgs of 1-benzenesulfonyl-2-cyclopent-1-enyl-4,5-dimethoxy-1H-indole (65%).

Step 4: To 291 mg (0.76 mmol) of the phenylsulfonamide intermediate from step 3 in 50 mL EtOH was added 5 mL 10% NaOH solution. The reaction was heated to reflux overnight and then concentrated. The residue was dissolved in EtOAc, washed with 2N $Na_2CO_3$ solution, $H_2O$, aqueous NaCl solution, dried ($MgSO_4$), and concentrated under vacuum to yield 180 mg of 2-cyclopent-1-enyl-4,5-dimethoxy-1H-indole (97%).

Step 5: The Diels-Alder reaction using 2-cyclopent-1-enyl-4,5-dimethoxy-1H-indole (step 4) and maleimide as described for 14k. Purification using silica gel chromatography (4% MeOH/$CH_2Cl_2$) gave 46 mg of the tetrahydrocarbazole imide (18%).

Step 6: To 46 mg (0.135 mmol) of the intermediate from step 5 in 0.5 mL AcOH was added 61 mg (0.27 mmol, 2 eq) DDQ and the reaction was heated to 70° C. for 1 h. The reaction mixture was concentrated, stirred with MeOH overnight, dried, and collected to yield 8 mg of 14l (18%). $^1$H NMR (DMSO-$d_6$) δ 13.5 (br s, 1H), 10.8 (br s, 1H), 6.01 (br m, 2H), 3.86 (br s, 6H), 3.19 (br m, 4H), 2.22 (br m, 2H); MS (m/z) 335 (M H).

Example 197

Preparation of 14m

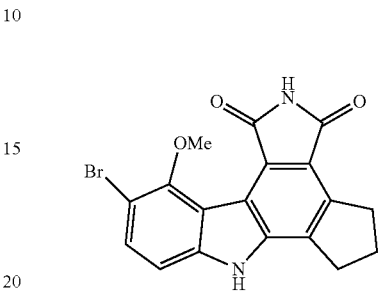

To a solution of example 14b (500 mg, 1.63 mmol) in DMF (40 mL) cooled in an ice-water bath was added dropwise a solution of pyridinium perbromide hydrobromide (522 mg, 1.63 mmol) in DMF (10 mL) over 5-10 minutes. The mixture was stirred while being allowed to warm slowly to ambient temperature over two hours, and then added to a stirred container of water (100 mL). The precipitate was filtered, washed with water and dried to constant weight to afford 600 mg of 14m as a pale yellow solid; $^1$H NMR (DMSO-d6) δ 11.80 (s, 1H), 10.70 (s, 1H), 7.65 (d, J=7 Hz, 1H), 6.75 (d, J=7 Hz, 1H), 4.00 (s, 3H), 3.30 (m, 4H), 2.25 (m, 2H). MS m/e 385/386.

Example 198

Preparation of 14n

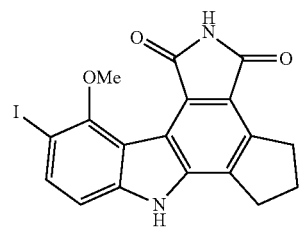 [SMILES: COc1c(I)ccc2[nH]c3c4c(c5c(c3c12)C(=O)NC5=O)CCC4]

To a solution of example 14b (500 mg, 1.63 mmol) in dichloromethane (70 mL) and methanol (30 mL) was added calcium carbonate (500 mg) followed by benzyltrimethylammonium chloride-iodonium chloride (625 mg, 1.80 mmol) with stirring. After 22 hours an additional 50 mg of benzyltrimethylammonium chloride-iodonium chloride was added and the mixture was stirred for six hours before being washed with 10% aqueous sodium thiosulfate (50 mL). The organic phase was concentrated and the residue was stirred in water (100 mL), acidified with 1N hydrochloric acid (50 mL), filtered and washed with water to neutrality and dried to constant weight to afford 770 mg of 14n as a yellow solid; $^1$H NMR (DMSO-d6) δ 11.40 (s, 1H), 10.70 (s, 1H), 7.80 (d, J=7 Hz, 1H), 6.65 (d, J=7 Hz, 1H), 4.00 (s, 3H), 3.30 (m, 4H), 2.25 (m, 2H); MS m/e 433.

Example 199

Preparation of 14o

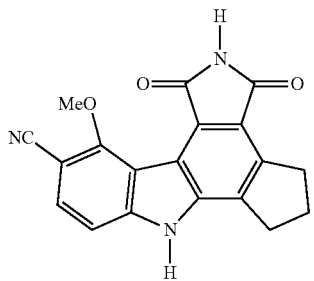 [SMILES: COc1c(C#N)ccc2[nH]c3c4c(c5c(c3c12)C(=O)NC5=O)CCC4]

A mixture of 14n (250 mg, 0.58 mmol) and copper(I) cyanide (266 mg, 1.7 mmol) in HMPA (4 mL) was stirred while being heated to 110° C. for 24 hours. The mixture was cooled to room temperature, added dropwise to 3N hydrochloric acid (25 mL) and filtered. The crude product was further purified by preparative thin layer chromatography in silica gel (5% MeOH/DCM) to give 185 mg of a brown semi-solid which was slurried in ether/MeOH (1/1, 5 mL), filtered, washed with ether/MeOH (1/1, 5 mL) and dried to constant weight to afford 68 mg of 14o as a mustard yellow solid; NMR (DMSO-d6) δ 12.65 (s, 1H), 10.80 (s, 1H), 7.95 (d, J=8 Hz, 1H), 6.95 (d, J=8 Hz, 1H), 4.05 (s, 3H), 3.30 (m, 4H), 2.25 (m, 2H). MS (m/e) 332.

Preparation of 15n-15p 15n-15p were prepared by the general procedure described for 15a-15m using the carbonate intermediate.

Example 200a

Preparation of 15n

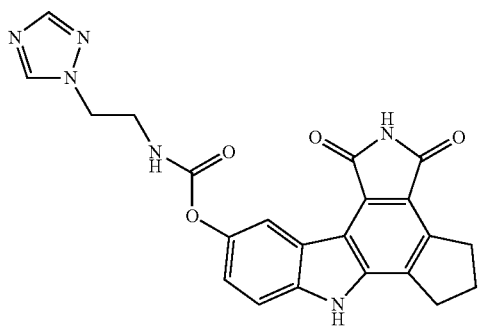 [SMILES: O=C(NCCn1cncn1)Oc1ccc2[nH]c3c4c(c5c(c3c2c1)C(=O)NC5=O)CCC4]

This compound was prepared by the general procedure described for 15a-15m using the carbonate intermediate. Prepared from 3-(4-nitrophenylcarbonate) intermediate (40 mg, 0.087 mmol) and 3-2'-aminoethyl-1,2,4-triazole dihydrochloride (19 mg, 0.17 mmol) in TFA (2 mL); $^1$H NMR (DMSO-d$_6$) δ 2.28-2.31 (m, 2H), 3.14-3.24 (m, 2H), 3.51-3.52 (m, 2H), 4.17-4.20 (m, 2H), 4.33-4.36 (m, 2H), 7.24-7.26 (d, 1H), 7.54-7.56 (d, 1H), 7.90 (m, 1H), 8.43 (s, 1H), 8.46 (s, 1H), 8.55 (s, 1H), 10.96 (s, 1H), 11.97 (s, 1H); MS (m/z)=429 (M−H).

Example 200b

Preparation of 15o

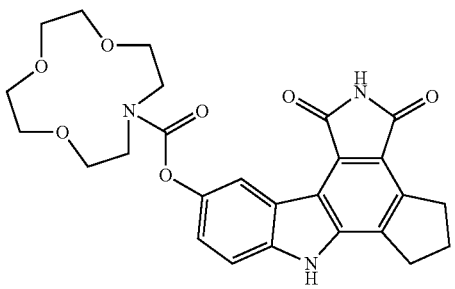 [SMILES: O=C1NC(=O)c2c1c1c(c3[nH]c4ccc(OC(=O)N5CCOCCOCCOCC5)cc4c23)CCC1]

This compound was prepared by the general procedure described for 15a-15m using the carbonate intermediate. Prepared from 3-(4-nitrophenylcarbonate) intermediate (40 mg, 0.087 mmol) and 1,4,7-trioxa-10-azacyclodecane (30 mg, 0.17 mmol); $^1$H NMR (DMSO-d$_6$) δ 2.28-2.32 (m, 2H), 3.17-3.18 (m, 2H), 3.87-3.89 (m, 2H), 7.26-7.29 (d, 1H), 7.54-7.57 (d, 1H), 8.47-8.48 (s, 1H), 10.96 (s, 1H), 11.97 (s, 1H); MS (m/z)=492 (M−H).

Example 200c

Preparation of 15p

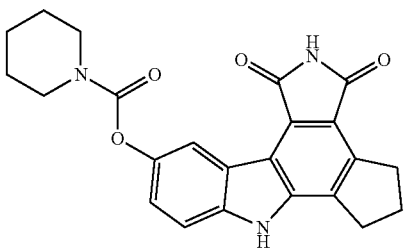 [SMILES: O=C1NC(=O)c2c1c1c(c3[nH]c4ccc(OC(=O)N5CCCCC5)cc4c23)CCC1]

This compound was prepared by the general procedure described for 15a-15m using the carbonate intermediate. Prepared from 3-(4-nitrophenylcarbonate) intermediate (35 mg, 0.076 mmol) and piperidine (13 mg, 0.15 mmol); $^1$H NMR (DMSO-d$_6$) δ 2.28-2.32 (m, 2H), 7.25-7.28 (d, 1H), 7.54-7.56 (d, 1H), 8.45-8.46 (d, 1H), 10.96 (d, 1H), 11.97 (s, 1H); MS (m/z)=401 (M–H).

Example 201

Preparation of 16a

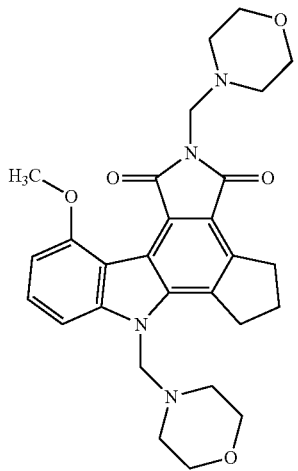 [SMILES: COc1cccc2c1c1c3c(c4c(c1n2CN1CCOCC1)CCC4)C(=O)N(CN1CCOCC1)C3=O]

To a slurry of 14b (15 mg, 0.049 mmol) in DMF (1 mL) was added paraformaldehyde (42 mg, 0.05 μL), morpholine (160 mg, 1.9 mmol) and heated at 70° C. for 18 hr. The mixture was evaporated. The residue was triturated with hexane, then dissolved in CH$_2$Cl$_2$, filtered and evaporated. The residue was triturated with Et$_2$O and 16a collected as a yellow solid (5 mg, 20%), $^1$HNMR (DMSO-d$_6$) 7.52 (t, 1H), 7.39 (d, 1H), 6.82 (d, 1H), 5.0 (s, 2H), 4.46 (s, 2H), 3.98 (s, 3H), 3.56 (s, 6H), 3.49 (s, 4H), 2.50 (s, 6H), 2.49 (s, 4H), 2.45 (m, 2H); MS m/z 505 (M+H).

Example 202

Preparation 16b and 16c

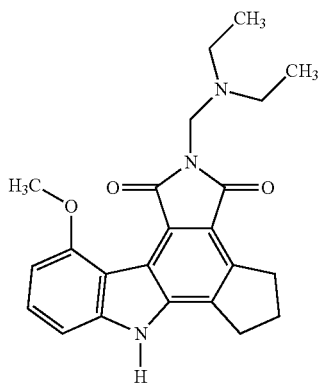

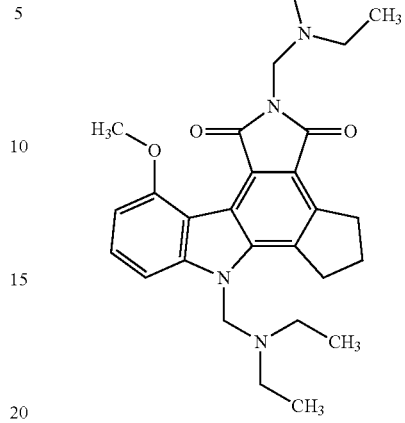

To a slurry of 14b (50 mg, 0.16 mmol) in DMF (5 mL) was added paraformaldehyde (73 mg, 0.81 mmol), diethylamine (84 μL, 0.81 mmol) and stirred at room temperature for 1 day. The reaction was evaporated and the residue triturated with hexane and evaporated to give two products as an oil, (ratio 6-1, 16b:16c). $^1$H-NMR (DMSO-d$_6$) 0.98 (t, 3H), 1.11 (t, 3H), 2.27 (m, 2H), 2.53 (m, 8H), 2.57 (m, 15H), 3.17 (t, 2H), 3.50 (m, 1H), 3.97 (s, 3H), 4.14 (d, 2H), 4.71 (d, 2H), 6.82 (t, 2H), 6.75 (d, 2H), 7.13 (d, 2H), 7.33 (m, 1H), 7.46 (t, 3H), 7.52 (m, 1H), 11.95 (s, 1H). 16b: MS m/z 392. 16c MS m/z 476.

Example 203

Preparation of 16d

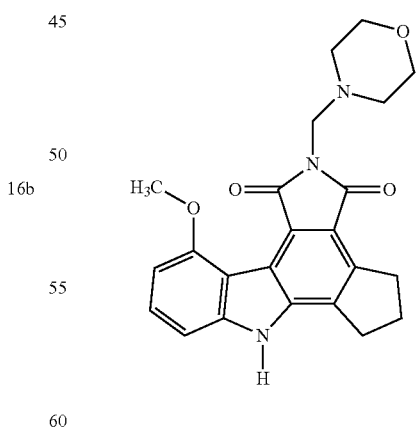

To a slurry of 14b (50 mg, 0.16 mmol) in ethanol (10 mL) was added paraformaldehyde (72 mg, 0.8 mmol), morpholine (100 g, 1.1 mol) and heated at 50° C. for 5 hr. The reaction was evaporated, water added (15 mL) and a yellow solid collected (59 mg). $^1$H NMR (DMSO-d$_6$) 11.98 (s, 1H), 7.45 (t, 1H), 7.13 (d, 1H), 6.75 (d, 1H), 4.44 (s, 2H), 3.97 (s, 3H), 3.56 (s, 4H), 3.18 (t, 2h), 2.29 (t, 2h). MS m/z 406 (M+H).

Example 204

Preparation of 16e

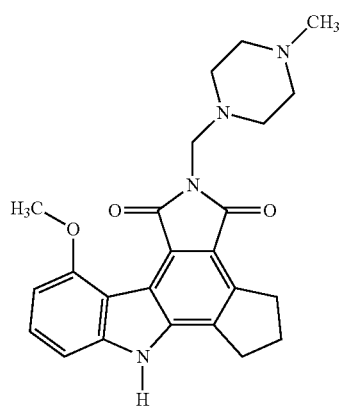

16e

To a slurry of 14b (10.0 g, 30 mmol) and N-methylpiperazine (12.4 g, 124 mmol) in ethanol (950 mL) was added paraformaldehyde (5.60 g, 62.4 mmol) in 0.5 hr and stirred 24 hr. The slurry was evaporated to dryness. To the residue was added hexane (500 mL), sonicated 15 min., stirred 1.5 hr. and cooled at 0° C. for 15 min. A yellow solid was collected and washed with cold hexane. This product was dissolved in warm THF (250 mL) and filtered. The filtrate was added dropwise into hexane (3 L), stirred 15 min., and 16e collected the precipitate and washed with hexane (12.0 g, 96% yield). $^1$H NMR (DMSO-$d_6$) 2.12 (s, 3H), 2.35 (m, 8H), 2.53 (m, 4H), 3.18 (m, 2H), 4.44 (s, 3H), 6.70 (d, 1H), 7.10 (d, 1H), 7.40 (t, 1H), 11.96 (s, 1H). MS m/z 419 (M+H).

Example 205

Preparation of 16f

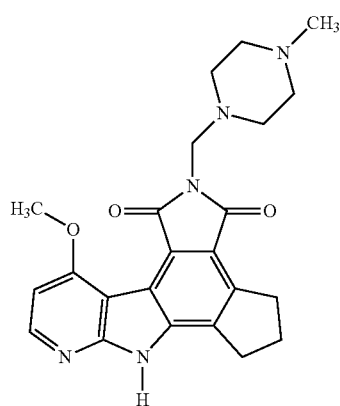

16f

A solution of 8x (90 mg, 0.3 mmol) in DMF (5 ml) was treated with N-methylpiperazine (30 μL, 0.3 mmol) and paraformaldehyde (10 mg, 0.1 mmol) and heated to 60° C. with stirring. After 24 hours the mixture was cooled to ambient temperature, 50% aqueous gluconic acid (w/w, 186 mL, 0.6 mmol) was added with stirring followed by deionized water (25 ml). The mixture was filtered and freeze-dried to give 234 mg of 16f as the di-gluconic acid salt; $^1$H NMR (DMSO-$d_6$): 12.5 (br, 2H), 10.80 (s, 1H), 8.35 (d, J=5 Hz, 1H), 6.85 (d, J=5 Hz, 1H), 4.40 (s, 2H), 4.25 (m, 2H), 4.10 (m, 4H), 3.90 (s, 3H), 3.60 (m, 4H), 3.35 (m, 4H), 3.25 (m, 2H), 2.75 (m, 4H), 2.70 (m, 4H), 2.35 (m, 2H), 2.20 (s, 3H); MS m/z 420 (M+H).

Example 206

Preparation of 16g

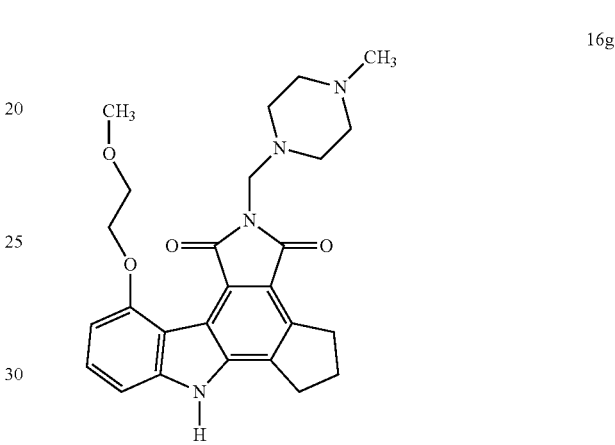

16g

To a slurry of 14f (2.0 g, 5.7 mmol) and N-methylpiperazine (2.28 g, 22.8 mmol) in ethanol (100 mL) at 55° C. was added paraformaldehyde (1.02 g, 11.4 mmol) in 10 min and stirred 5 hr. The slurry was cooled to 10° C. and 16g collected as a yellow solid, washed with cold ethanol and dried (2.5 g, 94%). $^1$H NMR (DMSO-$d_6$) 2.12 (s, 3H), 2.30 (m, 8H), 2.58 (s, 3H), 3.17 (t, 2H), 3.91 (t, 2H), 4.31 (t, 2H), 4.44 (s, 2H), 6.79 (d, 1H), 7.14 (d, 1H), 7.44 (t, 1H), 11.98 (s, 1H); MS m/z 463 (M+H).

Example 207

Preparation of 16h

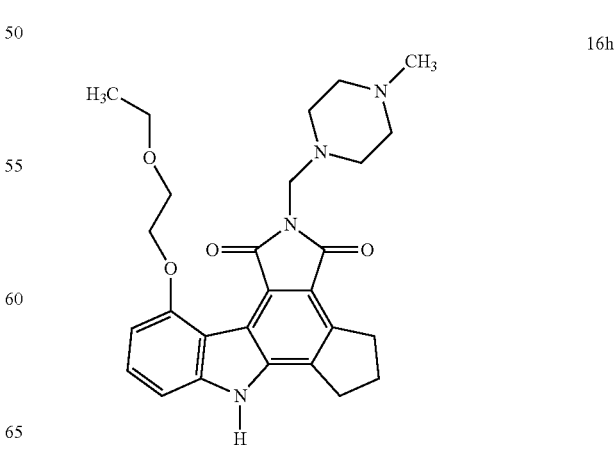

16h

To a slurry of 14i (2.4 g, 6.6 mmol) and N-methylpiperazine (2.64 g, 26.3 mol) in ethanol (100 mL) at 55° C. was added paraformaldehyde (1.18 g, 13.1 mmol) in 10 min and stirred hr. The slurry was concentrated and cooled to 10° C. The yellow solid was collected, washed with cold ethanol and dried (2.77 g, 88% yield). $^1$H NMR (DMSO-d$_6$) 1.10 (t, 3H), 2.12 (s, 3H), 2.29 (m, 6H), 2.59 (m, 4H), 3.17 (t, 2H), 3.50 (m, 4H), 3.95 (t, 2H), 4.30 (t, 2H), 4.46 (s, 2H), 6.79 (d, 1H), 7.14 (d, 1H), 7.44 (t, 1H), 11.98 (s, 1H); MS m/z 477 (M+H).

Example 208

Preparation of 16i

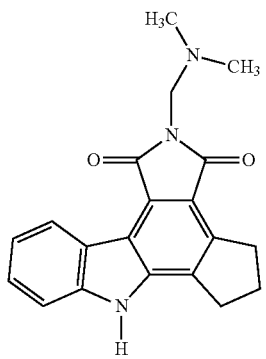

This compound was prepared using the procedure of 16h using 1a, dimethylamine HCl, and paraformaldehyde. $^1$H NMR (DMSO-d$_6$) 2.35 (m, 2H), 280 (s, 6H), 3.2-3.4 (m, 4H), 4.9 (s, 3H), 7.3 (d, 1H), 76 (m, 1H), 8.8 (d, 1H), 12.1 (s, 1H); MS m/z 334 (M+H).

TABLE 18

| Example | No. | PARP IC$_{50}$ |
|---|---|---|
| 171 | 8l | 38 |
| 172 | 8m | 17 |
| 173 | 8n | 6 |
| 174 | 8o | 4 |
| 175 | 8p | 20 |
| 176 | 8q/8r | 3 |
| 177 | 8s | 14 |
| 178 | 8t/8u | 6 |
| 179 | 8vi/8vii | 14 |
| 180 | 8w | 4 |
| 181 | 8x | 4 |
| 182 | 8y | 5 |
| 183 | 8z | 9 |
| 184 | 8aa | 10 |
| 185 | 8ab | 11 |
| 187 | 14c | 176 |
| 188 | 14d | 441 |
| 189 | 14e | 526 |
| 190 | 14f | 25 |
| 191 | 14g | 56 |
| 192 | 14h | 207 |
| 193 | 14i | 36 |
| 194 | 14j | 70 |
| 195 | 14k | 83 |
| 196 | 14l | 21 |
| 197 | 14m | 67 |
| 198 | 14n | 126 |
| 199 | 14o | 7 |
| 200a | 15n | 38 |
| 200b | 15o | 76 |
| 200c | 15p | 82 |

TABLE 18-continued

| Example | No. | PARP IC$_{50}$ |
|---|---|---|
| 201 | 16a | 10 |
| 202 | 16b/16c | 13 |
| 203 | 16d | 11 |
| 204 | 16e | 14 |
| 208 | 16i | 53 |

What is claimed is:
1. A compound of Formula IIIa:

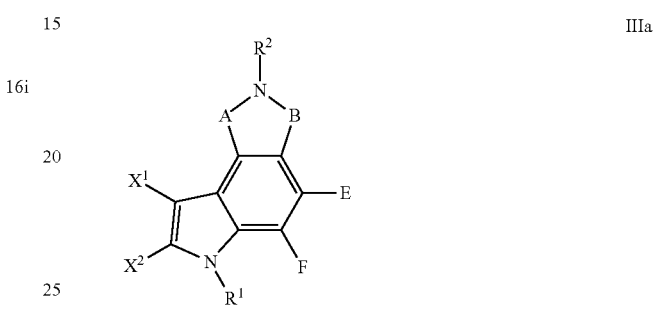

or a pharmacologically acceptable salt thereof, wherein:
each of A and B is, independently, C(=O);
E and F, together with the carbon atoms to which they are attached, form:
a substituted or unsubstituted C$_5$ cycloalkyl group;
R$^1$ is hydrogen;
R$^2$ is lower alkyl having at least one substituent J$^4$;
J is independently at each occurrence:
J$^3$-(J$^2$)$_n$-(J$^1$)$_m$- wherein each of n and m is, independently, 0 or 1;
each of J$^1$ and J$^2$ is, independently,
carbonyl, lower alkylcarbonyl, arylcarbonyl, carbonyloxy, amino, lower alkylamino, lower dialkylamino, amido, lower alkylamido, lower dialkylamido, lower alkoxy, lower alkyl, C$_3$ to C$_7$ cycloalkyl, heterocycloalkyl, aryl, or a heteroaryl; and
J$^3$ is:
hydrogen, halo, hydroxy, cyano, NO$_2$, carboxyl, lower alkyl, aryloxycarbonyl, alkyloxycarbonyl, heteroaryl, or heterocycloalkyl; and
J$^4$ is
lower alkylcarbonyl, arylcarbonyl, amino, lower alkylamino, lower dialkylamino, amido, lower alkylamido, lower dialkylamido, lower alkoxy, lower alkyl, C$_3$ to C$_7$ cycloalkyl, heterocycloalkyl, aryl, or a heteroaryl; and
X$^1$ and X$^2$, together with the atoms to which they are attached, form:
a substituted or unsubstituted phenyl group wherein said substituted phenyl group has at least one substituent J; or
a substituted or unsubstituted heteroaryl group wherein said substituted heteroaryl group has at least one substituent J and where said heteroaryl is pyridine or pyridine-N-oxide.
2. The compound of claim 1 wherein J$^4$ is amino, lower alkylamino, lower dialkylamino, or heterocycloalkyl.
3. The compound of claim 2 wherein X$^1$ and X$^2$, together with the atoms to which they are attached, form a phenyl with at least one substituent J.

4. The compound of claim 3 wherein J is lower alkoxy.

5. The compound of claim 1 wherein $J^4$ is dimethylamino-, diethylamino, 4-morpholin-4-yl, or 4-methylpiperazin-1-yl.

6. The compound of claim 1 wherein $J^4$ is 4-methylpiperazin-1-yl.

7. The compound of claim 6 wherein $X^1$ and $X^2$, together with the atoms to which they are attached, form a phenyl with at least one substituent J.

8. The compound of claim 7 where J is lower alkoxy.

9. The compound of claim 1 selected from:

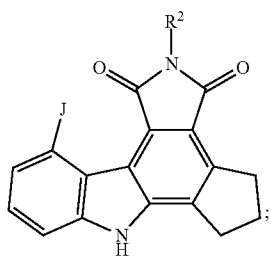

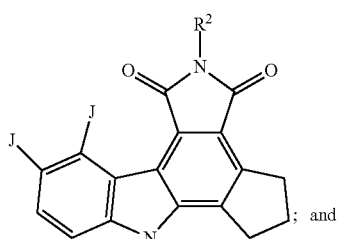

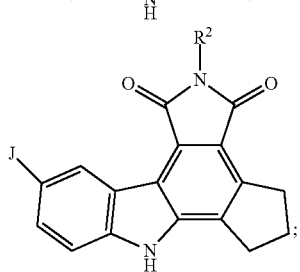

or a pharmacologically acceptable salt thereof.

10. The compound of claim 1 selected from:

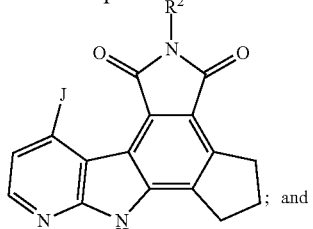

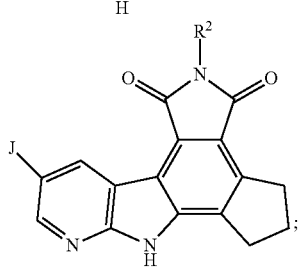

or a pharmacologically acceptable salt thereof.

11. A compound of claim 1 that is selected from:

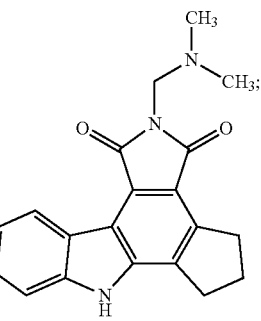

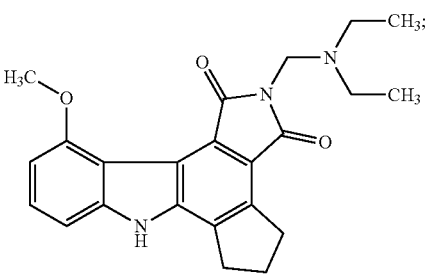

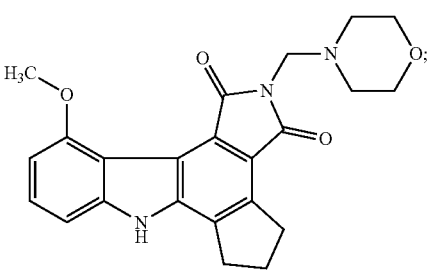

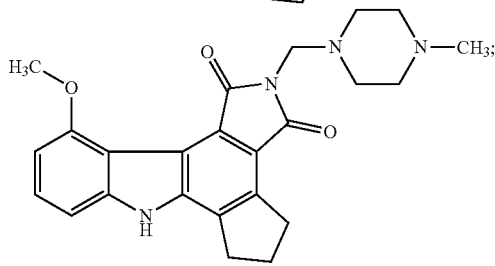

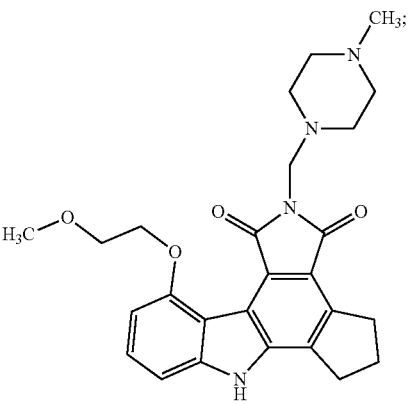

-continued

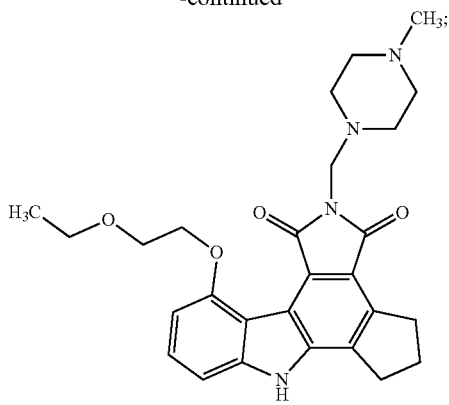

or a pharmacologically acceptable salt thereof.

12. A pharmaceutical composition comprising a compound of claim 1 or a pharmacologically acceptable salt thereof and a pharmaceutically acceptable carrier.

13. A pharmaceutical composition comprising a compound of claim 11 or a pharmacologically acceptable salt thereof and a pharmaceutically acceptable carrier.

14. A method of inhibiting PARP, VEGFR2, or MLK3 activity comprising contacting said PARP, VEGFR2, or MLK3 with a compound of claim 1.

15. A method for treating or preventing a neurodegenerative disease comprising administering to a mammal a therapeutically effective amount of a compound of claim 1.

16. The method of claim 15 wherein said neurodegenerative disease is Parkinson's, Huntington's, or Alzheimer's disease.

17. A method for treating traumatic central nervous system injuries or preventing neuronal degradation associated with traumatic central nervous system injuries comprising administering to a mammal a therapeutically effective amount of a compound of claim 1.

18. A method for treating cerebral ischemia, cardiac ischemia, inflammation, endotoxic shock, or diabetes comprising administering to a mammal a pharmaceutically effective amount of a compound of claim 1.

19. A method for suppressing the formation of blood vessels in a mammal comprising administering to a mammal a pharmaceutically effective amount of a compound of claim 1.

20. A method of treating cellular proliferative disorders comprising administering to a mammal a pharmaceutically effective amount of a compound of claim 1.

21. The method of claim 20 wherein said cellular proliferative disorders are related to solid tumors, diabetic retinopathy, intraocular neovascular syndromes, macular degeneration, rheumatoid arthritis, psoriasis, or endometriosis.

22. A method of treating cancer comprising administering to a mammal a pharmaceutically effective amount of a compound of claim 1.

23. The compound

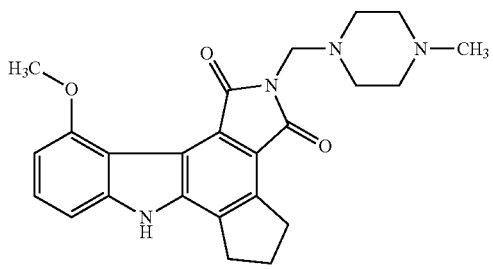 [SMILES: COc1cccc2[nH]c3c4c(c5c(c3c12)C(=O)N(CN1CCN(C)CC1)C5=O)CCC4]

or a salt thereof.

24. A pharmaceutical composition comprising the compound of claim 23 or a salt thereof and a pharmaceutically acceptable carrier.

25. A method of treating cancer comprising administering to a mammal a pharmaceutically effective amount of a compound of claim 1.

26. A method of treating cancer comprising administering to a mammal a pharmaceutically effective amount of the compound of claim 23.

27. A method of treating cancer comprising administering to a mammal a pharmaceutically effective amount of the pharmaceutical composition of claim 24.

* * * * *